(12) United States Patent
Miyaji et al.

(10) Patent No.: US 8,053,453 B2
(45) Date of Patent: Nov. 8, 2011

(54) PYRAZOLONE COMPOUNDS AND THROMBOPOIETIN RECEPTOR ACTIVATOR

(75) Inventors: Katsuaki Miyaji, Chiba (JP); Norihisa Ishiwata, Saitama (JP); Takanori Nakamura, Saitama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 184 days.

(21) Appl. No.: 10/530,482

(22) PCT Filed: Oct. 9, 2003

(86) PCT No.: PCT/JP03/12985
§ 371 (c)(1),
(2), (4) Date: Apr. 6, 2005

(87) PCT Pub. No.: WO2004/033433
PCT Pub. Date: Apr. 22, 2004

(65) Prior Publication Data
US 2006/0069140 A1    Mar. 30, 2006

(30) Foreign Application Priority Data

Oct. 9, 2002  (JP) .................................. 2002-296468
Jul. 24, 2003  (JP) .................................. 2003-278811
Aug. 1, 2003  (JP) .................................. 2003-285316

(51) Int. Cl.
*A61K 31/416*    (2006.01)
*A61K 31/4152*   (2006.01)
*C07D 231/36*    (2006.01)

(52) U.S. Cl. ....................... 514/381; 548/253; 548/367.1

(58) Field of Classification Search .......................... None
See application file for complete search history.

(56) References Cited

U.S. PATENT DOCUMENTS

| 4,065,481 A | 12/1977 | L'Eplattenier et al. |
| 5,066,695 A | 11/1991 | Cseh et al. |

FOREIGN PATENT DOCUMENTS

| JP | A 51-88539 | 8/1976 |
| JP | 10-072492 | 3/1998 |
| JP | 11-001477 | 1/1999 |
| JP | 11-152276 | 6/1999 |
| JP | 2001-097948 | 4/2001 |
| WO | 96/40189 | 12/1996 |
| WO | 96/40750 | 12/1996 |
| WO | 98/25965 | 6/1998 |
| WO | 99/11262 | 3/1999 |
| WO | 00/35446 | 6/2000 |
| WO | 00/66112 | 11/2000 |
| WO | 01/07423 | 2/2001 |
| WO | 01/17349 | 3/2001 |
| WO | 01/21180 | 3/2001 |
| WO | 01/34585 | 5/2001 |
| WO | 01/39773 | 6/2001 |
| WO | 01/53267 | 7/2001 |
| WO | 01/89457 | 11/2001 |
| WO | 02/49413 | 6/2002 |
| WO | 02/059099 | 8/2002 |
| WO | 02/059100 | 8/2002 |
| WO | 02/062775 | 8/2002 |
| WO | 02/085343 | 10/2002 |

OTHER PUBLICATIONS

Nardi et al., CAPLUS AN 1970:31685 (1 page only).*
Jelic et al., CAPLUS AN 2007:287704, abstract.*
Michel, M. CAPLUS AN 2007:194747, abstract.*
Sundell et al, CAPLUS AN 2006:70894, abstract.*
http://www.tirgan.com/thrpenia.htm, p. 1 of 11 through 10 of 11 (10 Pgs).*
Simon et al, "HIV/AIDS epidemiology, pathogenesis, prevention, and treatment", ww.thelancet.com, vol. 368, Aug. 5, 2006, p. 489-504.*
Maitland, Organic Chemistry, W.W.Norton & Company, 1997, p. 786.*
L'Eplattenier et al., caplus an 1977:30991.*
Pain et al, caplus an 1966:27488.*
Chawla et al., "Challenges in Polymorphism of Pharmaceuticals", CRIPS vol. 5, No. 1, Jan.-Mar. 2004 (4 Pages.*
Newman et al., "Solid-state analysis of the active pharmaceutical ingredient in drug products", DDT vol. 8, No. 19, Oct. 2003, p. 898-905.*
Liu et al., caplus an 2003:483572.*
599166-81-1; registry information, Oct. 6, 2003.*
Nardi, Dante et al: "Pyrazoline-5-one and pyrazolidine-3, 5-dione derivatives with antiphlogistic activity" Arzneimittel-Forschung vol. 19, No. 10, p. 1721-23, Oct. 1969.

(Continued)

*Primary Examiner* — Sun Jae Loewe
(74) *Attorney, Agent, or Firm* — Oblon, Spivak, McClelland, Maier & Neustadt, L.L.P.

(57) ABSTRACT

A preventive, therapeutic or improving agent for diseases against which activation of the thrombopoietin receptor is effective or a platelet increasing agent, which contains a thrombopoietin receptor activator represented by the formula (1): wherein A is a C?2-14#191 aryl group, B is a hydrogen atom, a C?1-6#191 alkyl group, a C?1-3#191 alkyl group substituted with one or more fluorine atoms or a C?2-14#191 aryl group, D is a hydrogen atom, a C?1-6#191 alkyl group, a C?1-3#191 alkyl group substituted with one or more fluorine atoms or a C?2-14#191 aryl group, and E is a C?2-14#191 aryl group, a tautomer, prodrug or pharmaceutically acceptable salt of the activator or a solvate thereof, as an active ingredient.

(1)

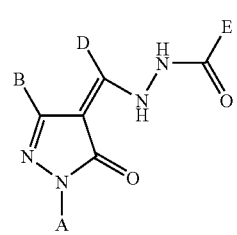

21 Claims, 2 Drawing Sheets

OTHER PUBLICATIONS

Database Chemcats 'Online!, Chemical Abstract Service, "LaboTest Stock", pp. 1-12, Jan. 2, 2002.
Database Chemcats 'Online!, Chemical Abstract Service, "Interchim Intermediates", pp. 1-79, Jul. 9, 2002.
Database Chemcats 'Online!, Chemical Abstract Service, "Enamine Product Listing", pp. 1-6, Nov. 15, 2001.
Cardier, Jose E. "Effects of Megakaryocyte Growth and Development Factor (Thrombopoietin) on Liver Endothelial Cells in Vitro", Microvascular Research, vol. 58, pp. 108-113 1999.
Brizzi, Maria et al. "Thrombopoietin Stimulates Endothelial Cell Motility and Neoangiogenesis by a Platelet-Activating Factor-Dependent Mechanism", Circ Res., vol. 84, pp. 785-796 1999.
"Blood", Journal of the American Society of Hematology, vol. 98, No. 11, pp. 71a-72a 2001.
Lang, Liu et al. "Synthesis and crystal structure of the derivatives of hydrazide containing pyrazolone", Huaxue Xuebao, SciFinder, vol. 59, No. 9, pp. 1495-1501 2001.
Yang, Zheng-yin. "Synthesis, Characterization and Scavenger Effects on $O_2^{-}$ of 3d Transition Metal Complexes of Isonicotinoyl Hydrazone Derived from Isoniazid with PMBP", Synth. React. Inorg. Met.-Org. Chem, vol. 30, No. 7, pp. 1265-1271 2000.
Lang, Liu et al. "Synthesis and Characterization of Metal Complexes of N-(1-Phenyl-3-Methyl-4-Benzal-5-Pyrazolone)-p-Methoxy-Benzoylhydrazine", Synth. React. Inorg. Met.-Org. Chem., vol. 32, No. 4, pp. 739-751 2002.
Yang, Zheng-Yin. "Synthesis, Characterization, and Biological Activity of Rare Earth Complexes of 1-Phenyl-3-Methyl-4-Benzoyl-5-Pyrazolone Benzoylhydrazone", Synth. React. Inorg. Met.-Org. Chem., vol. 32, No. 5, pp. 903-912 2002.
Ji, Ya-Li et al. "Synthesis and crystal structure of N-(1-phenyl-3-methyl-4-benzylidene-5-pyrazolone) p-nitrobenzoylhydrazide", Jiegou Huaxue, SciFinder, vol. 21, No. 5, pp. 553-556 2002.
Rao, Sumita N. et al. "Oxovanadium binuclear (IV) Schiff base complexes derived from aroyl hydrazones having subnormal magnetic moments", Polyhedron, vol. 16, No. 11, pp. 1825-1829 1997.
Nardi, D. et al. "Pyrazoline-5-one and Pyrazolidine-3,5-dione Derivatives with Antiphlogistic and Analgesic Activity", Arzneim-Forsch, vol. 19, No. 10, pp. 1721-1723 1969.
Sawusch, S. et al. "Ligand Exchange Reactions of ReOCl3(PPh3)2 with Tridentate Diacidic Ligands with the Donor Set O⁻N⁻O(N): Molecular and Electronic Structures of the Resulting Oxo-rhenium(V) Complexes", Structural Chemistry, vol. 10, No. 2, pp. 105-119 1999.
Kraudelt, Heide et al. "Titanium- and Vanadium Complexes of 4-[1-(N'-Benzoylhydrazino)-1-phenyl-methylidene]-3-methyl-1-phenyl-pyrazol-5-one. Structure of 4-[1-(N'-Benzoylhydrazino)-1-phenyl-methylidene]-3-methyl-1-phenyl-pyrazol-5-one", Chemical Sciences, vol. 51, No. 9, pp. 1240-1244, with English abstract 1996.
Bansse, Wolfgang et al. "Tin(IV) Complexes with Diacidic Azo(hydrazono) Compounds. Crystal Structure of Bis[4-(2'-hydroxyphenylazo]-3-methyl-1-phenyl-pyrazol-5-onato(2−)]tin(IV)", Chemical Sciences, vol. 52, No. 2, pp. 237-242, with English abstract 1997.
Pain, D. L., et al, "Isothiazoles. Part X[1] Some Sulphonic Acid Derivatives," Journal of the Chemical Society, 1965, Part V, pp. 7283-7284.
Nardi, D., et al., "Pyrazoline-5-one and Pyrazolidine-3,5-dione Derivatives with Antiphlogistic and Analgesic Activity," Arzneimittel-Forschung, 19(10, 1969, pp. 1721-1723.
Zhurnal Obshchei Khimii, 34(9), 1964, pp. 3005-3013.
U.S. Appl. No. 12/492,435, filed Jun. 26, 2009, Owada, et al.
Chinese J. Struct. Chem., vol. 21, 553-556 (2002).

* cited by examiner

PYRAZOLONE COMPOUNDS AND THROMBOPOIETIN RECEPTOR ACTIVATOR

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document to patent document 22).

1) Applications filed by Hokuriku Seiyaku Co., Ltd. relating to 1,4-benzodiazepine derivatives (patent documents 5 and 6)
2) International Laid-open Patent Applications filed by Shionogi & Co., Ltd. (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application filed by Roche Diagnostics GMBH (patent document 21)
6) International Laid-open Patent Application filed by Yamanouchi Pharmaceutical Co., Ltd. (patent document 22)

Some reports have been made about pyrazolone compounds (such as non-patent documents 4-13).

Patent Document 1
JP-A-10-72492
Patent Document 2
WO96/40750
Patent Document 3
WO96/40189
Patent Document 4
WO98/25965
Patent Document 5
JP-A-11-1477
Patent Document 6
JP-A-11-152276
Patent Document 7
WO01/07423
Patent Document 8
WO01/53267
Patent Document 9
WO02/059099
Patent Document 10
WO02/059100
Patent Document 11
WO00/35446
Patent Document 12
WO00/66112
Patent Document 13
WO01/34585
Patent Document 14
WO01/17349
Patent Document 15
WO01/39773
Patent Document 16
WO01/21180
Patent Document 17
WO01/89457
Patent Document 18
WO02/49413
Patent Document 19
WO02/085343
Patent Document 20
JP-A-2001-97948
Patent Document 21
WO99/11262
Patent Document 22
WO02/062775
Non-Patent Document 1
Microvasc. Res., 1999: 58, p. 108-113
Non-Patent Document 2
Circ. Res., 1999: 84, p. 785-796
Non-Patent Document 3
Blood 2001:98, p. 71a
Non-Patent Document 4
Huaxue Xuebao (2001), 59(9) p. 1495-1501
Non-Patent Document 5
Synthesis and Reactivity in Inorganic and Metal Organic Chemistry (2000), 30(7) p. 1265-1271
Non-Patent Document 6
Synthesis and Reactivity in Inorganic and Metal Organic Chemistry (2002), 32(4) p. 739-751
Non-Patent Document 7
Synthesis and Reactivity in Inorganic and Metal Organic Chemistry (2002), 32(5) p. 903-912
Non-Patent Document 8
Jiegou Huaxue (2002), 21(5), p. 553-556
Non-Patent Document 9
Polyhedroon (1997), 16(11) p. 1825-1829
Non-Patent Document 10
Arzneim-Forsch (1969), 19(10) p. 1721-1723
Non-Patent Document 11
Structural Chemistry (1999), 10(2), 105-119
Non-Patent Document 12
Chemical Sciences (1996), 51(9), 1240-1244
Non-Patent Document 13
Chemical Sciences (1997), 52(2), 237-242

DISCLOSURE OF THE INVENTION

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to a pyrazolone compound represented by the formula (1)

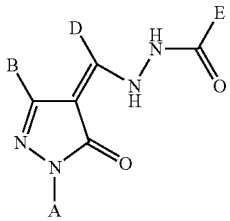

Formula (1)

wherein A is a $C_{2-14}$ aryl group (the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups (the hydroxyl group and the amino group may be substituted with a $C_{1-6}$ alkyl group or a $C_{1-6}$ alkylcarbonyl group)), B is a hydrogen atom, a $C_{1-6}$ alkyl group, a $C_{1-3}$ alkyl group substituted with one or more fluorine atoms or a $C_{2-14}$ aryl group, D is a hydrogen atom, a $C_{1-6}$ alkyl group, a $C_{1-3}$ alkyl group substituted with one or more fluorine atoms or a $C_{2-14}$ aryl group, and E is a $C_{2-14}$ aryl group (the $C_{2-14}$ aryl group is optionally substituted with one or more hydroxyl groups, one or more nitro groups, one or more halogen atoms, one or more cyano groups, one or more $C_{1-3}$ alkyl groups substituted with one or more fluorine atoms, $NG^1G^2$ (wherein $G^1$ and $G^2$ are independently hydrogen atoms, formyl groups, $C_{1-6}$ alkyl groups or $C_{1-6}$ alkylcarbonyl groups), one or more carboxyl groups, one or more sulfonic acid groups, one or more phosphonic acid groups, one or more carbamido groups (the carbamido group may be substituted with a $C_{1-6}$ alkyl group), one or more sulfamido groups (the sulfamido group may be substituted with a $C_{1-6}$ alkyl group), one or more hydroxycarbamido groups, one or more hydroxysulfamido groups, one or more tetrazole groups, one or more $C_{1-6}$ alkoxycarbonyl groups or $X(CYZ)_nco_2H$ (wherein X is $CH_2$, O, S or $NG^3$ ($G^3$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3)), a tautomer, prodrug or pharmaceutically acceptable salt of the compound or a solvate thereof, a thrombopoietin receptor activator, a preventive, therapeutic or improving agent for diseases against which activation of the thrombopoietin receptor is effective which contains the thrombopoietin receptor activator, a tautomer, prodrug or pharmaceutically acceptable salt of the thrombopoietin receptor activator or a solvate thereof as an active ingredient, and a platelet increasing agent containing the thrombopoietin receptor activator, a tautomer, prodrug or pharmaceutically acceptable salt of the thrombopoietin receptor activator or a solvate thereof as an active ingredient. It also relates to a pyrazolone compound represented by the formula (2)

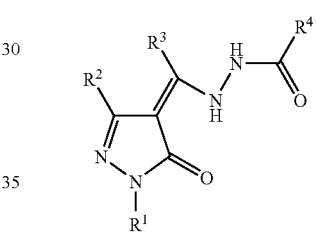

Formula (2)

wherein $R^1$ is a $C_{2-14}$ aryl group (the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups (the hydroxyl group and the amino group may be substituted with a $C_{1-6}$ alkyl group or a $C_{1-6}$ alkylcarbonyl group)), $R^2$ is a hydrogen atom, a $C_{1-6}$ alkyl group, a $C_{1-3}$ alkyl group substituted with one or more fluorine atoms or a $C_{2-14}$ aryl group, $R^3$ is a hydrogen atom, a $C_{1-6}$ alkyl group, a $C_{1-3}$ alkyl group substituted with one or more fluorine atoms or a $C_{2-14}$ aryl group, and $R^4$ is a $C_{2-14}$ aryl group (the $C_{2-14}$ aryl group is optionally substituted with one or more hydroxyl groups, one or more nitro groups or $NR^5R^6$ (wherein $R^5$ and $R^6$ are independently hydrogen atoms, formyl groups, $C_{1-6}$ alkyl groups or $C_{1-6}$ alkylcarbonyl groups)), a tautomer prodrug or pharmaceutically acceptable salt of the compound or a solvate thereof, a thrombopoietin receptor activator, a preventive, therapeutic or improving agent for diseases against which activation of the thrombopoietin receptor is effective which contains the thrombopoietin receptor activator, a tautomer, prodrug or pharmaceutically acceptable salt of the thrombopoietin receptor activator or a solvate thereof as an active ingredient, and a platelet increasing agent containing the thrombopoietin receptor activator, a tautomer, prodrug or pharmaceutically acceptable salt of the thrombopoietin receptor activator or a solvate thereof as an active ingredient. It further relates to a pyrazolone compound represented by the formula (3)

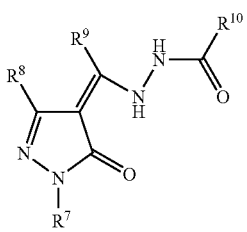

Formula (3)

wherein $R^7$ is a $C_{2-14}$ aryl group (the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups (the hydroxyl group and the amino group may be substituted with a $C_{1-6}$ alkyl group or a $C_{1-6}$ alkylcarbonyl group)), $R^8$ is a hydrogen atom, a $C_{1-6}$ alkyl group, a $C_{1-3}$ alkyl group substituted with one or more fluorine atoms or a $C_{2-14}$ aryl group, $R^9$ is a hydrogen atom, a $C_{1-6}$ alkyl group, a $C_{1-3}$ alkyl group substituted with one or more fluorine atoms or a $C_{2-14}$ aryl group, and $R^{10}$ is a $C_{2-14}$ aryl group (the $C_{2-14}$ aryl group is optionally substituted with one or more carboxyl groups, one or more sulfonic acid groups, one or more phosphonic acid groups, one or more carbamido groups, one or more sulfamido groups, one or more hydroxycarbamido groups, one or more hydroxysulfamido groups, one or more tetrazole groups, one or more $C_{1-6}$ alkoxycarbonyl groups or $X(CYZ)_nCO_2H$ (wherein X is $CH_2$, O, S or $NR^{11}$ ($R^{11}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3)), a tautomer, prodrug or pharmaceutically acceptable salt of the compound or a solvate thereof, a thrombopoietin receptor activator, a preventive, therapeutic or improving agent for diseases against which activation of the thrombopoietin receptor is effective which contains the thrombopoietin receptor activator, a tautomer, prodrug or pharmaceutically acceptable salt of the thrombopoietin receptor activator or a solvate thereof as an active ingredient, and a platelet increasing agent containing the thrombopoietin receptor activator, a tautomer, prodrug or pharmaceutically acceptable salt of the thrombopoietin receptor activator or a solvate thereof as an active ingredient. It still further relates to a pyrazolone compound represented by the formula (4)

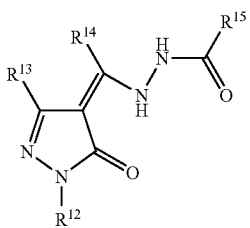

Formula (4)

wherein $R^{12}$ is a $C_{2-14}$ aryl group (the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups (the hydroxyl group and the amino group may be substituted with a $C_{1-6}$ alkyl group or a $C_{1-6}$ alkylcarbonyl group)), $R^{13}$ is a hydrogen atom, a $C_{1-6}$ alkyl group, a $C_{1-3}$ alkyl group substituted with one or more fluorine atoms or a $C_{2-14}$ aryl group, $R^{14}$ is a hydrogen atom, a $C_{1-6}$ alkyl group, a $C_{1-3}$ alkyl group substituted with one or more fluorine atoms or a $C_{2-14}$ aryl group, and $R^{15}$ is a $C_{2-14}$ aryl group (the $C_{2-14}$ aryl group is substituted with a substituent selected from a hydroxyl group, an amino group, a nitro group, a halogen atom, a cyano group, a $C_{1-3}$ alkyl group substituted with one or more fluorine atoms, a carbamido group and a sulfamido group (the carbamido group and the sulfamido group may be substituted with a $C_{1-6}$ alkyl group) and with a substituent selected from a carboxyl group, a sulfonic acid group, a phosphonic acid group, a carbamido group, a sulfamido group, a hydroxycarbamido group, a hydroxysulfamido group, a tetrazole group, a $C_{1-6}$ alkoxycarbonyl group and $X(CYZ)_nCO_2H$ (wherein X is $CH_2$, O, S or $NR^{16}$ ($R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3)), a tautomer, prodrug or pharmaceutically acceptable salt of the compound or a solvate thereof, a thrombopoietin receptor activator, a preventive, therapeutic or improving agent for diseases against which activation of the thrombopoietin receptor is effective which contains the thrombopoietin receptor activator, a tautomer, prodrug or pharmaceutically acceptable salt of the thrombopoietin receptor activator or a solvate thereof as an active ingredient, and a platelet increasing agent containing the thrombopoietin receptor activator, a tautomer, prodrug or pharmaceutically acceptable salt of the thrombopoietin receptor activator or a solvate thereof as an active ingredient.

Though WO99/11262 (patent document 21), WO01/34585 (patent document 13), WO02/49413 (patent document 18) disclose pyrazolone compounds having platelet increasing action, there is no specific disclosure of the pyrazolone compounds of the present invention. The compounds of the present invention showed high activity that could not be expected from the disclosure in WO99/11262 (patent document 21), WO01/34585 (patent document 13) or WO02/49413 (patent document 18).

BEST MODE FOR CARRYING OUT THE INVENTION

Figure 1:
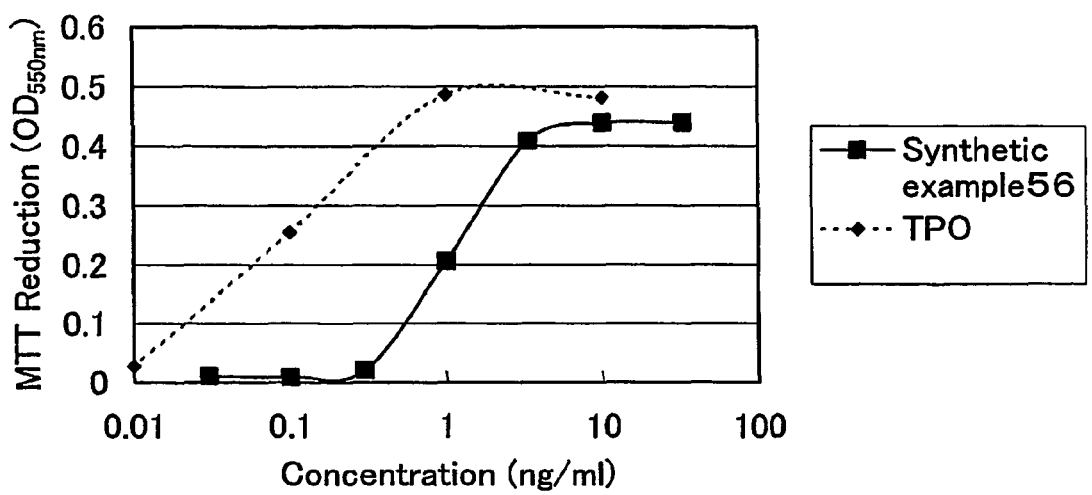
FIG. 1: The proliferation of UT7/EPO-mpl cells when stimulated by Synthetic Example 56 assayed by the MTT method is shown in FIG. 1.

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, and "Bu" denotes butyl.

First, the terms in the respective substituents A, B, D, E, $G^1$, $G^2$, $G^3$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ will be explained.

As a halogen atom, fluorine, chlorine, bromine or iodine may be mentioned.

A $C_{1-3}$ alkyl group may be linear, branched or a $C_3$ cycloalkyl group, and methyl, ethyl, n-propyl, i-propyl and c-propyl and the like may be mentioned. A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenyl group, m-biphenyl group, a p-biphenyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered $C_{5-9}$ fused heterocyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A $C_{1-3}$ alkyl group substituted with one or more fluorine atoms may be a trifluoromethyl group, a difluoromethyl group, a monofluoromethyl group, a pentafluoroethyl group, a 1,1-difluoro-2,2-difluoroethyl group, a heptafluoropropyl group or the like.

A $C_{1-6}$ alkylcarbonyl group may be methylcarbonyl, ethylcarbonyl, n-propylcarbonyl, i-propylcarbonyl, n-butylcarbonyl, i-butylcarbonyl, s-butylcarbonyl, t-butylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl or the like.

A $C_{1-6}$ alkoxycarbonyl group may be methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl or the like.

Specific preferred examples of the substituents A, $R^1$, $R^7$ and $R^{12}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a $C_{1-6}$ alkyl group, a halogen atom, a $C_{1-3}$ alkyl group substituted with one or more fluorine atoms, a nitro group, an amino group, an amino group substituted with a $C_{1-6}$ alkyl group, an amino group substituted with a $C_{1-6}$ alkylcarbonyl group, a hydroxyl group, a hydroxyl group substituted with a $C_{1-6}$ alkyl group, a hydroxyl group substituted with a $C_{1-6}$ alkylcarbonyl group and a $C_{1-6}$ alkylcarbonyl group.

Particularly preferred examples of the substituents A, $R^1$, $R^7$ and $R^{12}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group) and pyridyl groups (a 2-pyridyl group, a 3-pyridyl group and a 4-pyridyl group) optionally substituted with one or more of the following substituents.

Substituents: a $C_{1-6}$ alkyl group, a halogen atom, a $C_{1-3}$ alkyl group substituted with one or more fluorine atoms, a nitro group, an amino group, an amino group substituted with a $C_{1-6}$ alkyl group, an amino group substituted with an $C_{1-6}$ alkylcarbonyl group, a hydroxyl group, a hydroxyl group substituted with a $C_{1-6}$ alkyl group, a hydroxyl group substituted with a $C_{1-6}$ alkylcarbonyl group and a $C_{1-6}$ alkylcarbonyl group.

Still further preferred specific examples of the substituents A, $R^1$, $R^7$ and $R^{12}$ are a 3-methyl-phenyl group, a 4-methyl-phenyl group, a 3,4-dimethyl-phenyl group, a 3-t-butyl-phenyl group, a 4-t-butyl-phenyl group, a 3-trifluoromethyl-phenyl group, a 4-trifluoromethyl-phenyl group, a 3,4-ditrifluoromethyl-phenyl group, a 3-chloro-phenyl group, a 4-chloro-phenyl group, a 3-iodo-phenyl group, a 4-iodo-phenyl group, a 3-fluoro-phenyl group, a 4-fluoro-phenyl group, a 3,4-dichloro-phenyl group, a 3,4-diiode-phenyl group, a 3,4-difluoro-phenyl group, a 3-nitro-phenyl group, a 4-nitro-phenyl group, a α-naphthyl group, a β-naphthyl group and the like.

Specific preferable examples of the substituents B, $R^2$, $R^8$ and $R^{13}$ are a hydrogen atom, a methyl group, an ethyl group, a n-propyl group, an i-propyl group, a trifluoromethyl group and a phenyl group, and particularly preferred examples are a hydrogen atom, a methyl group, an ethyl group and a trifluoromethyl group.

Specific preferable examples of the substituents D, $R^3$, $R^9$ and $R^{14}$ are a hydrogen atom, a methyl group, an ethyl group, a n-propyl group, an i-propyl group, a c-propyl group and a phenyl group, and particularly preferable examples are a hydrogen atom, a methyl group and an ethyl group.

Specific preferable examples of the substituent $R^4$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) substituted with one or more of the following substituents.

Substituents: a hydroxyl group, an amino group and a nitro group.

Specific particularly preferred examples of the substituent $R^4$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group) and pyridyl groups (a 2-pyridyl group, a 3-pyridyl group and a 4-pyridyl group) substituted with one or more of the following substituents.

Substituents: a hydroxyl group, an amino group and a nitro group.

Specific preferable example of the substituent $R^{10}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinoyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) substituted with one or more of the following substituents.

Substituents: a carboxyl group, sulfonic acid group, a phosphonic acid group, a carbamido group, a sulfamide group, a hydroxycarbamido group, a hydroxysulfamido group, $CH_2CO_2H$, $OCH_2CO_2H$, $NHCH_2CO_2H$, $CH_2CH_2CO_2H$ and a tetrazole group.

Specific particularly preferred examples of the substituent $R^{10}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group) and pyridyl groups (a 2-pyridyl group, a 3-pyridyl group and a 4-pyridyl group) substituted with one or more of the following substituents.

Substituents: a carboxyl group, a sulfonic acid group, a phosphonic acid group, a carbamido group, a sulfamido group, a hydroxycarbamido group, a hydroxysulfamido group, $CH_2CO_2H$, $OCH_2CO_2H$, $NHCH_2CO_2H$, $CH_2CH_2CO_2H$ and a tetrazole group.

Specific preferable examples of the substituent $R^{15}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) substituted with a substituent selected from substituent set A and with a substituent selected from substituent set B.

Substituent set A: a hydroxyl group, an amino group, a nitro group, a cyano group, a halogen atom, a $C_{1-3}$ alkyl group substituted with one or more fluorine atoms, a carbamido group and a sulfamido group (the carbamido group and the sulfamido group may be substituted with a $C_{1-6}$ alkyl group).

Substituent set B: a carboxyl group, a sulfonic acid group, a phosphonic acid group, a carbamido group, a sulfamido group, a hydroxycarbamido group, a hydroxysulfamido group, $CH_2CO_2H$, $OCH_2CO_2H$, $NHCH_2CO_2H$, $CH_2CH_2CO_2H$ and a tetrazole group.

Specific particularly preferred examples of the substituent $R^{15}$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group) and pyridyl groups (a 2-pyridyl group, a 3-pyridyl group and a 4-pyridyl group) substituted with a substituent selected from substituent set A and with a substituent selected from substituent set B.

Substituent set A: a hydroxyl group, an amino group, a nitro group, a cyano group, a halogen atom, a $C_{1-3}$ alkyl group substituted with one or more fluorine atoms, a carbamido group and a sulfamido group (the carbamido group and the sulfamido group may be substituted with a $C_{1-6}$ alkyl group).

Substituent set B: a carboxyl group, a sulfonic acid group, a phosphonic acid group, a carbamido group, a sulfamido group, a hydroxycarbamido group, a hydroxysulfamido group, $CH_2CO_2H$, $OCH_2CO_2H$, $NHCH_2CO_2H$, $CH_2CH_2CO_2H$ and a tetrazole group.

Favorable compounds as the thrombopoietin receptor activator, the preventive, therapeutic or improving agent for diseases against which activation of the thrombopoietin receptor is effective and the platelet increasing agent of the present invention are as follows.

1) Pyrazolone compounds represented by the formula (2) wherein $R^4$ is a $C_{2-14}$ aryl group substituted with one or more hydroxyl groups, tautomers, prodrugs or pharmaceutically acceptable salts of the compounds or solvates thereof.

2) Pyrazolone compounds represented by the formula (2) wherein $R^4$ is a $C_{2-14}$ aryl group substituted with $NR^5R^6$ (wherein $R^5$ and $R^6$ are independently hydrogen atoms, formyl groups, $C_{1-6}$ alkyl groups or $C_{1-6}$ alkylcarbonyl groups), tautomers, prodrugs or pharmaceutically acceptable salts of the compounds or solvates thereof.

3) Pyrazolone compounds represented by the formula (2) wherein $R^4$ is a phenyl group or pyridyl group substituted with one or more hydroxyl groups, tautomers, prodrugs or pharmaceutically acceptable salts of the compounds or solvates thereof.

4) Pyrazolone compounds represented by the formula (2) wherein $R^4$ is a phenyl group or pyridyl group substituted with $NR^5R^6$ (wherein $R^5$ and $R^6$ are independently hydrogen atoms, formyl groups, $C_{1-6}$ alkyl groups or $C_{1-6}$ alkylcarbonyl groups), tautomers, prodrugs or pharmaceutically acceptable salts of the compounds or solvates thereof.

5) Pyrazolone compounds represented by the formula (2) wherein $R^4$ is a thienyl group, furyl group or pyridazinyl group substituted with one or more hydroxyl groups, tautomers, prodrugs or pharmaceutically acceptable salts of the compounds or solvates thereof.

6) Pyrazolone compounds represented by the formula (2) wherein $R^4$ is a thienyl, furyl group or pyridazinyl group substituted with $NR^5R^6$ (wherein $R^5$ and $R^6$ are independently hydrogen atoms, formyl groups, $C_{1-6}$ alkyl groups or $C_{1-6}$ alkylcarbonyl groups), tautomers, prodrugs or pharmaceutically acceptable salts of the compounds or solvates thereof.

7) Pyrazolone compounds represented by the formula (3) wherein $R^{10}$ is a $C_{2-14}$ aryl group substituted with $X(CYZ)_nCO_2H$ (wherein X is $CH_2$, O, S or $NR^{11}$ (wherein $R^{11}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3), tautomers, prodrugs or pharmaceutically acceptable salts of the compounds or solvates thereof.

8) Pyrazolone compounds represented by the formula (3) wherein $R^{10}$ is a phenyl group or pyridyl group substituted with $X(CYZ)_nCO_2H$ (wherein X is $CH_2$, O, S or $NR^{11}$ (wherein $R^{11}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3), tautomers, prodrugs or pharmaceutically acceptable salts of the compounds or solvates thereof.

9) Pyrazolone compounds represented by the formula (3) wherein $R^{10}$ is a thienyl group, furyl group or a pyridazinyl group substituted with $X(CYZ)_nCO_2H$ (wherein X is $CH_2$, O, S or $NR^{11}$ (wherein $R^{11}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3), tautomers, prodrugs or pharmaceutically acceptable salts of the compounds or solvates thereof.

10) Pyrazolone compounds represented by the formula (3) wherein $R^{10}$ is a $C_{2-14}$ aryl group substituted with a carboxyl group, tautomers, prodrugs or pharmaceutically acceptable salts of the compounds or solvates thereof.

11) Pyrazolone compounds represented by the formula (3) wherein $R^{10}$ is a phenyl group or pyridyl group substituted with a carboxyl group, tautomers, prodrugs or pharmaceutically acceptable salts of the compounds or solvates thereof.

12) Pyrazolone compounds represented by the formula (3) wherein $R^{10}$ is a thienyl group, furyl group or pyridazinyl group substituted with a carboxyl group, tautomers, prodrugs or pharmaceutically acceptable salts of the compounds or solvates thereof.

13) Pyrazolone compounds represented by the formula (3) wherein $R^{10}$ is a $C_{2-14}$ aryl group substituted with a sulfonic acid group, tautomers, prodrugs or pharmaceutically acceptable salts of the compounds or solvates thereof.

14) Pyrazolone compounds represented by the formula (3) wherein $R^{10}$ is a phenyl group or pyridyl group substituted with a sulfonic acid group, tautomers, prodrugs or pharmaceutically acceptable salts of the compounds or solvates thereof.

15) Pyrazolone compounds represented by the formula (3) wherein $R^{10}$ is a thienyl group, furyl group or pyridazinyl group substituted with a sulfonic acid group, tautomers, prodrugs or pharmaceutically acceptable salts of the compounds or solvates thereof.

16) Pyrazolone compounds represented by the formula (3) wherein $R^{10}$ is a $C_{2-14}$ aryl group substituted with a phosphonic acid group, tautomers, prodrugs or pharmaceutically acceptable salts of the compounds or solvates thereof.

17) Pyrazolone compounds represented by the formula (3) wherein $R^{10}$ is a phenyl group or pyridyl group substituted with a phosphonic acid group, tautomers, prodrugs or pharmaceutically acceptable salts of the compounds or solvates thereof.

18) Pyrazolone compounds represented by the formula (3) wherein $R^{10}$ is a thienyl group, furyl group or pyridazinyl group substituted with a phosphonic acid group, tautomers, prodrugs or pharmaceutically acceptable salts of the compounds or solvates thereof.

19) Pyrazolone compounds represented by the formula (3) wherein $R^{10}$ is a $C_{2-14}$ aryl group substituted with a carbamido group, tautomers, prodrugs or pharmaceutically acceptable salts of the compounds or solvates thereof.

20) Pyrazolone compounds represented by the formula (3) wherein $R^{10}$ is a phenyl group or pyridyl group substituted with a carbamido group, tautomers, prodrugs or pharmaceutically acceptable salts of the compounds or solvates thereof.

21) Pyrazolone compounds represented by the formula (3) wherein $R^{10}$ is a thienyl group, furyl group or pyridazinyl group substituted with a carbamido group, tautomers, prodrugs or pharmaceutically acceptable salts of the compounds or solvates thereof.

22) Pyrazolone compounds represented by the formula (3) wherein $R^{10}$ is a $C_{2-14}$ aryl group substituted with a sulfamido group, tautomers, prodrugs or pharmaceutically acceptable salts of the compounds or solvates thereof.

23) Pyrazolone compounds represented by the formula (3) wherein $R^{10}$ is a phenyl group or pyridyl group substituted with a sulfamido group, tautomers, prodrugs or pharmaceutically acceptable salts of the compounds or solvates thereof.

24) Pyrazolone compounds represented by the formula (3) wherein $R^{10}$ is a thienyl group, furyl group or pyridazinyl group substituted with a sulfamido group, tautomers, prodrugs or pharmaceutically acceptable salts of the compounds or solvates thereof.

25) Pyrazolone compounds represented by the formula (3) wherein $R^{10}$ is a $C_{2-14}$ aryl group substituted with a hydroxycarbamido group, tautomers, prodrugs or pharmaceutically acceptable salts of the compounds or solvates thereof.

26) Pyrazolone compounds represented by the formula (3) wherein $R^{10}$ is a phenyl group or pyridyl group substituted with a hydroxycarbamido group, tautomers, prodrugs or pharmaceutically acceptable salts of the compounds or solvates thereof.

27) Pyrazolone compounds represented by the formula (3) wherein $R^{10}$ is a thienyl group, furyl group or pyridazinyl group substituted with a hydroxycarbamido group, tautomers, prodrugs or pharmaceutically acceptable salts of the compounds or solvates thereof.

28) Pyrazolone compounds represented by the formula (3) wherein $R^{10}$ is a $C_{2-14}$ aryl group substituted with a hydroxysulfamido group, tautomers, prodrugs or pharmaceutically acceptable salts of the compounds or solvates thereof.

29) Pyrazolone compounds represented by the formula (3) wherein $R^{10}$ is a phenyl group or pyridyl group substituted with a hydroxysulfamido group, tautomers, prodrugs or pharmaceutically acceptable salts of the compounds or solvates thereof.

30) Pyrazolone compounds represented by the formula (3) wherein $R^{10}$ is a thienyl group, furyl group or pyridazinyl group substituted with a hydroxysulfamido group, tautomers, prodrugs or pharmaceutically acceptable salts of the compounds or solvates thereof.

31) Pyrazolone compounds represented by the formula (3) wherein $R^{10}$ is a $C_{2-14}$ aryl group substituted with a tetrazole group, tautomers, prodrugs or pharmaceutically acceptable salts of the compounds or solvates thereof.

32) Pyrazolone compounds represented by the formula (3) wherein $R^{10}$ is a phenyl group or pyridyl group substituted with a tetrazole group, tautomers, prodrugs or pharmaceutically acceptable salts of the compounds or solvates thereof.

33) Pyrazolone compounds represented by the formula (3) wherein $R^{10}$ is a thienyl group, furyl group or pyridazinyl group substituted with a tetrazole group, tautomers, prodrugs or pharmaceutically acceptable salts of the compounds or solvates thereof.

34) Pyrazolone compounds represented by the formula (4) wherein $R^{15}$ is a $C_{2-14}$ aryl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with a hydroxyl group, tautomers, prodrugs or pharmaceutically acceptable salts of the compounds or solvates thereof.

35) Pyrazolone compounds represented by the formula (4) wherein $R^{15}$ is a phenyl or pyridyl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with a hydroxyl group, tautomers, prodrugs or pharmaceutically acceptable salts of the compounds or solvates thereof.

36) Pyrazolone compounds represented by the formula (4) wherein $R^{15}$ is a thienyl group, furyl group or pyridazinyl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with a hydroxyl group, tautomers, prodrugs or pharmaceutically acceptable salts of the compounds or solvates thereof.

37) Pyrazolone compounds represented by the formula (4) wherein $R^{15}$ is a $C_{2-14}$ aryl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with an amino group, tautomers, prodrugs or pharmaceutically acceptable salts of the compounds or solvates thereof.

38) Pyrazolone compounds represented by the formula (4) wherein $R^{15}$ is a phenyl or pyridyl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with an amino group, tautomers, prodrugs or pharmaceutically acceptable salts of the compounds or solvates thereof.

39) Pyrazolone compounds represented by the formula (4) wherein $R^{15}$ is a thienyl group, furyl group or pyridazinyl group substituted with $X(CYZ)_nCO_2H$ (wherein X is $CH_2$, O, S or $NR^{16}$ (wherein $R^{16}$ is a hydrogen atom, a $C_{1-6}$ alkyl group, a formyl group or a $C_{1-6}$ alkylcarbonyl group), Y and Z are independently hydrogen atoms or $C_{1-3}$ alkyl groups, and n is 0, 1, 2 or 3) and with an amino group, tautomers, prodrugs or pharmaceutically acceptable salts of the compounds or solvates thereof.

40) Pyrazolone compounds represented by the formula (4) wherein $R^{15}$ is a $C_{2-14}$ aryl group substituted with a substituent selected from a nitro group, a cyano group, a $C_{1-3}$ alkyl group substituted with one or more fluorine atoms, a carbamido group and a sulfamido group (the carbamido group and the sulfamido group may be substituted with a $C_{1-6}$ alkyl group) and a halogen atom and with a carboxyl group, tautomers, prodrugs or pharmaceutically acceptable salts of the compounds or solvates thereof.

41) Pyrazolone compounds represented by the formula (4) wherein $R^{15}$ is a phenyl or pyridyl group substituted with a substituent selected from a nitro group, a cyano group, a $C_{1-3}$ alkyl group substituted with one or more fluorine atoms, a carbamido group and a sulfamido group (the carbamido group and the sulfamido group may be substituted with a $C_{1-6}$ alkyl group) and a halogen atom and with a carboxyl group, tautomers, prodrugs or pharmaceutically acceptable salts of the compounds or solvates thereof.

42) Pyrazolone compounds represented by the formula (4) wherein $R^{15}$ is a thienyl group, furyl group or pyridazinyl group substituted with a substituent selected from a nitro group, a cyano group, a $C_{1-3}$ alkyl group substituted with one or more fluorine atoms, a carbamido group and a sulfamido group (the carbamido group and the sulfamido group may be substituted with a $C_{1-6}$ alkyl group) and a halogen atom and with a carboxyl group, tautomers, prodrugs or pharmaceutically acceptable salts of the compounds or solvates thereof.

43) The pyrazolone compounds according to 1), 2), 3), 4), 5) or 6), wherein $R^2$ is a $C_{1-3}$ alkyl group substituted with one or more fluorine atoms, tautomers, prodrugs or pharmaceutically acceptable salts of the compounds or solvates thereof.

44) The pyrazolone compounds according to 1), 2), 3), 4), 5) or 6), wherein $R^2$ is a $C_{1-6}$ alkyl group, tautomers, prodrugs or pharmaceutically acceptable salts of the compounds or solvates thereof.

45) The pyrazolone compounds according to 1), 2), 3), 4), 5) or 6), wherein $R^2$ is a hydrogen atom, tautomers, prodrugs or pharmaceutically acceptable salts of the compounds or solvates thereof.

46) The pyrazolone compounds according to 7), 8), 9), 10), 11), 12), 13) 14), 15), 16), 17), 18), 19), 20), 21), 22), 23), 24), 25), 26), 27), 28), 29), 30), 31), 32) or 33), wherein $R^8$ is a $C_{1-3}$ alkyl group substituted with one or more fluorine atoms, tautomers, prodrugs or pharmaceutically acceptable salts of the compounds or solvates thereof.

47) The pyrazolone compounds according to 7), 8), 9), 10), 11), 12), 13) 14), 15), 16), 17), 18), 19), 20), 21), 22), 23), 24), 25), 26), 27), 28), 29), 30), 31), 32) or 33), wherein $R^8$ is a $C_{1-6}$ alkyl group, tautomers, prodrugs or pharmaceutically acceptable salts of the compounds or solvates thereof.

48) The pyrazolone compounds according to 7), 8), 9), 10), 11), 12), 13) 14), 15), 16), 17), 18), 19), 20), 21), 22), 23), 24), 25), 26), 27), 28), 29), 30), 31), 32) or 33), wherein $R^8$ is a hydrogen atom, tautomers, prodrugs or pharmaceutically acceptable salts of the compounds or solvates thereof.

49) The pyrazolone compounds according to 34), 35), 36), 37), 38), 39), 40), 41) or 42), wherein $R^{13}$ is a $C_{1-3}$ alkyl group substituted with one or more fluorine atoms, tautomers, prodrugs or pharmaceutically acceptable salts of the compounds or solvates thereof.

50) The pyrazolone compounds according to 34), 35), 36), 37), 38), 39), 40), 41) or 42), wherein $R^{13}$ is a $C_{1-6}$ alkyl group, tautomers, prodrugs or pharmaceutically acceptable salts of the compounds or solvates thereof.

51) The pyrazolone compounds according to 34), 35), 36), 37), 38), 39), 40), 41) or 42), wherein $R^{13}$ is a hydrogen atom, tautomers, prodrugs or pharmaceutically acceptable salts of the compounds or solvates thereof.

52) The pyrazolone compounds according to 1), 2), 3), 4), 5), 6), 43), 44) or 45), wherein $R^3$ is a hydrogen atom, tautomers, prodrugs or pharmaceutically acceptable salts of the compounds or solvates thereof.

53) The pyrazolone compounds according to 1), 2), 3), 4), 5), 6), 43), 44) or 45), wherein $R^3$ is a $C_{1-6}$ alkyl group, tautomers, prodrugs or pharmaceutically acceptable salts of the compounds or solvates thereof.

54) The pyrazolone compounds according to 7), 8), 9), 10), 11), 12), 13), 14), 15), 16), 17), 18), 19), 20), 21), 22), 23), 24), 25), 26), 27), 28), 29), 30), 31), 32), 33), 46), 47) or 48), wherein $R^9$ is a hydrogen atom, tautomers, prodrugs or pharmaceutically acceptable salts of the compounds or solvates thereof.

55) The pyrazolone compounds according to 7), 8), 9), 10), 11), 12), 13), 14), 15), 16), 17), 18), 19), 20), 21), 22), 23), 24), 25), 26), 27), 28), 29), 30), 31), 32), 33), 46), 47) or 48), wherein $R^9$ is a $C_{1-6}$ alkyl group, tautomers, prodrugs or pharmaceutically acceptable salts of the compounds or solvates thereof.

56) The pyrazolone compounds according to 34), 35), 36), 37), 38), 39), 40), 41), 42), 49), 50) or 51), wherein $R^{14}$ is a hydrogen atom, tautomers, prodrugs or pharmaceutically acceptable salts of the compounds or solvates thereof.

57) The pyrazolone compounds according to 34), 35), 36), 37), 38), 39), 40), 41), 42), 49), 50) or 51), wherein $R^{14}$ is a $C_{1-6}$ alkyl group, tautomers, prodrugs or pharmaceutically acceptable salts of the compounds or solvates thereof.

58) The pyrazolone compounds according to 52) or 53), wherein $R^1$ is a $C_{2-14}$ aryl group substituted with one or more $C_{3-6}$ alkyl groups, tautomers, prodrugs or pharmaceutically acceptable salts of the compounds or solvates thereof.

59) The pyrazolone compounds according to 52) or 53), wherein $R^1$ is a phenyl group or pyridyl group substituted with one or more $C_{1-6}$ alkyl groups, tautomers, prodrugs or pharmaceutically acceptable salts of the compounds or solvates thereof.

60) The pyrazolone compounds according to 52) or 53), wherein $R^1$ is a thienyl group, furyl group or pyridazinyl group substituted with one or more $C_{1-6}$ alkyl groups, tautomers, prodrugs or pharmaceutically acceptable salts of the compounds or solvates thereof.

61) The pyrazolone compounds according to 54) or 55), wherein $R^7$ is a $C_{2-14}$ aryl group substituted with one or more $C_{1-6}$ alkyl groups, tautomers, prodrugs or pharmaceutically acceptable salts of the compounds or solvates thereof.

62) The pyrazolone compounds according to 54) or 55), wherein $R^7$ is a phenyl group or pyridyl group substituted with one or more $C_{1-6}$ alkyl groups, tautomers, prodrugs or pharmaceutically acceptable salts of the compounds or solvates thereof.

63) The pyrazolone compounds according to 54) or 55), wherein $R^7$ is a thienyl group, furyl group or pyridazinyl group substituted with one or more $C_{1-6}$ alkyl groups, tautomers, prodrugs or pharmaceutically acceptable salts of the compounds or solvates thereof.

64) The pyrazolone compounds according to 56) or 57), wherein $R^{12}$ is a $C_{2-14}$ aryl group substituted with one or more $C_{1-6}$ alkyl groups, tautomers, prodrugs or pharmaceutically acceptable salts of the compounds or solvates thereof.

65) The pyrazolone compounds according to 56) or 57), wherein $R^{12}$ is a phenyl group or pyridyl group substituted with one or more C$_{1-6}$ alkyl groups, tautomers, prodrugs or pharmaceutically acceptable salts of the compounds or solvates thereof.

66) The pyrazolone compounds according to 56) or 57), wherein R$^{12}$ is a thienyl group, furyl group or pyridazinyl group substituted with one or more C$_{1-6}$ alkyl groups, tautomers, prodrugs or pharmaceutically acceptable salts of the compounds or solvates thereof.

67) The pyrazolone compounds according to 52) or 53) wherein R$^1$ is a C$_{2-14}$ aryl group substituted with one or more halogen atoms, tautomers, prodrugs or pharmaceutically acceptable salts of the compounds or solvates thereof.

68) The pyrazolone compounds according to 52) or 53) wherein R$^1$ is a phenyl group or pyridyl group substituted with one or more halogen atoms, tautomers, prodrugs or pharmaceutically acceptable salts of the compounds or solvates thereof.

69) The pyrazolone compounds according to 52) or 53) wherein R$^1$ is a thienyl group, furyl group or pyridazinyl group substituted with one or more halogen atoms, tautomers, prodrugs or pharmaceutically acceptable salts of the compounds or solvates thereof.

70) The pyrazolone compounds according to 54) or 55), wherein R$^7$ is a C$_{2-14}$ aryl group substituted with one or more halogen atoms, tautomers, prodrugs or pharmaceutically acceptable salts of the compounds or solvates thereof.

71) The pyrazolone compounds according to 54) or 55), wherein R$^7$ is a phenyl group or pyridyl group substituted with one or more halogen atoms, tautomers, prodrugs or pharmaceutically acceptable salts of the compounds or solvates thereof.

72) The pyrazolone compounds according to 54) or 55), wherein R$^7$ is a thienyl group, furyl group or pyridazinyl group substituted with one or more halogen atoms, tautomers, prodrugs or pharmaceutically acceptable salts of the compounds or solvates thereof.

73) The pyrazolone compounds according to 56) or 57), wherein R$^{12}$ is a C$_{2-14}$ aryl group substituted with one or more halogen atoms, tautomers, prodrugs or pharmaceutically acceptable salts of the compounds or solvates thereof.

74) The pyrazolone compounds according to 56) or 57), wherein R$^{12}$ is a phenyl group or pyridyl group substituted with one or more halogen atoms, tautomers, prodrugs or pharmaceutically acceptable salts of the compounds or solvates thereof.

75) The pyrazolone compounds according to 56) or 57), wherein R$^{12}$ is a thienyl group, furyl group or pyridazinyl group substituted with one or more halogen atoms, tautomers, prodrugs or pharmaceutically acceptable salts of the compounds or solvates thereof.

76) The pyrazolone compounds according to 52) or 53), wherein R$^1$ is a C$_{2-14}$ aryl group substituted with one or more C$_{1-3}$ alkyl groups substituted with one or more fluorine atoms, tautomers, prodrugs or pharmaceutically acceptable salts of the compounds or solvates thereof.

77) The pyrazolone compounds according to 52) or 53), wherein R$^1$ is a phenyl group or pyridyl group substituted with one or more C$_{1-3}$ alkyl groups substituted with one or more fluorine atoms, tautomers, prodrugs or pharmaceutically acceptable salts of the compounds or solvates thereof.

78) The pyrazolone compounds according to 52) or 53), wherein R$^1$ is a thienyl group, furyl group or pyridazinyl group substituted with one or more C$_{1-3}$ alkyl groups substituted with one or more fluorine atoms, tautomers, prodrugs or pharmaceutically acceptable salts of the compounds or solvates thereof.

79) The pyrazolone compounds according to 54) or 55), wherein R$^7$ is a C$_{2-14}$ aryl group substituted with one or more C$_{1-3}$ alkyl groups substituted with one or more fluorine atoms, tautomers, prodrugs or pharmaceutically acceptable salts of the compounds or solvates thereof.

80) The pyrazolone compounds according to 54) or 55), wherein R$^7$ is a phenyl group or pyridyl group substituted with one or more C$_{1-3}$ alkyl groups substituted with one or more fluorine atoms, tautomers, prodrugs or pharmaceutically acceptable salts of the compounds or solvates thereof.

81) The pyrazolone compounds according to 54) or 55), wherein R$^7$ is a thienyl group, furyl group or pyridazinyl group substituted with one or more C$_{1-3}$ alkyl groups substituted with one or more fluorine atoms, tautomers, prodrugs or pharmaceutically acceptable salts of the compounds or solvates thereof.

82) The pyrazolone compounds according to 56) or 57), wherein R$^{12}$ is a C$_{2-14}$ aryl group substituted with one or more C$_{1-3}$ alkyl groups substituted with one or more fluorine atoms, tautomers, prodrugs or pharmaceutically acceptable salts of the compounds or solvates thereof.

83) The pyrazolone compounds according to 56) or 57), wherein R$^{12}$ is a phenyl group or pyridyl group substituted with one or more C$_{1-3}$ alkyl groups substituted with one or more fluorine atoms, tautomers, prodrugs or pharmaceutically acceptable salts of the compounds or solvates thereof.

84) The pyrazolone compounds according to 56) or 57), wherein R$^{12}$ is a thienyl group, furyl group or pyridazinyl group substituted with one or more C$_{1-3}$ alkyl groups substituted with one or more fluorine atoms, tautomers, prodrugs or pharmaceutically acceptable salts of the compounds or solvates thereof.

85) The pyrazolone compounds according to 52) or 53), wherein R$^1$ is a C$_{2-14}$ aryl group substituted with a hydroxyl group substituted with a C$_{1-6}$ alkyl group, tautomers, prodrugs or pharmaceutically acceptable salts of the compounds or solvates thereof.

86) The pyrazolone compounds according to 52) or 53), wherein R$^1$ is a phenyl group or pyridyl group substituted with a hydroxyl group substituted with a C$_{1-6}$ alkyl group, tautomers, prodrugs or pharmaceutically acceptable salts of the compounds or solvates thereof.

87) The pyrazolone compounds according to 52) or 53), wherein R$^1$ is a thienyl group, furyl group or pyridazinyl group substituted with a hydroxyl group substituted with a C$_{1-6}$ alkyl group, tautomers, prodrugs or pharmaceutically acceptable salts of the compounds or solvates thereof.

88) The pyrazolone compounds according to 54) or 55), wherein R$^7$ is a C$_{2-14}$ aryl group substituted with a hydroxyl group substituted with a C$_{1-6}$ alkyl group, tautomers, prodrugs or pharmaceutically acceptable salts of the compounds or solvates thereof.

89) The pyrazolone compounds according to 54) or 55), wherein R$^7$ is a phenyl group or pyridyl group substituted with a hydroxyl group substituted with a C$_{1-6}$ alkyl group, tautomers, prodrugs or pharmaceutically acceptable salts of the compounds or solvates thereof.

90) The pyrazolone compounds according to 54) or 55), wherein R$^7$ is a thienyl group, furyl group or pyridazinyl group substituted with a hydroxyl group substituted with a C$_{1-6}$ alkyl group, tautomers, prodrugs or pharmaceutically acceptable salts of the compounds or solvates thereof.

91) The pyrazolone compounds according to 56) or 57), wherein R$^{12}$ is a C$_{2-14}$ aryl group substituted with a hydroxyl group substituted with a C$_{1-6}$ alkyl group, tautomers, prodrugs or pharmaceutically acceptable salts of the compounds or solvates thereof.

92) The pyrazolone compounds according to 56) or 57), wherein $R^{12}$ is a phenyl group or pyridyl group substituted with a hydroxyl group substituted with a $C_{1-6}$ alkyl group, tautomers, prodrugs or pharmaceutically acceptable salts of the compounds or solvates thereof.

93) The pyrazolone compounds according to 56) or 57), wherein $R^{12}$ is a thienyl group, furyl group or pyridazinyl group substituted with a hydroxyl group substituted with a $C_{1-6}$ alkyl group, tautomers, prodrugs or pharmaceutically acceptable salts of the compounds or solvates thereof.

94) The pyrazolone compounds according to 52) or 53), wherein $R^1$ is a $C_{2-14}$ aryl group substituted with an amino group substituted with a $C_{1-6}$ alkyl group, tautomers, prodrugs or pharmaceutically acceptable salts of the compounds or solvates thereof.

95) The pyrazolone compounds according to 52) or 53), wherein $R^1$ is a phenyl group or pyridyl group substituted with an amino group substituted with a $C_{1-6}$ alkyl group, tautomers, prodrugs or pharmaceutically acceptable salts of the compounds or solvates thereof.

96) The pyrazolone compounds according to 52) or 53), wherein $R^1$ is a thienyl group, furyl group or pyridazinyl group substituted with an amino group substituted with a $C_{1-6}$ alkyl group, tautomers, prodrugs or pharmaceutically acceptable salts of the compounds or solvates thereof.

97) The pyrazolone compounds according to 54) or 55), wherein $R^7$ is a $C_{2-14}$ aryl group substituted with an amino group substituted with a $C_{1-6}$ alkyl group, tautomers, prodrugs or pharmaceutically acceptable salts of the compounds or solvates thereof.

98) The pyrazolone compounds according to 54) or 55), wherein $R^7$ is a phenyl group or pyridyl group substituted with an amino group substituted with a $C_{1-6}$ alkyl group, tautomers, prodrugs or pharmaceutically acceptable salts of the compounds or solvates thereof.

99) The pyrazolone compounds according to 54) or 55), wherein $R^7$ is a thienyl group, furyl group or pyridazinyl group substituted with an amino group substituted with a $C_{1-6}$ alkyl group, tautomers, prodrugs or pharmaceutically acceptable salts of the compounds or solvates thereof.

100) The pyrazolone compounds according to 56) or 57), wherein $R^{12}$ is a $C_{2-14}$ aryl group substituted with an amino group substituted with a $C_{1-6}$ alkyl group, tautomers, prodrugs or pharmaceutically acceptable salts of the compounds or solvates thereof.

101) The pyrazolone compounds according to 56) or 57), wherein $R^{12}$ is a phenyl group or pyridyl group substituted with an amino group substituted with a $C_{1-6}$ alkyl group, tautomers, prodrugs or pharmaceutically acceptable salts of the compounds or solvates thereof.

102) The pyrazolone compounds according to 56) or 57), wherein $R^{12}$ is a thienyl group, furyl group or pyridazinyl group substituted with an amino group substituted with a $C_{1-6}$ alkyl group, tautomers, prodrugs or pharmaceutically acceptable salts of the compounds or solvates thereof.

103) The pyrazolone compounds according to 52) or 53), wherein $R^1$ is a $C_{2-14}$ aryl group substituted with a hydroxyl group substituted with a $C_{1-6}$ alkylcarbonyl group, tautomers, prodrugs or pharmaceutically acceptable salts of the compounds or solvates thereof.

104) The pyrazolone compounds according to 52) or 53), wherein $R^1$ is a phenyl group or pyridyl group substituted with a hydroxyl group substituted with a $C_{1-6}$ alkylcarbonyl group, tautomers, prodrugs or pharmaceutically acceptable salts of the compounds or solvates thereof.

105) The pyrazolone compounds according to 52) or 53), wherein $R^1$ is a thienyl group, furyl group or pyridazinyl group substituted with a hydroxyl group substituted with a $C_{1-6}$ alkylcarbonyl group, tautomers, prodrugs or pharmaceutically acceptable salts of the compounds or solvates thereof.

106) The pyrazolone compounds according to 54) or 55), wherein $R^7$ is a $C_{2-14}$ aryl group substituted with a hydroxyl group substituted with a $C_{1-6}$ alkylcarbonyl group, tautomers, prodrugs or pharmaceutically acceptable salts of the compounds or solvates thereof.

107) The pyrazolone compounds according to 54) or 55), wherein $R^7$ is a phenyl group or pyridyl group substituted with a hydroxyl group substituted with a $C_{1-6}$ alkylcarbonyl group, tautomers, prodrugs or pharmaceutically acceptable salts of the compounds or solvates thereof.

108) The pyrazolone compounds according to 54) or 55), wherein $R^7$ is a thienyl group, furyl group or pyridazinyl group substituted with a hydroxyl group substituted with a $C_{1-6}$ alkylcarbonyl group, tautomers, prodrugs or pharmaceutically acceptable salts of the compounds or solvates thereof.

109) The pyrazolone compounds according to 56) or 57), wherein $R^{12}$ is a $C_{2-14}$ aryl group substituted with a hydroxyl group substituted with a $C_{1-6}$ alkylcarbonyl group, tautomers, prodrugs or pharmaceutically acceptable salts of the compounds or solvates thereof.

110) The pyrazolone compounds according to 56) or 57), wherein $R^{12}$ is a phenyl group or pyridyl group substituted with a hydroxyl group substituted with a $C_{1-6}$ alkylcarbonyl group, tautomers, prodrugs or pharmaceutically acceptable salts of the compounds or solvates thereof.

111) The pyrazolone compounds according to 56) or 57), wherein $R^{12}$ is a thienyl group, furyl group or pyridazinyl group substituted with a hydroxyl group substituted with a $C_{1-6}$ alkylcarbonyl group, tautomers, prodrugs or pharmaceutically acceptable salts of the compounds or solvates thereof.

112) The pyrazolone compounds according to 52) or 53), wherein $R^1$ is a $C_{2-14}$ aryl group substituted with an amino group substituted with a $C_{1-6}$ alkylcarbonyl group, tautomers, prodrugs or pharmaceutically acceptable salts of the compounds or solvates thereof.

113) The pyrazolone compounds according to 52) or 53), wherein $R^1$ is a phenyl group or pyridyl group substituted with an amino group substituted with a $C_{1-6}$ alkylcarbonyl group, tautomers, prodrugs or pharmaceutically acceptable salts of the compounds or solvates thereof.

114) The pyrazolone compounds according to 52) or 53), wherein $R^1$ is a thienyl group, furyl group or pyridazinyl group substituted with an amino group substituted with a $C_{1-6}$ alkylcarbonyl group, tautomers, prodrugs or pharmaceutically acceptable salts of the compounds or solvates thereof.

115) The pyrazolone compounds according to 54) or 55), wherein $R^7$ is a $C_{2-14}$ aryl group substituted with an amino group substituted with a $C_{1-6}$ alkylcarbonyl group, tautomers, prodrugs or pharmaceutically acceptable salts of the compounds or solvates thereof.

116) The pyrazolone compounds according to 54) or 55), wherein $R^7$ is a phenyl group or pyridyl group substituted with an amino group substituted with a $C_{1-6}$ alkylcarbonyl group, tautomers, prodrugs or pharmaceutically acceptable salts of the compounds or solvates thereof.

117) The pyrazolone compounds according to 54) or 55), wherein $R^7$ is a thienyl group, furyl group or pyridazinyl group substituted with an amino group substituted with a $C_{1-6}$ alkylcarbonyl group, tautomers, prodrugs or pharmaceutically acceptable salts of the compounds or solvates thereof.

118) The pyrazolone compounds according to 56) or 57), wherein $R^{12}$ is a $C_{2-14}$ aryl group substituted with an amino group substituted with a $C_{1-6}$ alkylcarbonyl group, tautomers, prodrugs or pharmaceutically acceptable salts of the compounds or solvates thereof.

119) The pyrazolone compounds according to 56) or 57), wherein $R^{12}$ is a phenyl group or pyridyl group substituted with an amino group substituted with a $C_{1-6}$ alkylcarbonyl group, tautomers, prodrugs or pharmaceutically acceptable salts of the compounds or solvates thereof.

120) The pyrazolone compounds according to 56) or 57), wherein $R^{12}$ is a thienyl group, furyl group or pyridazinyl group substituted with an amino group substituted with a $C_{1-6}$ alkylcarbonyl group, tautomers, prodrugs or pharmaceutically acceptable salts of the compounds or solvates thereof.

121) The pyrazolone compounds according to 52) or 53), wherein $R^1$ is a $C_{2-14}$ aryl group substituted with a $C_{1-6}$ alkylcarbonyl group, tautomers, prodrugs or pharmaceutically acceptable salts of the compounds or solvates thereof.

122) The pyrazolone compounds according to 52) or 53), wherein $R^1$ is a phenyl group or pyridyl group substituted with a $C_{1-6}$ alkylcarbonyl group, tautomers, prodrugs or pharmaceutically acceptable salts of the compounds or solvates thereof.

123) The pyrazolone compounds according to 52) or 53), wherein $R^1$ is a thienyl group, furyl group or pyridazinyl group substituted with a $C_{1-6}$ alkylcarbonyl group, tautomers, prodrugs or pharmaceutically acceptable salts of the compounds or solvates thereof.

124) The pyrazolone compounds according to 54) or 55), wherein $R^7$ is a $C_{2-14}$ aryl group substituted with a $C_{1-6}$ alkylcarbonyl group, tautomers, prodrugs or pharmaceutically acceptable salts of the compounds or solvates thereof.

125) The pyrazolone compounds according to 54) or 55), wherein $R^7$ is a phenyl group or pyridyl group substituted with a $C_{1-6}$ alkylcarbonyl group, tautomers, prodrugs or pharmaceutically acceptable salts of the compounds or solvates thereof.

126) The pyrazolone compounds according to 54) or 55), wherein $R^7$ is a thienyl group, furyl group or pyridazinyl group substituted with a $C_{1-6}$ alkylcarbonyl group, tautomers, prodrugs or pharmaceutically acceptable salts of the compounds or solvates thereof.

127) The pyrazolone compounds according to 56) or 57), wherein $R^{12}$ is a $C_{2-14}$ aryl group substituted with a $C_{1-6}$ alkylcarbonyl group, tautomers, prodrugs or pharmaceutically acceptable salts of the compounds or solvates thereof.

128) The pyrazolone compounds according to 56) or 57), wherein $R^{12}$ is a phenyl group or pyridyl group substituted with a $C_{1-6}$ alkylcarbonyl group, tautomers, prodrugs or pharmaceutically acceptable salts of the compounds or solvates thereof.

129) The pyrazolone compounds according to 56) or 57), wherein $R^{12}$ is a thienyl group, furyl group or pyridazinyl group substituted with a $C_{1-6}$ alkylcarbonyl group, tautomers, prodrugs or pharmaceutically acceptable salts of the compounds or solvates thereof.

130) The compounds wherein $R^7$, $R^8$, $R^9$ and $R^{10}$ are any of the following combinations in Table 1, tautomers, prodrugs or pharmaceutically acceptable salts of the compounds or solvates thereof. The symbols in Table 1 denote the following substituents.

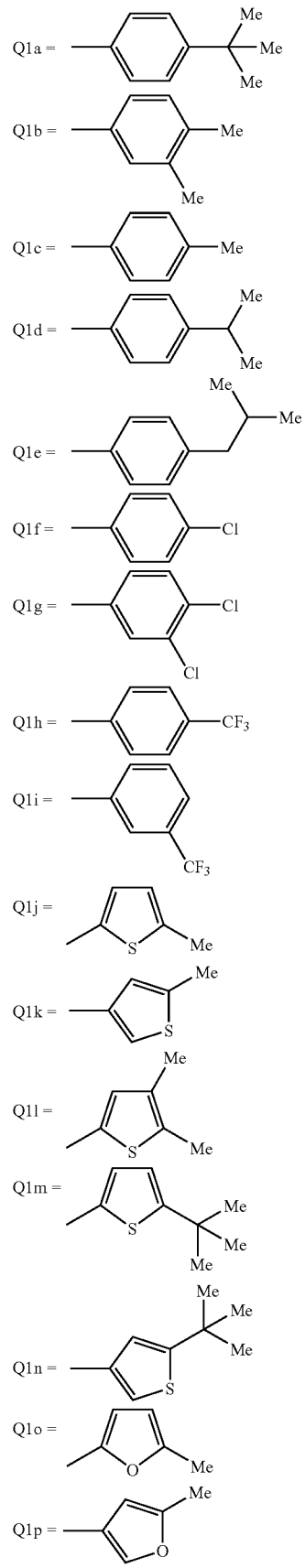

Formula 9

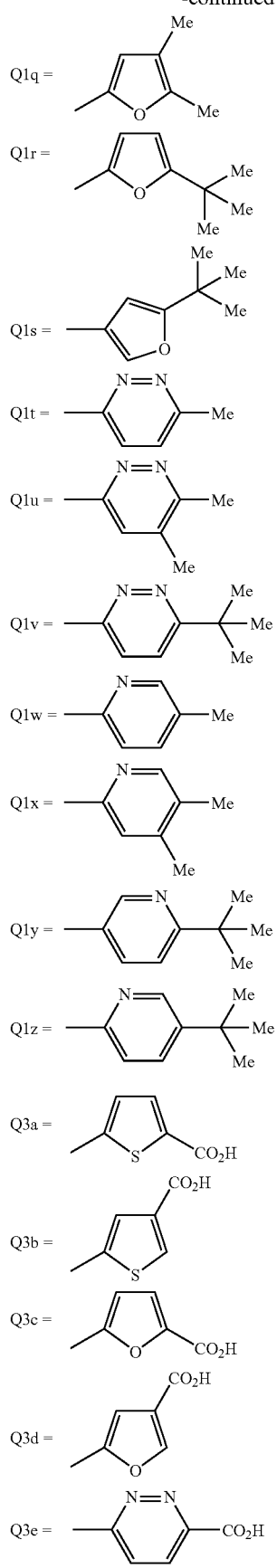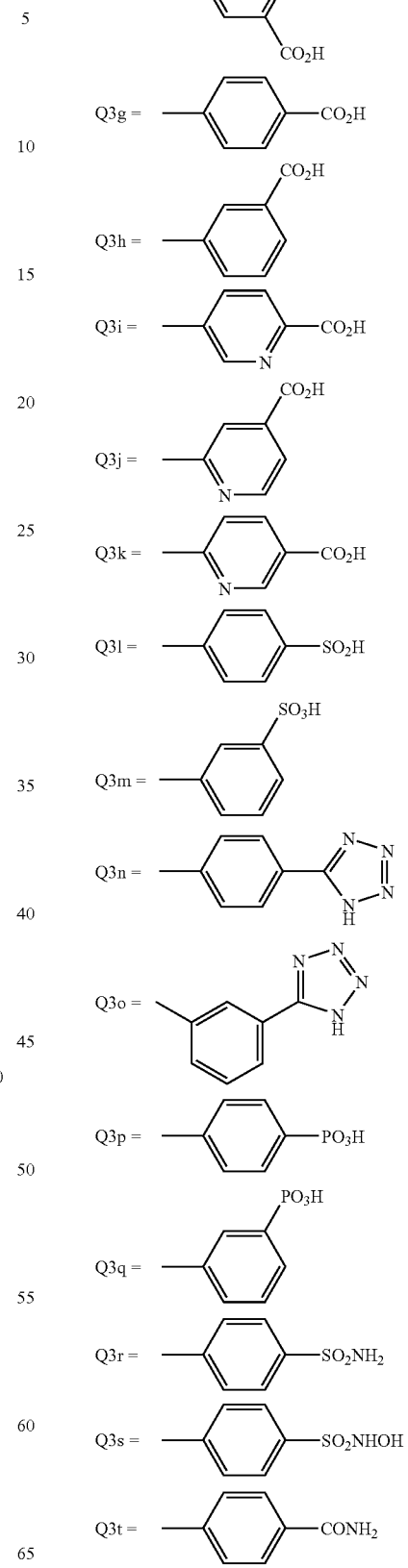

Q3u = —⟨C₆H₄⟩—CONHOH

TABLE 1

| No | R⁷ | R⁸ | R⁹ | R¹⁰ |
|---|---|---|---|---|
| 1 | Q1a | H | H | Q3a |
| 2 | Q1a | H | H | Q3b |
| 3 | Q1a | H | H | Q3c |
| 4 | Q1a | H | H | Q3d |
| 5 | Q1a | H | H | Q3e |
| 6 | Q1a | H | H | Q3f |
| 7 | Q1a | H | H | Q3g |
| 8 | Q1a | H | H | Q3h |
| 9 | Q1a | H | H | Q3i |
| 10 | Q1a | H | H | Q3j |
| 11 | Q1a | H | H | Q3k |
| 12 | Q1a | H | H | Q3l |
| 13 | Q1a | H | H | Q3m |
| 14 | Q1a | H | H | Q3n |
| 15 | Q1a | H | H | Q3o |
| 16 | Q1a | H | H | Q3p |
| 17 | Q1a | H | H | Q3q |
| 18 | Q1a | H | Me | Q3a |
| 19 | Q1a | H | Me | Q3b |
| 20 | Q1a | H | Me | Q3c |
| 21 | Q1a | H | Me | Q3d |
| 22 | Q1a | H | Me | Q3e |
| 23 | Q1a | H | Me | Q3f |
| 24 | Q1a | H | Me | Q3g |
| 25 | Q1a | H | Me | Q3h |
| 26 | Q1a | H | Me | Q3i |
| 27 | Q1a | H | Me | Q3j |
| 28 | Q1a | H | Me | Q3k |
| 29 | Q1a | H | Me | Q3l |
| 30 | Q1a | H | Me | Q3m |
| 31 | Q1a | H | Me | Q3n |
| 32 | Q1a | H | Me | Q3o |
| 33 | Q1a | H | Me | Q3p |
| 34 | Q1a | H | Me | Q3q |
| 35 | Q1a | Me | H | Q3a |
| 36 | Q1a | Me | H | Q3b |
| 37 | Q1a | Me | H | Q3c |
| 38 | Q1a | Me | H | Q3d |
| 39 | Q1a | Me | H | Q3e |
| 40 | Q1a | Me | H | Q3f |
| 41 | Q1a | Me | H | Q3g |
| 42 | Q1a | Me | H | Q3h |
| 43 | Q1a | Me | H | Q3i |
| 44 | Q1a | Me | H | Q3j |
| 45 | Q1a | Me | H | Q3k |
| 46 | Q1a | Me | H | Q3l |
| 47 | Q1a | Me | H | Q3m |
| 48 | Q1a | Me | H | Q3n |
| 49 | Q1a | Me | H | Q3o |
| 50 | Q1a | Me | H | Q3p |
| 51 | Q1a | Me | H | Q3q |
| 52 | Q1a | Me | Me | Q3a |
| 53 | Q1a | Me | Me | Q3b |
| 54 | Q1a | Me | Me | Q3c |
| 55 | Q1a | Me | Me | Q3d |
| 56 | Q1a | Me | Me | Q3e |
| 57 | Q1a | Me | Me | Q3f |
| 58 | Q1a | Me | Me | Q3g |
| 59 | Q1a | Me | Me | Q3h |
| 60 | Q1a | Me | Me | Q3i |
| 61 | Q1a | Me | Me | Q3j |
| 62 | Q1a | Me | Me | Q3k |
| 63 | Q1a | Me | Me | Q3l |
| 64 | Q1a | Me | Me | Q3m |
| 65 | Q1a | Me | Me | Q3n |
| 66 | Q1a | Me | Me | Q3o |
| 67 | Q1a | Me | Me | Q3p |
| 68 | Q1a | Me | Me | Q3q |
| 69 | Q1a | CF3 | H | Q3a |
| 70 | Q1a | CF3 | H | Q3b |
| 71 | Q1a | CF3 | H | Q3c |
| 72 | Q1a | CF3 | H | Q3d |
| 73 | Q1a | CF3 | H | Q3e |
| 74 | Q1a | CF3 | H | Q3f |
| 75 | Q1a | CF3 | H | Q3g |
| 76 | Q1a | CF3 | H | Q3h |
| 77 | Q1a | CF3 | H | Q3i |
| 78 | Q1a | CF3 | H | Q3j |
| 79 | Q1a | CF3 | H | Q3k |
| 80 | Q1a | CF3 | H | Q3l |
| 81 | Q1a | CF3 | H | Q3m |
| 82 | Q1a | CF3 | H | Q3n |
| 83 | Q1a | CF3 | H | Q3o |
| 84 | Q1a | CF3 | H | Q3p |
| 85 | Q1a | CF3 | H | Q3q |
| 86 | Q1a | CF3 | Me | Q3a |
| 87 | Q1a | CF3 | Me | Q3b |
| 88 | Q1a | CF3 | Me | Q3c |
| 89 | Q1a | CF3 | Me | Q3d |
| 90 | Q1a | CF3 | Me | Q3e |
| 91 | Q1a | CF3 | Me | Q3f |
| 92 | Q1a | CF3 | Me | Q3g |
| 93 | Q1a | CF3 | Me | Q3h |
| 94 | Q1a | CF3 | Me | Q3i |
| 95 | Q1a | CF3 | Me | Q3j |
| 96 | Q1a | CF3 | Me | Q3k |
| 97 | Q1a | CF3 | Me | Q3l |
| 98 | Q1a | CF3 | Me | Q3m |
| 99 | Q1a | CF3 | Me | Q3n |
| 100 | Q1a | CF3 | Me | Q3o |
| 101 | Q1a | CF3 | Me | Q3p |
| 102 | Q1a | CF3 | Me | Q3q |
| 103 | Q1b | H | H | Q3a |
| 104 | Q1b | H | H | Q3b |
| 105 | Q1b | H | H | Q3c |
| 106 | Q1b | H | H | Q3d |
| 107 | Q1b | H | H | Q3e |
| 108 | Q1b | H | H | Q3f |
| 109 | Q1b | H | H | Q3g |
| 110 | Q1b | H | H | Q3h |
| 111 | Q1b | H | H | Q3i |
| 112 | Q1b | H | H | Q3j |
| 113 | Q1b | H | H | Q3k |
| 114 | Q1b | H | H | Q3l |
| 115 | Q1b | H | H | Q3m |
| 116 | Q1b | H | H | Q3n |
| 117 | Q1b | H | H | Q3o |
| 118 | Q1b | H | H | Q3p |
| 119 | Q1b | H | H | Q3q |
| 120 | Q1b | H | Me | Q3a |
| 121 | Q1b | H | Me | Q3b |
| 122 | Q1b | H | Me | Q3c |
| 123 | Q1b | H | Me | Q3d |
| 124 | Q1b | H | Me | Q3e |
| 125 | Q1b | H | Me | Q3f |
| 126 | Q1b | H | Me | Q3g |
| 127 | Q1b | H | Me | Q3h |
| 128 | Q1b | H | Me | Q3i |
| 129 | Q1b | H | Me | Q3j |
| 130 | Q1b | H | Me | Q3k |
| 131 | Q1b | H | Me | Q3l |
| 132 | Q1b | H | Me | Q3m |
| 133 | Q1b | H | Me | Q3n |
| 134 | Q1b | H | Me | Q3o |
| 135 | Q1b | H | Me | Q3p |
| 136 | Q1b | H | Me | Q3q |
| 137 | Q1b | Me | H | Q3a |
| 138 | Q1b | Me | H | Q3b |
| 139 | Q1b | Me | H | Q3c |
| 140 | Q1b | Me | H | Q3d |
| 141 | Q1b | Me | H | Q3e |
| 142 | Q1b | Me | H | Q3f |
| 143 | Q1b | Me | H | Q3g |
| 144 | Q1b | Me | H | Q3h |
| 145 | Q1b | Me | H | Q3i |
| 146 | Q1b | Me | H | Q3j |
| 147 | Q1b | Me | H | Q3k |
| 148 | Q1b | Me | H | Q3l |

TABLE 1-continued

| No | R⁷ | R⁸ | R⁹ | R¹⁰ |
|---|---|---|---|---|
| 149 | Q1b | Me | H | Q3m |
| 150 | Q1b | Me | H | Q3n |
| 151 | Q1b | Me | H | Q3o |
| 152 | Q1b | Me | H | Q3p |
| 153 | Q1b | Me | H | Q3q |
| 154 | Q1b | Me | Me | Q3a |
| 155 | Q1b | Me | Me | Q3b |
| 156 | Q1b | Me | Me | Q3c |
| 157 | Q1b | Me | Me | Q3d |
| 158 | Q1b | Me | Me | Q3e |
| 159 | Q1b | Me | Me | Q3f |
| 160 | Q1b | Me | Me | Q3g |
| 161 | Q1b | Me | Me | Q3h |
| 162 | Q1b | Me | Me | Q3i |
| 163 | Q1b | Me | Me | Q3j |
| 164 | Q1b | Me | Me | Q3k |
| 165 | Q1b | Me | Me | Q3l |
| 166 | Q1b | Me | Me | Q3m |
| 167 | Q1b | Me | Me | Q3n |
| 168 | Q1b | Me | Me | Q3o |
| 169 | Q1b | Me | Me | Q3p |
| 170 | Q1b | Me | Me | Q3q |
| 171 | Q1b | CF3 | H | Q3a |
| 172 | Q1b | CF3 | H | Q3b |
| 173 | Q1b | CF3 | H | Q3c |
| 174 | Q1b | CF3 | H | Q3d |
| 175 | Q1b | CF3 | H | Q3e |
| 176 | Q1b | CF3 | H | Q3f |
| 177 | Q1b | CF3 | H | Q3g |
| 178 | Q1b | CF3 | H | Q3h |
| 179 | Q1b | CF3 | H | Q3i |
| 180 | Q1b | CF3 | H | Q3j |
| 181 | Q1b | CF3 | H | Q3k |
| 182 | Q1b | CF3 | H | Q3l |
| 183 | Q1b | CF3 | H | Q3m |
| 184 | Q1b | CF3 | H | Q3n |
| 185 | Q1b | CF3 | H | Q3o |
| 186 | Q1b | CF3 | H | Q3p |
| 187 | Q1b | CF3 | H | Q3q |
| 188 | Q1b | CF3 | Me | Q3a |
| 189 | Q1b | CF3 | Me | Q3b |
| 190 | Q1b | CF3 | Me | Q3c |
| 191 | Q1b | CF3 | Me | Q3d |
| 192 | Q1b | CF3 | Me | Q3e |
| 193 | Q1b | CF3 | Me | Q3f |
| 194 | Q1b | CF3 | Me | Q3g |
| 195 | Q1b | CF3 | Me | Q3h |
| 196 | Q1b | CF3 | Me | Q3i |
| 197 | Q1b | CF3 | Me | Q3j |
| 198 | Q1b | CF3 | Me | Q3k |
| 199 | Q1b | CF3 | Me | Q3l |
| 200 | Q1b | CF3 | Me | Q3m |
| 201 | Q1b | CF3 | Me | Q3n |
| 202 | Q1b | CF3 | Me | Q3o |
| 203 | Q1b | CF3 | Me | Q3p |
| 204 | Q1b | CF3 | Me | Q3q |
| 205 | Q1c | H | H | Q3a |
| 206 | Q1c | H | H | Q3b |
| 207 | Q1c | H | H | Q3c |
| 208 | Q1c | H | H | Q3d |
| 209 | Q1c | H | H | Q3e |
| 210 | Q1c | H | H | Q3f |
| 211 | Q1c | H | H | Q3g |
| 212 | Q1c | H | H | Q3h |
| 213 | Q1c | H | H | Q3i |
| 214 | Q1c | H | H | Q3j |
| 215 | Q1c | H | H | Q3k |
| 216 | Q1c | H | H | Q3l |
| 217 | Q1c | H | H | Q3m |
| 218 | Q1c | H | H | Q3n |
| 219 | Q1c | H | H | Q3o |
| 220 | Q1c | H | H | Q3p |
| 221 | Q1c | H | H | Q3q |
| 222 | Q1c | H | Me | Q3a |
| 223 | Q1c | H | Me | Q3b |
| 224 | Q1c | H | Me | Q3c |
| 225 | Q1c | H | Me | Q3d |
| 226 | Q1c | H | Me | Q3e |
| 227 | Q1c | H | Me | Q3f |
| 228 | Q1c | H | Me | Q3g |
| 229 | Q1c | H | Me | Q3h |
| 230 | Q1c | H | Me | Q3i |
| 231 | Q1c | H | Me | Q3j |
| 232 | Q1c | H | Me | Q3k |
| 233 | Q1c | H | Me | Q3l |
| 234 | Q1c | H | Me | Q3m |
| 235 | Q1c | H | Me | Q3n |
| 236 | Q1c | H | Me | Q3o |
| 237 | Q1c | H | Me | Q3p |
| 238 | Q1c | H | Me | Q3q |
| 239 | Q1c | Me | H | Q3a |
| 240 | Q1c | Me | H | Q3b |
| 241 | Q1c | Me | H | Q3c |
| 242 | Q1c | Me | H | Q3d |
| 243 | Q1c | Me | H | Q3e |
| 244 | Q1c | Me | H | Q3f |
| 245 | Q1c | Me | H | Q3g |
| 246 | Q1c | Me | H | Q3h |
| 247 | Q1c | Me | H | Q3i |
| 248 | Q1c | Me | H | Q3j |
| 249 | Q1c | Me | H | Q3k |
| 250 | Q1c | Me | H | Q3l |
| 251 | Q1c | Me | H | Q3m |
| 252 | Q1c | Me | H | Q3n |
| 253 | Q1c | Me | H | Q3o |
| 254 | Q1c | Me | H | Q3p |
| 255 | Q1c | Me | H | Q3q |
| 256 | Q1c | Me | Me | Q3a |
| 257 | Q1c | Me | Me | Q3b |
| 258 | Q1c | Me | Me | Q3c |
| 259 | Q1c | Me | Me | Q3d |
| 260 | Q1c | Me | Me | Q3e |
| 261 | Q1c | Me | Me | Q3f |
| 262 | Q1c | Me | Me | Q3g |
| 263 | Q1c | Me | Me | Q3h |
| 264 | Q1c | Me | Me | Q3i |
| 265 | Q1c | Me | Me | Q3j |
| 266 | Q1c | Me | Me | Q3k |
| 267 | Q1c | Me | Me | Q3l |
| 268 | Q1c | Me | Me | Q3m |
| 269 | Q1c | Me | Me | Q3n |
| 270 | Q1c | Me | Me | Q3o |
| 271 | Q1c | Me | Me | Q3p |
| 272 | Q1c | Me | Me | Q3q |
| 273 | Q1c | CF3 | H | Q3a |
| 274 | Q1c | CF3 | H | Q3b |
| 275 | Q1c | CF3 | H | Q3c |
| 276 | Q1c | CF3 | H | Q3d |
| 277 | Q1c | CF3 | H | Q3e |
| 278 | Q1c | CF3 | H | Q3f |
| 279 | Q1c | CF3 | H | Q3g |
| 280 | Q1c | CF3 | H | Q3h |
| 281 | Q1c | CF3 | H | Q3i |
| 282 | Q1c | CF3 | H | Q3j |
| 283 | Q1c | CF3 | H | Q3k |
| 284 | Q1c | CF3 | H | Q3l |
| 285 | Q1c | CF3 | H | Q3m |
| 286 | Q1c | CF3 | H | Q3n |
| 287 | Q1c | CF3 | H | Q3o |
| 288 | Q1c | CF3 | H | Q3p |
| 289 | Q1c | CF3 | H | Q3q |
| 290 | Q1c | CF3 | Me | Q3a |
| 291 | Q1c | CF3 | Me | Q3b |
| 292 | Q1c | CF3 | Me | Q3c |
| 293 | Q1c | CF3 | Me | Q3d |
| 294 | Q1c | CF3 | Me | Q3e |
| 295 | Q1c | CF3 | Me | Q3f |
| 296 | Q1c | CF3 | Me | Q3g |
| 297 | Q1c | CF3 | Me | Q3h |
| 298 | Q1c | CF3 | Me | Q3i |
| 299 | Q1c | CF3 | Me | Q3j |
| 300 | Q1c | CF3 | Me | Q3k |
| 301 | Q1c | CF3 | Me | Q3l |
| 302 | Q1c | CF3 | Me | Q3m |
| 303 | Q1c | CF3 | Me | Q3n |
| 304 | Q1c | CF3 | Me | Q3o |

TABLE 1-continued

| No | R⁷ | R⁸ | R⁹ | R¹⁰ |
|---|---|---|---|---|
| 305 | Q1c | CF3 | Me | Q3p |
| 306 | Q1c | CF3 | Me | Q3q |
| 307 | Q1d | H | H | Q3a |
| 308 | Q1d | H | H | Q3b |
| 309 | Q1d | H | H | Q3c |
| 310 | Q1d | H | H | Q3d |
| 311 | Q1d | H | H | Q3e |
| 312 | Q1d | H | H | Q3f |
| 313 | Q1d | H | H | Q3g |
| 314 | Q1d | H | H | Q3h |
| 315 | Q1d | H | H | Q3i |
| 316 | Q1d | H | H | Q3j |
| 317 | Q1d | H | H | Q3k |
| 318 | Q1d | H | H | Q3l |
| 319 | Q1d | H | H | Q3m |
| 320 | Q1d | H | H | Q3n |
| 321 | Q1d | H | H | Q3o |
| 322 | Q1d | H | H | Q3p |
| 323 | Q1d | H | H | Q3q |
| 324 | Q1d | H | Me | Q3a |
| 325 | Q1d | H | Me | Q3b |
| 326 | Q1d | H | Me | Q3c |
| 327 | Q1d | H | Me | Q3d |
| 328 | Q1d | H | Me | Q3e |
| 329 | Q1d | H | Me | Q3f |
| 330 | Q1d | H | Me | Q3g |
| 331 | Q1d | H | Me | Q3h |
| 332 | Q1d | H | Me | Q3i |
| 333 | Q1d | H | Me | Q3j |
| 334 | Q1d | H | Me | Q3k |
| 335 | Q1d | H | Me | Q3l |
| 336 | Q1d | H | Me | Q3m |
| 337 | Q1d | H | Me | Q3n |
| 338 | Q1d | H | Me | Q3o |
| 339 | Q1d | H | Me | Q3p |
| 340 | Q1d | H | Me | Q3q |
| 341 | Q1d | Me | H | Q3a |
| 342 | Q1d | Me | H | Q3b |
| 343 | Q1d | Me | H | Q3c |
| 344 | Q1d | Me | H | Q3d |
| 345 | Q1d | Me | H | Q3e |
| 346 | Q1d | Me | H | Q3f |
| 347 | Q1d | Me | H | Q3g |
| 348 | Q1d | Me | H | Q3h |
| 349 | Q1d | Me | H | Q3i |
| 350 | Q1d | Me | H | Q3j |
| 351 | Q1d | Me | H | Q3k |
| 352 | Q1d | Me | H | Q3l |
| 353 | Q1d | Me | H | Q3m |
| 354 | Q1d | Me | H | Q3n |
| 355 | Q1d | Me | H | Q3o |
| 356 | Q1d | Me | H | Q3p |
| 357 | Q1d | Me | H | Q3q |
| 358 | Q1d | Me | Me | Q3a |
| 359 | Q1d | Me | Me | Q3b |
| 360 | Q1d | Me | Me | Q3c |
| 361 | Q1d | Me | Me | Q3d |
| 362 | Q1d | Me | Me | Q3e |
| 363 | Q1d | Me | Me | Q3f |
| 364 | Q1d | Me | Me | Q3g |
| 365 | Q1d | Me | Me | Q3h |
| 366 | Q1d | Me | Me | Q3i |
| 367 | Q1d | Me | Me | Q3j |
| 368 | Q1d | Me | Me | Q3k |
| 369 | Q1d | Me | Me | Q3l |
| 370 | Q1d | Me | Me | Q3m |
| 371 | Q1d | Me | Me | Q3n |
| 372 | Q1d | Me | Me | Q3o |
| 373 | Q1d | Me | Me | Q3p |
| 374 | Q1d | Me | Me | Q3q |
| 375 | Q1d | CF3 | H | Q3a |
| 376 | Q1d | CF3 | H | Q3b |
| 377 | Q1d | CF3 | H | Q3c |
| 378 | Q1d | CF3 | H | Q3d |
| 379 | Q1d | CF3 | H | Q3e |
| 380 | Q1d | CF3 | H | Q3f |
| 381 | Q1d | CF3 | H | Q3g |
| 382 | Q1d | CF3 | H | Q3h |
| 383 | Q1d | CF3 | H | Q3i |
| 384 | Q1d | CF3 | H | Q3j |
| 385 | Q1d | CF3 | H | Q3k |
| 386 | Q1d | CF3 | H | Q3l |
| 387 | Q1d | CF3 | H | Q3m |
| 388 | Q1d | CF3 | H | Q3n |
| 389 | Q1d | CF3 | H | Q3o |
| 390 | Q1d | CF3 | H | Q3p |
| 391 | Q1d | CF3 | H | Q3q |
| 392 | Q1d | CF3 | Me | Q3a |
| 393 | Q1d | CF3 | Me | Q3b |
| 394 | Q1d | CF3 | Me | Q3c |
| 395 | Q1d | CF3 | Me | Q3d |
| 396 | Q1d | CF3 | Me | Q3e |
| 397 | Q1d | CF3 | Me | Q3f |
| 398 | Q1d | CF3 | Me | Q3g |
| 399 | Q1d | CF3 | Me | Q3h |
| 400 | Q1d | CF3 | Me | Q3i |
| 401 | Q1d | CF3 | Me | Q3j |
| 402 | Q1d | CF3 | Me | Q3k |
| 403 | Q1d | CF3 | Me | Q3l |
| 404 | Q1d | CF3 | Me | Q3m |
| 405 | Q1d | CF3 | Me | Q3n |
| 406 | Q1d | CF3 | Me | Q3o |
| 407 | Q1d | CF3 | Me | Q3p |
| 408 | Q1d | CF3 | Me | Q3q |
| 409 | Q1e | H | H | Q3a |
| 410 | Q1e | H | H | Q3b |
| 411 | Q1e | H | H | Q3c |
| 412 | Q1e | H | H | Q3d |
| 413 | Q1e | H | H | Q3e |
| 414 | Q1e | H | H | Q3f |
| 415 | Q1e | H | H | Q3g |
| 416 | Q1e | H | H | Q3h |
| 417 | Q1e | H | H | Q3i |
| 418 | Q1e | H | H | Q3j |
| 419 | Q1e | H | H | Q3k |
| 420 | Q1e | H | H | Q3l |
| 421 | Q1e | H | H | Q3m |
| 422 | Q1e | H | H | Q3n |
| 423 | Q1e | H | H | Q3o |
| 424 | Q1e | H | H | Q3p |
| 425 | Q1e | H | H | Q3q |
| 426 | Q1e | H | Me | Q3a |
| 427 | Q1e | H | Me | Q3b |
| 428 | Q1e | H | Me | Q3c |
| 429 | Q1e | H | Me | Q3d |
| 430 | Q1e | H | Me | Q3e |
| 431 | Q1e | H | Me | Q3f |
| 432 | Q1e | H | Me | Q3g |
| 433 | Q1e | H | Me | Q3h |
| 434 | Q1e | H | Me | Q3i |
| 435 | Q1e | H | Me | Q3j |
| 436 | Q1e | H | Me | Q3k |
| 437 | Q1e | H | Me | Q3l |
| 438 | Q1e | H | Me | Q3m |
| 439 | Q1e | H | Me | Q3n |
| 440 | Q1e | H | Me | Q3o |
| 441 | Q1e | H | Me | Q3p |
| 442 | Q1e | H | Me | Q3q |
| 443 | Q1e | Me | H | Q3a |
| 444 | Q1e | Me | H | Q3b |
| 445 | Q1e | Me | H | Q3c |
| 446 | Q1e | Me | H | Q3d |
| 447 | Q1e | Me | H | Q3e |
| 448 | Q1e | Me | H | Q3f |
| 449 | Q1e | Me | H | Q3g |
| 450 | Q1e | Me | H | Q3h |
| 451 | Q1e | Me | H | Q3i |
| 452 | Q1e | Me | H | Q3j |
| 453 | Q1e | Me | H | Q3k |
| 454 | Q1e | Me | H | Q3l |
| 455 | Q1e | Me | H | Q3m |
| 456 | Q1e | Me | H | Q3n |
| 457 | Q1e | Me | H | Q3o |
| 458 | Q1e | Me | H | Q3p |
| 459 | Q1e | Me | H | Q3q |
| 460 | Q1e | Me | Me | Q3a |

TABLE 1-continued

| No | R⁷ | R⁸ | R⁹ | R¹⁰ |
|---|---|---|---|---|
| 461 | Q1e | Me | Me | Q3b |
| 462 | Q1e | Me | Me | Q3c |
| 463 | Q1e | Me | Me | Q3d |
| 464 | Q1e | Me | Me | Q3e |
| 465 | Q1e | Me | Me | Q3f |
| 466 | Q1e | Me | Me | Q3g |
| 467 | Q1e | Me | Me | Q3h |
| 468 | Q1e | Me | Me | Q3i |
| 469 | Q1e | Me | Me | Q3j |
| 470 | Q1e | Me | Me | Q3k |
| 471 | Q1e | Me | Me | Q3l |
| 472 | Q1e | Me | Me | Q3m |
| 473 | Q1e | Me | Me | Q3n |
| 474 | Q1e | Me | Me | Q3o |
| 475 | Q1e | Me | Me | Q3p |
| 476 | Q1e | Me | Me | Q3q |
| 477 | Q1e | CF3 | H | Q3a |
| 478 | Q1e | CF3 | H | Q3b |
| 479 | Q1e | CF3 | H | Q3c |
| 480 | Q1e | CF3 | H | Q3d |
| 481 | Q1e | CF3 | H | Q3e |
| 482 | Q1e | CF3 | H | Q3f |
| 483 | Q1e | CF3 | H | Q3g |
| 484 | Q1e | CF3 | H | Q3h |
| 485 | Q1e | CF3 | H | Q3i |
| 486 | Q1e | CF3 | H | Q3j |
| 487 | Q1e | CF3 | H | Q3k |
| 488 | Q1e | CF3 | H | Q3l |
| 489 | Q1e | CF3 | H | Q3m |
| 490 | Q1e | CF3 | H | Q3n |
| 491 | Q1e | CF3 | H | Q3o |
| 492 | Q1e | CF3 | H | Q3p |
| 493 | Q1e | CF3 | H | Q3q |
| 494 | Q1e | CF3 | Me | Q3a |
| 495 | Q1e | CF3 | Me | Q3b |
| 496 | Q1e | CF3 | Me | Q3c |
| 497 | Q1e | CF3 | Me | Q3d |
| 498 | Q1e | CF3 | Me | Q3e |
| 499 | Q1e | CF3 | Me | Q3f |
| 500 | Q1e | CF3 | Me | Q3g |
| 501 | Q1e | CF3 | Me | Q3h |
| 502 | Q1e | CF3 | Me | Q3i |
| 503 | Q1e | CF3 | Me | Q3j |
| 504 | Q1e | CF3 | Me | Q3k |
| 505 | Q1e | CF3 | Me | Q3l |
| 506 | Q1e | CF3 | Me | Q3m |
| 507 | Q1e | CF3 | Me | Q3n |
| 508 | Q1e | CF3 | Me | Q3o |
| 509 | Q1e | CF3 | Me | Q3p |
| 510 | Q1e | CF3 | Me | Q3q |
| 511 | Q1f | H | H | Q3a |
| 512 | Q1f | H | H | Q3b |
| 513 | Q1f | H | H | Q3c |
| 514 | Q1f | H | H | Q3d |
| 515 | Q1f | H | H | Q3e |
| 516 | Q1f | H | H | Q3f |
| 517 | Q1f | H | H | Q3g |
| 518 | Q1f | H | H | Q3h |
| 519 | Q1f | H | H | Q3i |
| 520 | Q1f | H | H | Q3j |
| 521 | Q1f | H | H | Q3k |
| 522 | Q1f | H | H | Q3l |
| 523 | Q1f | H | H | Q3m |
| 524 | Q1f | H | H | Q3n |
| 525 | Q1f | H | H | Q3o |
| 526 | Q1f | H | H | Q3p |
| 527 | Q1f | H | H | Q3q |
| 528 | Q1f | H | Me | Q3a |
| 529 | Q1f | H | Me | Q3b |
| 530 | Q1f | H | Me | Q3c |
| 531 | Q1f | H | Me | Q3d |
| 532 | Q1f | H | Me | Q3e |
| 533 | Q1f | H | Me | Q3f |
| 534 | Q1f | H | Me | Q3g |
| 535 | Q1f | H | Me | Q3h |
| 536 | Q1f | H | Me | Q3i |
| 537 | Q1f | H | Me | Q3j |
| 538 | Q1f | H | Me | Q3k |
| 539 | Q1f | H | Me | Q3l |
| 540 | Q1f | H | Me | Q3m |
| 541 | Q1f | H | Me | Q3n |
| 542 | Q1f | H | Me | Q3o |
| 543 | Q1f | H | Me | Q3p |
| 544 | Q1f | H | Me | Q3q |
| 545 | Q1f | Me | H | Q3a |
| 546 | Q1f | Me | H | Q3b |
| 547 | Q1f | Me | H | Q3c |
| 548 | Q1f | Me | H | Q3d |
| 549 | Q1f | Me | H | Q3e |
| 550 | Q1f | Me | H | Q3f |
| 551 | Q1f | Me | H | Q3g |
| 552 | Q1f | Me | H | Q3h |
| 553 | Q1f | Me | H | Q3i |
| 554 | Q1f | Me | H | Q3j |
| 555 | Q1f | Me | H | Q3k |
| 556 | Q1f | Me | H | Q3l |
| 557 | Q1f | Me | H | Q3m |
| 558 | Q1f | Me | H | Q3n |
| 559 | Q1f | Me | H | Q3o |
| 560 | Q1f | Me | H | Q3p |
| 561 | Q1f | Me | H | Q3q |
| 562 | Q1f | Me | Me | Q3a |
| 563 | Q1f | Me | Me | Q3b |
| 564 | Q1f | Me | Me | Q3c |
| 565 | Q1f | Me | Me | Q3d |
| 566 | Q1f | Me | Me | Q3e |
| 567 | Q1f | Me | Me | Q3f |
| 568 | Q1f | Me | Me | Q3g |
| 569 | Q1f | Me | Me | Q3h |
| 570 | Q1f | Me | Me | Q3i |
| 571 | Q1f | Me | Me | Q3j |
| 572 | Q1f | Me | Me | Q3k |
| 573 | Q1f | Me | Me | Q3l |
| 574 | Q1f | Me | Me | Q3m |
| 575 | Q1f | Me | Me | Q3n |
| 576 | Q1f | Me | Me | Q3o |
| 577 | Q1f | Me | Me | Q3p |
| 578 | Q1f | Me | Me | Q3q |
| 579 | Q1f | CF3 | H | Q3a |
| 580 | Q1f | CF3 | H | Q3b |
| 581 | Q1f | CF3 | H | Q3c |
| 582 | Q1f | CF3 | H | Q3d |
| 583 | Q1f | CF3 | H | Q3e |
| 584 | Q1f | CF3 | H | Q3f |
| 585 | Q1f | CF3 | H | Q3g |
| 586 | Q1f | CF3 | H | Q3h |
| 587 | Q1f | CF3 | H | Q3i |
| 588 | Q1f | CF3 | H | Q3j |
| 589 | Q1f | CF3 | H | Q3k |
| 590 | Q1f | CF3 | H | Q3l |
| 591 | Q1f | CF3 | H | Q3m |
| 592 | Q1f | CF3 | H | Q3n |
| 593 | Q1f | CF3 | H | Q3o |
| 594 | Q1f | CF3 | H | Q3p |
| 595 | Q1f | CF3 | H | Q3q |
| 596 | Q1f | CF3 | Me | Q3a |
| 597 | Q1f | CF3 | Me | Q3b |
| 598 | Q1f | CF3 | Me | Q3c |
| 599 | Q1f | CF3 | Me | Q3d |
| 600 | Q1f | CF3 | Me | Q3e |
| 601 | Q1f | CF3 | Me | Q3f |
| 602 | Q1f | CF3 | Me | Q3g |
| 603 | Q1f | CF3 | Me | Q3h |
| 604 | Q1f | CF3 | Me | Q3i |
| 605 | Q1f | CF3 | Me | Q3j |
| 606 | Q1f | CF3 | Me | Q3k |
| 607 | Q1f | CF3 | Me | Q3l |
| 608 | Q1f | CF3 | Me | Q3m |
| 609 | Q1f | CF3 | Me | Q3n |
| 610 | Q1f | CF3 | Me | Q3o |
| 611 | Q1f | CF3 | Me | Q3p |
| 612 | Q1f | CF3 | Me | Q3q |
| 613 | Q1g | H | H | Q3a |
| 614 | Q1g | H | H | Q3b |
| 615 | Q1g | H | H | Q3c |
| 616 | Q1g | H | H | Q3d |

TABLE 1-continued

| No | R⁷ | R⁸ | R⁹ | R¹⁰ |
|---|---|---|---|---|
| 617 | Q1g | H | H | Q3e |
| 618 | Q1g | H | H | Q3f |
| 619 | Q1g | H | H | Q3g |
| 620 | Q1g | H | H | Q3h |
| 621 | Q1g | H | H | Q3i |
| 622 | Q1g | H | H | Q3j |
| 623 | Q1g | H | H | Q3k |
| 624 | Q1g | H | H | Q3l |
| 625 | Q1g | H | H | Q3m |
| 626 | Q1g | H | H | Q3n |
| 627 | Q1g | H | H | Q3o |
| 628 | Q1g | H | H | Q3p |
| 629 | Q1g | H | H | Q3q |
| 630 | Q1g | H | Me | Q3a |
| 631 | Q1g | H | Me | Q3b |
| 632 | Q1g | H | Me | Q3c |
| 633 | Q1g | H | Me | Q3d |
| 634 | Q1g | H | Me | Q3e |
| 635 | Q1g | H | Me | Q3f |
| 636 | Q1g | H | Me | Q3g |
| 637 | Q1g | H | Me | Q3h |
| 638 | Q1g | H | Me | Q3i |
| 639 | Q1g | H | Me | Q3j |
| 640 | Q1g | H | Me | Q3k |
| 641 | Q1g | H | Me | Q3l |
| 642 | Q1g | H | Me | Q3m |
| 643 | Q1g | H | Me | Q3n |
| 644 | Q1g | H | Me | Q3o |
| 645 | Q1g | H | Me | Q3p |
| 646 | Q1g | H | Me | Q3q |
| 647 | Q1g | Me | H | Q3a |
| 648 | Q1g | Me | H | Q3b |
| 649 | Q1g | Me | H | Q3c |
| 650 | Q1g | Me | H | Q3d |
| 651 | Q1g | Me | H | Q3e |
| 652 | Q1g | Me | H | Q3f |
| 653 | Q1g | Me | H | Q3g |
| 654 | Q1g | Me | H | Q3h |
| 655 | Q1g | Me | H | Q3i |
| 656 | Q1g | Me | H | Q3j |
| 657 | Q1g | Me | H | Q3k |
| 658 | Q1g | Me | H | Q3l |
| 659 | Q1g | Me | H | Q3m |
| 660 | Q1g | Me | H | Q3n |
| 661 | Q1g | Me | H | Q3o |
| 662 | Q1g | Me | H | Q3p |
| 663 | Q1g | Me | H | Q3q |
| 664 | Q1g | Me | Me | Q3a |
| 665 | Q1g | Me | Me | Q3b |
| 666 | Q1g | Me | Me | Q3c |
| 667 | Q1g | Me | Me | Q3d |
| 668 | Q1g | Me | Me | Q3e |
| 669 | Q1g | Me | Me | Q3f |
| 670 | Q1g | Me | Me | Q3g |
| 671 | Q1g | Me | Me | Q3h |
| 672 | Q1g | Me | Me | Q3i |
| 673 | Q1g | Me | Me | Q3j |
| 674 | Q1g | Me | Me | Q3k |
| 675 | Q1g | Me | Me | Q3l |
| 676 | Q1g | Me | Me | Q3m |
| 677 | Q1g | Me | Me | Q3n |
| 678 | Q1g | Me | Me | Q3o |
| 679 | Q1g | Me | Me | Q3p |
| 680 | Q1g | Me | Me | Q3q |
| 681 | Q1g | CF3 | H | Q3a |
| 682 | Q1g | CF3 | H | Q3b |
| 683 | Q1g | CF3 | H | Q3c |
| 684 | Q1g | CF3 | H | Q3d |
| 685 | Q1g | CF3 | H | Q3e |
| 686 | Q1g | CF3 | H | Q3f |
| 687 | Q1g | CF3 | H | Q3g |
| 688 | Q1g | CF3 | H | Q3h |
| 689 | Q1g | CF3 | H | Q3i |
| 690 | Q1g | CF3 | H | Q3j |
| 691 | Q1g | CF3 | H | Q3k |
| 692 | Q1g | CF3 | H | Q3l |
| 693 | Q1g | CF3 | H | Q3m |
| 694 | Q1g | CF3 | H | Q3n |
| 695 | Q1g | CF3 | H | Q3o |
| 696 | Q1g | CF3 | H | Q3p |
| 697 | Q1g | CF3 | H | Q3q |
| 698 | Q1g | CF3 | Me | Q3a |
| 699 | Q1g | CF3 | Me | Q3b |
| 700 | Q1g | CF3 | Me | Q3c |
| 701 | Q1g | CF3 | Me | Q3d |
| 702 | Q1g | CF3 | Me | Q3e |
| 703 | Q1g | CF3 | Me | Q3f |
| 704 | Q1g | CF3 | Me | Q3g |
| 705 | Q1g | CF3 | Me | Q3h |
| 706 | Q1g | CF3 | Me | Q3i |
| 707 | Q1g | CF3 | Me | Q3j |
| 708 | Q1g | CF3 | Me | Q3k |
| 709 | Q1g | CF3 | Me | Q3l |
| 710 | Q1g | CF3 | Me | Q3m |
| 711 | Q1g | CF3 | Me | Q3n |
| 712 | Q1g | CF3 | Me | Q3o |
| 713 | Q1g | CF3 | Me | Q3p |
| 714 | Q1g | CF3 | Me | Q3q |
| 715 | Q1h | H | H | Q3a |
| 716 | Q1h | H | H | Q3b |
| 717 | Q1h | H | H | Q3c |
| 718 | Q1h | H | H | Q3d |
| 719 | Q1h | H | H | Q3e |
| 720 | Q1h | H | H | Q3f |
| 721 | Q1h | H | H | Q3g |
| 722 | Q1h | H | H | Q3h |
| 723 | Q1h | H | H | Q3i |
| 724 | Q1h | H | H | Q3j |
| 725 | Q1h | H | H | Q3k |
| 726 | Q1h | H | H | Q3l |
| 727 | Q1h | H | H | Q3m |
| 728 | Q1h | H | H | Q3n |
| 729 | Q1h | H | H | Q3o |
| 730 | Q1h | H | H | Q3p |
| 731 | Q1h | H | H | Q3q |
| 732 | Q1h | H | Me | Q3a |
| 733 | Q1h | H | Me | Q3b |
| 734 | Q1h | H | Me | Q3c |
| 735 | Q1h | H | Me | Q3d |
| 736 | Q1h | H | Me | Q3e |
| 737 | Q1h | H | Me | Q3f |
| 738 | Q1h | H | Me | Q3g |
| 739 | Q1h | H | Me | Q3h |
| 740 | Q1h | H | Me | Q3i |
| 741 | Q1h | H | Me | Q3j |
| 742 | Q1h | H | Me | Q3k |
| 743 | Q1h | H | Me | Q3l |
| 744 | Q1h | H | Me | Q3m |
| 745 | Q1h | H | Me | Q3n |
| 746 | Q1h | H | Me | Q3o |
| 747 | Q1h | H | Me | Q3p |
| 748 | Q1h | H | Me | Q3q |
| 749 | Q1h | Me | H | Q3a |
| 750 | Q1h | Me | H | Q3b |
| 751 | Q1h | Me | H | Q3c |
| 752 | Q1h | Me | H | Q3d |
| 753 | Q1h | Me | H | Q3e |
| 754 | Q1h | Me | H | Q3f |
| 755 | Q1h | Me | H | Q3g |
| 756 | Q1h | Me | H | Q3h |
| 757 | Q1h | Me | H | Q3i |
| 758 | Q1h | Me | H | Q3j |
| 759 | Q1h | Me | H | Q3k |
| 760 | Q1h | Me | H | Q3l |
| 761 | Q1h | Me | H | Q3m |
| 762 | Q1h | Me | H | Q3n |
| 763 | Q1h | Me | H | Q3o |
| 764 | Q1h | Me | H | Q3p |
| 765 | Q1h | Me | H | Q3q |
| 766 | Q1h | Me | Me | Q3a |
| 767 | Q1h | Me | Me | Q3b |
| 768 | Q1h | Me | Me | Q3c |
| 769 | Q1h | Me | Me | Q3d |
| 770 | Q1h | Me | Me | Q3e |
| 771 | Q1h | Me | Me | Q3f |
| 772 | Q1h | Me | Me | Q3g |

TABLE 1-continued

| No | R⁷ | R⁸ | R⁹ | R¹⁰ |
|---|---|---|---|---|
| 773 | Q1h | Me | Me | Q3h |
| 774 | Q1h | Me | Me | Q3i |
| 775 | Q1h | Me | Me | Q3j |
| 776 | Q1h | Me | Me | Q3k |
| 777 | Q1h | Me | Me | Q3l |
| 778 | Q1h | Me | Me | Q3m |
| 779 | Q1h | Me | Me | Q3n |
| 780 | Q1h | Me | Me | Q3o |
| 781 | Q1h | Me | Me | Q3p |
| 782 | Q1h | Me | Me | Q3q |
| 783 | Q1h | CF3 | H | Q3a |
| 784 | Q1h | CF3 | H | Q3b |
| 785 | Q1h | CF3 | H | Q3c |
| 786 | Q1h | CF3 | H | Q3d |
| 787 | Q1h | CF3 | H | Q3e |
| 788 | Q1h | CF3 | H | Q3f |
| 789 | Q1h | CF3 | H | Q3g |
| 790 | Q1h | CF3 | H | Q3h |
| 791 | Q1h | CF3 | H | Q3i |
| 792 | Q1h | CF3 | H | Q3j |
| 793 | Q1h | CF3 | H | Q3k |
| 794 | Q1h | CF3 | H | Q3l |
| 795 | Q1h | CF3 | H | Q3m |
| 796 | Q1h | CF3 | H | Q3n |
| 797 | Q1h | CF3 | H | Q3o |
| 798 | Q1h | CF3 | H | Q3p |
| 799 | Q1h | CF3 | H | Q3q |
| 800 | Q1h | CF3 | Me | Q3a |
| 801 | Q1h | CF3 | Me | Q3b |
| 802 | Q1h | CF3 | Me | Q3c |
| 803 | Q1h | CF3 | Me | Q3d |
| 804 | Q1h | CF3 | Me | Q3e |
| 805 | Q1h | CF3 | Me | Q3f |
| 806 | Q1h | CF3 | Me | Q3g |
| 807 | Q1h | CF3 | Me | Q3h |
| 808 | Q1h | CF3 | Me | Q3i |
| 809 | Q1h | CF3 | Me | Q3j |
| 810 | Q1h | CF3 | Me | Q3k |
| 811 | Q1h | CF3 | Me | Q3l |
| 812 | Q1h | CF3 | Me | Q3m |
| 813 | Q1h | CF3 | Me | Q3n |
| 814 | Q1h | CF3 | Me | Q3o |
| 815 | Q1h | CF3 | Me | Q3p |
| 816 | Q1h | CF3 | Me | Q3q |
| 817 | Q1i | H | H | Q3a |
| 818 | Q1i | H | H | Q3b |
| 819 | Q1i | H | H | Q3c |
| 820 | Q1i | H | H | Q3d |
| 821 | Q1i | H | H | Q3e |
| 822 | Q1i | H | H | Q3f |
| 823 | Q1i | H | H | Q3g |
| 824 | Q1i | H | H | Q3h |
| 825 | Q1i | H | H | Q3i |
| 826 | Q1i | H | H | Q3j |
| 827 | Q1i | H | H | Q3k |
| 828 | Q1i | H | H | Q3l |
| 829 | Q1i | H | H | Q3m |
| 830 | Q1i | H | H | Q3n |
| 831 | Q1i | H | H | Q3o |
| 832 | Q1i | H | H | Q3p |
| 833 | Q1i | H | H | Q3q |
| 834 | Q1i | H | Me | Q3a |
| 835 | Q1i | H | Me | Q3b |
| 836 | Q1i | H | Me | Q3c |
| 837 | Q1i | H | Me | Q3d |
| 838 | Q1i | H | Me | Q3e |
| 839 | Q1i | H | Me | Q3f |
| 840 | Q1i | H | Me | Q3g |
| 841 | Q1i | H | Me | Q3h |
| 842 | Q1i | H | Me | Q3i |
| 843 | Q1i | H | Me | Q3j |
| 844 | Q1i | H | Me | Q3k |
| 845 | Q1i | H | Me | Q3l |
| 846 | Q1i | H | Me | Q3m |
| 847 | Q1i | H | Me | Q3n |
| 848 | Q1i | H | Me | Q3o |
| 849 | Q1i | H | Me | Q3p |
| 850 | Q1i | H | Me | Q3q |
| 851 | Q1i | Me | H | Q3a |
| 852 | Q1i | Me | H | Q3b |
| 853 | Q1i | Me | H | Q3c |
| 854 | Q1i | Me | H | Q3d |
| 855 | Q1i | Me | H | Q3e |
| 856 | Q1i | Me | H | Q3f |
| 857 | Q1i | Me | H | Q3g |
| 858 | Q1i | Me | H | Q3h |
| 859 | Q1i | Me | H | Q3i |
| 860 | Q1i | Me | H | Q3j |
| 861 | Q1i | Me | H | Q3k |
| 862 | Q1i | Me | H | Q3l |
| 863 | Q1i | Me | H | Q3m |
| 864 | Q1i | Me | H | Q3n |
| 865 | Q1i | Me | H | Q3o |
| 866 | Q1i | Me | H | Q3p |
| 867 | Q1i | Me | H | Q3q |
| 868 | Q1i | Me | Me | Q3a |
| 869 | Q1i | Me | Me | Q3b |
| 870 | Q1i | Me | Me | Q3c |
| 871 | Q1i | Me | Me | Q3d |
| 872 | Q1i | Me | Me | Q3e |
| 873 | Q1i | Me | Me | Q3f |
| 874 | Q1i | Me | Me | Q3g |
| 875 | Q1i | Me | Me | Q3h |
| 876 | Q1i | Me | Me | Q3i |
| 877 | Q1i | Me | Me | Q3j |
| 878 | Q1i | Me | Me | Q3k |
| 879 | Q1i | Me | Me | Q3l |
| 880 | Q1i | Me | Me | Q3m |
| 881 | Q1i | Me | Me | Q3n |
| 882 | Q1i | Me | Me | Q3o |
| 883 | Q1i | Me | Me | Q3p |
| 884 | Q1i | Me | Me | Q3q |
| 885 | Q1i | CF3 | H | Q3a |
| 886 | Q1i | CF3 | H | Q3b |
| 887 | Q1i | CF3 | H | Q3c |
| 888 | Q1i | CF3 | H | Q3d |
| 889 | Q1i | CF3 | H | Q3e |
| 890 | Q1i | CF3 | H | Q3f |
| 891 | Q1i | CF3 | H | Q3g |
| 892 | Q1i | CF3 | H | Q3h |
| 893 | Q1i | CF3 | H | Q3i |
| 894 | Q1i | CF3 | H | Q3j |
| 895 | Q1i | CF3 | H | Q3k |
| 896 | Q1i | CF3 | H | Q3l |
| 897 | Q1i | CF3 | H | Q3m |
| 898 | Q1i | CF3 | H | Q3n |
| 899 | Q1i | CF3 | H | Q3o |
| 900 | Q1i | CF3 | H | Q3p |
| 901 | Q1i | CF3 | H | Q3q |
| 902 | Q1i | CF3 | Me | Q3a |
| 903 | Q1i | CF3 | Me | Q3b |
| 904 | Q1i | CF3 | Me | Q3c |
| 905 | Q1i | CF3 | Me | Q3d |
| 906 | Q1i | CF3 | Me | Q3e |
| 907 | Q1i | CF3 | Me | Q3f |
| 908 | Q1i | CF3 | Me | Q3g |
| 909 | Q1i | CF3 | Me | Q3h |
| 910 | Q1i | CF3 | Me | Q3i |
| 911 | Q1i | CF3 | Me | Q3j |
| 912 | Q1i | CF3 | Me | Q3k |
| 913 | Q1i | CF3 | Me | Q3l |
| 914 | Q1i | CF3 | Me | Q3m |
| 915 | Q1i | CF3 | Me | Q3n |
| 916 | Q1i | CF3 | Me | Q3o |
| 917 | Q1i | CF3 | Me | Q3p |
| 918 | Q1i | CF3 | Me | Q3q |
| 919 | Q1j | H | H | Q3a |
| 920 | Q1j | H | H | Q3b |
| 921 | Q1j | H | H | Q3c |
| 922 | Q1j | H | H | Q3d |
| 923 | Q1j | H | H | Q3e |
| 924 | Q1j | H | H | Q3f |
| 925 | Q1j | H | H | Q3g |
| 926 | Q1j | H | H | Q3h |
| 927 | Q1j | H | H | Q3i |
| 928 | Q1j | H | H | Q3j |

TABLE 1-continued

| No | R⁷ | R⁸ | R⁹ | R¹⁰ |
|---|---|---|---|---|
| 929 | Q1j | H | H | Q3k |
| 930 | Q1j | H | H | Q3l |
| 931 | Q1j | H | H | Q3m |
| 932 | Q1j | H | H | Q3n |
| 933 | Q1j | H | H | Q3o |
| 934 | Q1j | H | H | Q3p |
| 935 | Q1j | H | H | Q3q |
| 936 | Q1j | H | Me | Q3a |
| 937 | Q1j | H | Me | Q3b |
| 938 | Q1j | H | Me | Q3c |
| 939 | Q1j | H | Me | Q3d |
| 940 | Q1j | H | Me | Q3e |
| 941 | Q1j | H | Me | Q3f |
| 942 | Q1j | H | Me | Q3g |
| 943 | Q1j | H | Me | Q3h |
| 944 | Q1j | H | Me | Q3i |
| 945 | Q1j | H | Me | Q3j |
| 946 | Q1j | H | Me | Q3k |
| 947 | Q1j | H | Me | Q3l |
| 948 | Q1j | H | Me | Q3m |
| 949 | Q1j | H | Me | Q3n |
| 950 | Q1j | H | Me | Q3o |
| 951 | Q1j | H | Me | Q3p |
| 952 | Q1j | H | Me | Q3q |
| 953 | Q1j | Me | H | Q3a |
| 954 | Q1j | Me | H | Q3b |
| 955 | Q1j | Me | H | Q3c |
| 956 | Q1j | Me | H | Q3d |
| 957 | Q1j | Me | H | Q3e |
| 958 | Q1j | Me | H | Q3f |
| 959 | Q1j | Me | H | Q3g |
| 960 | Q1j | Me | H | Q3h |
| 961 | Q1j | Me | H | Q3i |
| 962 | Q1j | Me | H | Q3j |
| 963 | Q1j | Me | H | Q3k |
| 964 | Q1j | Me | H | Q3l |
| 965 | Q1j | Me | H | Q3m |
| 966 | Q1j | Me | H | Q3n |
| 967 | Q1j | Me | H | Q3o |
| 968 | Q1j | Me | H | Q3p |
| 969 | Q1j | Me | H | Q3q |
| 970 | Q1j | Me | Me | Q3a |
| 971 | Q1j | Me | Me | Q3b |
| 972 | Q1j | Me | Me | Q3c |
| 973 | Q1j | Me | Me | Q3d |
| 974 | Q1j | Me | Me | Q3e |
| 975 | Q1j | Me | Me | Q3f |
| 976 | Q1j | Me | Me | Q3g |
| 977 | Q1j | Me | Me | Q3h |
| 978 | Q1j | Me | Me | Q3i |
| 979 | Q1j | Me | Me | Q3j |
| 980 | Q1j | Me | Me | Q3k |
| 981 | Q1j | Me | Me | Q3l |
| 982 | Q1j | Me | Me | Q3m |
| 983 | Q1j | Me | Me | Q3n |
| 984 | Q1j | Me | Me | Q3o |
| 985 | Q1j | Me | Me | Q3p |
| 986 | Q1j | Me | Me | Q3q |
| 987 | Q1j | CF3 | H | Q3a |
| 988 | Q1j | CF3 | H | Q3b |
| 989 | Q1j | CF3 | H | Q3c |
| 990 | Q1j | CF3 | H | Q3d |
| 991 | Q1j | CF3 | H | Q3e |
| 992 | Q1j | CF3 | H | Q3f |
| 993 | Q1j | CF3 | H | Q3g |
| 994 | Q1j | CF3 | H | Q3h |
| 995 | Q1j | CF3 | H | Q3i |
| 996 | Q1j | CF3 | H | Q3j |
| 997 | Q1j | CF3 | H | Q3k |
| 998 | Q1j | CF3 | H | Q3l |
| 999 | Q1j | CF3 | H | Q3m |
| 1000 | Q1j | CF3 | H | Q3n |
| 1001 | Q1j | CF3 | H | Q3o |
| 1002 | Q1j | CF3 | H | Q3p |
| 1003 | Q1j | CF3 | H | Q3q |
| 1004 | Q1j | CF3 | Me | Q3a |
| 1005 | Q1j | CF3 | Me | Q3b |
| 1006 | Q1j | CF3 | Me | Q3c |
| 1007 | Q1j | CF3 | Me | Q3d |
| 1008 | Q1j | CF3 | Me | Q3e |
| 1009 | Q1j | CF3 | Me | Q3f |
| 1010 | Q1j | CF3 | Me | Q3g |
| 1011 | Q1j | CF3 | Me | Q3h |
| 1012 | Q1j | CF3 | Me | Q3i |
| 1013 | Q1j | CF3 | Me | Q3j |
| 1014 | Q1j | CF3 | Me | Q3k |
| 1015 | Q1j | CF3 | Me | Q3l |
| 1016 | Q1j | CF3 | Me | Q3m |
| 1017 | Q1j | CF3 | Me | Q3n |
| 1018 | Q1j | CF3 | Me | Q3o |
| 1019 | Q1j | CF3 | Me | Q3p |
| 1020 | Q1j | CF3 | Me | Q3q |
| 1021 | Q1k | H | H | Q3a |
| 1022 | Q1k | H | H | Q3b |
| 1023 | Q1k | H | H | Q3c |
| 1024 | Q1k | H | H | Q3d |
| 1025 | Q1k | H | H | Q3e |
| 1026 | Q1k | H | H | Q3f |
| 1027 | Q1k | H | H | Q3g |
| 1028 | Q1k | H | H | Q3h |
| 1029 | Q1k | H | H | Q3i |
| 1030 | Q1k | H | H | Q3j |
| 1031 | Q1k | H | H | Q3k |
| 1032 | Q1k | H | H | Q3l |
| 1033 | Q1k | H | H | Q3m |
| 1034 | Q1k | H | H | Q3n |
| 1035 | Q1k | H | H | Q3o |
| 1036 | Q1k | H | H | Q3p |
| 1037 | Q1k | H | H | Q3q |
| 1038 | Q1k | H | Me | Q3a |
| 1039 | Q1k | H | Me | Q3b |
| 1040 | Q1k | H | Me | Q3c |
| 1041 | Q1k | H | Me | Q3d |
| 1042 | Q1k | H | Me | Q3e |
| 1043 | Q1k | H | Me | Q3f |
| 1044 | Q1k | H | Me | Q3g |
| 1045 | Q1k | H | Me | Q3h |
| 1046 | Q1k | H | Me | Q3i |
| 1047 | Q1k | H | Me | Q3j |
| 1048 | Q1k | H | Me | Q3k |
| 1049 | Q1k | H | Me | Q3l |
| 1050 | Q1k | H | Me | Q3m |
| 1051 | Q1k | H | Me | Q3n |
| 1052 | Q1k | H | Me | Q3o |
| 1053 | Q1k | H | Me | Q3p |
| 1054 | Q1k | H | Me | Q3q |
| 1055 | Q1k | Me | H | Q3a |
| 1056 | Q1k | Me | H | Q3b |
| 1057 | Q1k | Me | H | Q3c |
| 1058 | Q1k | Me | H | Q3d |
| 1059 | Q1k | Me | H | Q3e |
| 1060 | Q1k | Me | H | Q3f |
| 1061 | Q1k | Me | H | Q3g |
| 1062 | Q1k | Me | H | Q3h |
| 1063 | Q1k | Me | H | Q3i |
| 1064 | Q1k | Me | H | Q3j |
| 1065 | Q1k | Me | H | Q3k |
| 1066 | Q1k | Me | H | Q3l |
| 1067 | Q1k | Me | H | Q3m |
| 1068 | Q1k | Me | H | Q3n |
| 1069 | Q1k | Me | H | Q3o |
| 1070 | Q1k | Me | H | Q3p |
| 1071 | Q1k | Me | H | Q3q |
| 1072 | Q1k | Me | Me | Q3a |
| 1073 | Q1k | Me | Me | Q3b |
| 1074 | Q1k | Me | Me | Q3c |
| 1075 | Q1k | Me | Me | Q3d |
| 1076 | Q1k | Me | Me | Q3e |
| 1077 | Q1k | Me | Me | Q3f |
| 1078 | Q1k | Me | Me | Q3g |
| 1079 | Q1k | Me | Me | Q3h |
| 1080 | Q1k | Me | Me | Q3i |
| 1081 | Q1k | Me | Me | Q3j |
| 1082 | Q1k | Me | Me | Q3k |
| 1083 | Q1k | Me | Me | Q3l |
| 1084 | Q1k | Me | Me | Q3m |

TABLE 1-continued

| No | R⁷ | R⁸ | R⁹ | R¹⁰ |
|---|---|---|---|---|
| 1085 | Q1k | Me | Me | Q3n |
| 1086 | Q1k | Me | Me | Q3o |
| 1087 | Q1k | Me | Me | Q3p |
| 1088 | Q1k | Me | Me | Q3q |
| 1089 | Q1k | CF3 | H | Q3a |
| 1090 | Q1k | CF3 | H | Q3b |
| 1091 | Q1k | CF3 | H | Q3c |
| 1092 | Q1k | CF3 | H | Q3d |
| 1093 | Q1k | CF3 | H | Q3e |
| 1094 | Q1k | CF3 | H | Q3f |
| 1095 | Q1k | CF3 | H | Q3g |
| 1096 | Q1k | CF3 | H | Q3h |
| 1097 | Q1k | CF3 | H | Q3i |
| 1098 | Q1k | CF3 | H | Q3j |
| 1099 | Q1k | CF3 | H | Q3k |
| 1100 | Q1k | CF3 | H | Q3l |
| 1101 | Q1k | CF3 | H | Q3m |
| 1102 | Q1k | CF3 | H | Q3n |
| 1103 | Q1k | CF3 | H | Q3o |
| 1104 | Q1k | CF3 | H | Q3p |
| 1105 | Q1k | CF3 | H | Q3q |
| 1106 | Q1k | CF3 | Me | Q3a |
| 1107 | Q1k | CF3 | Me | Q3b |
| 1108 | Q1k | CF3 | Me | Q3c |
| 1109 | Q1k | CF3 | Me | Q3d |
| 1110 | Q1k | CF3 | Me | Q3e |
| 1111 | Q1k | CF3 | Me | Q3f |
| 1112 | Q1k | CF3 | Me | Q3g |
| 1113 | Q1k | CF3 | Me | Q3h |
| 1114 | Q1k | CF3 | Me | Q3i |
| 1115 | Q1k | CF3 | Me | Q3j |
| 1116 | Q1k | CF3 | Me | Q3k |
| 1117 | Q1k | CF3 | Me | Q3l |
| 1118 | Q1k | CF3 | Me | Q3m |
| 1119 | Q1k | CF3 | Me | Q3n |
| 1120 | Q1k | CF3 | Me | Q3o |
| 1121 | Q1k | CF3 | Me | Q3p |
| 1122 | Q1k | CF3 | Me | Q3q |
| 1123 | Q1l | H | H | Q3a |
| 1124 | Q1l | H | H | Q3b |
| 1125 | Q1l | H | H | Q3c |
| 1126 | Q1l | H | H | Q3d |
| 1127 | Q1l | H | H | Q3e |
| 1128 | Q1l | H | H | Q3f |
| 1129 | Q1l | H | H | Q3g |
| 1130 | Q1l | H | H | Q3h |
| 1131 | Q1l | H | H | Q3i |
| 1132 | Q1l | H | H | Q3j |
| 1133 | Q1l | H | H | Q3k |
| 1134 | Q1l | H | H | Q3l |
| 1135 | Q1l | H | H | Q3m |
| 1136 | Q1l | H | H | Q3n |
| 1137 | Q1l | H | H | Q3o |
| 1138 | Q1l | H | H | Q3p |
| 1139 | Q1l | H | H | Q3q |
| 1140 | Q1l | H | Me | Q3a |
| 1141 | Q1l | H | Me | Q3b |
| 1142 | Q1l | H | Me | Q3c |
| 1143 | Q1l | H | Me | Q3d |
| 1144 | Q1l | H | Me | Q3e |
| 1145 | Q1l | H | Me | Q3f |
| 1146 | Q1l | H | Me | Q3g |
| 1147 | Q1l | H | Me | Q3h |
| 1148 | Q1l | H | Me | Q3i |
| 1149 | Q1l | H | Me | Q3j |
| 1150 | Q1l | H | Me | Q3k |
| 1151 | Q1l | H | Me | Q3l |
| 1152 | Q1l | H | Me | Q3m |
| 1153 | Q1l | H | Me | Q3n |
| 1154 | Q1l | H | Me | Q3o |
| 1155 | Q1l | H | Me | Q3p |
| 1156 | Q1l | H | Me | Q3q |
| 1157 | Q1l | Me | H | Q3a |
| 1158 | Q1l | Me | H | Q3b |
| 1159 | Q1l | Me | H | Q3c |
| 1160 | Q1l | Me | H | Q3d |
| 1161 | Q1l | Me | H | Q3e |
| 1162 | Q1l | Me | H | Q3f |
| 1163 | Q1l | Me | H | Q3g |
| 1164 | Q1l | Me | H | Q3h |
| 1165 | Q1l | Me | H | Q3i |
| 1166 | Q1l | Me | H | Q3j |
| 1167 | Q1l | Me | H | Q3k |
| 1168 | Q1l | Me | H | Q3l |
| 1169 | Q1l | Me | H | Q3m |
| 1170 | Q1l | Me | H | Q3n |
| 1171 | Q1l | Me | H | Q3o |
| 1172 | Q1l | Me | H | Q3p |
| 1173 | Q1l | Me | H | Q3q |
| 1174 | Q1l | Me | Me | Q3a |
| 1175 | Q1l | Me | Me | Q3b |
| 1176 | Q1l | Me | Me | Q3c |
| 1177 | Q1l | Me | Me | Q3d |
| 1178 | Q1l | Me | Me | Q3e |
| 1179 | Q1l | Me | Me | Q3f |
| 1180 | Q1l | Me | Me | Q3g |
| 1181 | Q1l | Me | Me | Q3h |
| 1182 | Q1l | Me | Me | Q3i |
| 1183 | Q1l | Me | Me | Q3j |
| 1184 | Q1l | Me | Me | Q3k |
| 1185 | Q1l | Me | Me | Q3l |
| 1186 | Q1l | Me | Me | Q3m |
| 1187 | Q1l | Me | Me | Q3n |
| 1188 | Q1l | Me | Me | Q3o |
| 1189 | Q1l | Me | Me | Q3p |
| 1190 | Q1l | Me | Me | Q3q |
| 1191 | Q1l | CF3 | H | Q3a |
| 1192 | Q1l | CF3 | H | Q3b |
| 1193 | Q1l | CF3 | H | Q3c |
| 1194 | Q1l | CF3 | H | Q3d |
| 1195 | Q1l | CF3 | H | Q3e |
| 1196 | Q1l | CF3 | H | Q3f |
| 1197 | Q1l | CF3 | H | Q3g |
| 1198 | Q1l | CF3 | H | Q3h |
| 1199 | Q1l | CF3 | H | Q3i |
| 1200 | Q1l | CF3 | H | Q3j |
| 1201 | Q1l | CF3 | H | Q3k |
| 1202 | Q1l | CF3 | H | Q3l |
| 1203 | Q1l | CF3 | H | Q3m |
| 1204 | Q1l | CF3 | H | Q3n |
| 1205 | Q1l | CF3 | H | Q3o |
| 1206 | Q1l | CF3 | H | Q3p |
| 1207 | Q1l | CF3 | H | Q3q |
| 1208 | Q1l | CF3 | Me | Q3a |
| 1209 | Q1l | CF3 | Me | Q3b |
| 1210 | Q1l | CF3 | Me | Q3c |
| 1211 | Q1l | CF3 | Me | Q3d |
| 1212 | Q1l | CF3 | Me | Q3e |
| 1213 | Q1l | CF3 | Me | Q3f |
| 1214 | Q1l | CF3 | Me | Q3g |
| 1215 | Q1l | CF3 | Me | Q3h |
| 1216 | Q1l | CF3 | Me | Q3i |
| 1217 | Q1l | CF3 | Me | Q3j |
| 1218 | Q1l | CF3 | Me | Q3k |
| 1219 | Q1l | CF3 | Me | Q3l |
| 1220 | Q1l | CF3 | Me | Q3m |
| 1221 | Q1l | CF3 | Me | Q3n |
| 1222 | Q1l | CF3 | Me | Q3o |
| 1223 | Q1l | CF3 | Me | Q3p |
| 1224 | Q1l | CF3 | Me | Q3q |
| 1225 | Q1m | H | H | Q3a |
| 1226 | Q1m | H | H | Q3b |
| 1227 | Q1m | H | H | Q3c |
| 1228 | Q1m | H | H | Q3d |
| 1229 | Q1m | H | H | Q3e |
| 1230 | Q1m | H | H | Q3f |
| 1231 | Q1m | H | H | Q3g |
| 1232 | Q1m | H | H | Q3h |
| 1233 | Q1m | H | H | Q3i |
| 1234 | Q1m | H | H | Q3j |
| 1235 | Q1m | H | H | Q3k |
| 1236 | Q1m | H | H | Q3l |
| 1237 | Q1m | H | H | Q3m |
| 1238 | Q1m | H | H | Q3n |
| 1239 | Q1m | H | H | Q3o |
| 1240 | Q1m | H | H | Q3p |

TABLE 1-continued

| No | $R^7$ | $R^8$ | $R^9$ | $R^{10}$ |
|---|---|---|---|---|
| 1241 | Q1m | H | H | Q3q |
| 1242 | Q1m | H | Me | Q3a |
| 1243 | Q1m | H | Me | Q3b |
| 1244 | Q1m | H | Me | Q3c |
| 1245 | Q1m | H | Me | Q3d |
| 1246 | Q1m | H | Me | Q3e |
| 1247 | Q1m | H | Me | Q3f |
| 1248 | Q1m | H | Me | Q3g |
| 1249 | Q1m | H | Me | Q3h |
| 1250 | Q1m | H | Me | Q3i |
| 1251 | Q1m | H | Me | Q3j |
| 1252 | Q1m | H | Me | Q3k |
| 1253 | Q1m | H | Me | Q3l |
| 1254 | Q1m | H | Me | Q3m |
| 1255 | Q1m | H | Me | Q3n |
| 1256 | Q1m | H | Me | Q3o |
| 1257 | Q1m | H | Me | Q3p |
| 1258 | Q1m | H | Me | Q3q |
| 1259 | Q1m | Me | H | Q3a |
| 1260 | Q1m | Me | H | Q3b |
| 1261 | Q1m | Me | H | Q3c |
| 1262 | Q1m | Me | H | Q3d |
| 1263 | Q1m | Me | H | Q3e |
| 1264 | Q1m | Me | H | Q3f |
| 1265 | Q1m | Me | H | Q3g |
| 1266 | Q1m | Me | H | Q3h |
| 1267 | Q1m | Me | H | Q3i |
| 1268 | Q1m | Me | H | Q3j |
| 1269 | Q1m | Me | H | Q3k |
| 1270 | Q1m | Me | H | Q3l |
| 1271 | Q1m | Me | H | Q3m |
| 1272 | Q1m | Me | H | Q3n |
| 1273 | Q1m | Me | H | Q3o |
| 1274 | Q1m | Me | H | Q3p |
| 1275 | Q1m | Me | H | Q3q |
| 1276 | Q1m | Me | Me | Q3a |
| 1277 | Q1m | Me | Me | Q3b |
| 1278 | Q1m | Me | Me | Q3c |
| 1279 | Q1m | Me | Me | Q3d |
| 1280 | Q1m | Me | Me | Q3e |
| 1281 | Q1m | Me | Me | Q3f |
| 1282 | Q1m | Me | Me | Q3g |
| 1283 | Q1m | Me | Me | Q3h |
| 1284 | Q1m | Me | Me | Q3i |
| 1285 | Q1m | Me | Me | Q3j |
| 1286 | Q1m | Me | Me | Q3k |
| 1287 | Q1m | Me | Me | Q3l |
| 1288 | Q1m | Me | Me | Q3m |
| 1289 | Q1m | Me | Me | Q3n |
| 1290 | Q1m | Me | Me | Q3o |
| 1291 | Q1m | Me | Me | Q3p |
| 1292 | Q1m | Me | Me | Q3q |
| 1293 | Q1m | CF3 | H | Q3a |
| 1294 | Q1m | CF3 | H | Q3b |
| 1295 | Q1m | CF3 | H | Q3c |
| 1296 | Q1m | CF3 | H | Q3d |
| 1297 | Q1m | CF3 | H | Q3e |
| 1298 | Q1m | CF3 | H | Q3f |
| 1299 | Q1m | CF3 | H | Q3g |
| 1300 | Q1m | CF3 | H | Q3h |
| 1301 | Q1m | CF3 | H | Q3i |
| 1302 | Q1m | CF3 | H | Q3j |
| 1303 | Q1m | CF3 | H | Q3k |
| 1304 | Q1m | CF3 | H | Q3l |
| 1305 | Q1m | CF3 | H | Q3m |
| 1306 | Q1m | CF3 | H | Q3n |
| 1307 | Q1m | CF3 | H | Q3o |
| 1308 | Q1m | CF3 | H | Q3p |
| 1309 | Q1m | CF3 | H | Q3q |
| 1310 | Q1m | CF3 | Me | Q3a |
| 1311 | Q1m | CF3 | Me | Q3b |
| 1312 | Q1m | CF3 | Me | Q3c |
| 1313 | Q1m | CF3 | Me | Q3d |
| 1314 | Q1m | CF3 | Me | Q3e |
| 1315 | Q1m | CF3 | Me | Q3f |
| 1316 | Q1m | CF3 | Me | Q3g |
| 1317 | Q1m | CF3 | Me | Q3h |
| 1318 | Q1m | CF3 | Me | Q3i |
| 1319 | Q1m | CF3 | Me | Q3j |
| 1320 | Q1m | CF3 | Me | Q3k |
| 1321 | Q1m | CF3 | Me | Q3l |
| 1322 | Q1m | CF3 | Me | Q3m |
| 1323 | Q1m | CF3 | Me | Q3n |
| 1324 | Q1m | CF3 | Me | Q3o |
| 1325 | Q1m | CF3 | Me | Q3p |
| 1326 | Q1m | CF3 | Me | Q3q |
| 1327 | Q1n | H | H | Q3a |
| 1328 | Q1n | H | H | Q3b |
| 1329 | Q1n | H | H | Q3c |
| 1330 | Q1n | H | H | Q3d |
| 1331 | Q1n | H | H | Q3e |
| 1332 | Q1n | H | H | Q3f |
| 1333 | Q1n | H | H | Q3g |
| 1334 | Q1n | H | H | Q3h |
| 1335 | Q1n | H | H | Q3i |
| 1336 | Q1n | H | H | Q3j |
| 1337 | Q1n | H | H | Q3k |
| 1338 | Q1n | H | H | Q3l |
| 1339 | Q1n | H | H | Q3m |
| 1340 | Q1n | H | H | Q3n |
| 1341 | Q1n | H | H | Q3o |
| 1342 | Q1n | H | H | Q3p |
| 1343 | Q1n | H | H | Q3q |
| 1344 | Q1n | H | Me | Q3a |
| 1345 | Q1n | H | Me | Q3b |
| 1346 | Q1n | H | Me | Q3c |
| 1347 | Q1n | H | Me | Q3d |
| 1348 | Q1n | H | Me | Q3e |
| 1349 | Q1n | H | Me | Q3f |
| 1350 | Q1n | H | Me | Q3g |
| 1351 | Q1n | H | Me | Q3h |
| 1352 | Q1n | H | Me | Q3i |
| 1353 | Q1n | H | Me | Q3j |
| 1354 | Q1n | H | Me | Q3k |
| 1355 | Q1n | H | Me | Q3l |
| 1356 | Q1n | H | Me | Q3m |
| 1357 | Q1n | H | Me | Q3n |
| 1358 | Q1n | H | Me | Q3o |
| 1359 | Q1n | H | Me | Q3p |
| 1360 | Q1n | H | Me | Q3q |
| 1361 | Q1n | Me | H | Q3a |
| 1362 | Q1n | Me | H | Q3b |
| 1363 | Q1n | Me | H | Q3c |
| 1364 | Q1n | Me | H | Q3d |
| 1365 | Q1n | Me | H | Q3e |
| 1366 | Q1n | Me | H | Q3f |
| 1367 | Q1n | Me | H | Q3g |
| 1368 | Q1n | Me | H | Q3h |
| 1369 | Q1n | Me | H | Q3i |
| 1370 | Q1n | Me | H | Q3j |
| 1371 | Q1n | Me | H | Q3k |
| 1372 | Q1n | Me | H | Q3l |
| 1373 | Q1n | Me | H | Q3m |
| 1374 | Q1n | Me | H | Q3n |
| 1375 | Q1n | Me | H | Q3o |
| 1376 | Q1n | Me | H | Q3p |
| 1377 | Q1n | Me | H | Q3q |
| 1378 | Q1n | Me | Me | Q3a |
| 1379 | Q1n | Me | Me | Q3b |
| 1380 | Q1n | Me | Me | Q3c |
| 1381 | Q1n | Me | Me | Q3d |
| 1382 | Q1n | Me | Me | Q3e |
| 1383 | Q1n | Me | Me | Q3f |
| 1384 | Q1n | Me | Me | Q3g |
| 1385 | Q1n | Me | Me | Q3h |
| 1386 | Q1n | Me | Me | Q3i |
| 1387 | Q1n | Me | Me | Q3j |
| 1388 | Q1n | Me | Me | Q3k |
| 1389 | Q1n | Me | Me | Q3l |
| 1390 | Q1n | Me | Me | Q3m |
| 1391 | Q1n | Me | Me | Q3n |
| 1392 | Q1n | Me | Me | Q3o |
| 1393 | Q1n | Me | Me | Q3p |
| 1394 | Q1n | Me | Me | Q3q |
| 1395 | Q1n | CF3 | H | Q3a |
| 1396 | Q1n | CF3 | H | Q3b |

TABLE 1-continued

| No | R⁷ | R⁸ | R⁹ | R¹⁰ |
|---|---|---|---|---|
| 1397 | Q1n | CF3 | H | Q3c |
| 1398 | Q1n | CF3 | H | Q3d |
| 1399 | Q1n | CF3 | H | Q3e |
| 1400 | Q1n | CF3 | H | Q3f |
| 1401 | Q1n | CF3 | H | Q3g |
| 1402 | Q1n | CF3 | H | Q3h |
| 1403 | Q1n | CF3 | H | Q3i |
| 1404 | Q1n | CF3 | H | Q3j |
| 1405 | Q1n | CF3 | H | Q3k |
| 1406 | Q1n | CF3 | H | Q3l |
| 1407 | Q1n | CF3 | H | Q3m |
| 1408 | Q1n | CF3 | H | Q3n |
| 1409 | Q1n | CF3 | H | Q3o |
| 1410 | Q1n | CF3 | H | Q3p |
| 1411 | Q1n | CF3 | H | Q3q |
| 1412 | Q1n | CF3 | Me | Q3a |
| 1413 | Q1n | CF3 | Me | Q3b |
| 1414 | Q1n | CF3 | Me | Q3c |
| 1415 | Q1n | CF3 | Me | Q3d |
| 1416 | Q1n | CF3 | Me | Q3e |
| 1417 | Q1n | CF3 | Me | Q3f |
| 1418 | Q1n | CF3 | Me | Q3g |
| 1419 | Q1n | CF3 | Me | Q3h |
| 1420 | Q1n | CF3 | Me | Q3i |
| 1421 | Q1n | CF3 | Me | Q3j |
| 1422 | Q1n | CF3 | Me | Q3k |
| 1423 | Q1n | CF3 | Me | Q3l |
| 1424 | Q1n | CF3 | Me | Q3m |
| 1425 | Q1n | CF3 | Me | Q3n |
| 1426 | Q1n | CF3 | Me | Q3o |
| 1427 | Q1n | CF3 | Me | Q3p |
| 1428 | Q1n | CF3 | Me | Q3q |
| 1429 | Q1o | H | H | Q3a |
| 1430 | Q1o | H | H | Q3b |
| 1431 | Q1o | H | H | Q3c |
| 1432 | Q1o | H | H | Q3d |
| 1433 | Q1o | H | H | Q3e |
| 1434 | Q1o | H | H | Q3f |
| 1435 | Q1o | H | H | Q3g |
| 1436 | Q1o | H | H | Q3h |
| 1437 | Q1o | H | H | Q3i |
| 1438 | Q1o | H | H | Q3j |
| 1439 | Q1o | H | H | Q3k |
| 1440 | Q1o | H | H | Q3l |
| 1441 | Q1o | H | H | Q3m |
| 1442 | Q1o | H | H | Q3n |
| 1443 | Q1o | H | H | Q3o |
| 1444 | Q1o | H | H | Q3p |
| 1445 | Q1o | H | H | Q3q |
| 1446 | Q1o | H | Me | Q3a |
| 1447 | Q1o | H | Me | Q3b |
| 1448 | Q1o | H | Me | Q3c |
| 1449 | Q1o | H | Me | Q3d |
| 1450 | Q1o | H | Me | Q3e |
| 1451 | Q1o | H | Me | Q3f |
| 1452 | Q1o | H | Me | Q3g |
| 1453 | Q1o | H | Me | Q3h |
| 1454 | Q1o | H | Me | Q3i |
| 1455 | Q1o | H | Me | Q3j |
| 1456 | Q1o | H | Me | Q3k |
| 1457 | Q1o | H | Me | Q3l |
| 1458 | Q1o | H | Me | Q3m |
| 1459 | Q1o | H | Me | Q3n |
| 1460 | Q1o | H | Me | Q3o |
| 1461 | Q1o | H | Me | Q3p |
| 1462 | Q1o | H | Me | Q3q |
| 1463 | Q1o | Me | H | Q3a |
| 1464 | Q1o | Me | H | Q3b |
| 1465 | Q1o | Me | H | Q3c |
| 1466 | Q1o | Me | H | Q3d |
| 1467 | Q1o | Me | H | Q3e |
| 1468 | Q1o | Me | H | Q3f |
| 1469 | Q1o | Me | H | Q3g |
| 1470 | Q1o | Me | H | Q3h |
| 1471 | Q1o | Me | H | Q3i |
| 1472 | Q1o | Me | H | Q3j |
| 1473 | Q1o | Me | H | Q3k |
| 1474 | Q1o | Me | H | Q3l |
| 1475 | Q1o | Me | H | Q3m |
| 1476 | Q1o | Me | H | Q3n |
| 1477 | Q1o | Me | H | Q3o |
| 1478 | Q1o | Me | H | Q3p |
| 1479 | Q1o | Me | H | Q3q |
| 1480 | Q1o | Me | Me | Q3a |
| 1481 | Q1o | Me | Me | Q3b |
| 1482 | Q1o | Me | Me | Q3c |
| 1483 | Q1o | Me | Me | Q3d |
| 1484 | Q1o | Me | Me | Q3e |
| 1485 | Q1o | Me | Me | Q3f |
| 1486 | Q1o | Me | Me | Q3g |
| 1487 | Q1o | Me | Me | Q3h |
| 1488 | Q1o | Me | Me | Q3i |
| 1489 | Q1o | Me | Me | Q3j |
| 1490 | Q1o | Me | Me | Q3k |
| 1491 | Q1o | Me | Me | Q3l |
| 1492 | Q1o | Me | Me | Q3m |
| 1493 | Q1o | Me | Me | Q3n |
| 1494 | Q1o | Me | Me | Q3o |
| 1495 | Q1o | Me | Me | Q3p |
| 1496 | Q1o | Me | Me | Q3q |
| 1497 | Q1o | CF3 | H | Q3a |
| 1498 | Q1o | CF3 | H | Q3b |
| 1499 | Q1o | CF3 | H | Q3c |
| 1500 | Q1o | CF3 | H | Q3d |
| 1501 | Q1o | CF3 | H | Q3e |
| 1502 | Q1o | CF3 | H | Q3f |
| 1503 | Q1o | CF3 | H | Q3g |
| 1504 | Q1o | CF3 | H | Q3h |
| 1505 | Q1o | CF3 | H | Q3i |
| 1506 | Q1o | CF3 | H | Q3j |
| 1507 | Q1o | CF3 | H | Q3k |
| 1508 | Q1o | CF3 | H | Q3l |
| 1509 | Q1o | CF3 | H | Q3m |
| 1510 | Q1o | CF3 | H | Q3n |
| 1511 | Q1o | CF3 | H | Q3o |
| 1512 | Q1o | CF3 | H | Q3p |
| 1513 | Q1o | CF3 | H | Q3q |
| 1514 | Q1o | CF3 | Me | Q3a |
| 1515 | Q1o | CF3 | Me | Q3b |
| 1516 | Q1o | CF3 | Me | Q3c |
| 1517 | Q1o | CF3 | Me | Q3d |
| 1518 | Q1o | CF3 | Me | Q3e |
| 1519 | Q1o | CF3 | Me | Q3f |
| 1520 | Q1o | CF3 | Me | Q3g |
| 1521 | Q1o | CF3 | Me | Q3h |
| 1522 | Q1o | CF3 | Me | Q3i |
| 1523 | Q1o | CF3 | Me | Q3j |
| 1524 | Q1o | CF3 | Me | Q3k |
| 1525 | Q1o | CF3 | Me | Q3l |
| 1526 | Q1o | CF3 | Me | Q3m |
| 1527 | Q1o | CF3 | Me | Q3n |
| 1528 | Q1o | CF3 | Me | Q3o |
| 1529 | Q1o | CF3 | Me | Q3p |
| 1530 | Q1o | CF3 | Me | Q3q |
| 1531 | Q1p | H | H | Q3a |
| 1532 | Q1p | H | H | Q3b |
| 1533 | Q1p | H | H | Q3c |
| 1534 | Q1p | H | H | Q3d |
| 1535 | Q1p | H | H | Q3e |
| 1536 | Q1p | H | H | Q3f |
| 1537 | Q1p | H | H | Q3g |
| 1538 | Q1p | H | H | Q3h |
| 1539 | Q1p | H | H | Q3i |
| 1540 | Q1p | H | H | Q3j |
| 1541 | Q1p | H | H | Q3k |
| 1542 | Q1p | H | H | Q3l |
| 1543 | Q1p | H | H | Q3m |
| 1544 | Q1p | H | H | Q3n |
| 1545 | Q1p | H | H | Q3o |
| 1546 | Q1p | H | H | Q3p |
| 1547 | Q1p | H | H | Q3q |
| 1548 | Q1p | H | Me | Q3a |
| 1549 | Q1p | H | Me | Q3b |
| 1550 | Q1p | H | Me | Q3c |
| 1551 | Q1p | H | Me | Q3d |
| 1552 | Q1p | H | Me | Q3e |

TABLE 1-continued

| No | R⁷ | R⁸ | R⁹ | R¹⁰ |
|---|---|---|---|---|
| 1553 | Q1p | H | Me | Q3f |
| 1554 | Q1p | H | Me | Q3g |
| 1555 | Q1p | H | Me | Q3h |
| 1556 | Q1p | H | Me | Q3i |
| 1557 | Q1p | H | Me | Q3j |
| 1558 | Q1p | H | Me | Q3k |
| 1559 | Q1p | H | Me | Q3l |
| 1560 | Q1p | H | Me | Q3m |
| 1561 | Q1p | H | Me | Q3n |
| 1562 | Q1p | H | Me | Q3o |
| 1563 | Q1p | H | Me | Q3p |
| 1564 | Q1p | H | Me | Q3q |
| 1565 | Q1p | Me | H | Q3a |
| 1566 | Q1p | Me | H | Q3b |
| 1567 | Q1p | Me | H | Q3c |
| 1568 | Q1p | Me | H | Q3d |
| 1569 | Q1p | Me | H | Q3e |
| 1570 | Q1p | Me | H | Q3f |
| 1571 | Q1p | Me | H | Q3g |
| 1572 | Q1p | Me | H | Q3h |
| 1573 | Q1p | Me | H | Q3i |
| 1574 | Q1p | Me | H | Q3j |
| 1575 | Q1p | Me | H | Q3k |
| 1576 | Q1p | Me | H | Q3l |
| 1577 | Q1p | Me | H | Q3m |
| 1578 | Q1p | Me | H | Q3n |
| 1579 | Q1p | Me | H | Q3o |
| 1580 | Q1p | Me | H | Q3p |
| 1581 | Q1p | Me | H | Q3q |
| 1582 | Q1p | Me | Me | Q3a |
| 1583 | Q1p | Me | Me | Q3b |
| 1584 | Q1p | Me | Me | Q3c |
| 1585 | Q1p | Me | Me | Q3d |
| 1586 | Q1p | Me | Me | Q3e |
| 1587 | Q1p | Me | Me | Q3f |
| 1588 | Q1p | Me | Me | Q3g |
| 1589 | Q1p | Me | Me | Q3h |
| 1590 | Q1p | Me | Me | Q3i |
| 1591 | Q1p | Me | Me | Q3j |
| 1592 | Q1p | Me | Me | Q3k |
| 1593 | Q1p | Me | Me | Q3l |
| 1594 | Q1p | Me | Me | Q3m |
| 1595 | Q1p | Me | Me | Q3n |
| 1596 | Q1p | Me | Me | Q3o |
| 1597 | Q1p | Me | Me | Q3p |
| 1598 | Q1p | Me | Me | Q3q |
| 1599 | Q1p | CF3 | H | Q3a |
| 1600 | Q1p | CF3 | H | Q3b |
| 1601 | Q1p | CF3 | H | Q3c |
| 1602 | Q1p | CF3 | H | Q3d |
| 1603 | Q1p | CF3 | H | Q3e |
| 1604 | Q1p | CF3 | H | Q3f |
| 1605 | Q1p | CF3 | H | Q3g |
| 1606 | Q1p | CF3 | H | Q3h |
| 1607 | Q1p | CF3 | H | Q3i |
| 1608 | Q1p | CF3 | H | Q3j |
| 1609 | Q1p | CF3 | H | Q3k |
| 1610 | Q1p | CF3 | H | Q3l |
| 1611 | Q1p | CF3 | H | Q3m |
| 1612 | Q1p | CF3 | H | Q3n |
| 1613 | Q1p | CF3 | H | Q3o |
| 1614 | Q1p | CF3 | H | Q3p |
| 1615 | Q1p | CF3 | H | Q3q |
| 1616 | Q1p | CF3 | Me | Q3a |
| 1617 | Q1p | CF3 | Me | Q3b |
| 1618 | Q1p | CF3 | Me | Q3c |
| 1619 | Q1p | CF3 | Me | Q3d |
| 1620 | Q1p | CF3 | Me | Q3e |
| 1621 | Q1p | CF3 | Me | Q3f |
| 1622 | Q1p | CF3 | Me | Q3g |
| 1623 | Q1p | CF3 | Me | Q3h |
| 1624 | Q1p | CF3 | Me | Q3i |
| 1625 | Q1p | CF3 | Me | Q3j |
| 1626 | Q1p | CF3 | Me | Q3k |
| 1627 | Q1p | CF3 | Me | Q3l |
| 1628 | Q1p | CF3 | Me | Q3m |
| 1629 | Q1p | CF3 | Me | Q3n |
| 1630 | Q1p | CF3 | Me | Q3o |
| 1631 | Q1p | CF3 | Me | Q3p |
| 1632 | Q1p | CF3 | Me | Q3q |
| 1633 | Q1q | H | H | Q3a |
| 1634 | Q1q | H | H | Q3b |
| 1635 | Q1q | H | H | Q3c |
| 1636 | Q1q | H | H | Q3d |
| 1637 | Q1q | H | H | Q3e |
| 1638 | Q1q | H | H | Q3f |
| 1639 | Q1q | H | H | Q3g |
| 1640 | Q1q | H | H | Q3h |
| 1641 | Q1q | H | H | Q3i |
| 1642 | Q1q | H | H | Q3j |
| 1643 | Q1q | H | H | Q3k |
| 1644 | Q1q | H | H | Q3l |
| 1645 | Q1q | H | H | Q3m |
| 1646 | Q1q | H | H | Q3n |
| 1647 | Q1q | H | H | Q3o |
| 1648 | Q1q | H | H | Q3p |
| 1649 | Q1q | H | H | Q3q |
| 1650 | Q1q | H | Me | Q3a |
| 1651 | Q1q | H | Me | Q3b |
| 1652 | Q1q | H | Me | Q3c |
| 1653 | Q1q | H | Me | Q3d |
| 1654 | Q1q | H | Me | Q3e |
| 1655 | Q1q | H | Me | Q3f |
| 1656 | Q1q | H | Me | Q3g |
| 1657 | Q1q | H | Me | Q3h |
| 1658 | Q1q | H | Me | Q3i |
| 1659 | Q1q | H | Me | Q3j |
| 1660 | Q1q | H | Me | Q3k |
| 1661 | Q1q | H | Me | Q3l |
| 1662 | Q1q | H | Me | Q3m |
| 1663 | Q1q | H | Me | Q3n |
| 1664 | Q1q | H | Me | Q3o |
| 1665 | Q1q | H | Me | Q3p |
| 1666 | Q1q | H | Me | Q3q |
| 1667 | Q1q | Me | H | Q3a |
| 1668 | Q1q | Me | H | Q3b |
| 1669 | Q1q | Me | H | Q3c |
| 1670 | Q1q | Me | H | Q3d |
| 1671 | Q1q | Me | H | Q3e |
| 1672 | Q1q | Me | H | Q3f |
| 1673 | Q1q | Me | H | Q3g |
| 1674 | Q1q | Me | H | Q3h |
| 1675 | Q1q | Me | H | Q3i |
| 1676 | Q1q | Me | H | Q3j |
| 1677 | Q1q | Me | H | Q3k |
| 1678 | Q1q | Me | H | Q3l |
| 1679 | Q1q | Me | H | Q3m |
| 1680 | Q1q | Me | H | Q3n |
| 1681 | Q1q | Me | H | Q3o |
| 1682 | Q1q | Me | H | Q3p |
| 1683 | Q1q | Me | H | Q3q |
| 1684 | Q1q | Me | Me | Q3a |
| 1685 | Q1q | Me | Me | Q3b |
| 1686 | Q1q | Me | Me | Q3c |
| 1687 | Q1q | Me | Me | Q3d |
| 1688 | Q1q | Me | Me | Q3e |
| 1689 | Q1q | Me | Me | Q3f |
| 1690 | Q1q | Me | Me | Q3g |
| 1691 | Q1q | Me | Me | Q3h |
| 1692 | Q1q | Me | Me | Q3i |
| 1693 | Q1q | Me | Me | Q3j |
| 1694 | Q1q | Me | Me | Q3k |
| 1695 | Q1q | Me | Me | Q3l |
| 1696 | Q1q | Me | Me | Q3m |
| 1697 | Q1q | Me | Me | Q3n |
| 1698 | Q1q | Me | Me | Q3o |
| 1699 | Q1q | Me | Me | Q3p |
| 1700 | Q1q | Me | Me | Q3q |
| 1701 | Q1q | CF3 | H | Q3a |
| 1702 | Q1q | CF3 | H | Q3b |
| 1703 | Q1q | CF3 | H | Q3c |
| 1704 | Q1q | CF3 | H | Q3d |
| 1705 | Q1q | CF3 | H | Q3e |
| 1706 | Q1q | CF3 | H | Q3f |
| 1707 | Q1q | CF3 | H | Q3g |
| 1708 | Q1q | CF3 | H | Q3h |

TABLE 1-continued

| No | R⁷ | R⁸ | R⁹ | R¹⁰ |
|---|---|---|---|---|
| 1709 | Q1q | CF3 | H | Q3i |
| 1710 | Q1q | CF3 | H | Q3j |
| 1711 | Q1q | CF3 | H | Q3k |
| 1712 | Q1q | CF3 | H | Q3l |
| 1713 | Q1q | CF3 | H | Q3m |
| 1714 | Q1q | CF3 | H | Q3n |
| 1715 | Q1q | CF3 | H | Q3o |
| 1716 | Q1q | CF3 | H | Q3p |
| 1717 | Q1q | CF3 | H | Q3q |
| 1718 | Q1q | CF3 | Me | Q3a |
| 1719 | Q1q | CF3 | Me | Q3b |
| 1720 | Q1q | CF3 | Me | Q3c |
| 1721 | Q1q | CF3 | Me | Q3d |
| 1722 | Q1q | CF3 | Me | Q3e |
| 1723 | Q1q | CF3 | Me | Q3f |
| 1724 | Q1q | CF3 | Me | Q3g |
| 1725 | Q1q | CF3 | Me | Q3h |
| 1726 | Q1q | CF3 | Me | Q3i |
| 1727 | Q1q | CF3 | Me | Q3j |
| 1728 | Q1q | CF3 | Me | Q3k |
| 1729 | Q1q | CF3 | Me | Q3l |
| 1730 | Q1q | CF3 | Me | Q3m |
| 1731 | Q1q | CF3 | Me | Q3n |
| 1732 | Q1q | CF3 | Me | Q3o |
| 1733 | Q1q | CF3 | Me | Q3p |
| 1734 | Q1q | CF3 | Me | Q3q |
| 1735 | Q1r | H | H | Q3a |
| 1736 | Q1r | H | H | Q3b |
| 1737 | Q1r | H | H | Q3c |
| 1738 | Q1r | H | H | Q3d |
| 1739 | Q1r | H | H | Q3e |
| 1740 | Q1r | H | H | Q3f |
| 1741 | Q1r | H | H | Q3g |
| 1742 | Q1r | H | H | Q3h |
| 1743 | Q1r | H | H | Q3i |
| 1744 | Q1r | H | H | Q3j |
| 1745 | Q1r | H | H | Q3k |
| 1746 | Q1r | H | H | Q3l |
| 1747 | Q1r | H | H | Q3m |
| 1748 | Q1r | H | H | Q3n |
| 1749 | Q1r | H | H | Q3o |
| 1750 | Q1r | H | H | Q3p |
| 1751 | Q1r | H | H | Q3q |
| 1752 | Q1r | H | Me | Q3a |
| 1753 | Q1r | H | Me | Q3b |
| 1754 | Q1r | H | Me | Q3c |
| 1755 | Q1r | H | Me | Q3d |
| 1756 | Q1r | H | Me | Q3e |
| 1757 | Q1r | H | Me | Q3f |
| 1758 | Q1r | H | Me | Q3g |
| 1759 | Q1r | H | Me | Q3h |
| 1760 | Q1r | H | Me | Q3i |
| 1761 | Q1r | H | Me | Q3j |
| 1762 | Q1r | H | Me | Q3k |
| 1763 | Q1r | H | Me | Q3l |
| 1764 | Q1r | H | Me | Q3m |
| 1765 | Q1r | H | Me | Q3n |
| 1766 | Q1r | H | Me | Q3o |
| 1767 | Q1r | H | Me | Q3p |
| 1768 | Q1r | H | Me | Q3q |
| 1769 | Q1r | Me | H | Q3a |
| 1770 | Q1r | Me | H | Q3b |
| 1771 | Q1r | Me | H | Q3c |
| 1772 | Q1r | Me | H | Q3d |
| 1773 | Q1r | Me | H | Q3e |
| 1774 | Q1r | Me | H | Q3f |
| 1775 | Q1r | Me | H | Q3g |
| 1776 | Q1r | Me | H | Q3h |
| 1777 | Q1r | Me | H | Q3i |
| 1778 | Q1r | Me | H | Q3j |
| 1779 | Q1r | Me | H | Q3k |
| 1780 | Q1r | Me | H | Q3l |
| 1781 | Q1r | Me | H | Q3m |
| 1782 | Q1r | Me | H | Q3n |
| 1783 | Q1r | Me | H | Q3o |
| 1784 | Q1r | Me | H | Q3p |
| 1785 | Q1r | Me | H | Q3q |
| 1786 | Q1r | Me | Me | Q3a |
| 1787 | Q1r | Me | Me | Q3b |
| 1788 | Q1r | Me | Me | Q3c |
| 1789 | Q1r | Me | Me | Q3d |
| 1790 | Q1r | Me | Me | Q3e |
| 1791 | Q1r | Me | Me | Q3f |
| 1792 | Q1r | Me | Me | Q3g |
| 1793 | Q1r | Me | Me | Q3h |
| 1794 | Q1r | Me | Me | Q3i |
| 1795 | Q1r | Me | Me | Q3j |
| 1796 | Q1r | Me | Me | Q3k |
| 1797 | Q1r | Me | Me | Q3l |
| 1798 | Q1r | Me | Me | Q3m |
| 1799 | Q1r | Me | Me | Q3n |
| 1800 | Q1r | Me | Me | Q3o |
| 1801 | Q1r | Me | Me | Q3p |
| 1802 | Q1r | Me | Me | Q3q |
| 1803 | Q1r | CF3 | H | Q3a |
| 1804 | Q1r | CF3 | H | Q3b |
| 1805 | Q1r | CF3 | H | Q3c |
| 1806 | Q1r | CF3 | H | Q3d |
| 1807 | Q1r | CF3 | H | Q3e |
| 1808 | Q1r | CF3 | H | Q3f |
| 1809 | Q1r | CF3 | H | Q3g |
| 1810 | Q1r | CF3 | H | Q3h |
| 1811 | Q1r | CF3 | H | Q3i |
| 1812 | Q1r | CF3 | H | Q3j |
| 1813 | Q1r | CF3 | H | Q3k |
| 1814 | Q1r | CF3 | H | Q3l |
| 1815 | Q1r | CF3 | H | Q3m |
| 1816 | Q1r | CF3 | H | Q3n |
| 1817 | Q1r | CF3 | H | Q3o |
| 1818 | Q1r | CF3 | H | Q3p |
| 1819 | Q1r | CF3 | H | Q3q |
| 1820 | Q1r | CF3 | Me | Q3a |
| 1821 | Q1r | CF3 | Me | Q3b |
| 1822 | Q1r | CF3 | Me | Q3c |
| 1823 | Q1r | CF3 | Me | Q3d |
| 1824 | Q1r | CF3 | Me | Q3e |
| 1825 | Q1r | CF3 | Me | Q3f |
| 1826 | Q1r | CF3 | Me | Q3g |
| 1827 | Q1r | CF3 | Me | Q3h |
| 1828 | Q1r | CF3 | Me | Q3i |
| 1829 | Q1r | CF3 | Me | Q3j |
| 1830 | Q1r | CF3 | Me | Q3k |
| 1831 | Q1r | CF3 | Me | Q3l |
| 1832 | Q1r | CF3 | Me | Q3m |
| 1833 | Q1r | CF3 | Me | Q3n |
| 1834 | Q1r | CF3 | Me | Q3o |
| 1835 | Q1r | CF3 | Me | Q3p |
| 1836 | Q1r | CF3 | Me | Q3q |
| 1837 | Q1s | H | H | Q3a |
| 1838 | Q1s | H | H | Q3b |
| 1839 | Q1s | H | H | Q3c |
| 1840 | Q1s | H | H | Q3d |
| 1841 | Q1s | H | H | Q3e |
| 1842 | Q1s | H | H | Q3f |
| 1843 | Q1s | H | H | Q3g |
| 1844 | Q1s | H | H | Q3h |
| 1845 | Q1s | H | H | Q3i |
| 1846 | Q1s | H | H | Q3j |
| 1847 | Q1s | H | H | Q3k |
| 1848 | Q1s | H | H | Q3l |
| 1849 | Q1s | H | H | Q3m |
| 1850 | Q1s | H | H | Q3n |
| 1851 | Q1s | H | H | Q3o |
| 1852 | Q1s | H | H | Q3p |
| 1853 | Q1s | H | H | Q3q |
| 1854 | Q1s | H | Me | Q3a |
| 1855 | Q1s | H | Me | Q3b |
| 1856 | Q1s | H | Me | Q3c |
| 1857 | Q1s | H | Me | Q3d |
| 1858 | Q1s | H | Me | Q3e |
| 1859 | Q1s | H | Me | Q3f |
| 1860 | Q1s | H | Me | Q3g |
| 1861 | Q1s | H | Me | Q3h |
| 1862 | Q1s | H | Me | Q3i |
| 1863 | Q1s | H | Me | Q3j |
| 1864 | Q1s | H | Me | Q3k |

TABLE 1-continued

| No | R⁷ | R⁸ | R⁹ | R¹⁰ |
|---|---|---|---|---|
| 1865 | Q1s | H | Me | Q3l |
| 1866 | Q1s | H | Me | Q3m |
| 1867 | Q1s | H | Me | Q3n |
| 1868 | Q1s | H | Me | Q3o |
| 1869 | Q1s | H | Me | Q3p |
| 1870 | Q1s | H | Me | Q3q |
| 1871 | Q1s | Me | H | Q3a |
| 1872 | Q1s | Me | H | Q3b |
| 1873 | Q1s | Me | H | Q3c |
| 1874 | Q1s | Me | H | Q3d |
| 1875 | Q1s | Me | H | Q3e |
| 1876 | Q1s | Me | H | Q3f |
| 1877 | Q1s | Me | H | Q3g |
| 1878 | Q1s | Me | H | Q3h |
| 1879 | Q1s | Me | H | Q3i |
| 1880 | Q1s | Me | H | Q3j |
| 1881 | Q1s | Me | H | Q3k |
| 1882 | Q1s | Me | H | Q3l |
| 1883 | Q1s | Me | H | Q3m |
| 1884 | Q1s | Me | H | Q3n |
| 1885 | Q1s | Me | H | Q3o |
| 1886 | Q1s | Me | H | Q3p |
| 1887 | Q1s | Me | H | Q3q |
| 1888 | Q1s | Me | Me | Q3a |
| 1889 | Q1s | Me | Me | Q3b |
| 1890 | Q1s | Me | Me | Q3c |
| 1891 | Q1s | Me | Me | Q3d |
| 1892 | Q1s | Me | Me | Q3e |
| 1893 | Q1s | Me | Me | Q3f |
| 1894 | Q1s | Me | Me | Q3g |
| 1895 | Q1s | Me | Me | Q3h |
| 1896 | Q1s | Me | Me | Q3i |
| 1897 | Q1s | Me | Me | Q3j |
| 1898 | Q1s | Me | Me | Q3k |
| 1899 | Q1s | Me | Me | Q3l |
| 1900 | Q1s | Me | Me | Q3m |
| 1901 | Q1s | Me | Me | Q3n |
| 1902 | Q1s | Me | Me | Q3o |
| 1903 | Q1s | Me | Me | Q3p |
| 1904 | Q1s | Me | Me | Q3q |
| 1905 | Q1s | CF3 | H | Q3a |
| 1906 | Q1s | CF3 | H | Q3b |
| 1907 | Q1s | CF3 | H | Q3c |
| 1908 | Q1s | CF3 | H | Q3d |
| 1909 | Q1s | CF3 | H | Q3e |
| 1910 | Q1s | CF3 | H | Q3f |
| 1911 | Q1s | CF3 | H | Q3g |
| 1912 | Q1s | CF3 | H | Q3h |
| 1913 | Q1s | CF3 | H | Q3i |
| 1914 | Q1s | CF3 | H | Q3j |
| 1915 | Q1s | CF3 | H | Q3k |
| 1916 | Q1s | CF3 | H | Q3l |
| 1917 | Q1s | CF3 | H | Q3m |
| 1918 | Q1s | CF3 | H | Q3n |
| 1919 | Q1s | CF3 | H | Q3o |
| 1920 | Q1s | CF3 | H | Q3p |
| 1921 | Q1s | CF3 | H | Q3q |
| 1922 | Q1s | CF3 | Me | Q3a |
| 1923 | Q1s | CF3 | Me | Q3b |
| 1924 | Q1s | CF3 | Me | Q3c |
| 1925 | Q1s | CF3 | Me | Q3d |
| 1926 | Q1s | CF3 | Me | Q3e |
| 1927 | Q1s | CF3 | Me | Q3f |
| 1928 | Q1s | CF3 | Me | Q3g |
| 1929 | Q1s | CF3 | Me | Q3h |
| 1930 | Q1s | CF3 | Me | Q3i |
| 1931 | Q1s | CF3 | Me | Q3j |
| 1932 | Q1s | CF3 | Me | Q3k |
| 1933 | Q1s | CF3 | Me | Q3l |
| 1934 | Q1s | CF3 | Me | Q3m |
| 1935 | Q1s | CF3 | Me | Q3n |
| 1936 | Q1s | CF3 | Me | Q3o |
| 1937 | Q1s | CF3 | Me | Q3p |
| 1938 | Q1s | CF3 | Me | Q3q |
| 1939 | Q1t | H | H | Q3a |
| 1940 | Q1t | H | H | Q3b |
| 1941 | Q1t | H | H | Q3c |
| 1942 | Q1t | H | H | Q3d |
| 1943 | Q1t | H | H | Q3e |
| 1944 | Q1t | H | H | Q3f |
| 1945 | Q1t | H | H | Q3g |
| 1946 | Q1t | H | H | Q3h |
| 1947 | Q1t | H | H | Q3i |
| 1948 | Q1t | H | H | Q3j |
| 1949 | Q1t | H | H | Q3k |
| 1950 | Q1t | H | H | Q3l |
| 1951 | Q1t | H | H | Q3m |
| 1952 | Q1t | H | H | Q3n |
| 1953 | Q1t | H | H | Q3o |
| 1954 | Q1t | H | H | Q3p |
| 1955 | Q1t | H | H | Q3q |
| 1956 | Q1t | H | Me | Q3a |
| 1957 | Q1t | H | Me | Q3b |
| 1958 | Q1t | H | Me | Q3c |
| 1959 | Q1t | H | Me | Q3d |
| 1960 | Q1t | H | Me | Q3e |
| 1961 | Q1t | H | Me | Q3f |
| 1962 | Q1t | H | Me | Q3g |
| 1963 | Q1t | H | Me | Q3h |
| 1964 | Q1t | H | Me | Q3i |
| 1965 | Q1t | H | Me | Q3j |
| 1966 | Q1t | H | Me | Q3k |
| 1967 | Q1t | H | Me | Q3l |
| 1968 | Q1t | H | Me | Q3m |
| 1969 | Q1t | H | Me | Q3n |
| 1970 | Q1t | H | Me | Q3o |
| 1971 | Q1t | H | Me | Q3p |
| 1972 | Q1t | H | Me | Q3q |
| 1973 | Q1t | Me | H | Q3a |
| 1974 | Q1t | Me | H | Q3b |
| 1975 | Q1t | Me | H | Q3c |
| 1976 | Q1t | Me | H | Q3d |
| 1977 | Q1t | Me | H | Q3e |
| 1978 | Q1t | Me | H | Q3f |
| 1979 | Q1t | Me | H | Q3g |
| 1980 | Q1t | Me | H | Q3h |
| 1981 | Q1t | Me | H | Q3i |
| 1982 | Q1t | Me | H | Q3j |
| 1983 | Q1t | Me | H | Q3k |
| 1984 | Q1t | Me | H | Q3l |
| 1985 | Q1t | Me | H | Q3m |
| 1986 | Q1t | Me | H | Q3n |
| 1987 | Q1t | Me | H | Q3o |
| 1988 | Q1t | Me | H | Q3p |
| 1989 | Q1t | Me | H | Q3q |
| 1990 | Q1t | Me | Me | Q3a |
| 1991 | Q1t | Me | Me | Q3b |
| 1992 | Q1t | Me | Me | Q3c |
| 1993 | Q1t | Me | Me | Q3d |
| 1994 | Q1t | Me | Me | Q3e |
| 1995 | Q1t | Me | Me | Q3f |
| 1996 | Q1t | Me | Me | Q3g |
| 1997 | Q1t | Me | Me | Q3h |
| 1998 | Q1t | Me | Me | Q3i |
| 1999 | Q1t | Me | Me | Q3j |
| 2000 | Q1t | Me | Me | Q3k |
| 2001 | Q1t | Me | Me | Q3l |
| 2002 | Q1t | Me | Me | Q3m |
| 2003 | Q1t | Me | Me | Q3n |
| 2004 | Q1t | Me | Me | Q3o |
| 2005 | Q1t | Me | Me | Q3p |
| 2006 | Q1t | Me | Me | Q3q |
| 2007 | Q1t | CF3 | H | Q3a |
| 2008 | Q1t | CF3 | H | Q3b |
| 2009 | Q1t | CF3 | H | Q3c |
| 2010 | Q1t | CF3 | H | Q3d |
| 2011 | Q1t | CF3 | H | Q3e |
| 2012 | Q1t | CF3 | H | Q3f |
| 2013 | Q1t | CF3 | H | Q3g |
| 2014 | Q1t | CF3 | H | Q3h |
| 2015 | Q1t | CF3 | H | Q3i |
| 2016 | Q1t | CF3 | H | Q3j |
| 2017 | Q1t | CF3 | H | Q3k |
| 2018 | Q1t | CF3 | H | Q3l |
| 2019 | Q1t | CF3 | H | Q3m |
| 2020 | Q1t | CF3 | H | Q3n |

TABLE 1-continued

| No | R⁷ | R⁸ | R⁹ | R¹⁰ |
|---|---|---|---|---|
| 2021 | Q1t | CF3 | H | Q3o |
| 2022 | Q1t | CF3 | H | Q3p |
| 2023 | Q1t | CF3 | H | Q3q |
| 2024 | Q1t | CF3 | Me | Q3a |
| 2025 | Q1t | CF3 | Me | Q3b |
| 2026 | Q1t | CF3 | Me | Q3c |
| 2027 | Q1t | CF3 | Me | Q3d |
| 2028 | Q1t | CF3 | Me | Q3e |
| 2029 | Q1t | CF3 | Me | Q3f |
| 2030 | Q1t | CF3 | Me | Q3g |
| 2031 | Q1t | CF3 | Me | Q3h |
| 2032 | Q1t | CF3 | Me | Q3i |
| 2033 | Q1t | CF3 | Me | Q3j |
| 2034 | Q1t | CF3 | Me | Q3k |
| 2035 | Q1t | CF3 | Me | Q3l |
| 2036 | Q1t | CF3 | Me | Q3m |
| 2037 | Q1t | CF3 | Me | Q3n |
| 2038 | Q1t | CF3 | Me | Q3o |
| 2039 | Q1t | CF3 | Me | Q3p |
| 2040 | Q1t | CF3 | Me | Q3q |
| 2041 | Q1u | H | H | Q3a |
| 2042 | Q1u | H | H | Q3b |
| 2043 | Q1u | H | H | Q3c |
| 2044 | Q1u | H | H | Q3d |
| 2045 | Q1u | H | H | Q3e |
| 2046 | Q1u | H | H | Q3f |
| 2047 | Q1u | H | H | Q3g |
| 2048 | Q1u | H | H | Q3h |
| 2049 | Q1u | H | H | Q3i |
| 2050 | Q1u | H | H | Q3j |
| 2051 | Q1u | H | H | Q3k |
| 2052 | Q1u | H | H | Q3l |
| 2053 | Q1u | H | H | Q3m |
| 2054 | Q1u | H | H | Q3n |
| 2055 | Q1u | H | H | Q3o |
| 2056 | Q1u | H | H | Q3p |
| 2057 | Q1u | H | H | Q3q |
| 2058 | Q1u | H | Me | Q3a |
| 2059 | Q1u | H | Me | Q3b |
| 2060 | Q1u | H | Me | Q3c |
| 2061 | Q1u | H | Me | Q3d |
| 2062 | Q1u | H | Me | Q3e |
| 2063 | Q1u | H | Me | Q3f |
| 2064 | Q1u | H | Me | Q3g |
| 2065 | Q1u | H | Me | Q3h |
| 2066 | Q1u | H | Me | Q3i |
| 2067 | Q1u | H | Me | Q3j |
| 2068 | Q1u | H | Me | Q3k |
| 2069 | Q1u | H | Me | Q3l |
| 2670 | Q1u | H | Me | Q3m |
| 2071 | Q1u | H | Me | Q3n |
| 2072 | Q1u | H | Me | Q3o |
| 2073 | Q1u | H | Me | Q3p |
| 2074 | Q1u | H | Me | Q3q |
| 2075 | Q1u | Me | H | Q3a |
| 2076 | Q1u | Me | H | Q3b |
| 2077 | Q1u | Me | H | Q3c |
| 2078 | Q1u | Me | H | Q3d |
| 2079 | Q1u | Me | H | Q3e |
| 2080 | Q1u | Me | H | Q3f |
| 2081 | Q1u | Me | H | Q3g |
| 2082 | Q1u | Me | H | Q3h |
| 2083 | Q1u | Me | H | Q3i |
| 2084 | Q1u | Me | H | Q3j |
| 2085 | Q1u | Me | H | Q3k |
| 2086 | Q1u | Me | H | Q3l |
| 2087 | Q1u | Me | H | Q3m |
| 2088 | Q1u | Me | H | Q3n |
| 2089 | Q1u | Me | H | Q3o |
| 2090 | Q1u | Me | H | Q3p |
| 2091 | Q1u | Me | H | Q3q |
| 2092 | Q1u | Me | Me | Q3a |
| 2093 | Q1u | Me | Me | Q3b |
| 2094 | Q1u | Me | Me | Q3c |
| 2095 | Q1u | Me | Me | Q3d |
| 2096 | Q1u | Me | Me | Q3e |
| 2097 | Q1u | Me | Me | Q3f |
| 2098 | Q1u | Me | Me | Q3g |
| 2099 | Q1u | Me | Me | Q3h |
| 2100 | Q1u | Me | Me | Q3i |
| 2101 | Q1u | Me | Me | Q3j |
| 2102 | Q1u | Me | Me | Q3k |
| 2103 | Q1u | Me | Me | Q3l |
| 2104 | Q1u | Me | Me | Q3m |
| 2105 | Q1u | Me | Me | Q3n |
| 2106 | Q1u | Me | Me | Q3o |
| 2107 | Q1u | Me | Me | Q3p |
| 2108 | Q1u | Me | Me | Q3q |
| 2109 | Q1u | CF3 | H | Q3a |
| 2110 | Q1u | CF3 | H | Q3b |
| 2111 | Q1u | CF3 | H | Q3c |
| 2112 | Q1u | CF3 | H | Q3d |
| 2113 | Q1u | CF3 | H | Q3e |
| 2114 | Q1u | CF3 | H | Q3f |
| 2115 | Q1u | CF3 | H | Q3g |
| 2116 | Q1u | CF3 | H | Q3h |
| 2117 | Q1u | CF3 | H | Q3i |
| 2118 | Q1u | CF3 | H | Q3j |
| 2119 | Q1u | CF3 | H | Q3k |
| 2120 | Q1u | CF3 | H | Q3l |
| 2121 | Q1u | CF3 | H | Q3m |
| 2122 | Q1u | CF3 | H | Q3n |
| 2123 | Q1u | CF3 | H | Q3o |
| 2124 | Q1u | CF3 | H | Q3p |
| 2125 | Q1u | CF3 | H | Q3q |
| 2126 | Q1u | CF3 | Me | Q3a |
| 2127 | Q1u | CF3 | Me | Q3b |
| 2128 | Q1u | CF3 | Me | Q3c |
| 2129 | Q1u | CF3 | Me | Q3d |
| 2130 | Q1u | CF3 | Me | Q3e |
| 2131 | Q1u | CF3 | Me | Q3f |
| 2132 | Q1u | CF3 | Me | Q3g |
| 2133 | Q1u | CF3 | Me | Q3h |
| 2134 | Q1u | CF3 | Me | Q3i |
| 2135 | Q1u | CF3 | Me | Q3j |
| 2136 | Q1u | CF3 | Me | Q3k |
| 2137 | Q1u | CF3 | Me | Q3l |
| 2138 | Q1u | CF3 | Me | Q3m |
| 2139 | Q1u | CF3 | Me | Q3n |
| 2140 | Q1u | CF3 | Me | Q3o |
| 2141 | Q1u | CF3 | Me | Q3p |
| 2142 | Q1u | CF3 | Me | Q3q |
| 2143 | Q1v | H | H | Q3a |
| 2144 | Q1v | H | H | Q3b |
| 2145 | Q1v | H | H | Q3c |
| 2146 | Q1v | H | H | Q3d |
| 2147 | Q1v | H | H | Q3e |
| 2148 | Q1v | H | H | Q3f |
| 2149 | Q1v | H | H | Q3g |
| 2150 | Q1v | H | H | Q3h |
| 2151 | Q1v | H | H | Q3i |
| 2152 | Q1v | H | H | Q3j |
| 2153 | Q1v | H | H | Q3k |
| 2154 | Q1v | H | H | Q3l |
| 2155 | Q1v | H | H | Q3m |
| 2156 | Q1v | H | H | Q3n |
| 2157 | Q1v | H | H | Q3o |
| 2158 | Q1v | H | H | Q3p |
| 2159 | Q1v | H | H | Q3q |
| 2160 | Q1v | H | Me | Q3a |
| 2161 | Q1v | H | Me | Q3b |
| 2162 | Q1v | H | Me | Q3c |
| 2163 | Q1v | H | Me | Q3d |
| 2164 | Q1v | H | Me | Q3e |
| 2165 | Q1v | H | Me | Q3f |
| 2166 | Q1v | H | Me | Q3g |
| 2167 | Q1v | H | Me | Q3h |
| 2168 | Q1v | H | Me | Q3i |
| 2169 | Q1v | H | Me | Q3j |
| 2170 | Q1v | H | Me | Q3k |
| 2171 | Q1v | H | Me | Q3l |
| 2172 | Q1v | H | Me | Q3m |
| 2173 | Q1v | H | Me | Q3n |
| 2174 | Q1v | H | Me | Q3o |
| 2175 | Q1v | H | Me | Q3p |
| 2176 | Q1v | H | Me | Q3q |

TABLE 1-continued

| No | R⁷ | R⁸ | R⁹ | R¹⁰ |
|---|---|---|---|---|
| 2177 | Q1v | Me | H | Q3a |
| 2178 | Q1v | Me | H | Q3b |
| 2179 | Q1v | Me | H | Q3c |
| 2180 | Q1v | Me | H | Q3d |
| 2181 | Q1v | Me | H | Q3e |
| 2182 | Q1v | Me | H | Q3f |
| 2183 | Q1v | Me | H | Q3g |
| 2184 | Q1v | Me | H | Q3h |
| 2185 | Q1v | Me | H | Q3i |
| 2186 | Q1v | Me | H | Q3j |
| 2187 | Q1v | Me | H | Q3k |
| 2188 | Q1v | Me | H | Q3l |
| 2189 | Q1v | Me | H | Q3m |
| 2190 | Q1v | Me | H | Q3n |
| 2191 | Q1v | Me | H | Q3o |
| 2192 | Q1v | Me | H | Q3p |
| 2193 | Q1v | Me | H | Q3q |
| 2194 | Q1v | Me | Me | Q3a |
| 2195 | Q1v | Me | Me | Q3b |
| 2196 | Q1v | Me | Me | Q3c |
| 2197 | Q1v | Me | Me | Q3d |
| 2198 | Q1v | Me | Me | Q3e |
| 2199 | Q1v | Me | Me | Q3f |
| 2200 | Q1v | Me | Me | Q3g |
| 2201 | Q1v | Me | Me | Q3h |
| 2202 | Q1v | Me | Me | Q3i |
| 2203 | Q1v | Me | Me | Q3j |
| 2204 | Q1v | Me | Me | Q3k |
| 2205 | Q1v | Me | Me | Q3l |
| 2206 | Q1v | Me | Me | Q3m |
| 2207 | Q1v | Me | Me | Q3n |
| 2208 | Q1v | Me | Me | Q3o |
| 2209 | Q1v | Me | Me | Q3p |
| 2210 | Q1v | Me | Me | Q3q |
| 2211 | Q1v | CF3 | H | Q3a |
| 2212 | Q1v | CF3 | H | Q3b |
| 2213 | Q1v | CF3 | H | Q3c |
| 2214 | Q1v | CF3 | H | Q3d |
| 2215 | Q1v | CF3 | H | Q3e |
| 2216 | Q1v | CF3 | H | Q3f |
| 2217 | Q1v | CF3 | H | Q3g |
| 2218 | Q1v | CF3 | H | Q3h |
| 2219 | Q1v | CF3 | H | Q3i |
| 2220 | Q1v | CF3 | H | Q3j |
| 2221 | Q1v | CF3 | H | Q3k |
| 2222 | Q1v | CF3 | H | Q3l |
| 2223 | Q1v | CF3 | H | Q3m |
| 2224 | Q1v | CF3 | H | Q3n |
| 2225 | Q1v | CF3 | H | Q3o |
| 2226 | Q1v | CF3 | H | Q3p |
| 2227 | Q1v | CF3 | H | Q3q |
| 2228 | Q1v | CF3 | Me | Q3a |
| 2229 | Q1v | CF3 | Me | Q3b |
| 2230 | Q1v | CF3 | Me | Q3c |
| 2231 | Q1v | CF3 | Me | Q3d |
| 2232 | Q1v | CF3 | Me | Q3e |
| 2233 | Q1v | CF3 | Me | Q3f |
| 2234 | Q1v | CF3 | Me | Q3g |
| 2235 | Q1v | CF3 | Me | Q3h |
| 2236 | Q1v | CF3 | Me | Q3i |
| 2237 | Q1v | CF3 | Me | Q3j |
| 2238 | Q1v | CF3 | Me | Q3k |
| 2239 | Q1v | CF3 | Me | Q3l |
| 2240 | Q1v | CF3 | Me | Q3m |
| 2241 | Q1v | CF3 | Me | Q3n |
| 2242 | Q1v | CF3 | Me | Q3o |
| 2243 | Q1v | CF3 | Me | Q3p |
| 2244 | Q1v | CF3 | Me | Q3q |
| 2245 | Q1w | H | H | Q3a |
| 2246 | Q1w | H | H | Q3b |
| 2247 | Q1w | H | H | Q3c |
| 2248 | Q1w | H | H | Q3d |
| 2249 | Q1w | H | H | Q3e |
| 2250 | Q1w | H | H | Q3f |
| 2251 | Q1w | H | H | Q3g |
| 2252 | Q1w | H | H | Q3h |
| 2253 | Q1w | H | H | Q3i |
| 2254 | Q1w | H | H | Q3j |
| 2255 | Q1w | H | H | Q3k |
| 2256 | Q1w | H | H | Q3l |
| 2257 | Q1w | H | H | Q3m |
| 2258 | Q1w | H | H | Q3n |
| 2259 | Q1w | H | H | Q3o |
| 2260 | Q1w | H | H | Q3p |
| 2261 | Q1w | H | H | Q3q |
| 2262 | Q1w | H | Me | Q3a |
| 2263 | Q1w | H | Me | Q3b |
| 2264 | Q1w | H | Me | Q3c |
| 2265 | Q1w | H | Me | Q3d |
| 2266 | Q1w | H | Me | Q3e |
| 2267 | Q1w | H | Me | Q3f |
| 2268 | Q1w | H | Me | Q3g |
| 2269 | Q1w | H | Me | Q3h |
| 2270 | Q1w | H | Me | Q3i |
| 2271 | Q1w | H | Me | Q3j |
| 2272 | Q1w | H | Me | Q3k |
| 2273 | Q1w | H | Me | Q3l |
| 2274 | Q1w | H | Me | Q3m |
| 2275 | Q1w | H | Me | Q3n |
| 2276 | Q1w | H | Me | Q3o |
| 2277 | Q1w | H | Me | Q3p |
| 2278 | Q1w | H | Me | Q3q |
| 2279 | Q1w | Me | H | Q3a |
| 2280 | Q1w | Me | H | Q3b |
| 2281 | Q1w | Me | H | Q3c |
| 2282 | Q1w | Me | H | Q3d |
| 2283 | Q1w | Me | H | Q3e |
| 2284 | Q1w | Me | H | Q3f |
| 2285 | Q1w | Me | H | Q3g |
| 2286 | Q1w | Me | H | Q3h |
| 2287 | Q1w | Me | H | Q3i |
| 2288 | Q1w | Me | H | Q3j |
| 2289 | Q1w | Me | H | Q3k |
| 2290 | Q1w | Me | H | Q3l |
| 2291 | Q1w | Me | H | Q3m |
| 2292 | Q1w | Me | H | Q3n |
| 2293 | Q1w | Me | H | Q3o |
| 2294 | Q1w | Me | H | Q3p |
| 2295 | Q1w | Me | H | Q3q |
| 2296 | Q1w | Me | Me | Q3a |
| 2297 | Q1w | Me | Me | Q3b |
| 2298 | Q1w | Me | Me | Q3c |
| 2299 | Q1w | Me | Me | Q3d |
| 2300 | Q1w | Me | Me | Q3e |
| 2301 | Q1w | Me | Me | Q3f |
| 2302 | Q1w | Me | Me | Q3g |
| 2303 | Q1w | Me | Me | Q3h |
| 2304 | Q1w | Me | Me | Q3i |
| 2305 | Q1w | Me | Me | Q3j |
| 2306 | Q1w | Me | Me | Q3k |
| 2307 | Q1w | Me | Me | Q3l |
| 2308 | Q1w | Me | Me | Q3m |
| 2309 | Q1w | Me | Me | Q3n |
| 2310 | Q1w | Me | Me | Q3o |
| 2311 | Q1w | Me | Me | Q3p |
| 2312 | Q1w | Me | Me | Q3q |
| 2313 | Q1w | CF3 | H | Q3a |
| 2314 | Q1w | CF3 | H | Q3b |
| 2315 | Q1w | CF3 | H | Q3c |
| 2316 | Q1w | CF3 | H | Q3d |
| 2317 | Q1w | CF3 | H | Q3e |
| 2318 | Q1w | CF3 | H | Q3f |
| 2319 | Q1w | CF3 | H | Q3g |
| 2320 | Q1w | CF3 | H | Q3h |
| 2321 | Q1w | CF3 | H | Q3i |
| 2322 | Q1w | CF3 | H | Q3j |
| 2323 | Q1w | CF3 | H | Q3k |
| 2324 | Q1w | CF3 | H | Q3l |
| 2325 | Q1w | CF3 | H | Q3m |
| 2326 | Q1w | CF3 | H | Q3n |
| 2327 | Q1w | CF3 | H | Q3o |
| 2328 | Q1w | CF3 | H | Q3p |
| 2329 | Q1w | CF3 | H | Q3q |
| 2330 | Q1w | CF3 | Me | Q3a |
| 2331 | Q1w | CF3 | Me | Q3b |
| 2332 | Q1w | CF3 | Me | Q3c |

TABLE 1-continued

| No | R⁷ | R⁸ | R⁹ | R¹⁰ |
|---|---|---|---|---|
| 2333 | Q1w | CF3 | Me | Q3d |
| 2334 | Q1w | CF3 | Me | Q3e |
| 2335 | Q1w | CF3 | Me | Q3f |
| 2336 | Q1w | CF3 | Me | Q3g |
| 2337 | Q1w | CF3 | Me | Q3h |
| 2338 | Q1w | CF3 | Me | Q3i |
| 2339 | Q1w | CF3 | Me | Q3j |
| 2340 | Q1w | CF3 | Me | Q3k |
| 2341 | Q1w | CF3 | Me | Q3l |
| 2342 | Q1w | CF3 | Me | Q3m |
| 2343 | Q1w | CF3 | Me | Q3n |
| 2344 | Q1w | CF3 | Me | Q3o |
| 2345 | Q1w | CF3 | Me | Q3p |
| 2346 | Q1w | CF3 | Me | Q3q |
| 2347 | Q1x | H | H | Q3a |
| 2348 | Q1x | H | H | Q3b |
| 2349 | Q1x | H | H | Q3c |
| 2350 | Q1x | H | H | Q3d |
| 2351 | Q1x | H | H | Q3e |
| 2352 | Q1x | H | H | Q3f |
| 2353 | Q1x | H | H | Q3g |
| 2354 | Q1x | H | H | Q3h |
| 2355 | Q1x | H | H | Q3i |
| 2356 | Q1x | H | H | Q3j |
| 2357 | Q1x | H | H | Q3k |
| 2358 | Q1x | H | H | Q3l |
| 2359 | Q1x | H | H | Q3m |
| 2360 | Q1x | H | H | Q3n |
| 2361 | Q1x | H | H | Q3o |
| 2362 | Q1x | H | H | Q3p |
| 2363 | Q1x | H | H | Q3q |
| 2364 | Q1x | H | Me | Q3a |
| 2365 | Q1x | H | Me | Q3b |
| 2366 | Q1x | H | Me | Q3c |
| 2367 | Q1x | H | Me | Q3d |
| 2368 | Q1x | H | Me | Q3e |
| 2369 | Q1x | H | Me | Q3f |
| 2370 | Q1x | H | Me | Q3g |
| 2371 | Q1x | H | Me | Q3h |
| 2372 | Q1x | H | Me | Q3i |
| 2373 | Q1x | H | Me | Q3j |
| 2374 | Q1x | H | Me | Q3k |
| 2375 | Q1x | H | Me | Q3l |
| 2376 | Q1x | H | Me | Q3m |
| 2377 | Q1x | H | Me | Q3n |
| 2378 | Q1x | H | Me | Q3o |
| 2379 | Q1x | H | Me | Q3p |
| 2380 | Q1x | H | Me | Q3q |
| 2381 | Q1x | Me | H | Q3a |
| 2382 | Q1x | Me | H | Q3b |
| 2383 | Q1x | Me | H | Q3c |
| 2384 | Q1x | Me | H | Q3d |
| 2385 | Q1x | Me | H | Q3e |
| 2386 | Q1x | Me | H | Q3f |
| 2387 | Q1x | Me | H | Q3g |
| 2388 | Q1x | Me | H | Q3h |
| 2389 | Q1x | Me | H | Q3i |
| 2390 | Q1x | Me | H | Q3j |
| 2391 | Q1x | Me | H | Q3k |
| 2392 | Q1x | Me | H | Q3l |
| 2393 | Q1x | Me | H | Q3m |
| 2394 | Q1x | Me | H | Q3n |
| 2395 | Q1x | Me | H | Q3o |
| 2396 | Q1x | Me | H | Q3p |
| 2397 | Q1x | Me | H | Q3q |
| 2398 | Q1x | Me | Me | Q3a |
| 2399 | Q1x | Me | Me | Q3b |
| 2400 | Q1x | Me | Me | Q3c |
| 2401 | Q1x | Me | Me | Q3d |
| 2402 | Q1x | Me | Me | Q3e |
| 2403 | Q1x | Me | Me | Q3f |
| 2404 | Q1x | Me | Me | Q3g |
| 2405 | Q1x | Me | Me | Q3h |
| 2406 | Q1x | Me | Me | Q3i |
| 2407 | Q1x | Me | Me | Q3j |
| 2408 | Q1x | Me | Me | Q3k |
| 2409 | Q1x | Me | Me | Q3l |
| 2410 | Q1x | Me | Me | Q3m |
| 2411 | Q1x | Me | Me | Q3n |
| 2412 | Q1x | Me | Me | Q3o |
| 2413 | Q1x | Me | Me | Q3p |
| 2414 | Q1x | Me | Me | Q3q |
| 2415 | Q1x | CF3 | H | Q3a |
| 2416 | Q1x | CF3 | H | Q3b |
| 2417 | Q1x | CF3 | H | Q3c |
| 2418 | Q1x | CF3 | H | Q3d |
| 2419 | Q1x | CF3 | H | Q3e |
| 2420 | Q1x | CF3 | H | Q3f |
| 2421 | Q1x | CF3 | H | Q3g |
| 2422 | Q1x | CF3 | H | Q3h |
| 2423 | Q1x | CF3 | H | Q3i |
| 2424 | Q1x | CF3 | H | Q3j |
| 2425 | Q1x | CF3 | H | Q3k |
| 2426 | Q1x | CF3 | H | Q3l |
| 2427 | Q1x | CF3 | H | Q3m |
| 2428 | Q1x | CF3 | H | Q3n |
| 2429 | Q1x | CF3 | H | Q3o |
| 2430 | Q1x | CF3 | H | Q3p |
| 2431 | Q1x | CF3 | H | Q3q |
| 2432 | Q1x | CF3 | Me | Q3a |
| 2433 | Q1x | CF3 | Me | Q3b |
| 2434 | Q1x | CF3 | Me | Q3c |
| 2435 | Q1x | CF3 | Me | Q3d |
| 2436 | Q1x | CF3 | Me | Q3e |
| 2437 | Q1x | CF3 | Me | Q3f |
| 2438 | Q1x | CF3 | Me | Q3g |
| 2439 | Q1x | CF3 | Me | Q3h |
| 2440 | Q1x | CF3 | Me | Q3i |
| 2441 | Q1x | CF3 | Me | Q3j |
| 2442 | Q1x | CF3 | Me | Q3k |
| 2443 | Q1x | CF3 | Me | Q3l |
| 2444 | Q1x | CF3 | Me | Q3m |
| 2445 | Q1x | CF3 | Me | Q3n |
| 2446 | Q1x | CF3 | Me | Q3o |
| 2447 | Q1x | CF3 | Me | Q3p |
| 2448 | Q1x | CF3 | Me | Q3q |
| 2449 | Q1y | H | H | Q3a |
| 2450 | Q1y | H | H | Q3b |
| 2451 | Q1y | H | H | Q3c |
| 2452 | Q1y | H | H | Q3d |
| 2453 | Q1y | H | H | Q3e |
| 2454 | Q1y | H | H | Q3f |
| 2455 | Q1y | H | H | Q3g |
| 2456 | Q1y | H | H | Q3h |
| 2457 | Q1y | H | H | Q3i |
| 2458 | Q1y | H | H | Q3j |
| 2459 | Q1y | H | H | Q3k |
| 2460 | Q1y | H | H | Q3l |
| 2461 | Q1y | H | H | Q3m |
| 2462 | Q1y | H | H | Q3n |
| 2463 | Q1y | H | H | Q3o |
| 2464 | Q1y | H | H | Q3p |
| 2465 | Q1y | H | H | Q3q |
| 2466 | Q1y | H | Me | Q3a |
| 2467 | Q1y | H | Me | Q3b |
| 2468 | Q1y | H | Me | Q3c |
| 2469 | Q1y | H | Me | Q3d |
| 2470 | Q1y | H | Me | Q3e |
| 2471 | Q1y | H | Me | Q3f |
| 2472 | Q1y | H | Me | Q3g |
| 2473 | Q1y | H | Me | Q3h |
| 2474 | Q1y | H | Me | Q3i |
| 2475 | Q1y | H | Me | Q3j |
| 2476 | Q1y | H | Me | Q3k |
| 2477 | Q1y | H | Me | Q3l |
| 2478 | Q1y | H | Me | Q3m |
| 2479 | Q1y | H | Me | Q3n |
| 2480 | Q1y | H | Me | Q3o |
| 2481 | Q1y | H | Me | Q3p |
| 2482 | Q1y | H | Me | Q3q |
| 2483 | Q1y | Me | H | Q3a |
| 2484 | Q1y | Me | H | Q3b |
| 2485 | Q1y | Me | H | Q3c |
| 2486 | Q1y | Me | H | Q3d |
| 2487 | Q1y | Me | H | Q3e |
| 2488 | Q1y | Me | H | Q3f |

TABLE 1-continued

| No | R⁷ | R⁸ | R⁹ | R¹⁰ |
|---|---|---|---|---|
| 2489 | Q1y | Me | H | Q3g |
| 2490 | Q1y | Me | H | Q3h |
| 2491 | Q1y | Me | H | Q3i |
| 2492 | Q1y | Me | H | Q3j |
| 2493 | Q1y | Me | H | Q3k |
| 2494 | Q1y | Me | H | Q3l |
| 2495 | Q1y | Me | H | Q3m |
| 2496 | Q1y | Me | H | Q3n |
| 2497 | Q1y | Me | H | Q3o |
| 2498 | Q1y | Me | H | Q3p |
| 2499 | Q1y | Me | H | Q3q |
| 2500 | Q1y | Me | Me | Q3a |
| 2501 | Q1y | Me | Me | Q3b |
| 2502 | Q1y | Me | Me | Q3c |
| 2503 | Q1y | Me | Me | Q3d |
| 2504 | Q1y | Me | Me | Q3e |
| 2505 | Q1y | Me | Me | Q3f |
| 2506 | Q1y | Me | Me | Q3g |
| 2507 | Q1y | Me | Me | Q3h |
| 2508 | Q1y | Me | Me | Q3i |
| 2509 | Q1y | Me | Me | Q3j |
| 2510 | Q1y | Me | Me | Q3k |
| 2511 | Q1y | Me | Me | Q3l |
| 2512 | Q1y | Me | Me | Q3m |
| 2513 | Q1y | Me | Me | Q3n |
| 2514 | Q1y | Me | Me | Q3o |
| 2515 | Q1y | Me | Me | Q3p |
| 2516 | Q1y | Me | Me | Q3q |
| 2517 | Q1y | CF3 | H | Q3a |
| 2518 | Q1y | CF3 | H | Q3b |
| 2519 | Q1y | CF3 | H | Q3c |
| 2520 | Q1y | CF3 | H | Q3d |
| 2521 | Q1y | CF3 | H | Q3e |
| 2522 | Q1y | CF3 | H | Q3f |
| 2523 | Q1y | CF3 | H | Q3g |
| 2524 | Q1y | CF3 | H | Q3h |
| 2525 | Q1y | CF3 | H | Q3i |
| 2526 | Q1y | CF3 | H | Q3j |
| 2527 | Q1y | CF3 | H | Q3k |
| 2528 | Q1y | CF3 | H | Q3l |
| 2529 | Q1y | CF3 | H | Q3m |
| 2530 | Q1y | CF3 | H | Q3n |
| 2531 | Q1y | CF3 | H | Q3o |
| 2532 | Q1y | CF3 | H | Q3p |
| 2533 | Q1y | CF3 | H | Q3q |
| 2534 | Q1y | CF3 | Me | Q3a |
| 2535 | Q1y | CF3 | Me | Q3b |
| 2536 | Q1y | CF3 | Me | Q3c |
| 2537 | Q1y | CF3 | Me | Q3d |
| 2538 | Q1y | CF3 | Me | Q3e |
| 2539 | Q1y | CF3 | Me | Q3f |
| 2540 | Q1y | CF3 | Me | Q3g |
| 2541 | Q1y | CF3 | Me | Q3h |
| 2542 | Q1y | CF3 | Me | Q3i |
| 2543 | Q1y | CF3 | Me | Q3j |
| 2544 | Q1y | CF3 | Me | Q3k |
| 2545 | Q1y | CF3 | Me | Q3l |
| 2546 | Q1y | CF3 | Me | Q3m |
| 2547 | Q1y | CF3 | Me | Q3n |
| 2548 | Q1y | CF3 | Me | Q3o |
| 2549 | Q1y | CF3 | Me | Q3p |
| 2550 | Q1y | CF3 | Me | Q3q |
| 2551 | Q1z | H | H | Q3a |
| 2552 | Q1z | H | H | Q3b |
| 2553 | Q1z | H | H | Q3c |
| 2554 | Q1z | H | H | Q3d |
| 2555 | Q1z | H | H | Q3e |
| 2556 | Q1z | H | H | Q3f |
| 2557 | Q1z | H | H | Q3g |
| 2558 | Q1z | H | H | Q3h |
| 2559 | Q1z | H | H | Q3i |
| 2560 | Q1z | H | H | Q3j |
| 2561 | Q1z | H | H | Q3k |
| 2562 | Q1z | H | H | Q3l |
| 2563 | Q1z | H | H | Q3m |
| 2564 | Q1z | H | H | Q3n |
| 2565 | Q1z | H | H | Q3o |
| 2566 | Q1z | H | H | Q3p |
| 2567 | Q1z | H | H | Q3q |
| 2568 | Q1z | H | Me | Q3a |
| 2569 | Q1z | H | Me | Q3b |
| 2570 | Q1z | H | Me | Q3c |
| 2571 | Q1z | H | Me | Q3d |
| 2572 | Q1z | H | Me | Q3e |
| 2573 | Q1z | H | Me | Q3f |
| 2574 | Q1z | H | Me | Q3g |
| 2575 | Q1z | H | Me | Q3h |
| 2576 | Q1z | H | Me | Q3i |
| 2577 | Q1z | H | Me | Q3j |
| 2578 | Q1z | H | Me | Q3k |
| 2579 | Q1z | H | Me | Q3l |
| 2580 | Q1z | H | Me | Q3m |
| 2581 | Q1z | H | Me | Q3n |
| 2582 | Q1z | H | Me | Q3o |
| 2583 | Q1z | H | Me | Q3p |
| 2584 | Q1z | H | Me | Q3q |
| 2585 | Q1z | Me | H | Q3a |
| 2586 | Q1z | Me | H | Q3b |
| 2587 | Q1z | Me | H | Q3c |
| 2588 | Q1z | Me | H | Q3d |
| 2589 | Q1z | Me | H | Q3e |
| 2590 | Q1z | Me | H | Q3f |
| 2591 | Q1z | Me | H | Q3g |
| 2592 | Q1z | Me | H | Q3h |
| 2593 | Q1z | Me | H | Q3i |
| 2594 | Q1z | Me | H | Q3j |
| 2595 | Q1z | Me | H | Q3k |
| 2596 | Q1z | Me | H | Q3l |
| 2597 | Q1z | Me | H | Q3m |
| 2598 | Q1z | Me | H | Q3n |
| 2599 | Q1z | Me | H | Q3o |
| 2600 | Q1z | Me | H | Q3p |
| 2601 | Q1z | Me | H | Q3q |
| 2602 | Q1z | Me | Me | Q3a |
| 2603 | Q1z | Me | Me | Q3b |
| 2604 | Q1z | Me | Me | Q3c |
| 2605 | Q1z | Me | Me | Q3d |
| 2606 | Q1z | Me | Me | Q3e |
| 2607 | Q1z | Me | Me | Q3f |
| 2608 | Q1z | Me | Me | Q3g |
| 2609 | Q1z | Me | Me | Q3h |
| 2610 | Q1z | Me | Me | Q3i |
| 2611 | Q1z | Me | Me | Q3j |
| 2612 | Q1z | Me | Me | Q3k |
| 2613 | Q1z | Me | Me | Q3l |
| 2614 | Q1z | Me | Me | Q3m |
| 2615 | Q1z | Me | Me | Q3n |
| 2616 | Q1z | Me | Me | Q3o |
| 2617 | Q1z | Me | Me | Q3p |
| 2618 | Q1z | Me | Me | Q3q |
| 2619 | Q1z | CF3 | H | Q3a |
| 2620 | Q1z | CF3 | H | Q3b |
| 2621 | Q1z | CF3 | H | Q3c |
| 2622 | Q1z | CF3 | H | Q3d |
| 2623 | Q1z | CF3 | H | Q3e |
| 2624 | Q1z | CF3 | H | Q3f |
| 2625 | Q1z | CF3 | H | Q3g |
| 2626 | Q1z | CF3 | H | Q3h |
| 2627 | Q1z | CF3 | H | Q3i |
| 2628 | Q1z | CF3 | H | Q3j |
| 2629 | Q1z | CF3 | H | Q3k |
| 2630 | Q1z | CF3 | H | Q3l |
| 2631 | Q1z | CF3 | H | Q3m |
| 2632 | Q1z | CF3 | H | Q3n |
| 2633 | Q1z | CF3 | H | Q3o |
| 2634 | Q1z | CF3 | H | Q3p |
| 2635 | Q1z | CF3 | H | Q3q |
| 2636 | Q1z | CF3 | Me | Q3a |
| 2637 | Q1z | CF3 | Me | Q3b |
| 2638 | Q1z | CF3 | Me | Q3c |
| 2639 | Q1z | CF3 | Me | Q3d |
| 2640 | Q1z | CF3 | Me | Q3e |
| 2641 | Q1z | CF3 | Me | Q3f |
| 2642 | Q1z | CF3 | Me | Q3g |
| 2643 | Q1z | CF3 | Me | Q3h |
| 2644 | Q1z | CF3 | Me | Q3i |

TABLE 1-continued

| No | R7 | R8 | R9 | R10 |
|---|---|---|---|---|
| 2645 | Q1z | CF3 | Me | Q3j |
| 2646 | Q1z | CF3 | Me | Q3k |
| 2647 | Q1z | CF3 | Me | Q3l |
| 2648 | Q1z | CF3 | Me | Q3m |
| 2649 | Q1z | CF3 | Me | Q3n |
| 2650 | Q1z | CF3 | Me | Q3o |
| 2651 | Q1z | CF3 | Me | Q3p |
| 2652 | Q1z | CF3 | Me | Q3q |
| 2653 | Q1a | H | H | Q3r |
| 2654 | Q1a | H | H | Q3s |
| 2655 | Q1a | H | H | Q3t |
| 2656 | Q1a | H | H | Q3u |
| 2657 | Q1a | H | Me | Q3r |
| 2658 | Q1a | H | Me | Q3s |
| 2659 | Q1a | H | Me | Q3t |
| 2660 | Q1a | H | Me | Q3u |
| 2661 | Q1a | Me | H | Q3r |
| 2662 | Q1a | Me | H | Q3s |
| 2663 | Q1a | Me | H | Q3t |
| 2664 | Q1a | Me | H | Q3u |
| 2665 | Q1a | Me | Me | Q3r |
| 2666 | Q1a | Me | Me | Q3s |
| 2667 | Q1a | Me | Me | Q3t |
| 2668 | Q1a | Me | Me | Q3u |
| 2669 | Q1a | CF3 | H | Q3r |
| 2670 | Q1a | CF3 | H | Q3s |
| 2671 | Q1a | CF3 | H | Q3t |
| 2672 | Q1a | CF3 | H | Q3u |
| 2673 | Q1a | CF3 | Me | Q3r |
| 2674 | Q1a | CF3 | Me | Q3s |
| 2675 | Q1a | CF3 | Me | Q3t |
| 2676 | Q1a | CF3 | Me | Q3u |
| 2677 | Q1b | H | H | Q3r |
| 2678 | Q1b | H | H | Q3s |
| 2679 | Q1b | H | H | Q3t |
| 2680 | Q1b | H | H | Q3u |
| 2681 | Q1b | H | Me | Q3r |
| 2682 | Q1b | H | Me | Q3s |
| 2683 | Q1b | H | Me | Q3t |
| 2684 | Q1b | H | Me | Q3u |
| 2685 | Q1b | Me | H | Q3r |
| 2686 | Q1b | Me | H | Q3s |
| 2687 | Q1b | Me | H | Q3t |
| 2688 | Q1b | Me | H | Q3u |
| 2689 | Q1b | Me | Me | Q3r |
| 2690 | Q1b | Me | Me | Q3s |
| 2691 | Q1b | Me | Me | Q3t |
| 2692 | Q1b | Me | Me | Q3u |
| 2693 | Q1b | CF3 | H | Q3r |
| 2694 | Q1b | CF3 | H | Q3s |
| 2695 | Q1b | CF3 | H | Q3t |
| 2696 | Q1b | CF3 | H | Q3u |
| 2697 | Q1b | CF3 | Me | Q3r |
| 2698 | Q1b | CF3 | Me | Q3s |
| 2699 | Q1b | CF3 | Me | Q3t |
| 2700 | Q1b | CF3 | Me | Q3u |
| 2701 | Q1c | H | H | Q3r |
| 2702 | Q1c | H | H | Q3s |
| 2703 | Q1c | H | H | Q3t |
| 2704 | Q1c | H | H | Q3u |
| 2705 | Q1c | H | Me | Q3r |
| 2706 | Q1c | H | Me | Q3s |
| 2707 | Q1c | H | Me | Q3t |
| 2708 | Q1c | H | Me | Q3u |
| 2709 | Q1c | Me | H | Q3r |
| 2710 | Q1c | Me | H | Q3s |
| 2711 | Q1c | Me | H | Q3t |
| 2712 | Q1c | Me | H | Q3u |
| 2713 | Q1c | Me | Me | Q3r |
| 2714 | Q1c | Me | Me | Q3s |
| 2715 | Q1c | Me | Me | Q3t |
| 2716 | Q1c | Me | Me | Q3u |
| 2717 | Q1c | CF3 | H | Q3r |
| 2718 | Q1c | CF3 | H | Q3s |
| 2719 | Q1c | CF3 | H | Q3t |
| 2720 | Q1c | CF3 | H | Q3u |
| 2721 | Q1c | CF3 | Me | Q3r |
| 2722 | Q1c | CF3 | Me | Q3s |
| 2723 | Q1c | CF3 | Me | Q3t |
| 2724 | Q1c | CF3 | Me | Q3u |
| 2725 | Q1d | H | H | Q3r |
| 2726 | Q1d | H | H | Q3s |
| 2727 | Q1d | H | H | Q3t |
| 2728 | Q1d | H | H | Q3u |
| 2729 | Q1d | H | Me | Q3r |
| 2730 | Q1d | H | Me | Q3s |
| 2731 | Q1d | H | Me | Q3t |
| 2732 | Q1d | H | Me | Q3u |
| 2733 | Q1d | Me | H | Q3r |
| 2734 | Q1d | Me | H | Q3s |
| 2735 | Q1d | Me | H | Q3t |
| 2736 | Q1d | Me | H | Q3u |
| 2737 | Q1d | Me | Me | Q3r |
| 2738 | Q1d | Me | Me | Q3s |
| 2739 | Q1d | Me | Me | Q3t |
| 2740 | Q1d | Me | Me | Q3u |
| 2741 | Q1d | CF3 | H | Q3r |
| 2742 | Q1d | CF3 | H | Q3s |
| 2743 | Q1d | CF3 | H | Q3t |
| 2744 | Q1d | CF3 | H | Q3u |
| 2745 | Q1d | CF3 | Me | Q3r |
| 2746 | Q1d | CF3 | Me | Q3s |
| 2747 | Q1d | CF3 | Me | Q3t |
| 2748 | Q1d | CF3 | Me | Q3u |
| 2749 | Q1e | H | H | Q3r |
| 2750 | Q1e | H | H | Q3s |
| 2751 | Q1e | H | H | Q3t |
| 2752 | Q1e | H | H | Q3u |
| 2753 | Q1e | H | Me | Q3r |
| 2754 | Q1e | H | Me | Q3s |
| 2755 | Q1e | H | Me | Q3t |
| 2756 | Q1e | H | Me | Q3u |
| 2757 | Q1e | Me | H | Q3r |
| 2758 | Q1e | Me | H | Q3s |
| 2759 | Q1e | Me | H | Q3t |
| 2760 | Q1e | Me | H | Q3u |
| 2761 | Q1e | Me | Me | Q3r |
| 2762 | Q1e | Me | Me | Q3s |
| 2763 | Q1e | Me | Me | Q3t |
| 2764 | Q1e | Me | Me | Q3u |
| 2765 | Q1e | CF3 | H | Q3r |
| 2766 | Q1e | CF3 | H | Q3s |
| 2767 | Q1e | CF3 | H | Q3t |
| 2768 | Q1e | CF3 | H | Q3u |
| 2769 | Q1e | CF3 | Me | Q3r |
| 2770 | Q1e | CF3 | Me | Q3s |
| 2771 | Q1e | CF3 | Me | Q3t |
| 2772 | Q1e | CF3 | Me | Q3u |
| 2773 | Q1f | H | H | Q3r |
| 2774 | Q1f | H | H | Q3s |
| 2775 | Q1f | H | H | Q3t |
| 2776 | Q1f | H | H | Q3u |
| 2777 | Q1f | H | Me | Q3r |
| 2778 | Q1f | H | Me | Q3s |
| 2779 | Q1f | H | Me | Q3t |
| 2780 | Q1f | H | Me | Q3u |
| 2781 | Q1f | Me | H | Q3r |
| 2782 | Q1f | Me | H | Q3s |
| 2783 | Q1f | Me | H | Q3t |
| 2784 | Q1f | Me | H | Q3u |
| 2785 | Q1f | Me | Me | Q3r |
| 2786 | Q1f | Me | Me | Q3s |
| 2787 | Q1f | Me | Me | Q3t |
| 2788 | Q1f | Me | Me | Q3u |
| 2789 | Q1f | CF3 | H | Q3r |
| 2790 | Q1f | CF3 | H | Q3s |
| 2791 | Q1f | CF3 | H | Q3t |
| 2792 | Q1f | CF3 | H | Q3u |
| 2793 | Q1f | CF3 | Me | Q3r |
| 2794 | Q1f | CF3 | Me | Q3s |
| 2795 | Q1f | CF3 | Me | Q3t |
| 2796 | Q1f | CF3 | Me | Q3u |
| 2797 | Q1g | H | H | Q3r |
| 2798 | Q1g | H | H | Q3s |
| 2799 | Q1g | H | H | Q3t |
| 2800 | Q1g | H | H | Q3u |

TABLE 1-continued

| No | R⁷ | R⁸ | R⁹ | R¹⁰ |
|---|---|---|---|---|
| 2801 | Q1g | H | Me | Q3r |
| 2802 | Q1g | H | Me | Q3s |
| 2803 | Q1g | H | Me | Q3t |
| 2804 | Q1g | H | Me | Q3u |
| 2805 | Q1g | Me | H | Q3r |
| 2806 | Q1g | Me | H | Q3s |
| 2807 | Q1g | Me | H | Q3t |
| 2808 | Q1g | Me | H | Q3u |
| 2809 | Q1g | Me | Me | Q3r |
| 2810 | Q1g | Me | Me | Q3s |
| 2811 | Q1g | Me | Me | Q3t |
| 2812 | Q1g | Me | Me | Q3u |
| 2813 | Q1g | CF3 | H | Q3r |
| 2814 | Q1g | CF3 | H | Q3s |
| 2815 | Q1g | CF3 | H | Q3t |
| 2816 | Q1g | CF3 | H | Q3u |
| 2817 | Q1g | CF3 | Me | Q3r |
| 2818 | Q1g | CF3 | Me | Q3s |
| 2819 | Q1g | CF3 | Me | Q3t |
| 2820 | Q1g | CF3 | Me | Q3u |
| 2821 | Q1h | H | H | Q3r |
| 2822 | Q1h | H | H | Q3s |
| 2823 | Q1h | H | H | Q3t |
| 2824 | Q1h | H | H | Q3u |
| 2825 | Q1h | H | Me | Q3r |
| 2826 | Q1h | H | Me | Q3s |
| 2827 | Q1h | H | Me | Q3t |
| 2828 | Q1h | H | Me | Q3u |
| 2829 | Q1h | Me | H | Q3r |
| 2830 | Q1h | Me | H | Q3s |
| 2831 | Q1h | Me | H | Q3t |
| 2832 | Q1h | Me | H | Q3u |
| 2833 | Q1h | Me | Me | Q3r |
| 2834 | Q1h | Me | Me | Q3s |
| 2835 | Q1h | Me | Me | Q3t |
| 2836 | Q1h | Me | Me | Q3u |
| 2837 | Q1h | CF3 | H | Q3r |
| 2838 | Q1h | CF3 | H | Q3s |
| 2839 | Q1h | CF3 | H | Q3t |
| 2840 | Q1h | CF3 | H | Q3u |
| 2841 | Q1h | CF3 | Me | Q3r |
| 2842 | Q1h | CF3 | Me | Q3s |
| 2843 | Q1h | CF3 | Me | Q3t |
| 2844 | Q1h | CF3 | Me | Q3u |
| 2845 | Q1i | H | H | Q3r |
| 2846 | Q1i | H | H | Q3s |
| 2847 | Q1i | H | H | Q3t |
| 2848 | Q1i | H | H | Q3u |
| 2849 | Q1i | H | Me | Q3r |
| 2850 | Q1i | H | Me | Q3s |
| 2851 | Q1i | H | Me | Q3t |
| 2852 | Q1i | H | Me | Q3u |
| 2853 | Q1i | Me | H | Q3r |
| 2854 | Q1i | Me | H | Q3s |
| 2855 | Q1i | Me | H | Q3t |
| 2856 | Q1i | Me | H | Q3u |
| 2857 | Q1i | Me | Me | Q3r |
| 2858 | Q1i | Me | Me | Q3s |
| 2859 | Q1i | Me | Me | Q3t |
| 2860 | Q1i | Me | Me | Q3u |
| 2861 | Q1i | CF3 | H | Q3r |
| 2862 | Q1i | CF3 | H | Q3s |
| 2863 | Q1i | CF3 | H | Q3t |
| 2864 | Q1i | CF3 | H | Q3u |
| 2865 | Q1i | CF3 | Me | Q3r |
| 2866 | Q1i | CF3 | Me | Q3s |
| 2867 | Q1i | CF3 | Me | Q3t |
| 2868 | Q1i | CF3 | Me | Q3u |
| 2869 | Q1j | H | H | Q3r |
| 2870 | Q1j | H | H | Q3s |
| 2871 | Q1j | H | H | Q3t |
| 2872 | Q1j | H | H | Q3u |
| 2873 | Q1j | H | Me | Q3r |
| 2874 | Q1j | H | Me | Q3s |
| 2875 | Q1j | H | Me | Q3t |
| 2876 | Q1j | H | Me | Q3u |
| 2877 | Q1j | Me | H | Q3r |
| 2878 | Q1j | Me | H | Q3s |
| 2879 | Q1j | Me | H | Q3t |
| 2880 | Q1j | Me | H | Q3u |
| 2881 | Q1j | Me | Me | Q3r |
| 2882 | Q1j | Me | Me | Q3s |
| 2883 | Q1j | Me | Me | Q3t |
| 2884 | Q1j | Me | Me | Q3u |
| 2885 | Q1j | CF3 | H | Q3r |
| 2886 | Q1j | CF3 | H | Q3s |
| 2887 | Q1j | CF3 | H | Q3t |
| 2888 | Q1j | CF3 | H | Q3u |
| 2889 | Q1j | CF3 | Me | Q3r |
| 2890 | Q1j | CF3 | Me | Q3s |
| 2891 | Q1j | CF3 | Me | Q3t |
| 2892 | Q1j | CF3 | Me | Q3u |
| 2893 | Q1k | H | H | Q3r |
| 2894 | Q1k | H | H | Q3s |
| 2895 | Q1k | H | H | Q3t |
| 2896 | Q1k | H | H | Q3u |
| 2897 | Q1k | H | Me | Q3r |
| 2898 | Q1k | H | Me | Q3s |
| 2899 | Q1k | H | Me | Q3t |
| 2900 | Q1k | H | Me | Q3u |
| 2901 | Q1k | Me | H | Q3r |
| 2902 | Q1k | Me | H | Q3s |
| 2903 | Q1k | Me | H | Q3t |
| 2904 | Q1k | Me | H | Q3u |
| 2905 | Q1k | Me | Me | Q3r |
| 2906 | Q1k | Me | Me | Q3s |
| 2907 | Q1k | Me | Me | Q3t |
| 2908 | Q1k | Me | Me | Q3u |
| 2909 | Q1k | CF3 | H | Q3r |
| 2910 | Q1k | CF3 | H | Q3s |
| 2911 | Q1k | CF3 | H | Q3t |
| 2912 | Q1k | CF3 | H | Q3u |
| 2913 | Q1k | CF3 | Me | Q3r |
| 2914 | Q1k | CF3 | Me | Q3s |
| 2915 | Q1k | CF3 | Me | Q3t |
| 2916 | Q1k | CF3 | Me | Q3u |
| 2917 | Q1l | H | H | Q3r |
| 2918 | Q1l | H | H | Q3s |
| 2919 | Q1l | H | H | Q3t |
| 2920 | Q1l | H | H | Q3u |
| 2921 | Q1l | H | Me | Q3r |
| 2922 | Q1l | H | Me | Q3s |
| 2923 | Q1l | H | Me | Q3t |
| 2924 | Q1l | H | Me | Q3u |
| 2925 | Q1l | Me | H | Q3r |
| 2926 | Q1l | Me | H | Q3s |
| 2927 | Q1l | Me | H | Q3t |
| 2928 | Q1l | Me | H | Q3u |
| 2929 | Q1l | Me | Me | Q3r |
| 2930 | Q1l | Me | Me | Q3s |
| 2931 | Q1l | Me | Me | Q3t |
| 2932 | Q1l | Me | Me | Q3u |
| 2933 | Q1l | CF3 | H | Q3r |
| 2934 | Q1l | CF3 | H | Q3s |
| 2935 | Q1l | CF3 | H | Q3t |
| 2936 | Q1l | CF3 | H | Q3u |
| 2937 | Q1l | CF3 | Me | Q3r |
| 2938 | Q1l | CF3 | Me | Q3s |
| 2939 | Q1l | CF3 | Me | Q3t |
| 2940 | Q1l | CF3 | Me | Q3u |
| 2941 | Q1m | H | H | Q3r |
| 2942 | Q1m | H | H | Q3s |
| 2943 | Q1m | H | H | Q3t |
| 2944 | Q1m | H | H | Q3u |
| 2945 | Q1m | H | Me | Q3r |
| 2946 | Q1m | H | Me | Q3s |
| 2947 | Q1m | H | Me | Q3t |
| 2948 | Q1m | H | Me | Q3u |
| 2949 | Q1m | Me | H | Q3r |
| 2950 | Q1m | Me | H | Q3s |
| 2951 | Q1m | Me | H | Q3t |
| 2952 | Q1m | Me | H | Q3u |
| 2953 | Q1m | Me | Me | Q3r |
| 2954 | Q1m | Me | Me | Q3s |
| 2955 | Q1m | Me | Me | Q3t |
| 2956 | Q1m | Me | Me | Q3u |

TABLE 1-continued

| No | R⁷ | R⁸ | R⁹ | R¹⁰ |
|---|---|---|---|---|
| 2957 | Q1m | CF3 | H | Q3r |
| 2958 | Q1m | CF3 | H | Q3s |
| 2959 | Q1m | CF3 | H | Q3t |
| 2960 | Q1m | CF3 | H | Q3u |
| 2961 | Q1m | CF3 | Me | Q3r |
| 2962 | Q1m | CF3 | Me | Q3s |
| 2963 | Q1m | CF3 | Me | Q3t |
| 2964 | Q1m | CF3 | Me | Q3u |
| 2965 | Q1n | H | H | Q3r |
| 2966 | Q1n | H | H | Q3s |
| 2967 | Q1n | H | H | Q3t |
| 2968 | Q1n | H | H | Q3u |
| 2969 | Q1n | H | Me | Q3r |
| 2970 | Q1n | H | Me | Q3s |
| 2971 | Q1n | H | Me | Q3t |
| 2972 | Q1n | H | Me | Q3u |
| 2973 | Q1n | Me | H | Q3r |
| 2974 | Q1n | Me | H | Q3s |
| 2975 | Q1n | Me | H | Q3t |
| 2976 | Q1n | Me | H | Q3u |
| 2977 | Q1n | Me | Me | Q3r |
| 2978 | Q1n | Me | Me | Q3s |
| 2979 | Q1n | Me | Me | Q3t |
| 2980 | Q1n | Me | Me | Q3u |
| 2981 | Q1n | CF3 | H | Q3r |
| 2982 | Q1n | CF3 | H | Q3s |
| 2983 | Q1n | CF3 | H | Q3t |
| 2984 | Q1n | CF3 | H | Q3u |
| 2985 | Q1n | CF3 | Me | Q3r |
| 2986 | Q1n | CF3 | Me | Q3s |
| 2987 | Q1n | CF3 | Me | Q3t |
| 2988 | Q1n | CF3 | Me | Q3u |
| 2989 | Q1o | H | H | Q3r |
| 2990 | Q1o | H | H | Q3s |
| 2991 | Q1o | H | H | Q3t |
| 2992 | Q1o | H | H | Q3u |
| 2993 | Q1o | H | Me | Q3r |
| 2994 | Q1o | H | Me | Q3s |
| 2995 | Q1o | H | Me | Q3t |
| 2996 | Q1o | H | Me | Q3u |
| 2997 | Q1o | Me | H | Q3r |
| 2998 | Q1o | Me | H | Q3s |
| 2999 | Q1o | Me | H | Q3t |
| 3000 | Q1o | Me | H | Q3u |
| 3001 | Q1o | Me | Me | Q3r |
| 3002 | Q1o | Me | Me | Q3s |
| 3003 | Q1o | Me | Me | Q3t |
| 3004 | Q1o | Me | Me | Q3u |
| 3005 | Q1o | CF3 | H | Q3r |
| 3006 | Q1o | CF3 | H | Q3s |
| 3007 | Q1o | CF3 | H | Q3t |
| 3008 | Q1o | CF3 | H | Q3u |
| 3009 | Q1o | CF3 | Me | Q3r |
| 3010 | Q1o | CF3 | Me | Q3s |
| 3011 | Q1o | CF3 | Me | Q3t |
| 3012 | Q1o | CF3 | Me | Q3u |
| 3013 | Q1p | H | H | Q3r |
| 3014 | Q1p | H | H | Q3s |
| 3015 | Q1p | H | H | Q3t |
| 3016 | Q1p | H | H | Q3u |
| 3017 | Q1p | H | Me | Q3r |
| 3018 | Q1p | H | Me | Q3s |
| 3019 | Q1p | H | Me | Q3t |
| 3020 | Q1p | H | Me | Q3u |
| 3021 | Q1p | Me | H | Q3r |
| 3022 | Q1p | Me | H | Q3s |
| 3023 | Q1p | Me | H | Q3t |
| 3024 | Q1p | Me | H | Q3u |
| 3025 | Q1p | Me | Me | Q3r |
| 3026 | Q1p | Me | Me | Q3s |
| 3027 | Q1p | Me | Me | Q3t |
| 3028 | Q1p | Me | Me | Q3u |
| 3029 | Q1p | CF3 | H | Q3r |
| 3030 | Q1p | CF3 | H | Q3s |
| 3031 | Q1p | CF3 | H | Q3t |
| 3032 | Q1p | CF3 | H | Q3u |
| 3033 | Q1p | CF3 | Me | Q3r |
| 3034 | Q1p | CF3 | Me | Q3s |
| 3035 | Q1p | CF3 | Me | Q3t |
| 3036 | Q1p | CF3 | Me | Q3u |
| 3037 | Q1q | H | H | Q3r |
| 3038 | Q1q | H | H | Q3s |
| 3039 | Q1q | H | H | Q3t |
| 3040 | Q1q | H | H | Q3u |
| 3041 | Q1q | H | Me | Q3r |
| 3042 | Q1q | H | Me | Q3s |
| 3043 | Q1q | H | Me | Q3t |
| 3044 | Q1q | H | Me | Q3u |
| 3045 | Q1q | Me | H | Q3r |
| 3046 | Q1q | Me | H | Q3s |
| 3047 | Q1q | Me | H | Q3t |
| 3048 | Q1q | Me | H | Q3u |
| 3049 | Q1q | Me | Me | Q3r |
| 3050 | Q1q | Me | Me | Q3s |
| 3051 | Q1q | Me | Me | Q3t |
| 3052 | Q1q | Me | Me | Q3u |
| 3053 | Q1q | CF3 | H | Q3r |
| 3054 | Q1q | CF3 | H | Q3s |
| 3055 | Q1q | CF3 | H | Q3t |
| 3056 | Q1q | CF3 | H | Q3u |
| 3057 | Q1q | CF3 | Me | Q3r |
| 3058 | Q1q | CF3 | Me | Q3s |
| 3059 | Q1q | CF3 | Me | Q3t |
| 3060 | Q1q | CF3 | Me | Q3u |
| 3061 | Q1r | H | H | Q3r |
| 3062 | Q1r | H | H | Q3s |
| 3063 | Q1r | H | H | Q3t |
| 3064 | Q1r | H | H | Q3u |
| 3065 | Q1r | H | Me | Q3r |
| 3066 | Q1r | H | Me | Q3s |
| 3067 | Q1r | H | Me | Q3t |
| 3068 | Q1r | H | Me | Q3u |
| 3069 | Q1r | Me | H | Q3r |
| 3070 | Q1r | Me | H | Q3s |
| 3071 | Q1r | Me | H | Q3t |
| 3072 | Q1r | Me | H | Q3u |
| 3073 | Q1r | Me | Me | Q3r |
| 3074 | Q1r | Me | Me | Q3s |
| 3075 | Q1r | Me | Me | Q3t |
| 3076 | Q1r | Me | Me | Q3u |
| 3077 | Q1r | CF3 | H | Q3r |
| 3078 | Q1r | CF3 | H | Q3s |
| 3079 | Q1r | CF3 | H | Q3t |
| 3080 | Q1r | CF3 | H | Q3u |
| 3081 | Q1r | CF3 | Me | Q3r |
| 3082 | Q1r | CF3 | Me | Q3s |
| 3083 | Q1r | CF3 | Me | Q3t |
| 3084 | Q1r | CF3 | Me | Q3u |
| 3085 | Q1s | H | H | Q3r |
| 3086 | Q1s | H | H | Q3s |
| 3087 | Q1s | H | H | Q3t |
| 3088 | Q1s | H | H | Q3u |
| 3089 | Q1s | H | Me | Q3r |
| 3090 | Q1s | H | Me | Q3s |
| 3091 | Q1s | H | Me | Q3t |
| 3092 | Q1s | H | Me | Q3u |
| 3093 | Q1s | Me | H | Q3r |
| 3094 | Q1s | Me | H | Q3s |
| 3095 | Q1s | Me | H | Q3t |
| 3096 | Q1s | Me | H | Q3u |
| 3097 | Q1s | Me | Me | Q3r |
| 3098 | Q1s | Me | Me | Q3s |
| 3099 | Q1s | Me | Me | Q3t |
| 3100 | Q1s | Me | Me | Q3u |
| 3101 | Q1s | CF3 | H | Q3r |
| 3102 | Q1s | CF3 | H | Q3s |
| 3103 | Q1s | CF3 | H | Q3t |
| 3104 | Q1s | CF3 | H | Q3u |
| 3105 | Q1s | CF3 | Me | Q3r |
| 3106 | Q1s | CF3 | Me | Q3s |
| 3107 | Q1s | CF3 | Me | Q3t |
| 3108 | Q1s | CF3 | Me | Q3u |
| 3109 | Q1t | H | H | Q3r |
| 3110 | Q1t | H | H | Q3s |
| 3111 | Q1t | H | H | Q3t |
| 3112 | Q1t | H | H | Q3u |

TABLE 1-continued

| No | R⁷ | R⁸ | R⁹ | R¹⁰ |
|---|---|---|---|---|
| 3113 | Q1t | H | Me | Q3r |
| 3114 | Q1t | H | Me | Q3s |
| 3115 | Q1t | H | Me | Q3t |
| 3116 | Q1t | H | Me | Q3u |
| 3117 | Q1t | Me | H | Q3r |
| 3118 | Q1t | Me | H | Q3s |
| 3119 | Q1t | Me | H | Q3t |
| 3120 | Q1t | Me | H | Q3u |
| 3121 | Q1t | Me | Me | Q3r |
| 3122 | Q1t | Me | Me | Q3s |
| 3123 | Q1t | Me | Me | Q3t |
| 3124 | Q1t | Me | Me | Q3u |
| 3125 | Q1t | CF3 | H | Q3r |
| 3126 | Q1t | CF3 | H | Q3s |
| 3127 | Q1t | CF3 | H | Q3t |
| 3128 | Q1t | CF3 | H | Q3u |
| 3129 | Q1t | CF3 | Me | Q3r |
| 3130 | Q1t | CF3 | Me | Q3s |
| 3131 | Q1t | CF3 | Me | Q3t |
| 3132 | Q1t | CF3 | Me | Q3u |
| 3133 | Q1u | H | H | Q3r |
| 3134 | Q1u | H | H | Q3s |
| 3135 | Q1u | H | H | Q3t |
| 3136 | Q1u | H | H | Q3u |
| 3137 | Q1u | H | Me | Q3r |
| 3138 | Q1u | H | Me | Q3s |
| 3139 | Q1u | H | Me | Q3t |
| 3140 | Q1u | H | Me | Q3u |
| 3141 | Q1u | Me | H | Q3r |
| 3142 | Q1u | Me | H | Q3s |
| 3143 | Q1u | Me | H | Q3t |
| 3144 | Q1u | Me | H | Q3u |
| 3145 | Q1u | Me | Me | Q3r |
| 3146 | Q1u | Me | Me | Q3s |
| 3147 | Q1u | Me | Me | Q3t |
| 3148 | Q1u | Me | Me | Q3u |
| 3149 | Q1u | CF3 | H | Q3r |
| 3150 | Q1u | CF3 | H | Q3s |
| 3151 | Q1u | CF3 | H | Q3t |
| 3152 | Q1u | CF3 | H | Q3u |
| 3153 | Q1u | CF3 | Me | Q3r |
| 3154 | Q1u | CF3 | Me | Q3s |
| 3155 | Q1u | CF3 | Me | Q3t |
| 3156 | Q1u | CF3 | Me | Q3u |
| 3157 | Q1v | H | H | Q3r |
| 3158 | Q1v | H | H | Q3s |
| 3159 | Q1v | H | H | Q3t |
| 3160 | Q1v | H | H | Q3u |
| 3161 | Q1v | H | Me | Q3r |
| 3162 | Q1v | H | Me | Q3s |
| 3163 | Q1v | H | Me | Q3t |
| 3164 | Q1v | H | Me | Q3u |
| 3165 | Q1v | Me | H | Q3r |
| 3166 | Q1v | Me | H | Q3s |
| 3167 | Q1v | Me | H | Q3t |
| 3168 | Q1v | Me | H | Q3u |
| 3169 | Q1v | Me | Me | Q3r |
| 3170 | Q1v | Me | Me | Q3s |
| 3171 | Q1v | Me | Me | Q3t |
| 3172 | Q1v | Me | Me | Q3u |
| 3173 | Q1v | CF3 | H | Q3r |
| 3174 | Q1v | CF3 | H | Q3s |
| 3175 | Q1v | CF3 | H | Q3t |
| 3176 | Q1v | CF3 | H | Q3u |
| 3177 | Q1v | CF3 | Me | Q3r |
| 3178 | Q1v | CF3 | Me | Q3s |
| 3179 | Q1v | CF3 | Me | Q3t |
| 3180 | Q1v | CF3 | Me | Q3u |
| 3181 | Q1w | H | H | Q3r |
| 3182 | Q1w | H | H | Q3s |
| 3183 | Q1w | H | H | Q3t |
| 3184 | Q1w | H | H | Q3u |
| 3185 | Q1w | H | Me | Q3r |
| 3186 | Q1w | H | Me | Q3s |
| 3187 | Q1w | H | Me | Q3t |
| 3188 | Q1w | H | Me | Q3u |
| 3189 | Q1w | Me | H | Q3r |
| 3190 | Q1w | Me | H | Q3s |
| 3191 | Q1w | Me | H | Q3t |
| 3192 | Q1w | Me | H | Q3u |
| 3193 | Q1w | Me | Me | Q3r |
| 3194 | Q1w | Me | Me | Q3s |
| 3195 | Q1w | Me | Me | Q3t |
| 3196 | Q1w | Me | Me | Q3u |
| 3197 | Q1w | CF3 | H | Q3r |
| 3198 | Q1w | CF3 | H | Q3s |
| 3199 | Q1w | CF3 | H | Q3t |
| 3200 | Q1w | CF3 | H | Q3u |
| 3201 | Q1w | CF3 | Me | Q3r |
| 3202 | Q1w | CF3 | Me | Q3s |
| 3203 | Q1w | CF3 | Me | Q3t |
| 3204 | Q1w | CF3 | Me | Q3u |
| 3205 | Q1x | H | H | Q3r |
| 3206 | Q1x | H | H | Q3s |
| 3207 | Q1x | H | H | Q3t |
| 3208 | Q1x | H | H | Q3u |
| 3209 | Q1x | H | Me | Q3r |
| 3210 | Q1x | H | Me | Q3s |
| 3211 | Q1x | H | Me | Q3t |
| 3212 | Q1x | H | Me | Q3u |
| 3213 | Q1x | Me | H | Q3r |
| 3214 | Q1x | Me | H | Q3s |
| 3215 | Q1x | Me | H | Q3t |
| 3216 | Q1x | Me | H | Q3u |
| 3217 | Q1x | Me | Me | Q3r |
| 3218 | Q1x | Me | Me | Q3s |
| 3219 | Q1x | Me | Me | Q3t |
| 3220 | Q1x | Me | Me | Q3u |
| 3221 | Q1x | CF3 | H | Q3r |
| 3222 | Q1x | CF3 | H | Q3s |
| 3223 | Q1x | CF3 | H | Q3t |
| 3224 | Q1x | CF3 | H | Q3u |
| 3225 | Q1x | CF3 | Me | Q3r |
| 3226 | Q1x | CF3 | Me | Q3s |
| 3227 | Q1x | CF3 | Me | Q3t |
| 3228 | Q1x | CF3 | Me | Q3u |
| 3229 | Q1y | H | H | Q3r |
| 3230 | Q1y | H | H | Q3s |
| 3231 | Q1y | H | H | Q3t |
| 3232 | Q1y | H | H | Q3u |
| 3233 | Q1y | H | Me | Q3r |
| 3234 | Q1y | H | Me | Q3s |
| 3235 | Q1y | H | Me | Q3t |
| 3236 | Q1y | H | Me | Q3u |
| 3237 | Q1y | Me | H | Q3r |
| 3238 | Q1y | Me | H | Q3s |
| 3239 | Q1y | Me | H | Q3t |
| 3240 | Q1y | Me | H | Q3u |
| 3241 | Q1y | Me | Me | Q3r |
| 3242 | Q1y | Me | Me | Q3s |
| 3243 | Q1y | Me | Me | Q3t |
| 3244 | Q1y | Me | Me | Q3u |
| 3245 | Q1y | CF3 | H | Q3r |
| 3246 | Q1y | CF3 | H | Q3s |
| 3247 | Q1y | CF3 | H | Q3t |
| 3248 | Q1y | CF3 | H | Q3u |
| 3249 | Q1y | CF3 | Me | Q3r |
| 3250 | Q1y | CF3 | Me | Q3s |
| 3251 | Q1y | CF3 | Me | Q3t |
| 3252 | Q1y | CF3 | Me | Q3u |
| 3253 | Q1z | H | H | Q3r |
| 3254 | Q1z | H | H | Q3s |
| 3255 | Q1z | H | H | Q3t |
| 3256 | Q1z | H | H | Q3u |
| 3257 | Q1z | H | Me | Q3r |
| 3258 | Q1z | H | Me | Q3s |
| 3259 | Q1z | H | Me | Q3t |
| 3260 | Q1z | H | Me | Q3u |
| 3261 | Q1z | Me | H | Q3r |
| 3262 | Q1z | Me | H | Q3s |
| 3263 | Q1z | Me | H | Q3t |
| 3264 | Q1z | Me | H | Q3u |
| 3265 | Q1z | Me | Me | Q3r |
| 3266 | Q1z | Me | Me | Q3s |
| 3267 | Q1z | Me | Me | Q3t |
| 3268 | Q1z | Me | Me | Q3u |

TABLE 1-continued
| No | R⁷ | R⁸ | R⁹ | R¹⁰ |
|---|---|---|---|---|
| 3269 | Q1z | CF3 | H | Q3r |
| 3270 | Q1z | CF3 | H | Q3s |
| 3271 | Q1z | CF3 | H | Q3t |
| 3272 | Q1z | CF3 | H | Q3u |
| 3273 | Q1z | CF3 | Me | Q3r |
| 3274 | Q1z | CF3 | Me | Q3s |
| 3275 | Q1z | CF3 | Me | Q3t |
| 3276 | Q1z | CF3 | Me | Q3u |
131) The compounds wherein $R^1$, $R^2$, $R^3$ and $R^4$ are any of the following combinations in Table 2, tautomers, prodrugs or pharmaceutically acceptable salts of the compounds or solvates thereof. The symbols in Table 2 denote the following substituents.
Formula 11
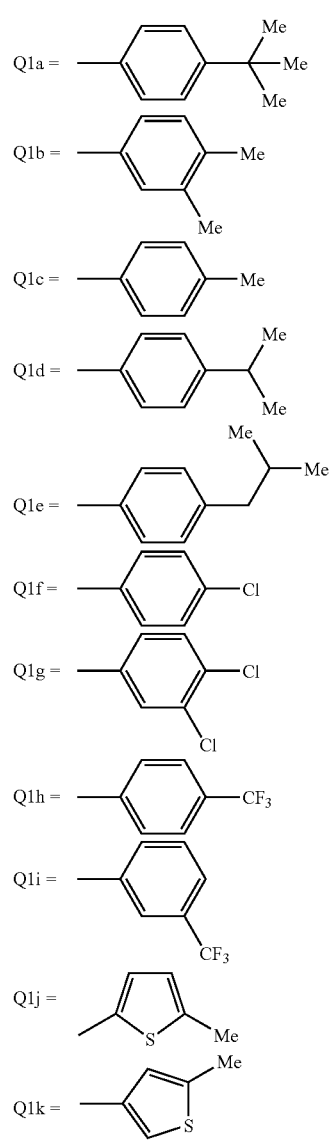
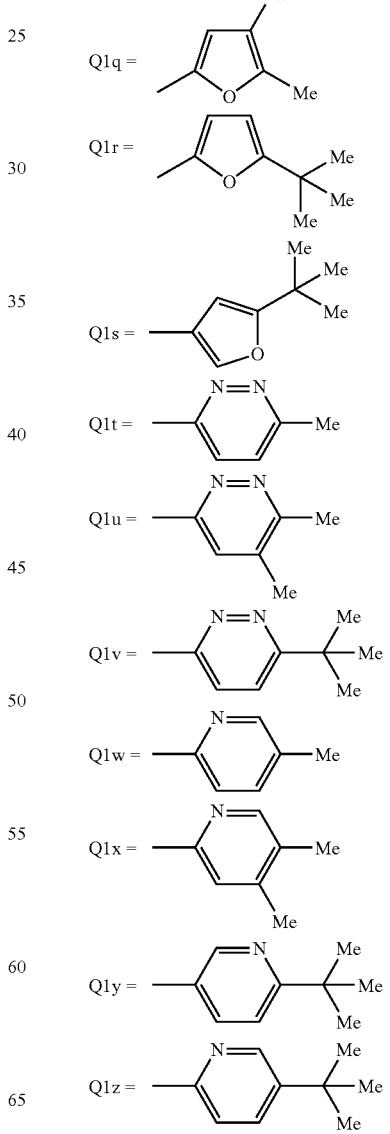

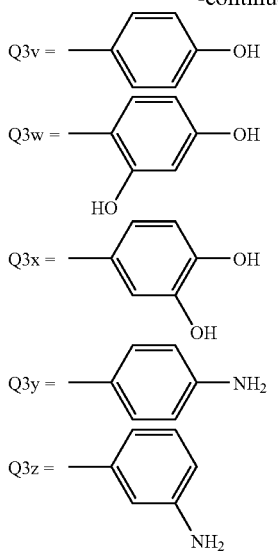

| Q3v = | phenol (4-OH) |
| Q3w = | benzene-1,3,5-... (actually 2,4-di-OH) |
| Q3x = | catechol-type (3,4-di-OH) |
| Q3y = | 4-NH2 aniline |
| Q3z = | 4-NH2 aniline (para) |

TABLE 2

| No | R¹ | R² | R³ | R⁴ |
|---|---|---|---|---|
| 1 | Q1a | H | H | Q3v |
| 2 | Q1a | H | H | Q3w |
| 3 | Q1a | H | H | Q3x |
| 4 | Q1a | H | H | Q3y |
| 5 | Q1a | H | H | Q3z |
| 6 | Q1a | H | Me | Q3v |
| 7 | Q1a | H | Me | Q3w |
| 8 | Q1a | H | Me | Q3x |
| 9 | Q1a | H | Me | Q3y |
| 10 | Q1a | H | Me | Q3z |
| 11 | Q1a | Me | H | Q3v |
| 12 | Q1a | Me | H | Q3w |
| 13 | Q1a | Me | H | Q3x |
| 14 | Q1a | Me | H | Q3y |
| 15 | Q1a | Me | H | Q3z |
| 16 | Q1a | Me | Me | Q3v |
| 17 | Q1a | Me | Me | Q3w |
| 18 | Q1a | Me | Me | Q3x |
| 19 | Q1a | Me | Me | Q3y |
| 20 | Q1a | Me | Me | Q3z |
| 21 | Q1a | CF3 | H | Q3v |
| 22 | Q1a | CF3 | H | Q3w |
| 23 | Q1a | CF3 | H | Q3x |
| 24 | Q1a | CF3 | H | Q3y |
| 25 | Q1a | CF3 | H | Q3z |
| 26 | Q1a | CF3 | Me | Q3v |
| 27 | Q1a | CF3 | Me | Q3w |
| 28 | Q1a | CF3 | Me | Q3x |
| 29 | Q1a | CF3 | Me | Q3y |
| 30 | Q1a | CF3 | Me | Q3z |
| 31 | Q1b | H | H | Q3v |
| 32 | Q1b | H | H | Q3w |
| 33 | Q1b | H | H | Q3x |
| 34 | Q1b | H | H | Q3y |
| 35 | Q1b | H | H | Q3z |
| 36 | Q1b | H | Me | Q3v |
| 37 | Q1b | H | Me | Q3w |
| 38 | Q1b | H | Me | Q3x |
| 39 | Q1b | H | Me | Q3y |
| 40 | Q1b | H | Me | Q3z |
| 41 | Q1b | Me | H | Q3v |
| 42 | Q1b | Me | H | Q3w |
| 43 | Q1b | Me | H | Q3x |
| 44 | Q1b | Me | H | Q3y |
| 45 | Q1b | Me | H | Q3z |
| 46 | Q1b | Me | Me | Q3v |
| 47 | Q1b | Me | Me | Q3w |
| 48 | Q1b | Me | Me | Q3x |
| 49 | Q1b | Me | Me | Q3y |
| 50 | Q1b | Me | Me | Q3z |
| 51 | Q1b | CF3 | H | Q3v |
| 52 | Q1b | CF3 | H | Q3w |
| 53 | Q1b | CF3 | H | Q3x |
| 54 | Q1b | CF3 | H | Q3y |
| 55 | Q1b | CF3 | H | Q3z |
| 56 | Q1b | CF3 | Me | Q3v |
| 57 | Q1b | CF3 | Me | Q3w |
| 58 | Q1b | CF3 | Me | Q3x |
| 59 | Q1b | CF3 | Me | Q3y |
| 60 | Q1b | CF3 | Me | Q3z |
| 61 | Q1c | H | H | Q3v |
| 62 | Q1c | H | H | Q3w |
| 63 | Q1c | H | H | Q3x |
| 64 | Q1c | H | H | Q3y |
| 65 | Q1c | H | H | Q3z |
| 66 | Q1c | H | Me | Q3v |
| 67 | Q1c | H | Me | Q3w |
| 68 | Q1c | H | Me | Q3x |
| 69 | Q1c | H | Me | Q3y |
| 70 | Q1c | H | Me | Q3z |
| 71 | Q1c | Me | H | Q3v |
| 72 | Q1c | Me | H | Q3w |
| 73 | Q1c | Me | H | Q3x |
| 74 | Q1c | Me | H | Q3y |
| 75 | Q1c | Me | H | Q3z |
| 76 | Q1c | Me | Me | Q3v |
| 77 | Q1c | Me | Me | Q3w |
| 78 | Q1c | Me | Me | Q3x |
| 79 | Q1c | Me | Me | Q3y |
| 80 | Q1c | Me | Me | Q3z |
| 81 | Q1c | CF3 | H | Q3v |
| 82 | Q1c | CF3 | H | Q3w |
| 83 | Q1c | CF3 | H | Q3x |
| 84 | Q1c | CF3 | H | Q3y |
| 85 | Q1c | CF3 | H | Q3z |
| 86 | Q1c | CF3 | Me | Q3v |
| 87 | Q1c | CF3 | Me | Q3w |
| 88 | Q1c | CF3 | Me | Q3x |
| 89 | Q1c | CF3 | Me | Q3y |
| 90 | Q1c | CF3 | Me | Q3z |
| 91 | Q1d | H | H | Q3v |
| 92 | Q1d | H | H | Q3w |
| 93 | Q1d | H | H | Q3x |
| 94 | Q1d | H | H | Q3y |
| 95 | Q1d | H | H | Q3z |
| 96 | Q1d | H | Me | Q3v |
| 97 | Q1d | H | Me | Q3w |
| 98 | Q1d | H | Me | Q3x |
| 99 | Q1d | H | Me | Q3y |
| 100 | Q1d | H | Me | Q3z |
| 101 | Q1d | Me | H | Q3v |
| 102 | Q1d | Me | H | Q3w |
| 103 | Q1d | Me | H | Q3x |
| 104 | Q1d | Me | H | Q3y |
| 105 | Q1d | Me | H | Q3z |
| 106 | Q1d | Me | Me | Q3v |
| 107 | Q1d | Me | Me | Q3w |
| 108 | Q1d | Me | Me | Q3x |
| 109 | Q1d | Me | Me | Q3y |
| 110 | Q1d | Me | Me | Q3z |
| 111 | Q1d | CF3 | H | Q3v |
| 112 | Q1d | CF3 | H | Q3w |
| 113 | Q1d | CF3 | H | Q3x |
| 114 | Q1d | CF3 | H | Q3y |
| 115 | Q1d | CF3 | H | Q3z |
| 116 | Q1d | CF3 | Me | Q3v |
| 117 | Q1d | CF3 | Me | Q3w |
| 118 | Q1d | CF3 | Me | Q3x |
| 119 | Q1d | CF3 | Me | Q3y |
| 120 | Q1d | CF3 | Me | Q3z |
| 121 | Q1e | H | H | Q3v |
| 122 | Q1e | H | H | Q3w |
| 123 | Q1e | H | H | Q3x |
| 124 | Q1e | H | H | Q3y |
| 125 | Q1e | H | H | Q3z |
| 126 | Q1e | H | Me | Q3v |

TABLE 2-continued

| No | R¹ | R² | R³ | R⁴ |
|---|---|---|---|---|
| 127 | Q1e | H | Me | Q3w |
| 128 | Q1e | H | Me | Q3x |
| 129 | Q1e | H | Me | Q3y |
| 130 | Q1e | H | Me | Q3z |
| 131 | Q1e | Me | H | Q3v |
| 132 | Q1e | Me | H | Q3w |
| 133 | Q1e | Me | H | Q3x |
| 134 | Q1e | Me | H | Q3y |
| 135 | Q1e | Me | H | Q3z |
| 136 | Q1e | Me | Me | Q3v |
| 137 | Q1e | Me | Me | Q3w |
| 138 | Q1e | Me | Me | Q3x |
| 139 | Q1e | Me | Me | Q3y |
| 140 | Q1e | Me | Me | Q3z |
| 141 | Q1e | CF3 | H | Q3v |
| 142 | Q1e | CF3 | H | Q3w |
| 143 | Q1e | CF3 | H | Q3x |
| 144 | Q1e | CF3 | H | Q3y |
| 145 | Q1e | CF3 | H | Q3z |
| 146 | Q1e | CF3 | Me | Q3v |
| 147 | Q1e | CF3 | Me | Q3w |
| 148 | Q1e | CF3 | Me | Q3x |
| 149 | Q1e | CF3 | Me | Q3y |
| 150 | Q1e | CF3 | Me | Q3z |
| 151 | Q1f | H | H | Q3v |
| 152 | Q1f | H | H | Q3w |
| 153 | Q1f | H | H | Q3x |
| 154 | Q1f | H | H | Q3y |
| 155 | Q1f | H | H | Q3z |
| 156 | Q1f | H | Me | Q3v |
| 157 | Q1f | H | Me | Q3w |
| 158 | Q1f | H | Me | Q3x |
| 159 | Q1f | H | Me | Q3y |
| 160 | Q1f | H | Me | Q3z |
| 161 | Q1f | Me | H | Q3v |
| 162 | Q1f | Me | H | Q3w |
| 163 | Q1f | Me | H | Q3x |
| 164 | Q1f | Me | H | Q3y |
| 165 | Q1f | Me | H | Q3z |
| 166 | Q1f | Me | Me | Q3v |
| 167 | Q1f | Me | Me | Q3w |
| 168 | Q1f | Me | Me | Q3x |
| 169 | Q1f | Me | Me | Q3y |
| 170 | Q1f | Me | Me | Q3z |
| 171 | Q1f | CF3 | H | Q3v |
| 172 | Q1f | CF3 | H | Q3w |
| 173 | Q1f | CF3 | H | Q3x |
| 174 | Q1f | CF3 | H | Q3y |
| 175 | Q1f | CF3 | H | Q3z |
| 176 | Q1f | CF3 | Me | Q3v |
| 177 | Q1f | CF3 | Me | Q3w |
| 178 | Q1f | CF3 | Me | Q3x |
| 179 | Q1f | CF3 | Me | Q3y |
| 180 | Q1f | CF3 | Me | Q3z |
| 181 | Q1g | H | H | Q3v |
| 182 | Q1g | H | H | Q3w |
| 183 | Q1g | H | H | Q3x |
| 184 | Q1g | H | H | Q3y |
| 185 | Q1g | H | H | Q3z |
| 186 | Q1g | H | Me | Q3v |
| 187 | Q1g | H | Me | Q3w |
| 188 | Q1g | H | Me | Q3x |
| 189 | Q1g | H | Me | Q3y |
| 190 | Q1g | H | Me | Q3z |
| 191 | Q1g | Me | H | Q3v |
| 192 | Q1g | Me | H | Q3w |
| 193 | Q1g | Me | H | Q3x |
| 194 | Q1g | Me | H | Q3y |
| 195 | Q1g | Me | H | Q3z |
| 196 | Q1g | Me | Me | Q3v |
| 197 | Q1g | Me | Me | Q3w |
| 198 | Q1g | Me | Me | Q3x |
| 199 | Q1g | Me | Me | Q3y |
| 200 | Q1g | Me | Me | Q3z |
| 201 | Q1g | CF3 | H | Q3v |
| 202 | Q1g | CF3 | H | Q3w |
| 203 | Q1g | CF3 | H | Q3x |
| 204 | Q1g | CF3 | H | Q3y |
| 205 | Q1g | CF3 | H | Q3z |
| 206 | Q1g | CF3 | Me | Q3v |
| 207 | Q1g | CF3 | Me | Q3w |
| 208 | Q1g | CF3 | Me | Q3x |
| 209 | Q1g | CF3 | Me | Q3y |
| 210 | Q1g | CF3 | Me | Q3z |
| 211 | Q1h | H | H | Q3v |
| 212 | Q1h | H | H | Q3w |
| 213 | Q1h | H | H | Q3x |
| 214 | Q1h | H | H | Q3y |
| 215 | Q1h | H | H | Q3z |
| 216 | Q1h | H | Me | Q3v |
| 217 | Q1h | H | Me | Q3w |
| 218 | Q1h | H | Me | Q3x |
| 219 | Q1h | H | Me | Q3y |
| 220 | Q1h | H | Me | Q3z |
| 221 | Q1h | Me | H | Q3v |
| 222 | Q1h | Me | H | Q3w |
| 223 | Q1h | Me | H | Q3x |
| 224 | Q1h | Me | H | Q3y |
| 225 | Q1h | Me | H | Q3z |
| 226 | Q1h | Me | Me | Q3v |
| 227 | Q1h | Me | Me | Q3w |
| 228 | Q1h | Me | Me | Q3x |
| 229 | Q1h | Me | Me | Q3y |
| 230 | Q1h | Me | Me | Q3z |
| 231 | Q1h | CF3 | H | Q3v |
| 232 | Q1h | CF3 | H | Q3w |
| 233 | Q1h | CF3 | H | Q3x |
| 234 | Q1h | CF3 | H | Q3y |
| 235 | Q1h | CF3 | H | Q3z |
| 236 | Q1h | CF3 | Me | Q3v |
| 237 | Q1h | CF3 | Me | Q3w |
| 238 | Q1h | CF3 | Me | Q3x |
| 239 | Q1h | CF3 | Me | Q3y |
| 240 | Q1h | CF3 | Me | Q3z |
| 241 | Q1i | H | H | Q3v |
| 242 | Q1i | H | H | Q3w |
| 243 | Q1i | H | H | Q3x |
| 244 | Q1i | H | H | Q3y |
| 245 | Q1i | H | H | Q3z |
| 246 | Q1i | H | Me | Q3v |
| 247 | Q1i | H | Me | Q3w |
| 248 | Q1i | H | Me | Q3x |
| 249 | Q1i | H | Me | Q3y |
| 250 | Q1i | H | Me | Q3z |
| 251 | Q1i | Me | H | Q3v |
| 252 | Q1i | Me | H | Q3w |
| 253 | Q1i | Me | H | Q3x |
| 254 | Q1i | Me | H | Q3y |
| 255 | Q1i | Me | H | Q3z |
| 256 | Q1i | Me | Me | Q3v |
| 257 | Q1i | Me | Me | Q3w |
| 258 | Q1i | Me | Me | Q3x |
| 259 | Q1i | Me | Me | Q3y |
| 260 | Q1i | Me | Me | Q3z |
| 261 | Q1i | CF3 | H | Q3v |
| 262 | Q1i | CF3 | H | Q3w |
| 263 | Q1i | CF3 | H | Q3x |
| 264 | Q1i | CF3 | H | Q3y |
| 265 | Q1i | CF3 | H | Q3z |
| 266 | Q1i | CF3 | Me | Q3v |
| 267 | Q1i | CF3 | Me | Q3w |
| 268 | Q1i | CF3 | Me | Q3x |
| 269 | Q1i | CF3 | Me | Q3y |
| 270 | Q1i | CF3 | Me | Q3z |
| 271 | Q1j | H | H | Q3v |
| 272 | Q1j | H | H | Q3w |
| 273 | Q1j | H | H | Q3x |
| 274 | Q1j | H | H | Q3y |
| 275 | Q1j | H | H | Q3z |
| 276 | Q1j | H | Me | Q3v |
| 277 | Q1j | H | Me | Q3w |
| 278 | Q1j | H | Me | Q3x |
| 279 | Q1j | H | Me | Q3y |
| 280 | Q1j | H | Me | Q3z |
| 281 | Q1j | Me | H | Q3v |
| 282 | Q1j | Me | H | Q3w |

TABLE 2-continued

| No | R$^1$ | R$^2$ | R$^3$ | R$^4$ |
|---|---|---|---|---|
| 283 | Q1j | Me | H | Q3x |
| 284 | Q1j | Me | H | Q3y |
| 285 | Q1j | Me | H | Q3z |
| 286 | Q1j | Me | Me | Q3v |
| 287 | Q1j | Me | Me | Q3w |
| 288 | Q1j | Me | Me | Q3x |
| 289 | Q1j | Me | Me | Q3y |
| 290 | Q1j | Me | Me | Q3z |
| 291 | Q1j | CF3 | H | Q3v |
| 292 | Q1j | CF3 | H | Q3w |
| 293 | Q1j | CF3 | H | Q3x |
| 294 | Q1j | CF3 | H | Q3y |
| 295 | Q1j | CF3 | H | Q3z |
| 296 | Q1j | CF3 | Me | Q3v |
| 297 | Q1j | CF3 | Me | Q3w |
| 298 | Q1j | CF3 | Me | Q3x |
| 299 | Q1j | CF3 | Me | Q3y |
| 300 | Q1j | CF3 | Me | Q3z |
| 301 | Q1k | H | H | Q3v |
| 302 | Q1k | H | H | Q3w |
| 303 | Q1k | H | H | Q3x |
| 304 | Q1k | H | H | Q3y |
| 305 | Q1k | H | H | Q3z |
| 306 | Q1k | H | Me | Q3v |
| 307 | Q1k | H | Me | Q3w |
| 308 | Q1k | H | Me | Q3x |
| 309 | Q1k | H | Me | Q3y |
| 310 | Q1k | H | Me | Q3z |
| 311 | Q1k | Me | H | Q3v |
| 312 | Q1k | Me | H | Q3w |
| 313 | Q1k | Me | H | Q3x |
| 314 | Q1k | Me | H | Q3y |
| 315 | Q1k | Me | H | Q3z |
| 316 | Q1k | Me | Me | Q3v |
| 317 | Q1k | Me | Me | Q3w |
| 318 | Q1k | Me | Me | Q3x |
| 319 | Q1k | Me | Me | Q3y |
| 320 | Q1k | Me | Me | Q3z |
| 321 | Q1k | CF3 | H | Q3v |
| 322 | Q1k | CF3 | H | Q3w |
| 323 | Q1k | CF3 | H | Q3x |
| 324 | Q1k | CF3 | H | Q3y |
| 325 | Q1k | CF3 | H | Q3z |
| 326 | Q1k | CF3 | Me | Q3v |
| 327 | Q1k | CF3 | Me | Q3w |
| 328 | Q1k | CF3 | Me | Q3x |
| 329 | Q1k | CF3 | Me | Q3y |
| 330 | Q1k | CF3 | Me | Q3z |
| 331 | Q1l | H | H | Q3v |
| 332 | Q1l | H | H | Q3w |
| 333 | Q1l | H | H | Q3x |
| 334 | Q1l | H | H | Q3y |
| 335 | Q1l | H | H | Q3z |
| 336 | Q1l | H | Me | Q3v |
| 337 | Q1l | H | Me | Q3w |
| 338 | Q1l | H | Me | Q3x |
| 339 | Q1l | H | Me | Q3y |
| 340 | Q1l | H | Me | Q3z |
| 341 | Q1l | Me | H | Q3v |
| 342 | Q1l | Me | H | Q3w |
| 343 | Q1l | Me | H | Q3x |
| 344 | Q1l | Me | H | Q3y |
| 345 | Q1l | Me | H | Q3z |
| 346 | Q1l | Me | Me | Q3v |
| 347 | Q1l | Me | Me | Q3w |
| 348 | Q1l | Me | Me | Q3x |
| 349 | Q1l | Me | Me | Q3y |
| 350 | Q1l | Me | Me | Q3z |
| 351 | Q1l | CF3 | H | Q3v |
| 352 | Q1l | CF3 | H | Q3w |
| 353 | Q1l | CF3 | H | Q3x |
| 354 | Q1l | CF3 | H | Q3y |
| 355 | Q1l | CF3 | H | Q3z |
| 356 | Q1l | CF3 | Me | Q3v |
| 357 | Q1l | CF3 | Me | Q3w |
| 358 | Q1l | CF3 | Me | Q3x |
| 359 | Q1l | CF3 | Me | Q3y |
| 360 | Q1l | CF3 | Me | Q3z |
| 361 | Q1m | H | H | Q3v |
| 362 | Q1m | H | H | Q3w |
| 363 | Q1m | H | H | Q3x |
| 364 | Q1m | H | H | Q3y |
| 365 | Q1m | H | H | Q3z |
| 366 | Q1m | H | Me | Q3v |
| 367 | Q1m | H | Me | Q3w |
| 368 | Q1m | H | Me | Q3x |
| 369 | Q1m | H | Me | Q3y |
| 370 | Q1m | H | Me | Q3z |
| 371 | Q1m | Me | H | Q3v |
| 372 | Q1m | Me | H | Q3w |
| 373 | Q1m | Me | H | Q3x |
| 374 | Q1m | Me | H | Q3y |
| 375 | Q1m | Me | H | Q3z |
| 376 | Q1m | Me | Me | Q3v |
| 377 | Q1m | Me | Me | Q3w |
| 378 | Q1m | Me | Me | Q3x |
| 379 | Q1m | Me | Me | Q3y |
| 380 | Q1m | Me | Me | Q3z |
| 381 | Q1m | CF3 | H | Q3v |
| 382 | Q1m | CF3 | H | Q3w |
| 383 | Q1m | CF3 | H | Q3x |
| 384 | Q1m | CF3 | H | Q3y |
| 385 | Q1m | CF3 | H | Q3z |
| 386 | Q1m | CF3 | Me | Q3v |
| 387 | Q1m | CF3 | Me | Q3w |
| 388 | Q1m | CF3 | Me | Q3x |
| 389 | Q1m | CF3 | Me | Q3y |
| 390 | Q1m | CF3 | Me | Q3z |
| 391 | Q1n | H | H | Q3v |
| 392 | Q1n | H | H | Q3w |
| 393 | Q1n | H | H | Q3x |
| 394 | Q1n | H | H | Q3y |
| 395 | Q1n | H | H | Q3z |
| 396 | Q1n | H | Me | Q3v |
| 397 | Q1n | H | Me | Q3w |
| 398 | Q1n | H | Me | Q3x |
| 399 | Q1n | H | Me | Q3y |
| 400 | Q1n | H | Me | Q3z |
| 401 | Q1n | Me | H | Q3v |
| 402 | Q1n | Me | H | Q3w |
| 403 | Q1n | Me | H | Q3x |
| 404 | Q1n | Me | H | Q3y |
| 405 | Q1n | Me | H | Q3z |
| 406 | Q1n | Me | Me | Q3v |
| 407 | Q1n | Me | Me | Q3w |
| 408 | Q1n | Me | Me | Q3x |
| 409 | Q1n | Me | Me | Q3y |
| 410 | Q1n | Me | Me | Q3z |
| 411 | Q1n | CF3 | H | Q3v |
| 412 | Q1n | CF3 | H | Q3w |
| 413 | Q1n | CF3 | H | Q3x |
| 414 | Q1n | CF3 | H | Q3y |
| 415 | Q1n | CF3 | H | Q3z |
| 416 | Q1n | CF3 | Me | Q3v |
| 417 | Q1n | CF3 | Me | Q3w |
| 418 | Q1n | CF3 | Me | Q3x |
| 419 | Q1n | CF3 | Me | Q3y |
| 420 | Q1n | CF3 | Me | Q3z |
| 421 | Q1o | H | H | Q3v |
| 422 | Q1o | H | H | Q3w |
| 423 | Q1o | H | H | Q3x |
| 424 | Q1o | H | H | Q3y |
| 425 | Q1o | H | H | Q3z |
| 426 | Q1o | H | Me | Q3v |
| 427 | Q1o | H | Me | Q3w |
| 428 | Q1o | H | Me | Q3x |
| 429 | Q1o | H | Me | Q3y |
| 430 | Q1o | H | Me | Q3z |
| 431 | Q1o | Me | H | Q3v |
| 432 | Q1o | Me | H | Q3w |
| 433 | Q1o | Me | H | Q3x |
| 434 | Q1o | Me | H | Q3y |
| 435 | Q1o | Me | H | Q3z |
| 436 | Q1o | Me | Me | Q3v |
| 437 | Q1o | Me | Me | Q3w |
| 438 | Q1o | Me | Me | Q3x |

TABLE 2-continued

| No | R¹ | R² | R³ | R⁴ |
|---|---|---|---|---|
| 439 | Q1o | Me | Me | Q3y |
| 440 | Q1o | Me | Me | Q3z |
| 441 | Q1o | CF3 | H | Q3v |
| 442 | Q1o | CF3 | H | Q3w |
| 443 | Q1o | CF3 | H | Q3x |
| 444 | Q1o | CF3 | H | Q3y |
| 445 | Q1o | CF3 | H | Q3z |
| 446 | Q1o | CF3 | Me | Q3v |
| 447 | Q1o | CF3 | Me | Q3w |
| 448 | Q1o | CF3 | Me | Q3x |
| 449 | Q1o | CF3 | Me | Q3y |
| 450 | Q1o | CF3 | Me | Q3z |
| 451 | Q1p | H | H | Q3v |
| 452 | Q1p | H | H | Q3w |
| 453 | Q1p | H | H | Q3x |
| 454 | Q1p | H | H | Q3y |
| 455 | Q1p | H | H | Q3z |
| 456 | Q1p | H | Me | Q3v |
| 457 | Q1p | H | Me | Q3w |
| 458 | Q1p | H | Me | Q3x |
| 459 | Q1p | H | Me | Q3y |
| 460 | Q1p | H | Me | Q3z |
| 461 | Q1p | Me | H | Q3v |
| 462 | Q1p | Me | H | Q3w |
| 463 | Q1p | Me | H | Q3x |
| 464 | Q1p | Me | H | Q3y |
| 465 | Q1p | Me | H | Q3z |
| 466 | Q1p | Me | Me | Q3v |
| 467 | Q1p | Me | Me | Q3w |
| 468 | Q1p | Me | Me | Q3x |
| 469 | Q1p | Me | Me | Q3y |
| 470 | Q1p | Me | Me | Q3z |
| 471 | Q1p | CF3 | H | Q3v |
| 472 | Q1p | CF3 | H | Q3w |
| 473 | Q1p | CF3 | H | Q3x |
| 474 | Q1p | CF3 | H | Q3y |
| 475 | Q1p | CF3 | H | Q3z |
| 476 | Q1p | CF3 | Me | Q3v |
| 477 | Q1p | CF3 | Me | Q3w |
| 478 | Q1p | CF3 | Me | Q3x |
| 479 | Q1p | CF3 | Me | Q3y |
| 480 | Q1p | CF3 | Me | Q3z |
| 481 | Q1q | H | H | Q3v |
| 482 | Q1q | H | H | Q3w |
| 483 | Q1q | H | H | Q3x |
| 484 | Q1q | H | H | Q3y |
| 485 | Q1q | H | H | Q3z |
| 486 | Q1q | H | Me | Q3v |
| 487 | Q1q | H | Me | Q3w |
| 488 | Q1q | H | Me | Q3x |
| 489 | Q1q | H | Me | Q3y |
| 490 | Q1q | H | Me | Q3z |
| 491 | Q1q | Me | H | Q3v |
| 492 | Q1q | Me | H | Q3w |
| 493 | Q1q | Me | H | Q3x |
| 494 | Q1q | Me | H | Q3y |
| 495 | Q1q | Me | H | Q3z |
| 496 | Q1q | Me | Me | Q3v |
| 497 | Q1q | Me | Me | Q3w |
| 498 | Q1q | Me | Me | Q3x |
| 499 | Q1q | Me | Me | Q3y |
| 500 | Q1q | Me | Me | Q3z |
| 501 | Q1q | CF3 | H | Q3v |
| 502 | Q1q | CF3 | H | Q3w |
| 503 | Q1q | CF3 | H | Q3x |
| 504 | Q1q | CF3 | H | Q3y |
| 505 | Q1q | CF3 | H | Q3z |
| 506 | Q1q | CF3 | Me | Q3v |
| 507 | Q1q | CF3 | Me | Q3w |
| 508 | Q1q | CF3 | Me | Q3x |
| 509 | Q1q | CF3 | Me | Q3y |
| 510 | Q1q | CF3 | Me | Q3z |
| 511 | Q1r | H | H | Q3v |
| 512 | Q1r | H | H | Q3w |
| 513 | Q1r | H | H | Q3x |
| 514 | Q1r | H | H | Q3y |
| 515 | Q1r | H | H | Q3z |
| 516 | Q1r | H | Me | Q3v |
| 517 | Q1r | H | Me | Q3w |
| 518 | Q1r | H | Me | Q3x |
| 519 | Q1r | H | Me | Q3y |
| 520 | Q1r | H | Me | Q3z |
| 521 | Q1r | Me | H | Q3v |
| 522 | Q1r | Me | H | Q3w |
| 523 | Q1r | Me | H | Q3x |
| 524 | Q1r | Me | H | Q3y |
| 525 | Q1r | Me | H | Q3z |
| 526 | Q1r | Me | Me | Q3v |
| 527 | Q1r | Me | Me | Q3w |
| 528 | Q1r | Me | Me | Q3x |
| 529 | Q1r | Me | Me | Q3y |
| 530 | Q1r | Me | Me | Q3z |
| 531 | Q1r | CF3 | H | Q3v |
| 532 | Q1r | CF3 | H | Q3w |
| 533 | Q1r | CF3 | H | Q3x |
| 534 | Q1r | CF3 | H | Q3y |
| 535 | Q1r | CF3 | H | Q3z |
| 536 | Q1r | CF3 | Me | Q3v |
| 537 | Q1r | CF3 | Me | Q3w |
| 538 | Q1r | CF3 | Me | Q3x |
| 539 | Q1r | CF3 | Me | Q3y |
| 540 | Q1r | CF3 | Me | Q3z |
| 541 | Q1s | H | H | Q3v |
| 542 | Q1s | H | H | Q3w |
| 543 | Q1s | H | H | Q3x |
| 544 | Q1s | H | H | Q3y |
| 545 | Q1s | H | H | Q3z |
| 546 | Q1s | H | Me | Q3v |
| 547 | Q1s | H | Me | Q3w |
| 548 | Q1s | H | Me | Q3x |
| 549 | Q1s | H | Me | Q3y |
| 550 | Q1s | H | Me | Q3z |
| 551 | Q1s | Me | H | Q3v |
| 552 | Q1s | Me | H | Q3w |
| 553 | Q1s | Me | H | Q3x |
| 554 | Q1s | Me | H | Q3y |
| 555 | Q1s | Me | H | Q3z |
| 556 | Q1s | Me | Me | Q3v |
| 557 | Q1s | Me | Me | Q3w |
| 558 | Q1s | Me | Me | Q3x |
| 559 | Q1s | Me | Me | Q3y |
| 560 | Q1s | Me | Me | Q3z |
| 561 | Q1s | CF3 | H | Q3v |
| 562 | Q1s | CF3 | H | Q3w |
| 563 | Q1s | CF3 | H | Q3x |
| 564 | Q1s | CF3 | H | Q3y |
| 565 | Q1s | CF3 | H | Q3z |
| 566 | Q1s | CF3 | Me | Q3v |
| 567 | Q1s | CF3 | Me | Q3w |
| 568 | Q1s | CF3 | Me | Q3x |
| 569 | Q1s | CF3 | Me | Q3y |
| 570 | Q1s | CF3 | Me | Q3z |
| 571 | Q1t | H | H | Q3v |
| 572 | Q1t | H | H | Q3w |
| 573 | Q1t | H | H | Q3x |
| 574 | Q1t | H | H | Q3y |
| 575 | Q1t | H | H | Q3z |
| 576 | Q1t | H | Me | Q3v |
| 577 | Q1t | H | Me | Q3w |
| 578 | Q1t | H | Me | Q3x |
| 579 | Q1t | H | Me | Q3y |
| 580 | Q1t | H | Me | Q3z |
| 581 | Q1t | Me | H | Q3v |
| 582 | Q1t | Me | H | Q3w |
| 583 | Q1t | Me | H | Q3x |
| 584 | Q1t | Me | H | Q3y |
| 585 | Q1t | Me | H | Q3z |
| 586 | Q1t | Me | Me | Q3v |
| 587 | Q1t | Me | Me | Q3w |
| 588 | Q1t | Me | Me | Q3x |
| 589 | Q1t | Me | Me | Q3y |
| 590 | Q1t | Me | Me | Q3z |
| 591 | Q1t | CF3 | H | Q3v |
| 592 | Q1t | CF3 | H | Q3w |
| 593 | Q1t | CF3 | H | Q3x |
| 594 | Q1t | CF3 | H | Q3y |

TABLE 2-continued

| No | R¹ | R² | R³ | R⁴ |
|---|---|---|---|---|
| 595 | Q1t | CF3 | H | Q3z |
| 596 | Q1t | CF3 | Me | Q3v |
| 597 | Q1t | CF3 | Me | Q3w |
| 598 | Q1t | CF3 | Me | Q3x |
| 599 | Q1t | CF3 | Me | Q3y |
| 600 | Q1t | CF3 | Me | Q3z |
| 601 | Q1u | H | H | Q3v |
| 602 | Q1u | H | H | Q3w |
| 603 | Q1u | H | H | Q3x |
| 604 | Q1u | H | H | Q3y |
| 605 | Q1u | H | H | Q3z |
| 606 | Q1u | H | Me | Q3v |
| 607 | Q1u | H | Me | Q3w |
| 608 | Q1u | H | Me | Q3x |
| 609 | Q1u | H | Me | Q3y |
| 610 | Q1u | H | Me | Q3z |
| 611 | Q1u | Me | H | Q3v |
| 612 | Q1u | Me | H | Q3w |
| 613 | Q1u | Me | H | Q3x |
| 614 | Q1u | Me | H | Q3y |
| 615 | Q1u | Me | H | Q3z |
| 616 | Q1u | Me | Me | Q3v |
| 617 | Q1u | Me | Me | Q3w |
| 618 | Q1u | Me | Me | Q3x |
| 619 | Q1u | Me | Me | Q3y |
| 620 | Q1u | Me | Me | Q3z |
| 621 | Q1u | CF3 | H | Q3v |
| 622 | Q1u | CF3 | H | Q3w |
| 623 | Q1u | CF3 | H | Q3x |
| 624 | Q1u | CF3 | H | Q3y |
| 625 | Q1u | CF3 | H | Q3z |
| 626 | Q1u | CF3 | Me | Q3v |
| 627 | Q1u | CF3 | Me | Q3w |
| 628 | Q1u | CF3 | Me | Q3x |
| 629 | Q1u | CF3 | Me | Q3y |
| 630 | Q1u | CF3 | Me | Q3z |
| 631 | Q1v | H | H | Q3v |
| 632 | Q1v | H | H | Q3w |
| 633 | Q1v | H | H | Q3x |
| 634 | Q1v | H | H | Q3y |
| 635 | Q1v | H | H | Q3z |
| 636 | Q1v | H | Me | Q3v |
| 637 | Q1v | H | Me | Q3w |
| 638 | Q1v | H | Me | Q3x |
| 639 | Q1v | H | Me | Q3y |
| 640 | Q1v | H | Me | Q3z |
| 641 | Q1v | Me | H | Q3v |
| 642 | Q1v | Me | H | Q3w |
| 643 | Q1v | Me | H | Q3x |
| 644 | Q1v | Me | H | Q3y |
| 645 | Q1v | Me | H | Q3z |
| 646 | Q1v | Me | Me | Q3v |
| 647 | Q1v | Me | Me | Q3w |
| 648 | Q1v | Me | Me | Q3x |
| 649 | Q1v | Me | Me | Q3y |
| 650 | Q1v | Me | Me | Q3z |
| 651 | Q1v | CF3 | H | Q3v |
| 652 | Q1v | CF3 | H | Q3w |
| 653 | Q1v | CF3 | H | Q3x |
| 654 | Q1v | CF3 | H | Q3y |
| 655 | Q1v | CF3 | H | Q3z |
| 656 | Q1v | CF3 | Me | Q3v |
| 657 | Q1v | CF3 | Me | Q3w |
| 658 | Q1v | CF3 | Me | Q3x |
| 659 | Q1v | CF3 | Me | Q3y |
| 660 | Q1v | CF3 | Me | Q3z |
| 661 | Q1w | H | H | Q3v |
| 662 | Q1w | H | H | Q3w |
| 663 | Q1w | H | H | Q3x |
| 664 | Q1w | H | H | Q3y |
| 665 | Q1w | H | H | Q3z |
| 666 | Q1w | H | Me | Q3v |
| 667 | Q1w | H | Me | Q3w |
| 668 | Q1w | H | Me | Q3x |
| 669 | Q1w | H | Me | Q3y |
| 670 | Q1w | H | Me | Q3z |
| 671 | Q1w | Me | H | Q3v |
| 672 | Q1w | Me | H | Q3w |
| 673 | Q1w | Me | H | Q3x |
| 674 | Q1w | Me | H | Q3y |
| 675 | Q1w | Me | H | Q3z |
| 676 | Q1w | Me | Me | Q3v |
| 677 | Q1w | Me | Me | Q3w |
| 678 | Q1w | Me | Me | Q3x |
| 679 | Q1w | Me | Me | Q3y |
| 680 | Q1w | Me | Me | Q3z |
| 681 | Q1w | CF3 | H | Q3v |
| 682 | Q1w | CF3 | H | Q3w |
| 683 | Q1w | CF3 | H | Q3x |
| 684 | Q1w | CF3 | H | Q3y |
| 685 | Q1w | CF3 | H | Q3z |
| 686 | Q1w | CF3 | Me | Q3v |
| 687 | Q1w | CF3 | Me | Q3w |
| 688 | Q1w | CF3 | Me | Q3x |
| 689 | Q1w | CF3 | Me | Q3y |
| 690 | Q1w | CF3 | Me | Q3z |
| 691 | Q1x | H | H | Q3v |
| 692 | Q1x | H | H | Q3w |
| 693 | Q1x | H | H | Q3x |
| 694 | Q1x | H | H | Q3y |
| 695 | Q1x | H | H | Q3z |
| 696 | Q1x | H | Me | Q3v |
| 697 | Q1x | H | Me | Q3w |
| 698 | Q1x | H | Me | Q3x |
| 699 | Q1x | H | Me | Q3y |
| 700 | Q1x | H | Me | Q3z |
| 701 | Q1x | Me | H | Q3v |
| 702 | Q1x | Me | H | Q3w |
| 703 | Q1x | Me | H | Q3x |
| 704 | Q1x | Me | H | Q3y |
| 705 | Q1x | Me | H | Q3z |
| 706 | Q1x | Me | Me | Q3v |
| 707 | Q1x | Me | Me | Q3w |
| 708 | Q1x | Me | Me | Q3x |
| 709 | Q1x | Me | Me | Q3y |
| 710 | Q1x | Me | Me | Q3z |
| 711 | Q1x | CF3 | H | Q3v |
| 712 | Q1x | CF3 | H | Q3w |
| 713 | Q1x | CF3 | H | Q3x |
| 714 | Q1x | CF3 | H | Q3y |
| 715 | Q1x | CF3 | H | Q3z |
| 716 | Q1x | CF3 | Me | Q3v |
| 717 | Q1x | CF3 | Me | Q3w |
| 718 | Q1x | CF3 | Me | Q3x |
| 719 | Q1x | CF3 | Me | Q3y |
| 720 | Q1x | CF3 | Me | Q3z |
| 721 | Q1y | H | H | Q3v |
| 722 | Q1y | H | H | Q3w |
| 723 | Q1y | H | H | Q3x |
| 724 | Q1y | H | H | Q3y |
| 725 | Q1y | H | H | Q3z |
| 726 | Q1y | H | Me | Q3v |
| 727 | Q1y | H | Me | Q3w |
| 728 | Q1y | H | Me | Q3x |
| 729 | Q1y | H | Me | Q3y |
| 730 | Q1y | H | Me | Q3z |
| 731 | Q1y | Me | H | Q3v |
| 732 | Q1y | Me | H | Q3w |
| 733 | Q1y | Me | H | Q3x |
| 734 | Q1y | Me | H | Q3y |
| 735 | Q1y | Me | H | Q3z |
| 736 | Q1y | Me | Me | Q3v |
| 737 | Q1y | Me | Me | Q3w |
| 738 | Q1y | Me | Me | Q3x |
| 739 | Q1y | Me | Me | Q3y |
| 740 | Q1y | Me | Me | Q3z |
| 741 | Q1y | CF3 | H | Q3v |
| 742 | Q1y | CF3 | H | Q3w |
| 743 | Q1y | CF3 | H | Q3x |
| 744 | Q1y | CF3 | H | Q3y |
| 745 | Q1y | CF3 | H | Q3z |
| 746 | Q1y | CF3 | Me | Q3v |
| 747 | Q1y | CF3 | Me | Q3w |
| 748 | Q1y | CF3 | Me | Q3x |
| 749 | Q1y | CF3 | Me | Q3y |
| 750 | Q1y | CF3 | Me | Q3z |

TABLE 2-continued

| No | R¹ | R² | R³ | R⁴ |
|---|---|---|---|---|
| 751 | Q1z | H | H | Q3v |
| 752 | Q1z | H | H | Q3w |
| 753 | Q1z | H | H | Q3x |
| 754 | Q1z | H | H | Q3y |
| 755 | Q1z | H | H | Q3z |
| 756 | Q1z | H | Me | Q3v |
| 757 | Q1z | H | Me | Q3w |
| 758 | Q1z | H | Me | Q3x |
| 759 | Q1z | H | Me | Q3y |
| 760 | Q1z | H | Me | Q3z |
| 761 | Q1z | Me | H | Q3v |
| 762 | Q1z | Me | H | Q3w |
| 763 | Q1z | Me | H | Q3x |
| 764 | Q1z | Me | H | Q3y |
| 765 | Q1z | Me | H | Q3z |
| 766 | Q1z | Me | Me | Q3v |
| 767 | Q1z | Me | Me | Q3w |
| 768 | Q1z | Me | Me | Q3x |
| 769 | Q1z | Me | Me | Q3y |
| 770 | Q1z | Me | Me | Q3z |
| 771 | Q1z | CF3 | H | Q3v |
| 772 | Q1z | CF3 | H | Q3w |
| 773 | Q1z | CF3 | H | Q3x |
| 774 | Q1z | CF3 | H | Q3y |
| 775 | Q1z | CF3 | H | Q3z |
| 776 | Q1z | CF3 | Me | Q3v |
| 777 | Q1z | CF3 | Me | Q3w |
| 778 | Q1z | CF3 | Me | Q3x |
| 779 | Q1z | CF3 | Me | Q3y |
| 780 | Q1z | CF3 | Me | Q3z |

132) The compounds wherein $R^7$, $R^8$, $R^9$ and $R^{10}$ are any of the following combinations in Table 3, tautomers, prodrugs or pharmaceutically acceptable salts of the compounds or solvates thereof. The symbols in Table 3 denote the following substituents.

Formula 12

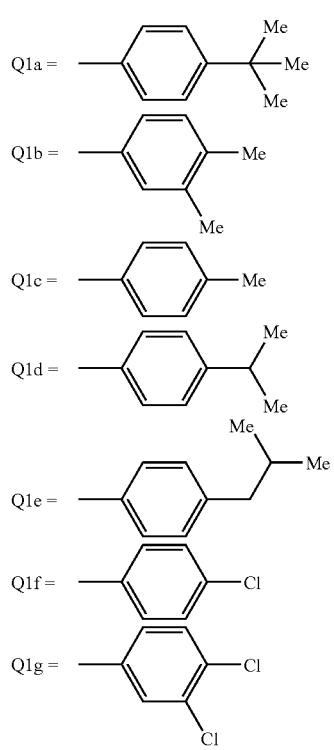

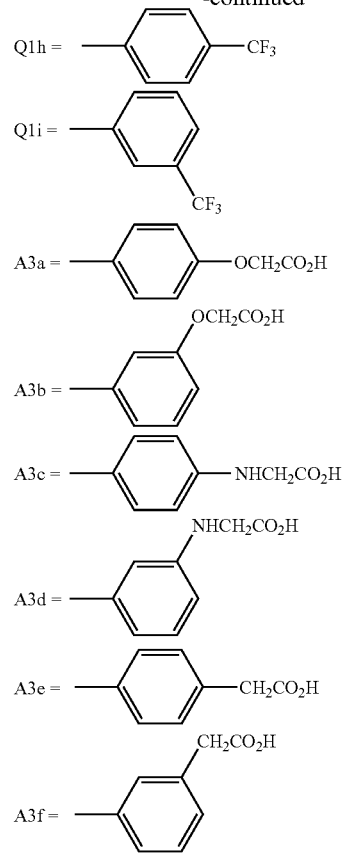

TABLE 3

| No | R⁷ | R⁸ | R⁹ | R¹⁰ |
|---|---|---|---|---|
| 1 | Q1a | Me | Me | A3a |
| 2 | Q1a | Me | Me | A3b |
| 3 | Q1a | Me | Me | A3c |
| 4 | Q1a | Me | Me | A3d |
| 5 | Q1a | Me | Me | A3e |
| 6 | Q1a | Me | Me | A3f |
| 7 | Q1a | Me | H | A3a |
| 8 | Q1a | Me | H | A3b |
| 9 | Q1a | Me | H | A3c |
| 10 | Q1a | Me | H | A3d |
| 11 | Q1a | Me | H | A3e |
| 12 | Q1a | Me | H | A3f |
| 13 | Q1a | CF3 | Me | A3a |
| 14 | Q1a | CF3 | Me | A3b |
| 15 | Q1a | CF3 | Me | A3c |
| 16 | Q1a | CF3 | Me | A3d |
| 17 | Q1a | CF3 | Me | A3e |
| 18 | Q1a | CF3 | Me | A3f |
| 19 | Q1a | CF3 | H | A3a |
| 20 | Q1a | CF3 | H | A3b |
| 21 | Q1a | CF3 | H | A3c |
| 22 | Q1a | CF3 | H | A3d |
| 23 | Q1a | CF3 | H | A3e |
| 24 | Q1a | CF3 | H | A3f |
| 25 | Q1b | Me | Me | A3a |
| 26 | Q1b | Me | Me | A3b |
| 27 | Q1b | Me | Me | A3c |
| 28 | Q1b | Me | Me | A3d |
| 29 | Q1b | Me | Me | A3e |
| 30 | Q1b | Me | Me | A3f |
| 31 | Q1b | Me | H | A3a |
| 32 | Q1b | Me | H | A3b |
| 33 | Q1b | Me | H | A3c |
| 34 | Q1b | Me | H | A3d |

TABLE 3-continued

| No | R⁷ | R⁸ | R⁹ | R¹⁰ |
|---|---|---|---|---|
| 35 | Q1b | Me | H | A3e |
| 36 | Q1b | Me | H | A3f |
| 37 | Q1b | CF3 | Me | A3a |
| 38 | Q1b | CF3 | Me | A3b |
| 39 | Q1b | CF3 | Me | A3c |
| 40 | Q1b | CF3 | Me | A3d |
| 41 | Q1b | CF3 | Me | A3e |
| 42 | Q1b | CF3 | Me | A3f |
| 43 | Q1b | CF3 | H | A3a |
| 44 | Q1b | CF3 | H | A3b |
| 45 | Q1b | CF3 | H | A3c |
| 46 | Q1b | CF3 | H | A3d |
| 47 | Q1b | CF3 | H | A3e |
| 48 | Q1b | CF3 | H | A3f |
| 49 | Q1c | Me | Me | A3a |
| 50 | Q1c | Me | Me | A3b |
| 51 | Q1c | Me | Me | A3c |
| 52 | Q1c | Me | Me | A3d |
| 53 | Q1c | Me | Me | A3e |
| 54 | Q1c | Me | Me | A3f |
| 55 | Q1c | Me | H | A3a |
| 56 | Q1c | Me | H | A3b |
| 57 | Q1c | Me | H | A3c |
| 58 | Q1c | Me | H | A3d |
| 59 | Q1c | Me | H | A3e |
| 60 | Q1c | Me | H | A3f |
| 61 | Q1c | CF3 | Me | A3a |
| 62 | Q1c | CF3 | Me | A3b |
| 63 | Q1c | CF3 | Me | A3c |
| 64 | Q1c | CF3 | Me | A3d |
| 65 | Q1c | CF3 | Me | A3e |
| 66 | Q1c | CF3 | Me | A3f |
| 67 | Q1c | CF3 | H | A3a |
| 68 | Q1c | CF3 | H | A3b |
| 69 | Q1c | CF3 | H | A3c |
| 70 | Q1c | CF3 | H | A3d |
| 71 | Q1c | CF3 | H | A3e |
| 72 | Q1c | CF3 | H | A3f |
| 73 | Q1d | Me | Me | A3a |
| 74 | Q1d | Me | Me | A3b |
| 75 | Q1d | Me | Me | A3c |
| 76 | Q1d | Me | Me | A3d |
| 77 | Q1d | Me | Me | A3e |
| 78 | Q1d | Me | Me | A3f |
| 79 | Q1d | Me | H | A3a |
| 80 | Q1d | Me | H | A3b |
| 81 | Q1d | Me | H | A3c |
| 82 | Q1d | Me | H | A3d |
| 83 | Q1d | Me | H | A3e |
| 84 | Q1d | Me | H | A3f |
| 85 | Q1d | CF3 | Me | A3a |
| 86 | Q1d | CF3 | Me | A3b |
| 87 | Q1d | CF3 | Me | A3c |
| 88 | Q1d | CF3 | Me | A3d |
| 89 | Q1d | CF3 | Me | A3e |
| 90 | Q1d | CF3 | Me | A3f |
| 91 | Q1d | CF3 | H | A3a |
| 92 | Q1d | CF3 | H | A3b |
| 93 | Q1d | CF3 | H | A3c |
| 94 | Q1d | CF3 | H | A3d |
| 95 | Q1d | CF3 | H | A3e |
| 96 | Q1d | CF3 | H | A3f |
| 97 | Q1e | Me | Me | A3a |
| 98 | Q1e | Me | Me | A3b |
| 99 | Q1e | Me | Me | A3c |
| 100 | Q1e | Me | Me | A3d |
| 101 | Q1e | Me | Me | A3e |
| 102 | Q1e | Me | Me | A3f |
| 103 | Q1e | Me | H | A3a |
| 104 | Q1e | Me | H | A3b |
| 105 | Q1e | Me | H | A3c |
| 106 | Q1e | Me | H | A3d |
| 107 | Q1e | Me | H | A3e |
| 108 | Q1e | Me | H | A3f |
| 109 | Q1e | CF3 | Me | A3a |
| 110 | Q1e | CF3 | Me | A3b |
| 111 | Q1e | CF3 | Me | A3c |
| 112 | Q1e | CF3 | Me | A3d |
| 113 | Q1e | CF3 | Me | A3e |
| 114 | Q1e | CF3 | Me | A3f |
| 115 | Q1e | CF3 | H | A3a |
| 116 | Q1e | CF3 | H | A3b |
| 117 | Q1e | CF3 | H | A3c |
| 118 | Q1e | CF3 | H | A3d |
| 119 | Q1e | CF3 | H | A3e |
| 120 | Q1e | CF3 | H | A3f |
| 121 | Q1f | Me | Me | A3a |
| 122 | Q1f | Me | Me | A3b |
| 123 | Q1f | Me | Me | A3c |
| 124 | Q1f | Me | Me | A3d |
| 125 | Q1f | Me | Me | A3e |
| 126 | Q1f | Me | Me | A3f |
| 127 | Q1f | Me | H | A3a |
| 128 | Q1f | Me | H | A3b |
| 129 | Q1f | Me | H | A3c |
| 130 | Q1f | Me | H | A3d |
| 131 | Q1f | Me | H | A3e |
| 132 | Q1f | Me | H | A3f |
| 133 | Q1f | CF3 | Me | A3a |
| 134 | Q1f | CF3 | Me | A3b |
| 135 | Q1f | CF3 | Me | A3c |
| 136 | Q1f | CF3 | Me | A3d |
| 137 | Q1f | CF3 | Me | A3e |
| 138 | Q1f | CF3 | Me | A3f |
| 139 | Q1f | CF3 | H | A3a |
| 140 | Q1f | CF3 | H | A3b |
| 141 | Q1f | CF3 | H | A3c |
| 142 | Q1f | CF3 | H | A3d |
| 143 | Q1f | CF3 | H | A3e |
| 144 | Q1f | CF3 | H | A3f |
| 145 | Q1g | Me | Me | A3a |
| 146 | Q1g | Me | Me | A3b |
| 147 | Q1g | Me | Me | A3c |
| 148 | Q1g | Me | Me | A3d |
| 149 | Q1g | Me | Me | A3e |
| 150 | Q1g | Me | Me | A3f |
| 151 | Q1g | Me | H | A3a |
| 152 | Q1g | Me | H | A3b |
| 153 | Q1g | Me | H | A3c |
| 154 | Q1g | Me | H | A3d |
| 155 | Q1g | Me | H | A3e |
| 156 | Q1g | Me | H | A3f |
| 157 | Q1g | CF3 | Me | A3a |
| 158 | Q1g | CF3 | Me | A3b |
| 159 | Q1g | CF3 | Me | A3c |
| 160 | Q1g | CF3 | Me | A3d |
| 161 | Q1g | CF3 | Me | A3e |
| 162 | Q1g | CF3 | Me | A3f |
| 163 | Q1g | CF3 | H | A3a |
| 164 | Q1g | CF3 | H | A3b |
| 165 | Q1g | CF3 | H | A3c |
| 166 | Q1g | CF3 | H | A3d |
| 167 | Q1g | CF3 | H | A3e |
| 168 | Q1g | CF3 | H | A3f |
| 169 | Q1h | Me | Me | A3a |
| 170 | Q1h | Me | Me | A3b |
| 171 | Q1h | Me | Me | A3c |
| 172 | Q1h | Me | Me | A3d |
| 173 | Q1h | Me | Me | A3e |
| 174 | Q1h | Me | Me | A3f |
| 175 | Q1h | Me | H | A3a |
| 176 | Q1h | Me | H | A3b |
| 177 | Q1h | Me | H | A3c |
| 178 | Q1h | Me | H | A3d |
| 179 | Q1h | Me | H | A3e |
| 180 | Q1h | Me | H | A3f |
| 181 | Q1h | CF3 | Me | A3a |
| 182 | Q1h | CF3 | Me | A3b |
| 183 | Q1h | CF3 | Me | A3c |
| 184 | Q1h | CF3 | Me | A3d |
| 185 | Q1h | CF3 | Me | A3e |
| 186 | Q1h | CF3 | Me | A3f |
| 187 | Q1h | CF3 | H | A3a |
| 188 | Q1h | CF3 | H | A3b |
| 189 | Q1h | CF3 | H | A3c |
| 190 | Q1h | CF3 | H | A3d |

TABLE 3-continued

| No | R⁷ | R⁸ | R⁹ | R¹⁰ |
|----|-----|-----|-----|------|
| 191 | Q1h | CF3 | H | A3e |
| 192 | Q1h | CF3 | H | A3f |
| 193 | Q1i | Me | Me | A3a |
| 194 | Q1i | Me | Me | A3b |
| 195 | Q1i | Me | Me | A3c |
| 196 | Q1i | Me | Me | A3d |
| 197 | Q1i | Me | Me | A3e |
| 198 | Q1i | Me | Me | A3f |
| 199 | Q1i | Me | H | A3a |
| 200 | Q1i | Me | H | A3b |
| 201 | O1i | Me | H | A3c |
| 202 | Q1i | Me | H | A3d |
| 203 | Q1i | Me | H | A3e |
| 204 | Q1i | Me | H | A3f |
| 205 | Q1i | CF3 | Me | A3a |
| 206 | Q1i | CF3 | Me | A3b |
| 207 | Q1i | CF3 | Me | A3c |
| 208 | Q1i | CF3 | Me | A3d |
| 209 | Q1i | CF3 | Me | A3e |
| 210 | Q1i | CF3 | Me | A3f |
| 211 | Q1i | CF3 | H | A3a |
| 212 | Q1i | CF3 | H | A3b |
| 213 | Q1i | CF3 | H | A3c |
| 214 | Q1i | CF3 | H | A3d |
| 215 | Q1i | CF3 | H | A3e |
| 216 | Q1i | CF3 | H | A3f |

133) The compounds wherein $R^{12}$, $R^{13}$, $R^{14}$ and $R^{15}$ are any of the following combinations in Table 4, tautomers, prodrugs or pharmaceutically acceptable salts of the compounds or solvates thereof. The symbols in Table 4 denote the following substituents.

Formula 13

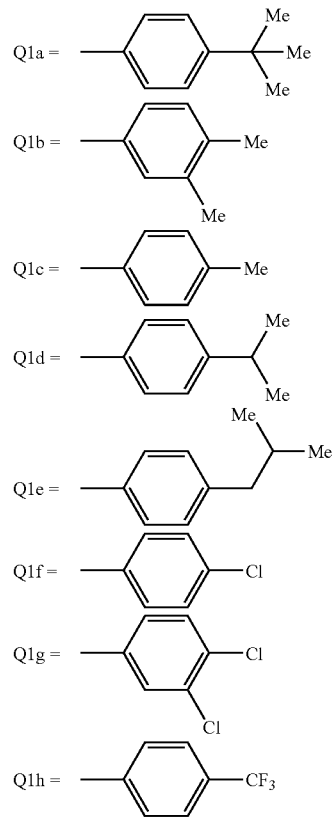

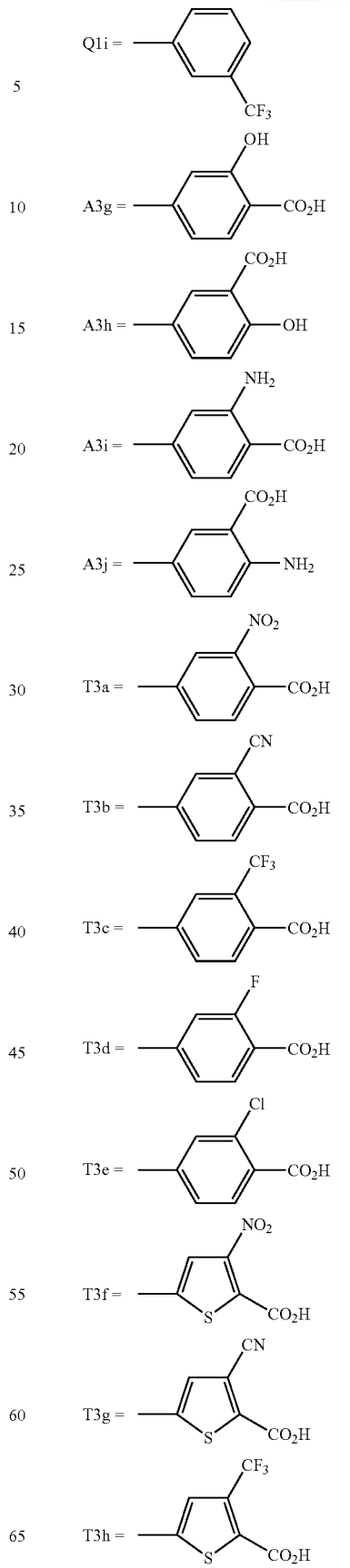

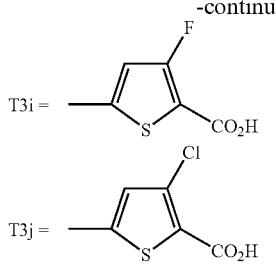

$$T3i = \text{3-fluoro-thiophene-2-carboxylic acid}$$

$$T3j = \text{3-chloro-thiophene-2-carboxylic acid}$$

TABLE 4

| No | R$^{12}$ | R$^{13}$ | R$^{14}$ | R$^{15}$ |
|---|---|---|---|---|
| 1 | Q1a | Me | H | A3g |
| 2 | Q1a | Me | H | A3h |
| 3 | Q1a | Me | H | A3i |
| 4 | Q1a | Me | H | A3j |
| 5 | Q1a | Me | Me | A3g |
| 6 | Q1a | Me | Me | A3h |
| 7 | Q1a | Me | Me | A3i |
| 8 | Q1a | Me | Me | A3j |
| 9 | Q1a | CF3 | H | A3g |
| 10 | Q1a | CF3 | H | A3h |
| 11 | Q1a | CF3 | H | A3i |
| 12 | Q1a | CF3 | H | A3j |
| 13 | Q1a | CF3 | Me | A3g |
| 14 | Q1a | CF3 | Me | A3h |
| 15 | Q1a | CF3 | Me | A3i |
| 16 | Q1a | CF3 | Me | A3j |
| 17 | Q1b | Me | H | A3g |
| 18 | Q1b | Me | H | A3h |
| 19 | Q1b | Me | H | A3i |
| 20 | Q1b | Me | H | A3j |
| 21 | Q1b | Me | Me | A3g |
| 22 | Q1b | Me | Me | A3h |
| 23 | Q1b | Me | Me | A3i |
| 24 | Q1b | Me | Me | A3j |
| 25 | Q1b | CF3 | H | A3g |
| 26 | Q1b | CF3 | H | A3h |
| 27 | Q1b | CF3 | H | A3i |
| 28 | Q1b | CF3 | H | A3j |
| 29 | Q1b | CF3 | Me | A3g |
| 30 | Q1b | CF3 | Me | A3h |
| 31 | Q1b | CF3 | Me | A3i |
| 32 | Q1b | CF3 | Me | A3j |
| 33 | Q1c | Me | H | A3g |
| 34 | Q1c | Me | H | A3h |
| 35 | Q1c | Me | H | A3i |
| 36 | Q1c | Me | H | A3j |
| 37 | Q1c | Me | Me | A3g |
| 38 | Q1c | Me | Me | A3h |
| 39 | Q1c | Me | Me | A3i |
| 40 | Q1c | Me | Me | A3j |
| 41 | Q1c | CF3 | H | A3g |
| 42 | Q1c | CF3 | H | A3h |
| 43 | Q1c | CF3 | H | A3i |
| 44 | Q1c | CF3 | H | A3j |
| 45 | Q1c | CF3 | Me | A3g |
| 46 | Q1c | CF3 | Me | A3h |
| 47 | Q1c | CF3 | Me | A3i |
| 48 | Q1c | CF3 | Me | A3j |
| 49 | Q1d | Me | H | A3g |
| 50 | Q1d | Me | H | A3h |
| 51 | Q1d | Me | H | A3i |
| 52 | Q1d | Me | H | A3j |
| 53 | Q1d | Me | Me | A3g |
| 54 | Q1d | Me | Me | A3h |
| 55 | Q1d | Me | Me | A3i |
| 56 | Q1d | Me | Me | A3j |
| 57 | Q1d | CF3 | H | A3g |
| 58 | Q1d | CF3 | H | A3h |
| 59 | Q1d | CF3 | H | A3i |
| 60 | Q1d | CF3 | H | A3j |
| 61 | Q1d | CF3 | Me | A3g |
| 62 | Q1d | CF3 | Me | A3h |
| 63 | Q1d | CF3 | Me | A3i |
| 64 | Q1d | CF3 | Me | A3j |
| 65 | Q1e | Me | H | A3g |
| 66 | Q1e | Me | H | A3h |
| 67 | Q1e | Me | H | A3i |
| 68 | Q1e | Me | H | A3j |
| 69 | Q1e | Me | Me | A3g |
| 70 | Q1e | Me | Me | A3h |
| 71 | Q1e | Me | Me | A3i |
| 72 | Q1e | Me | Me | A3j |
| 73 | Q1e | CF3 | H | A3g |
| 74 | Q1e | CF3 | H | A3h |
| 75 | Q1e | CF3 | H | A3i |
| 76 | Q1e | CF3 | H | A3j |
| 77 | Q1e | CF3 | Me | A3g |
| 78 | Q1e | CF3 | Me | A3h |
| 79 | Q1e | CF3 | Me | A3i |
| 80 | Q1e | CF3 | Me | A3j |
| 81 | Q1f | Me | H | A3g |
| 82 | Q1f | Me | H | A3h |
| 83 | Q1f | Me | H | A3i |
| 84 | Q1f | Me | H | A3j |
| 85 | Q1f | Me | Me | A3g |
| 86 | Q1f | Me | Me | A3h |
| 87 | Q1f | Me | Me | A3i |
| 88 | Q1f | Me | Me | A3j |
| 89 | Q1f | CF3 | H | A3g |
| 90 | Q1f | CF3 | H | A3h |
| 91 | Q1f | CF3 | H | A3i |
| 92 | Q1f | CF3 | H | A3j |
| 93 | Q1f | CF3 | Me | A3g |
| 94 | Q1f | CF3 | Me | A3h |
| 95 | Q1f | CF3 | Me | A3i |
| 96 | Q1f | CF3 | Me | A3j |
| 97 | Q1g | Me | H | A3g |
| 98 | Q1g | Me | H | A3h |
| 99 | Q1g | Me | H | A3i |
| 100 | Q1g | Me | H | A3j |
| 101 | Q1g | Me | Me | A3g |
| 102 | Q1g | Me | Me | A3h |
| 103 | Q1g | Me | Me | A3i |
| 104 | Q1g | Me | Me | A3j |
| 105 | Q1g | CF3 | H | A3g |
| 106 | Q1g | CF3 | H | A3h |
| 107 | Q1g | CF3 | H | A3i |
| 108 | Q1g | CF3 | H | A3j |
| 109 | Q1g | CF3 | Me | A3g |
| 110 | Q1g | CF3 | Me | A3h |
| 111 | Q1g | CF3 | Me | A3i |
| 112 | Q1g | CF3 | Me | A3j |
| 113 | Q1h | Me | H | A3g |
| 114 | Q1h | Me | H | A3h |
| 115 | Q1h | Me | H | A3i |
| 116 | Q1h | Me | H | A3j |
| 117 | Q1h | Me | Me | A3g |
| 118 | Q1h | Me | Me | A3h |
| 119 | Q1h | Me | Me | A3i |
| 120 | Q1h | Me | Me | A3j |
| 121 | Q1h | CF3 | H | A3g |
| 122 | Q1h | CF3 | H | A3h |
| 123 | Q1h | CF3 | H | A3i |
| 124 | Q1h | CF3 | H | A3j |
| 125 | Q1h | CF3 | Me | A3g |
| 126 | Q1h | CF3 | Me | A3h |
| 127 | Q1h | CF3 | Me | A3i |
| 128 | Q1h | CF3 | Me | A3j |
| 129 | Q1i | Me | H | A3g |
| 130 | Q1i | Me | H | A3h |
| 131 | Q1i | Me | H | A3i |
| 132 | Q1i | Me | H | A3j |
| 133 | Q1i | Me | Me | A3g |
| 134 | Q1i | Me | Me | A3h |
| 135 | Q1i | Me | Me | A3i |
| 136 | Q1i | Me | Me | A3j |
| 137 | Q1i | CF3 | H | A3g |
| 138 | Q1i | CF3 | H | A3h |
| 139 | Q1i | CF3 | H | A3i |
| 140 | Q1i | CF3 | H | A3j |

TABLE 4-continued

| No | R$^{12}$ | R$^{13}$ | R$^{14}$ | R$^{15}$ |
|---|---|---|---|---|
| 141 | Q1i | CF3 | Me | A3g |
| 142 | Q1i | CF3 | Me | A3h |
| 143 | Q1i | CF3 | Me | A3i |
| 144 | Q1i | CF3 | Me | A3j |
| 145 | Q1a | H | H | T3a |
| 146 | Q1a | H | H | T3b |
| 147 | Q1a | H | H | T3c |
| 148 | Q1a | H | H | T3d |
| 149 | Q1a | H | H | T3e |
| 150 | Q1a | H | H | T3f |
| 151 | Q1a | H | H | T3g |
| 152 | Q1a | H | H | T3h |
| 153 | Q1a | H | H | T3i |
| 154 | Q1a | H | H | T3j |
| 155 | Q1a | H | Me | T3a |
| 156 | Q1a | H | Me | T3b |
| 157 | Q1a | H | Me | T3c |
| 158 | Q1a | H | Me | T3d |
| 159 | Q1a | H | Me | T3e |
| 160 | Q1a | H | Me | T3f |
| 161 | Q1a | H | Me | T3g |
| 162 | Q1a | H | Me | T3h |
| 163 | Q1a | H | Me | T3i |
| 164 | Q1a | H | Me | T3j |
| 165 | Q1a | Me | H | T3a |
| 166 | Q1a | Me | H | T3b |
| 167 | Q1a | Me | H | T3c |
| 168 | Q1a | Me | H | T3d |
| 169 | Q1a | Me | H | T3e |
| 170 | Q1a | Me | H | T3f |
| 171 | Q1a | Me | H | T3g |
| 172 | Q1a | Me | H | T3h |
| 173 | Q1a | Me | H | T3i |
| 174 | Q1a | Me | H | T3j |
| 175 | Q1a | Me | Me | T3a |
| 176 | Q1a | Me | Me | T3b |
| 177 | Q1a | Me | Me | T3c |
| 178 | Q1a | Me | Me | T3d |
| 179 | Q1a | Me | Me | T3e |
| 180 | Q1a | Me | Me | T3f |
| 181 | Q1a | Me | Me | T3g |
| 182 | Q1a | Me | Me | T3h |
| 183 | Q1a | Me | Me | T3i |
| 184 | Q1a | Me | Me | T3j |
| 185 | Q1a | CF3 | H | T3a |
| 186 | Q1a | CF3 | H | T3b |
| 187 | Q1a | CF3 | H | T3c |
| 188 | Q1a | CF3 | H | T3d |
| 189 | Q1a | CF3 | H | T3e |
| 190 | Q1a | CF3 | H | T3f |
| 191 | Q1a | CF3 | H | T3g |
| 192 | Q1a | CF3 | H | T3h |
| 193 | Q1a | CF3 | H | T3i |
| 194 | Q1a | CF3 | H | T3j |
| 195 | Q1a | CF3 | Me | T3a |
| 196 | Q1a | CF3 | Me | T3b |
| 197 | Q1a | CF3 | Me | T3c |
| 198 | Q1a | CF3 | Me | T3d |
| 199 | Q1a | CF3 | Me | T3e |
| 200 | Q1a | CF3 | Me | T3f |
| 201 | Q1a | CF3 | Me | T3g |
| 202 | Q1a | CF3 | Me | T3h |
| 203 | Q1a | CF3 | Me | T3i |
| 204 | Q1a | CF3 | Me | T3j |
| 205 | Q1b | H | H | T3a |
| 206 | Q1b | H | H | T3b |
| 207 | Q1b | H | H | T3c |
| 208 | Q1b | H | H | T3d |
| 209 | Q1b | H | H | T3e |
| 210 | Q1b | H | H | T3f |
| 211 | Q1b | H | H | T3g |
| 212 | Q1b | H | H | T3h |
| 213 | Q1b | H | H | T3i |
| 214 | Q1b | H | H | T3j |
| 215 | Q1b | H | Me | T3a |
| 216 | Q1b | H | Me | T3b |
| 217 | Q1b | H | Me | T3c |
| 218 | Q1b | H | Me | T3d |
| 219 | Q1b | H | Me | T3e |
| 220 | Q1b | H | Me | T3f |
| 221 | Q1b | H | Me | T3g |
| 222 | Q1b | H | Me | T3h |
| 223 | Q1b | H | Me | T3i |
| 224 | Q1b | H | Me | T3j |
| 225 | Q1b | Me | H | T3a |
| 226 | Q1b | Me | H | T3b |
| 227 | Q1b | Me | H | T3c |
| 228 | Q1b | Me | H | T3d |
| 229 | Q1b | Me | H | T3e |
| 230 | Q1b | Me | H | T3f |
| 231 | Q1b | Me | H | T3g |
| 232 | Q1b | Me | H | T3h |
| 233 | Q1b | Me | H | T3i |
| 234 | Q1b | Me | H | T3j |
| 235 | Q1b | Me | Me | T3a |
| 236 | Q1b | Me | Me | T3b |
| 237 | Q1b | Me | Me | T3c |
| 238 | Q1b | Me | Me | T3d |
| 239 | Q1b | Me | Me | T3e |
| 240 | Q1b | Me | Me | T3f |
| 241 | Q1b | Me | Me | T3g |
| 242 | Q1b | Me | Me | T3h |
| 243 | Q1b | Me | Me | T3i |
| 244 | Q1b | Me | Me | T3j |
| 245 | Q1b | CF3 | H | T3a |
| 246 | Q1b | CF3 | H | T3b |
| 247 | Q1b | CF3 | H | T3c |
| 248 | Q1b | CF3 | H | T3d |
| 249 | Q1b | CF3 | H | T3e |
| 250 | Q1b | CF3 | H | T3f |
| 251 | Q1b | CF3 | H | T3g |
| 252 | Q1b | CF3 | H | T3h |
| 253 | Q1b | CF3 | H | T3i |
| 254 | Q1b | CF3 | H | T3j |
| 255 | Q1b | CF3 | Me | T3a |
| 256 | Q1b | CF3 | Me | T3b |
| 257 | Q1b | CF3 | Me | T3c |
| 258 | Q1b | CF3 | Me | T3d |
| 259 | Q1b | CF3 | Me | T3e |
| 260 | Q1b | CF3 | Me | T3f |
| 261 | Q1b | CF3 | Me | T3g |
| 262 | Q1b | CF3 | Me | T3h |
| 263 | Q1b | CF3 | Me | T3i |
| 264 | Q1b | CF3 | Me | T3j |
| 265 | Q1c | H | H | T3a |
| 266 | Q1c | H | H | T3b |
| 267 | Q1c | H | H | T3c |
| 268 | Q1c | H | H | T3d |
| 269 | Q1c | H | H | T3e |
| 270 | Q1c | H | H | T3f |
| 271 | Q1c | H | H | T3g |
| 272 | Q1c | H | H | T3h |
| 273 | Q1c | H | H | T3i |
| 274 | Q1c | H | H | T3j |
| 275 | Q1c | H | Me | T3a |
| 276 | Q1c | H | Me | T3b |
| 277 | Q1c | H | Me | T3c |
| 278 | Q1c | H | Me | T3d |
| 279 | Q1c | H | Me | T3e |
| 280 | Q1c | H | Me | T3f |
| 281 | Q1c | H | Me | T3g |
| 282 | Q1c | H | Me | T3h |
| 283 | Q1c | H | Me | T3i |
| 284 | Q1c | H | Me | T3j |
| 285 | Q1c | Me | H | T3a |
| 286 | Q1c | Me | H | T3b |
| 287 | Q1c | Me | H | T3c |
| 288 | Q1c | Me | H | T3d |
| 289 | Q1c | Me | H | T3e |
| 290 | Q1c | Me | H | T3f |
| 291 | Q1c | Me | H | T3g |
| 292 | Q1c | Me | H | T3h |
| 293 | Q1c | Me | H | T3i |
| 294 | Q1c | Me | H | T3j |
| 295 | Q1c | Me | Me | T3a |
| 296 | Q1c | Me | Me | T3b |

TABLE 4-continued

| No | $R^{12}$ | $R^{13}$ | $R^{14}$ | $R^{15}$ |
|---|---|---|---|---|
| 297 | Q1c | Me | Me | T3c |
| 298 | Q1c | Me | Me | T3d |
| 299 | Q1c | Me | Me | T3e |
| 300 | Q1c | Me | Me | T3f |
| 301 | Q1c | Me | Me | T3g |
| 302 | Q1c | Me | Me | T3h |
| 303 | Q1c | Me | Me | T3i |
| 304 | Q1c | Me | Me | T3j |
| 305 | Q1c | CF3 | H | T3a |
| 306 | Q1c | CF3 | H | T3b |
| 307 | Q1c | CF3 | H | T3c |
| 308 | Q1c | CF3 | H | T3d |
| 309 | Q1c | CF3 | H | T3e |
| 310 | Q1c | CF3 | H | T3f |
| 311 | Q1c | CF3 | H | T3g |
| 312 | Q1c | CF3 | H | T3h |
| 313 | Q1c | CF3 | H | T3i |
| 314 | Q1c | CF3 | H | T3j |
| 315 | Q1c | CF3 | Me | T3a |
| 316 | Q1c | CF3 | Me | T3b |
| 317 | Q1c | CF3 | Me | T3c |
| 318 | Q1c | CF3 | Me | T3d |
| 319 | Q1c | CF3 | Me | T3e |
| 320 | Q1c | CF3 | Me | T3f |
| 321 | Q1c | CF3 | Me | T3g |
| 322 | Q1c | CF3 | Me | T3h |
| 323 | Q1c | CF3 | Me | T3i |
| 324 | Q1c | CF3 | Me | T3j |
| 325 | Q1g | H | H | T3a |
| 326 | Q1g | H | H | T3b |
| 327 | Q1g | H | H | T3c |
| 328 | Q1g | H | H | T3d |
| 329 | Q1g | H | H | T3e |
| 330 | Q1g | H | H | T3f |
| 331 | Q1g | H | H | T3g |
| 332 | Q1g | H | H | T3h |
| 333 | Q1g | H | H | T3i |
| 334 | Q1g | H | H | T3j |
| 335 | Q1g | H | Me | T3a |
| 336 | Q1g | H | Me | T3b |
| 337 | Q1g | H | Me | T3c |
| 338 | Q1g | H | Me | T3d |
| 339 | Q1g | H | Me | T3e |
| 340 | Q1g | H | Me | T3f |
| 341 | Q1g | H | Me | T3g |
| 342 | Q1g | H | Me | T3h |
| 343 | Q1g | H | Me | T3i |
| 344 | Q1g | H | Me | T3j |
| 345 | Q1g | Me | H | T3a |
| 346 | Q1g | Me | H | T3b |
| 347 | Q1g | Me | H | T3c |
| 348 | Q1g | Me | H | T3d |
| 349 | Q1g | Me | H | T3e |
| 350 | Q1g | Me | H | T3f |
| 351 | Q1g | Me | H | T3g |
| 352 | Q1g | Me | H | T3h |
| 353 | Q1g | Me | H | T3i |
| 354 | Q1g | Me | H | T3j |
| 355 | Q1g | Me | Me | T3a |
| 356 | Q1g | Me | Me | T3b |
| 357 | Q1g | Me | Me | T3c |
| 358 | Q1g | Me | Me | T3d |
| 359 | Q1g | Me | Me | T3e |
| 360 | Q1g | Me | Me | T3f |
| 361 | Q1g | Me | Me | T3g |
| 362 | Q1g | Me | Me | T3h |
| 363 | Q1g | Me | Me | T3i |
| 364 | Q1g | Me | Me | T3j |
| 365 | Q1g | CF3 | H | T3a |
| 366 | Q1g | CF3 | H | T3b |
| 367 | Q1g | CF3 | H | T3c |
| 368 | Q1g | CF3 | H | T3d |
| 369 | Q1g | CF3 | H | T3e |
| 370 | Q1g | CF3 | H | T3f |
| 371 | Q1g | CF3 | H | T3g |
| 372 | Q1g | CF3 | H | T3h |
| 373 | Q1g | CF3 | H | T3i |
| 374 | Q1g | CF3 | H | T3j |
| 375 | Q1g | CF3 | Me | T3a |
| 376 | Q1g | CF3 | Me | T3b |
| 377 | Q1g | CF3 | Me | T3c |
| 378 | Q1g | CF3 | Me | T3d |
| 379 | Q1g | CF3 | Me | T3e |
| 380 | Q1g | CF3 | Me | T3f |
| 381 | Q1g | CF3 | Me | T3g |
| 382 | Q1g | CF3 | Me | T3h |
| 383 | Q1g | CF3 | Me | T3i |
| 384 | Q1g | CF3 | Me | T3j |
| 385 | Q1h | H | H | T3a |
| 386 | Q1h | H | H | T3b |
| 387 | Q1h | H | H | T3c |
| 388 | Q1h | H | H | T3d |
| 389 | Q1h | H | H | T3e |
| 390 | Q1h | H | H | T3f |
| 391 | Q1h | H | H | T3g |
| 392 | Q1h | H | H | T3h |
| 393 | Q1h | H | H | T3i |
| 394 | Q1h | H | H | T3j |
| 395 | Q1h | H | Me | T3a |
| 396 | Q1h | H | Me | T3b |
| 397 | Q1h | H | Me | T3c |
| 398 | Q1h | H | Me | T3d |
| 399 | Q1h | H | Me | T3e |
| 400 | Q1h | H | Me | T3f |
| 401 | Q1h | H | Me | T3g |
| 402 | Q1h | H | Me | T3h |
| 403 | Q1h | H | Me | T3i |
| 404 | Q1h | H | Me | T3j |
| 405 | Q1h | Me | H | T3a |
| 406 | Q1h | Me | H | T3b |
| 407 | Q1h | Me | H | T3c |
| 408 | Q1h | Me | H | T3d |
| 409 | Q1h | Me | H | T3e |
| 410 | Q1h | Me | H | T3f |
| 411 | Q1h | Me | H | T3g |
| 412 | Q1h | Me | H | T3h |
| 413 | Q1h | Me | H | T3i |
| 414 | Q1h | Me | H | T3j |
| 415 | Q1h | Me | Me | T3a |
| 416 | Q1h | Me | Me | T3b |
| 417 | Q1h | Me | Me | T3c |
| 418 | Q1h | Me | Me | T3d |
| 419 | Q1h | Me | Me | T3e |
| 420 | Q1h | Me | Me | T3f |
| 421 | Q1h | Me | Me | T3g |
| 422 | Q1h | Me | Me | T3h |
| 423 | Q1h | Me | Me | T3i |
| 424 | Q1h | Me | Me | T3j |
| 425 | Q1h | CF3 | H | T3a |
| 426 | Q1h | CF3 | H | T3b |
| 427 | Q1h | CF3 | H | T3c |
| 428 | Q1h | CF3 | H | T3d |
| 429 | Q1h | CF3 | H | T3e |
| 430 | Q1h | CF3 | H | T3f |
| 431 | Q1h | CF3 | H | T3g |
| 432 | Q1h | CF3 | H | T3h |
| 433 | Q1h | CF3 | H | T3i |
| 434 | Q1h | CF3 | H | T3j |
| 435 | Q1h | CF3 | Me | T3a |
| 436 | Q1h | CF3 | Me | T3b |
| 437 | Q1h | CF3 | Me | T3c |
| 438 | Q1h | CF3 | Me | T3d |
| 439 | Q1h | CF3 | Me | T3e |
| 440 | Q1h | CF3 | Me | T3f |
| 441 | Q1h | CF3 | Me | T3g |
| 442 | Q1h | CF3 | Me | T3h |
| 443 | Q1h | CF3 | Me | T3i |
| 444 | Q1h | CF3 | Me | T3j |

134) The compounds wherein $R^7$, $R^8$, $R^9$ and $R^{10}$ are any of the following combinations in Table 5, tautomers, prodrugs or pharmaceutically acceptable salts of the compounds or solvates thereof. The symbols in Table 5 denote the following substituents.

Formula 14
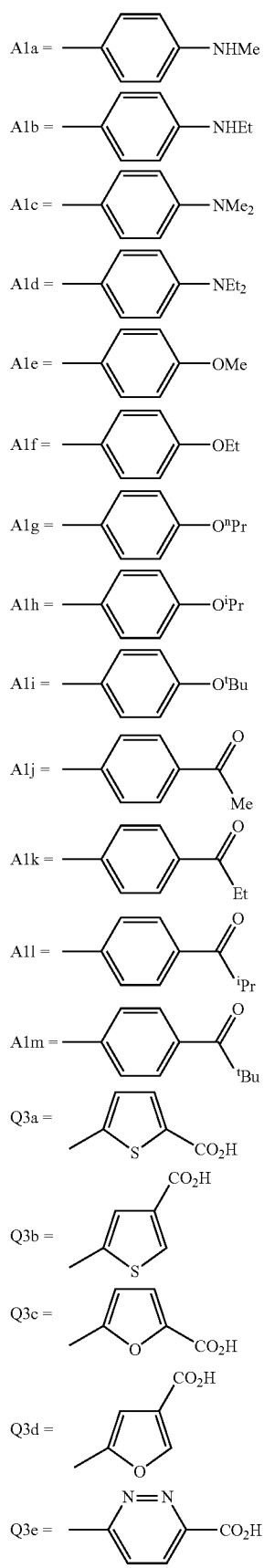
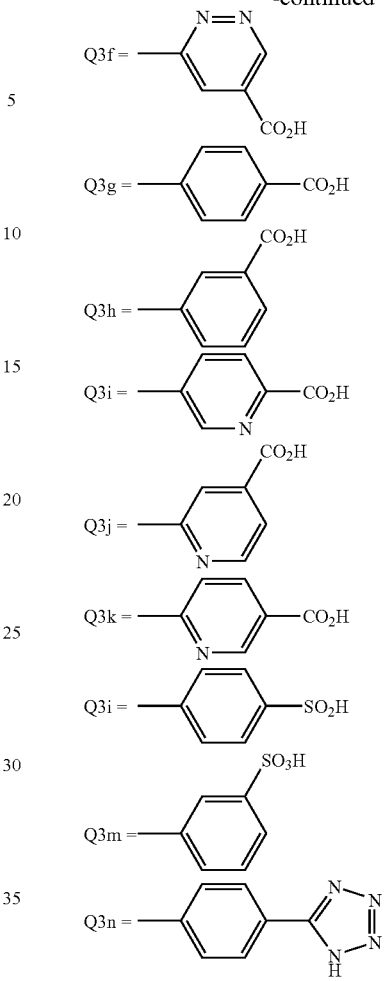
TABLE 5
| No | $R^7$ | $R^8$ | $R^9$ | $R^{10}$ |
|---|---|---|---|---|
| 1 | A1a | Me | H | Q3a |
| 2 | A1a | Me | H | Q3b |
| 3 | A1a | Me | H | Q3c |
| 4 | A1a | Me | H | Q3d |
| 5 | A1a | Me | H | Q3e |
| 6 | A1a | Me | H | Q3f |
| 7 | A1a | Me | H | Q3g |
| 8 | A1a | Me | H | Q3h |
| 9 | A1a | Me | H | Q3i |
| 10 | A1a | Me | H | Q3j |
| 11 | A1a | Me | H | Q3k |
| 12 | A1a | Me | H | Q3l |
| 13 | A1a | Me | H | Q3m |
| 14 | A1a | Me | H | Q3n |
| 15 | A1a | Me | Me | Q3a |
| 16 | A1a | Me | Me | Q3b |
| 17 | A1a | Me | Me | Q3c |
| 18 | A1a | Me | Me | Q3d |
| 19 | A1a | Me | Me | Q3e |
| 20 | A1a | Me | Me | Q3f |
| 21 | A1a | Me | Me | Q3g |
| 22 | A1a | Me | Me | Q3h |
| 23 | A1a | Me | Me | Q3i |
| 24 | A1a | Me | Me | Q3j |
| 25 | A1a | Me | Me | Q3k |
| 26 | A1a | Me | Me | Q3l |
| 27 | A1a | Me | Me | Q3m |
| 28 | A1a | Me | Me | Q3n |

TABLE 5-continued

| No | R⁷ | R⁸ | R⁹ | R¹⁰ |
|---|---|---|---|---|
| 29 | A1b | Me | H | Q3a |
| 30 | A1b | Me | H | Q3b |
| 31 | A1b | Me | H | Q3c |
| 32 | A1b | Me | H | Q3d |
| 33 | A1b | Me | H | Q3e |
| 34 | A1b | Me | H | Q3f |
| 35 | A1b | Me | H | Q3g |
| 36 | A1b | Me | H | Q3h |
| 37 | A1b | Me | H | Q3i |
| 38 | A1b | Me | H | Q3j |
| 39 | A1b | Me | H | Q3k |
| 40 | A1b | Me | H | Q3l |
| 41 | A1b | Me | H | Q3m |
| 42 | A1b | Me | H | Q3n |
| 43 | A1b | Me | Me | Q3a |
| 44 | A1b | Me | Me | Q3b |
| 45 | A1b | Me | Me | Q3c |
| 46 | A1b | Me | Me | Q3d |
| 47 | A1b | Me | Me | Q3e |
| 48 | A1b | Me | Me | Q3f |
| 49 | A1b | Me | Me | Q3g |
| 50 | A1b | Me | Me | Q3h |
| 51 | A1b | Me | Me | Q3i |
| 52 | A1b | Me | Me | Q3j |
| 53 | A1b | Me | Me | Q3k |
| 54 | A1b | Me | Me | Q3l |
| 55 | A1b | Me | Me | Q3m |
| 56 | A1b | Me | Me | Q3n |
| 57 | A1c | Me | H | Q3a |
| 58 | A1c | Me | H | Q3b |
| 59 | A1c | Me | H | Q3c |
| 60 | A1c | Me | H | Q3d |
| 61 | A1c | Me | H | Q3e |
| 62 | A1c | Me | H | Q3f |
| 63 | A1c | Me | H | Q3g |
| 64 | A1c | Me | H | Q3h |
| 65 | A1c | Me | H | Q3i |
| 66 | A1c | Me | H | Q3j |
| 67 | A1c | Me | H | Q3k |
| 68 | A1c | Me | H | Q3l |
| 69 | A1c | Me | H | Q3m |
| 70 | A1c | Me | H | Q3n |
| 71 | A1c | Me | Me | Q3a |
| 72 | A1c | Me | Me | Q3b |
| 73 | A1c | Me | Me | Q3c |
| 74 | A1c | Me | Me | Q3d |
| 75 | A1c | Me | Me | Q3e |
| 76 | A1c | Me | Me | Q3f |
| 77 | A1c | Me | Me | Q3g |
| 78 | A1c | Me | Me | Q3h |
| 79 | A1c | Me | Me | Q3i |
| 80 | A1c | Me | Me | Q3j |
| 81 | A1c | Me | Me | Q3k |
| 82 | A1c | Me | Me | Q3l |
| 83 | A1c | Me | Me | Q3m |
| 84 | A1c | Me | Me | Q3n |
| 85 | A1d | Me | H | Q3a |
| 86 | A1d | Me | H | Q3b |
| 87 | A1d | Me | H | Q3c |
| 88 | A1d | Me | H | Q3d |
| 89 | A1d | Me | H | Q3e |
| 90 | A1d | Me | H | Q3f |
| 91 | A1d | Me | H | Q3g |
| 92 | A1d | Me | H | Q3h |
| 93 | A1d | Me | H | Q3i |
| 94 | A1d | Me | H | Q3j |
| 95 | A1d | Me | H | Q3k |
| 96 | A1d | Me | H | Q3l |
| 97 | A1d | Me | H | Q3m |
| 98 | A1d | Me | H | Q3n |
| 99 | A1d | Me | Me | Q3a |
| 100 | A1d | Me | Me | Q3b |
| 101 | A1d | Me | Me | Q3c |
| 102 | A1d | Me | Me | Q3d |
| 103 | A1d | Me | Me | Q3e |
| 104 | A1d | Me | Me | Q3f |
| 105 | A1d | Me | Me | Q3g |
| 106 | A1d | Me | Me | Q3h |
| 107 | A1d | Me | Me | Q3i |
| 108 | A1d | Me | Me | Q3j |
| 109 | A1d | Me | Me | Q3k |
| 110 | A1d | Me | Me | Q3l |
| 111 | A1d | Me | Me | Q3m |
| 112 | A1d | Me | Me | Q3n |
| 113 | A1e | Me | H | Q3a |
| 114 | A1e | Me | H | Q3b |
| 115 | A1e | Me | H | Q3c |
| 116 | A1e | Me | H | Q3d |
| 117 | A1e | Me | H | Q3e |
| 118 | A1e | Me | H | Q3f |
| 119 | A1e | Me | H | Q3g |
| 120 | A1e | Me | H | Q3h |
| 121 | A1e | Me | H | Q3i |
| 122 | A1e | Me | H | Q3j |
| 123 | A1e | Me | H | Q3k |
| 124 | A1e | Me | H | Q3l |
| 125 | A1e | Me | H | Q3m |
| 126 | A1e | Me | H | Q3n |
| 127 | A1e | Me | Me | Q3a |
| 128 | A1e | Me | Me | Q3b |
| 129 | A1e | Me | Me | Q3c |
| 130 | A1e | Me | Me | Q3d |
| 131 | A1e | Me | Me | Q3e |
| 132 | A1e | Me | Me | Q3f |
| 133 | A1e | Me | Me | Q3g |
| 134 | A1e | Me | Me | Q3h |
| 135 | A1e | Me | Me | Q3i |
| 136 | A1e | Me | Me | Q3j |
| 137 | A1e | Me | Me | Q3k |
| 138 | A1e | Me | Me | Q3l |
| 139 | A1e | Me | Me | Q3m |
| 140 | A1e | Me | Me | Q3n |
| 141 | A1f | Me | H | Q3a |
| 142 | A1f | Me | H | Q3b |
| 143 | A1f | Me | H | Q3c |
| 144 | A1f | Me | H | Q3d |
| 145 | A1f | Me | H | Q3e |
| 146 | A1f | Me | H | Q3f |
| 147 | A1f | Me | H | Q3g |
| 148 | A1f | Me | H | Q3h |
| 149 | A1f | Me | H | Q3i |
| 150 | A1f | Me | H | Q3j |
| 151 | A1f | Me | H | Q3k |
| 152 | A1f | Me | H | Q3l |
| 153 | A1f | Me | H | Q3m |
| 154 | A1f | Me | H | Q3n |
| 155 | A1f | Me | Me | Q3a |
| 156 | A1f | Me | Me | Q3b |
| 157 | A1f | Me | Me | Q3c |
| 158 | A1f | Me | Me | Q3d |
| 159 | A1f | Me | Me | Q3e |
| 160 | A1f | Me | Me | Q3f |
| 161 | A1f | Me | Me | Q3g |
| 162 | A1f | Me | Me | Q3h |
| 163 | A1f | Me | Me | Q3i |
| 164 | A1f | Me | Me | Q3j |
| 165 | A1f | Me | Me | Q3k |
| 166 | A1f | Me | Me | Q3l |
| 167 | A1f | Me | Me | Q3m |
| 168 | A1f | Me | Me | Q3n |
| 169 | A1g | Me | H | Q3a |
| 170 | A1g | Me | H | Q3b |
| 171 | A1g | Me | H | Q3c |
| 172 | A1g | Me | H | Q3d |
| 173 | A1g | Me | H | Q3e |
| 174 | A1g | Me | H | Q3f |
| 175 | A1g | Me | H | Q3g |
| 176 | A1g | Me | H | Q3h |
| 177 | A1g | Me | H | Q3i |
| 178 | A1g | Me | H | Q3j |
| 179 | A1g | Me | H | Q3k |
| 180 | A1g | Me | H | Q3l |
| 181 | A1g | Me | H | Q3m |
| 182 | A1g | Me | H | Q3n |
| 183 | A1g | Me | Me | Q3a |
| 184 | A1g | Me | Me | Q3b |

TABLE 5-continued

| No | R⁷ | R⁸ | R⁹ | R¹⁰ |
|---|---|---|---|---|
| 185 | A1g | Me | Me | Q3c |
| 186 | A1g | Me | Me | Q3d |
| 187 | A1g | Me | Me | Q3e |
| 188 | A1g | Me | Me | Q3f |
| 189 | A1g | Me | Me | Q3g |
| 190 | A1g | Me | Me | Q3h |
| 191 | A1g | Me | Me | Q3i |
| 192 | A1g | Me | Me | Q3j |
| 193 | A1g | Me | Me | Q3k |
| 194 | A1g | Me | Me | Q3l |
| 195 | A1g | Me | Me | Q3m |
| 196 | A1g | Me | Me | Q3n |
| 197 | A1h | Me | H | Q3a |
| 198 | A1h | Me | H | Q3b |
| 199 | A1h | Me | H | Q3c |
| 200 | A1h | Me | H | Q3d |
| 201 | A1h | Me | H | Q3e |
| 202 | A1h | Me | H | Q3f |
| 203 | A1h | Me | H | Q3g |
| 204 | A1h | Me | H | Q3h |
| 205 | A1h | Me | H | Q3i |
| 206 | A1h | Me | H | Q3j |
| 207 | A1h | Me | H | Q3k |
| 208 | A1h | Me | H | Q3l |
| 209 | A1h | Me | H | Q3m |
| 210 | A1h | Me | H | Q3n |
| 211 | A1h | Me | Me | Q3a |
| 212 | A1h | Me | Me | Q3b |
| 213 | A1h | Me | Me | Q3c |
| 214 | A1h | Me | Me | Q3d |
| 215 | A1h | Me | Me | Q3e |
| 216 | A1h | Me | Me | Q3f |
| 217 | A1h | Me | Me | Q3g |
| 218 | A1h | Me | Me | Q3h |
| 219 | A1h | Me | Me | Q3i |
| 220 | A1h | Me | Me | Q3j |
| 221 | A1h | Me | Me | Q3k |
| 222 | A1h | Me | Me | Q3l |
| 223 | A1h | Me | Me | Q3m |
| 224 | A1h | Me | Me | Q3n |
| 225 | A1i | Me | H | Q3a |
| 226 | A1i | Me | H | Q3b |
| 227 | A1i | Me | H | Q3c |
| 228 | A1i | Me | H | Q3d |
| 229 | A1i | Me | H | Q3e |
| 230 | A1i | Me | H | Q3f |
| 231 | A1i | Me | H | Q3g |
| 232 | A1i | Me | H | Q3h |
| 233 | A1i | Me | H | Q3i |
| 234 | A1i | Me | H | Q3j |
| 235 | A1i | Me | H | Q3k |
| 236 | A1i | Me | H | Q3l |
| 237 | A1i | Me | H | Q3m |
| 238 | A1i | Me | H | Q3n |
| 239 | A1i | Me | Me | Q3a |
| 240 | A1i | Me | Me | Q3b |
| 241 | A1i | Me | Me | Q3c |
| 242 | A1i | Me | Me | Q3d |
| 243 | A1i | Me | Me | Q3e |
| 244 | A1i | Me | Me | Q3f |
| 245 | A1i | Me | Me | Q3g |
| 246 | A1i | Me | Me | Q3h |
| 247 | A1i | Me | Me | Q3i |
| 248 | A1i | Me | Me | Q3j |
| 249 | A1i | Me | Me | Q3k |
| 250 | A1i | Me | Me | Q3l |
| 251 | A1i | Me | Me | Q3m |
| 252 | A1i | Me | Me | Q3n |
| 253 | A1j | Me | H | Q3a |
| 254 | A1j | Me | H | Q3b |
| 255 | A1j | Me | H | Q3c |
| 256 | A1j | Me | H | Q3d |
| 257 | A1j | Me | H | Q3e |
| 258 | A1j | Me | H | Q3f |
| 259 | A1j | Me | H | Q3g |
| 260 | A1j | Me | H | Q3h |
| 261 | A1j | Me | H | Q3i |
| 262 | A1j | Me | H | Q3j |
| 263 | A1j | Me | H | Q3k |
| 264 | A1j | Me | H | Q3l |
| 265 | A1j | Me | H | Q3m |
| 266 | A1j | Me | H | Q3n |
| 267 | A1j | Me | Me | Q3a |
| 268 | A1j | Me | Me | Q3b |
| 269 | A1j | Me | Me | Q3c |
| 270 | A1j | Me | Me | Q3d |
| 271 | A1j | Me | Me | Q3e |
| 272 | A1j | Me | Me | Q3f |
| 273 | A1j | Me | Me | Q3g |
| 274 | A1j | Me | Me | Q3h |
| 275 | A1j | Me | Me | Q3i |
| 276 | A1j | Me | Me | Q3j |
| 277 | A1j | Me | Me | Q3k |
| 278 | A1j | Me | Me | Q3l |
| 279 | A1j | Me | Me | Q3m |
| 280 | A1j | Me | Me | Q3n |
| 281 | A1k | Me | H | Q3a |
| 282 | A1k | Me | H | Q3b |
| 283 | A1k | Me | H | Q3c |
| 284 | A1k | Me | H | Q3d |
| 285 | A1k | Me | H | Q3e |
| 286 | A1k | Me | H | Q3f |
| 287 | A1k | Me | H | Q3g |
| 288 | A1k | Me | H | Q3h |
| 289 | A1k | Me | H | Q3i |
| 290 | A1k | Me | H | Q3j |
| 291 | A1k | Me | H | Q3k |
| 292 | A1k | Me | H | Q3l |
| 293 | A1k | Me | H | Q3m |
| 294 | A1k | Me | H | Q3n |
| 295 | A1k | Me | Me | Q3a |
| 296 | A1k | Me | Me | Q3b |
| 297 | A1k | Me | Me | Q3c |
| 298 | A1k | Me | Me | Q3d |
| 299 | A1k | Me | Me | Q3e |
| 300 | A1k | Me | Me | Q3f |
| 301 | A1k | Me | Me | Q3g |
| 302 | A1k | Me | Me | Q3h |
| 303 | A1k | Me | Me | Q3i |
| 304 | A1k | Me | Me | Q3j |
| 305 | A1k | Me | Me | Q3k |
| 306 | A1k | Me | Me | Q3l |
| 307 | A1k | Me | Me | Q3m |
| 308 | A1k | Me | Me | Q3n |
| 309 | A1l | Me | H | Q3a |
| 310 | A1l | Me | H | Q3b |
| 311 | A1l | Me | H | Q3c |
| 312 | A1l | Me | H | Q3d |
| 313 | A1l | Me | H | Q3e |
| 314 | A1l | Me | H | Q3f |
| 315 | A1l | Me | H | Q3g |
| 316 | A1l | Me | H | Q3h |
| 317 | A1l | Me | H | Q3i |
| 318 | A1l | Me | H | Q3j |
| 319 | A1l | Me | H | Q3k |
| 320 | A1l | Me | H | Q3l |
| 321 | A1l | Me | H | Q3m |
| 322 | A1l | Me | H | Q3n |
| 323 | A1l | Me | Me | Q3a |
| 324 | A1l | Me | Me | Q3b |
| 325 | A1l | Me | Me | Q3c |
| 326 | A1l | Me | Me | Q3d |
| 327 | A1l | Me | Me | Q3e |
| 328 | A1l | Me | Me | Q3f |
| 329 | A1l | Me | Me | Q3g |
| 330 | A1l | Me | Me | Q3h |
| 331 | A1l | Me | Me | Q3i |
| 332 | A1l | Me | Me | Q3j |
| 333 | A1l | Me | Me | Q3k |
| 334 | A1l | Me | Me | Q3l |
| 335 | A1l | Me | Me | Q3m |
| 336 | A1l | Me | Me | Q3n |
| 337 | A1m | Me | H | Q3a |
| 338 | A1m | Me | H | Q3b |
| 339 | A1m | Me | H | Q3c |
| 340 | A1m | Me | H | Q3d |

TABLE 5-continued

| No | R⁷ | R⁸ | R⁹ | R¹⁰ |
|---|---|---|---|---|
| 341 | A1m | Me | H | Q3e |
| 342 | A1m | Me | H | Q3f |
| 343 | A1m | Me | H | Q3g |
| 344 | A1m | Me | H | Q3h |
| 345 | A1m | Me | H | Q3i |
| 346 | A1m | Me | H | Q3j |
| 347 | A1m | Me | H | Q3k |
| 348 | A1m | Me | H | Q3l |
| 349 | A1m | Me | H | Q3m |
| 350 | A1m | Me | H | Q3n |
| 351 | A1m | Me | Me | Q3a |
| 352 | A1m | Me | Me | Q3b |
| 353 | A1m | Me | Me | Q3c |
| 354 | A1m | Me | Me | Q3d |
| 355 | A1m | Me | Me | Q3e |
| 356 | A1m | Me | Me | Q3f |
| 357 | A1m | Me | Me | Q3g |
| 358 | A1m | Me | Me | Q3h |
| 359 | A1m | Me | Me | Q3i |
| 360 | A1m | Me | Me | Q3j |
| 361 | A1m | Me | Me | Q3k |
| 362 | A1m | Me | Me | Q3l |
| 363 | A1m | Me | Me | Q3m |
| 364 | A1m | Me | Me | Q3n |

135) The thrombopoietin receptor activators represented by 1).
136) The thrombopoietin receptor activators represented by 2).
137) The thrombopoietin receptor activators represented by 3).
138) The thrombopoietin receptor activators represented by 4).
139) The thrombopoietin receptor activators represented by 5).
140) The thrombopoietin receptor activators represented by 6).
141) The thrombopoietin receptor activators represented by 7).
142) The thrombopoietin receptor activators represented by 8).
143) The thrombopoietin receptor activators represented by 9).
144) The thrombopoietin receptor activators represented by 10).
145) The thrombopoietin receptor activators represented by 11).
146) The thrombopoietin receptor activators represented by 12).
147) The thrombopoietin receptor activators represented by 13).
148) The thrombopoietin receptor activators represented by 14).
149) The thrombopoietin receptor activators represented by 15).
150) The thrombopoietin receptor activators represented by 16).
151) The thrombopoietin receptor activators represented by 17).
152) The thrombopoietin receptor activators represented by 18).
153) The thrombopoietin receptor activators represented by 19).
154) The thrombopoietin receptor activators represented by 20).
155) The thrombopoietin receptor activators represented by 21).
156) The thrombopoietin receptor activators represented by 22).
157) The thrombopoietin receptor activators represented by 23).
158) The thrombopoietin receptor activators represented by 24).
159) The thrombopoietin receptor activators represented by 25).
160) The thrombopoietin receptor activators represented by 26).
161) The thrombopoietin receptor activators represented by 27).
162) The thrombopoietin receptor activators represented by 28).
163) The thrombopoietin receptor activators represented by 29).
164) The thrombopoietin receptor activators represented by 30).
165) The thrombopoietin receptor activators represented by 31).
166) The thrombopoietin receptor activators represented by 32).
167) The thrombopoietin receptor activators represented by 33).
168) The thrombopoietin receptor activators represented by 34).
169) The thrombopoietin receptor activators represented by 35).
170) The thrombopoietin receptor activators represented by 36).
171) The thrombopoietin receptor activators represented by 37).
172) The thrombopoietin receptor activators represented by 38).
173) The thrombopoietin receptor activators represented by 39).
174) The thrombopoietin receptor activators represented by 40).
175) The thrombopoietin receptor activators represented by 41).
176) The thrombopoietin receptor activators represented by 42).
177) The thrombopoietin receptor activators represented by 43).
178) The thrombopoietin receptor activators represented by 44).
179) The thrombopoietin receptor activators represented by 45).
180) The thrombopoietin receptor activators represented by 46).
181) The thrombopoietin receptor activators represented by 47).
182) The thrombopoietin receptor activators represented by 48).
183) The thrombopoietin receptor activators represented by 49).
184) The thrombopoietin receptor activators represented by 50).
185) The thrombopoietin receptor activators represented by 51).
186) The thrombopoietin receptor activators represented by 52).

187) The thrombopoietin receptor activators represented by 53).
188) The thrombopoietin receptor activators represented by 54).
189) The thrombopoietin receptor activators represented by 55).
190) The thrombopoietin receptor activators represented by 56).
191) The thrombopoietin receptor activators represented by 57).
192) The thrombopoietin receptor activators represented by 58).
193) The thrombopoietin receptor activators represented by 59).
194) The thrombopoietin receptor activators represented by 60).
195) The thrombopoietin receptor activators represented by 61).
196) The thrombopoietin receptor activators represented by 62).
197) The thrombopoietin receptor activators represented by 63).
198) The thrombopoietin receptor activators represented by 64).
199) The thrombopoietin receptor activators represented by 65).
200) The thrombopoietin receptor activators represented by 66).
201) The thrombopoietin receptor activators represented by 67).
202) The thrombopoietin receptor activators represented by 68).
203) The thrombopoietin receptor activators represented by 69).
204) The thrombopoietin receptor activators represented by 70).
205) The thrombopoietin receptor activators represented by 71).
206) The thrombopoietin receptor activators represented by 72).
207) The thrombopoietin receptor activators represented by 73).
208) The thrombopoietin receptor activators represented by 74).
209) The thrombopoietin receptor activators represented by 75).
210) The thrombopoietin receptor activators represented by 76).
211) The thrombopoietin receptor activators represented by 77).
212) The thrombopoietin receptor activators represented by 78).
213) The thrombopoietin receptor activators represented by 79).
214) The thrombopoietin receptor activators represented by 80).
215) The thrombopoietin receptor activators represented by 81).
216) The thrombopoietin receptor activators represented by 82).
217) The thrombopoietin receptor activators represented by 83).
218) The thrombopoietin receptor activators represented by 84).
219) The thrombopoietin receptor activators represented by 85).
220) The thrombopoietin receptor activators represented by 86).
221) The thrombopoietin receptor activators represented by 87).
222) The thrombopoietin receptor activators represented by 88).
223) The thrombopoietin receptor activators represented by 89).
224) The thrombopoietin receptor activators represented by 90).
225) The thrombopoietin receptor activators represented by 91).
226) The thrombopoietin receptor activators represented by 92).
227) The thrombopoietin receptor activators represented by 93).
228) The thrombopoietin receptor activators represented by 94).
229) The thrombopoietin receptor activators represented by 95).
230) The thrombopoietin receptor activators represented by 96).
231) The thrombopoietin receptor activators represented by 97).
232) The thrombopoietin receptor activators represented by 98).
233) The thrombopoietin receptor activators represented by 99).
234) The thrombopoietin receptor activators represented by 100).
235) The thrombopoietin receptor activators represented by 101).
236) The thrombopoietin receptor activators represented by 102).
237) The thrombopoietin receptor activators represented by 103).
238) The thrombopoietin receptor activators represented by 104).
239) The thrombopoietin receptor activators represented by 105).
240) The thrombopoietin receptor activators represented by 106).
241) The thrombopoietin receptor activators represented by 107).
242) The thrombopoietin receptor activators represented by 108).
243) The thrombopoietin receptor activators represented by 109).
244) The thrombopoietin receptor activators represented by 110).
245) The thrombopoietin receptor activators represented by 111).
246) The thrombopoietin receptor activators represented by 112).
247) The thrombopoietin receptor activators represented by 113).
248) The thrombopoietin receptor activators represented by 114).
249) The thrombopoietin receptor activators represented by 115).
250) The thrombopoietin receptor activators represented by 116).
251) The thrombopoietin receptor activators represented by 117).
252) The thrombopoietin receptor activators represented by 118).

253) The thrombopoietin receptor activators represented by 119).
254) The thrombopoietin receptor activators represented by 120).
255) The thrombopoietin receptor activators represented by 121).
256) The thrombopoietin receptor activators represented by 122).
257) The thrombopoietin receptor activators represented by 123).
258) The thrombopoietin receptor activators represented by 124).
259) The thrombopoietin receptor activators represented by 125).
260) The thrombopoietin receptor activators represented by 126).
261) The thrombopoietin receptor activators represented by 127).
262) The thrombopoietin receptor activators represented by 128).
263) The thrombopoietin receptor activators represented by 129).
264) The thrombopoietin receptor activators represented by 130).
265) The thrombopoietin receptor activators represented by 131).
266) The thrombopoietin receptor activators represented by 132).
267) The thrombopoietin receptor activators represented by 133).
268) The thrombopoietin receptor activators represented by 134).
269) Preventive, therapeutic and improving agents for diseases against which activation of the thrombopoietin receptor is effective which contain the thrombopoietin receptor activators represented by any of 135) to 268) or the formula (1), the formula (2), the formula (3) or the formula (4), tautomers, prodrugs or pharmaceutically acceptable salts of the activators or solvates thereof, as an active ingredient.

270) Platelet increasing agents containing the thrombopoietin receptor activators represented by any of 135) to 268) or the formula (1), the formula (2), the formula (3) or the formula (4), tautomers, prodrugs or pharmaceutically acceptable salts of the activators or solvates thereof, as an active ingredient.

The compounds of the present invention represented by the formula (1), the formula (2), the formula (3) or the formula (4) may be present in the form of pyrazoles which undergo the following tautomerizations, mixtures or mixtures of isomers thereof. When the compounds of the present invention have optical isomers, diastereomers or geometric isomers, the compounds of the present invention may be in the form of mixtures thereof or in the resolved form.

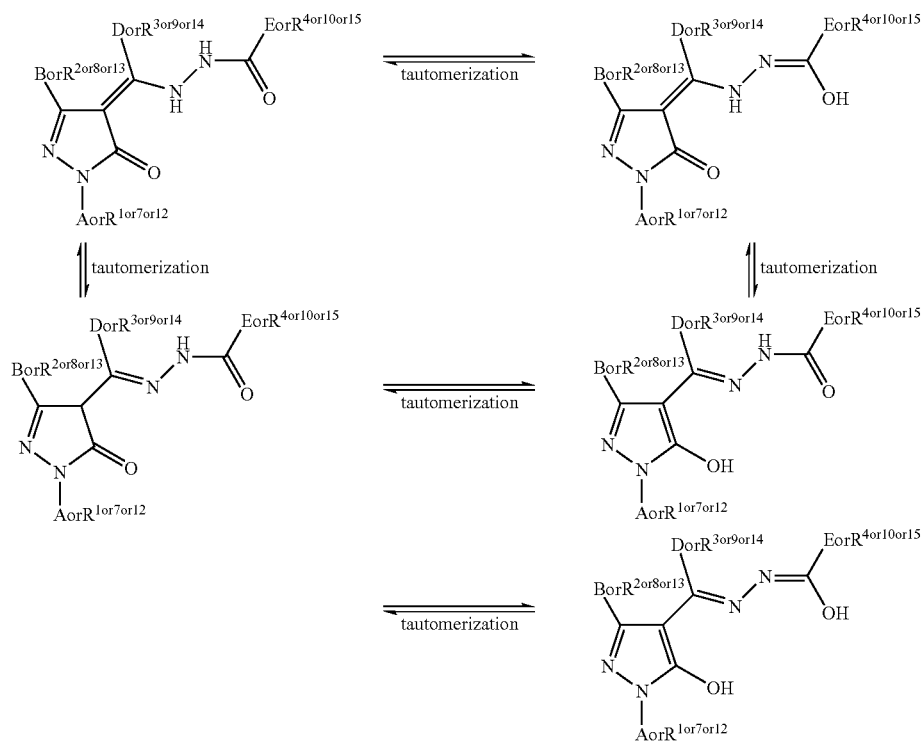

Formula 15

The compounds of the present invention represented by the formula (1), the formula (2), the formula (3) or the formula (4) or pharmaceutically acceptable salts thereof may be in the form of arbitrary crystals or arbitrary hydrates. The present invention covers these crystals, solvates and mixtures. They may be in the form of optional solvates with organic solvents such as acetone, ethanol and tetrahydrofuran, and the present invention covers any of these forms.

The compounds of the present invention represented by the formula (1), the formula (2), the formula (3) or the formula (4) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid). They may also be complexes with transition metals (such as copper and zinc).

The compounds which serve as prodrugs are derivatives of the present invention having chemically or metabolically degradable groups which give pharmacologically active compounds of the present invention upon hydrolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as a prodrug. Acyloxys particularly preferred as prodrugs include —OCOC$_2$H$_5$, —OCO(t-Bu), —OCOC$_{15}$H$_{31}$, —OCO(m-CO$_2$Na-Ph), —OCOCH$_2$CH$_2$CO$_2$Na, —OCOCH(NH$_2$)CH$_3$, —OCOCH$_2$N(CH$_3$)$_2$ and the like. When the compound of the present invention has an amino group, amide derivatives obtained by reacting the compound having an amino group with appropriate acid halides or appropriate mixed acid anhydrides may, for example, be mentioned as prodrugs. When the compound of the present invention has a carboxyl group, carboxylic acid esters with aliphatic alcohols or carboxylic acid esters obtained by the reaction of an alcoholic free hydroxyl group of 1,2- or 1,3-digylcerides may, for example, be mentioned as prodrugs. Particularly preferred prodrugs are methyl esters and ethyl esters.

The preventive, therapeutic and improving agents for diseases against which activation of the thrombopoietin receptor is effective or platelet increasing agents which contain the thrombopoietin receptor activators, tautomers, prodrugs or pharmaceutically acceptable salts of the activators or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may contain a solvent or a solubilizing agent such as an emulsifier, a suspending agent, a preservative and the like. For injections, pharmaceutical components such as distilled water for injection, physiological saline, 5% glucose solution and propylene glycol, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia caused by bone marrow transplantation, surgery and serious infection, or gastrointestinal bleeding, but such diseases are not restricted to these mentioned. Typical thrombocytopenias such as aplastic anemia, idiopathic thrombocytopenic purpura, myelodysplastic syndrome and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The pyrazolone compounds represented by the formula (1), the formula (2), the formula (3) or the formula (4) are prepared by the process illustrated below in reference to the pyrazolone compounds represented by the formula (3).

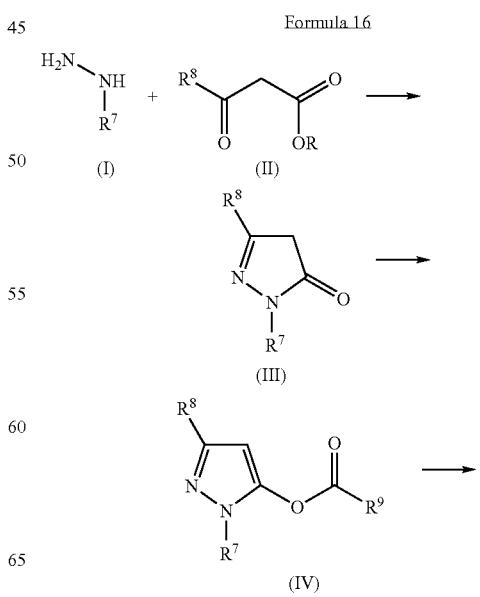

Formula 16

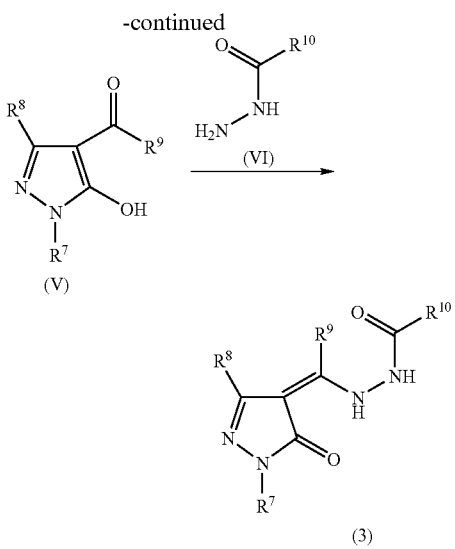

The pyrazolones (III) are obtained by known methods (Syn. Commun., 20(20), 3213 (1990), Chem. Ber., 59, 320 (1926), Monatsh. Chem., 89, 30 (1958)), for example, by reacting β-keto esters (II) with hydrazines ($R^7NHNH_2$ or salts thereof) in acetic acid with reflux. Acylation of them with acyl halides ($R^9COCl$) or acid anhydrides (($R^9CO)_2O$) to (IV) followed by Fries rearrangement in the presence of potassium carbonate in dioxane with heating gives 4-acyl-5-hydroxy-pyrazoles (V). 4-Formyl-5-hydroxypyrazole (V) ($R^9$=H) are obtainable by reacting the pyrazolones (III) with $POCl_3$-DMF. They are heated with hydrazides ($R^{10}CONHNH_2$ (VI) or salts thereof) optionally in the presence of a catalyst in a solvent to give the desired products. Syntheses of hydrazides (VI) are disclosed in the following documents.

1) Synthetic Commun., 28, (7) pp. 1223-1231 (1998)
2) J. Chem. Soc., 1225 (1948)
3) J. Chem. Soc., 2831 (1952)
4) WO03/7328
5) Nihon Kagaku Zasshi, 88(5), p. 73 (1967)
6) Journal of Heterocyclic Chemistry, 28(17), 17 (1991)

The compounds of the present invention are usually obtained with high purity by recrystallization or washing with solvents because most of them have good crystallizability. However, if necessary, they may be purified by column chromatography, thin layer chromatography, high performance liquid chromatography (HPLC) or high performance liquid chromatography-mass spectrometry (LC-MS).

EXAMPLES

Now, the present invention will be described in further detail with reference to Examples. However, it should be understood that the present invention is by no means restricted by these specific Examples.

DMSO denotes dimethyl sulfoxide, and DMF denotes dimethylformamide.

In high performance liquid chromatography-mass spectrometry (LC-MS), the retention time was measured under the following conditions.

Column: Waters Xterra MSC18 4.6×50 mm
Eluent: $H_2O:CH_3CN$=85:15→15:85

Syntheses of the compounds of Reference Synthetic Examples followed Examples 2-5 (pages 12-14) of WO01/34585.

Synthetic Example 1

Synthesis of 2,4-dihydroxybenzoic N'-(1-(3-methyl-5-oxo-1-(4-iodophenyl)-1,5-dihydropyrazol-4-ylidene)-ethyl)-hydrazide 1.03 g (3 mmol) of 1-(5-hydroxy-1-(4-iodophenyl)-3-methyl-1H-pyrazol-4-yl)-ethanone and 505 mg (3 mmol) of 2,4-dihydroxybenzoic hydrazide were dissolved in 50 ml of DMSO and heated at 85° C. for 9 hours with stirring. After cooling and evaporation of the solvent, the crude product was recrystallized from chloroform/ether to give 1.39 g of the desired product as a pale brown solid (yield 94%).

$^1$H-NMR (ppm in DMSO-$d_6$)
δ=2.36 (s, 3H), 2.42 (s, 3H), 6.36 (t, 1H, J=2 Hz), 6.40 (d, 1H, J=2 Hz), 7.68-7.76 (m, 3H), 7.86 (d, 2H, J=9 Hz)
LC/MS
$M^+$=492.27 (2.88 min)

Synthetic Example 2

Synthesis of 3,5-dihydroxybenzoic N'-(1-(1-(4-tert-butylphenyl)-3-methyl-5-oxo-1,5-dihydropyrazol-4-ylidene)-ethyl)-hydrazide From 1-(1-(4-tert-butylphenyl)-5-hydroxy-3-methyl-1H-pyrazol-4-yl)-ethanone and 3,5-dihydroxybenzoic hydrazide, 40.1 mg of the desired product was obtained in the same manner as in Synthetic Example 1 as a yellow solid (yield 40%).

$^1$H-NMR (ppm in DMSO-$d_6$)
δ=1.29 (s, 9H), 2.36 (s, 3H), 2.41 (s, 3H), 6.45 (s, 1H), 6.76 (s, 2H), 7.41 (d, 2H, J=8.8 Hz), 7.89 (d, 2H, J=8.8 Hz), 9.65 (s, 2H), 11.08 (s, 1H).
LC/MS
$M^+$=422 (2.19 min).

Synthetic Example 3

Synthesis of 3,5-dihydroxybenzoic N'-(1-(1-(3,4-dimethylphenyl)-3-methyl-5-oxo-1,5-dihydropyrazol-4-ylidene)-ethyl)-hydrazide From 1-(1-(3,4-dimethylphenyl)-5-hydroxy-3-methyl-1H-pyrazol-4-yl)-ethanone and 3,5-dihydroxybenzoic hydrazide, 57.0 mg of the desired product was obtained in the same manner as in Synthetic Example 1 as a pale red solid (yield 73%).

$^1$H-NMR (ppm in DMSO-$d_6$)
δ=2.21 (s, 3H), 2.24 (s, 3H), 2.35 (s, 3H), 2.41 (s, 3H), 6.45 (s, 1H), 6.75 (s, 1H), 6.76 (s, 1H), 7.14 (d, 1H, J=8.3 Hz), 7.70 (dd, 1H, J=1.9, 8.3 Hz), 7.77 (d, 1H, J=1.9 Hz), 9.66 (s, 2H), 11.09 (s, 1H).
LC/MS
$M^+$=394 (1.82 min).

Synthetic Example 4

Synthesis of 4-methoxycarbonyl-benzoic N'-(1-(1-(4-tert-butylphenyl)-3-methyl-5-oxo-1,5-dihydropyrazol-4-ylidene)-ethyl)-hydrazide 1) Synthesis of 4-methoxycarbonylbenzhydrazide The known procedure disclosed in the literature (Synthetic Communications, 28(7), 1223-1231, (1998)) was followed using monomethyl terephthalate and tetramethylfluoroformamidinium hexafluorophosphate to give 1.36 g of a colorless solid (yield 70%).

$^1$H-NMR (ppm in DMSO-$d_6$)

δ=3.86 (s, 3H), 4.56 (s, 2H), 7.93 (d, 2H, J=8.3 Hz), 8.02 (d, 2H, J=8.3 Hz), 9.96 (bs, 1H).

2) Synthesis of 4-methoxycarbonylbenzoic N'-(1-(1-(4-tert-butylphenyl)-3-methyl-5-oxo-1,5-dihydropyrazol-4-ylidene)-ethyl)-hydrazide 30.5 mg (0.11 mmol) of 1-(1-(4-tert-butylphenyl)-5-hydroxy-3-methyl-1H-pyrazol-4-yl)-ethanone and 23.1 mg (0.11 mmol) of 4-methoxycarbonylbenzhydrazide were dissolved in 3.0 ml of DMF and stirred at 100° C. for 3 hours. After cooling and evaporation of the solvent, the crude product was recrystallized from ethyl acetate/n-hexane to give 32.9 mg of the desired product as a yellow solid (yield 66%).

$^1$H-NMR (ppm in DMSO-$d_6$)

δ=1.29 (s, 9H), 2.37 (s, 3H), 2.46 (s, 3H), 3.90 (s, 3H), 7.41 (d, 2H, J=8.7 Hz), 7.89 (d, 2H, J=8.7 Hz), 8.05 (d, 2H, J=8.4 Hz), 8.12 (d, 2H, J=8.4 Hz).

LC/MS

M$^+$=448 (2.64 min).

Synthetic Example 5

Synthesis of 4-carboxybenzoic N'-(1-(1-(4-tert-butylphenyl)-3-methyl-5-oxo-1,5-dihydropyrazol-4-ylidene)-ethyl)-hydrazide To 23.2 mg (0.05 mmol) of the 4-methoxycarbonylbenzoic N'-(1-(1-(4-tert-butylphenyl)-3-methyl-5-oxo-1,5-dihydropyrazol-4-ylidene)-ethyl)-hydrazide synthesized in Synthetic Example 4 in 2.0 ml of methanol, 255 μl (0.255 mmol) of 1M aqueous sodium hydroxide was added at room temperature, and the mixture was heated at from 60° C. to 80° C. for 3.5 hours. After it was cooled to room temperature, 255 μl of 1M hydrochloric acid was added, and the precipitated solid was collected by filtration to obtain 13.9 mg of the desired product as a pale brown solid (yield 61%).

$^1$H-NMR (ppm in DMSO-$d_6$)

δ=1.29 (s, 9H), 2.37 (s, 3H), 2.45 (s, 3H), 7.41 (d, 2H, J=8.7 Hz), 7.89 (d, 2H, J=8.7 Hz), 8.03 (d, 2H, J=8.3 Hz), 8.09 (d, 2H, J=8.3 Hz), 11.44 (s, 1H).

LC/MS

M$^+$=434 (2.38 min).

Synthetic Example 6

Synthesis of 4-methoxycarbonylbenzoic N'-(1-(1-(3,4-dimethylphenyl)-3-methyl-5-oxo-1,5-dihydropyrazol-4-ylidene)-ethyl)-hydrazide From 1-(1-(3,4-dimethylphenyl)-5-hydroxy-3-methyl-1H-pyrazol-4-yl)-ethanone and 4-methoxycarbonylbenzhydrazide, 53.0 mg of the desired product was obtained in the same manner as in Synthetic Example 4 as a pale yellow solid (yield 64%).

$^1$H-NMR (ppm in DMSO-$d_6$)

δ=2.21 (s, 3H), 2.25 (s, 3H), 2.36 (s, 3H), 2.45 (s, 3H), 3.89 (s, 3H), 7.14 (d, 1H, J=8.5 Hz), 7.71 (dd, 1H, J=1.9, 8.5 Hz), 7.77 (d, 1H, J=1.9 Hz), 8.05 (d, 2H, J=8.5 Hz), 8.12 (d, 2H, J=8.5 Hz).

LC/MS

M$^+$=420 (2.34 min).

Synthetic Example 7

Synthesis of 4-carboxybenzoic N'-(1-(1-(3,4-dimethylphenyl)-3-methyl-5-oxo-1,5-dihydropyrazol-4-ylidene)-ethyl)-hydrazide From the 4-methoxycarbonylbenzoic N'-(1-(1-(3,4-dimethylphenyl)-3-methyl-5-oxo-1,5-dihydropyrazol-4-ylidene)-ethyl)-hydrazide synthesized in Synthetic Example 6, 21.5 mg of the desired product was obtained in the same manner as in Synthetic Example 5 as a pale yellow solid (yield 71%).

$^1$H-NMR (ppm in DMSO-$d_6$)

δ=2.21 (s, 3H), 2.25 (s, 3H), 2.36 (s, 3H), 2.45 (s, 3H), 7.14 (d, 1H, J=8.3 Hz), 7.70 (dd, 1H, J=1.9, 8.3 Hz), 7.77 (d, 1H, J=1.9 Hz), 8.03 (d, 2H, J=8.3 Hz), 8.10 (d, 2H, J=8.3 Hz), 11.45 (s, 1H).

LC/MS

M$^+$=406 (2.03 min).

Synthetic Example 8

Synthesis of 4-methoxycarbonylbenzoic N'-(1-(3-methyl-5-oxo-1-(3-trifluoromethylphenyl)-1,5-dihydropyrazol-4-ylidene)-ethyl)-hydrazide From 1-(5-hydroxy-3-methyl-1-(3-trifluoromethylphenyl)-1H-pyrazol-4-yl)-ethanone and 4-methoxycarbonylbenzhydrazide, 59.9 mg of the desired product was obtained in the same manner as in Synthetic Example 4 as a yellow solid (yield 65%).

$^1$H-NMR (ppm in DMSO-$d_6$)

δ=2.40 (s, 3H), 2.51 (s, 3H), 3.91 (s, 3H), 7.49 (d, 1H, J=7.4 Hz), 7.66 (dd, 1H, J=8.0, 8.3 Hz), 8.06 (d, 2H, J=8.3 Hz), 8.13 (d, 2H, J=8.3 Hz), 8.29 (d, 1H, J=8.0 Hz), 8.45 (s, 1H), 11.55 (bs, 1H), 12.47 (bs, 1H).

LC/MS

M$^+$=460.41 (2.69 min).

Synthetic Example 9

Synthesis of 4-carboxybenzoic N'-(1-(3-methyl-5-oxo-1-(3-trifluoromethylphenyl)-1,5-dihydropyrazol-4-ylidene)-ethyl)-hydrazide From the 4-methoxycarbonylbenzoic N'-(1-(3-methyl-5-oxo-1-(3-trifluoromethylphenyl)-1,5-dihydropyrazol-4-ylidene)-ethyl)-hydrazide synthesized in Synthetic Example 8, 26.5 mg of the desired product was obtained in the same manner as in Synthetic Example 5 as a pale yellow solid (yield 78%).

$^1$H-NMR (ppm in DMSO-$d_6$)

δ=2.41 (s, 3H), 2.51 (s, 3H), 7.49 (d, 1H, J=8.0 Hz), 7.66 (dd, 1H, J=8.0 Hz, 8.0 Hz), 8.03 (d, 2H, J=8.3 Hz), 8.10 (d, 2H, J=8.3 Hz), 8.29 (d, 1H, J=8.0 Hz), 8.45 (s, 1H), 11.52 (bs, 1H), 12.46 (bs, 1H).

LC/MS

M$^+$=446.38 (2.29 min).

Synthetic Example 10

Synthesis of 4-methoxycarbonylbenzoic N'-(1-(3-methyl-5-oxo-1-(4-trifluoromethylphenyl)-1,5-dihydropyrazol-4-ylidene)-ethyl)-hydrazide From 1-(5-hydroxy-3-methyl-1-(4-trifluoromethylphenyl)-1H-pyrazol-4-yl)-ethanone and 4-methoxycarbonylbenzhydrazide, 58.9 mg of the desired product was obtained in the same manner as in Synthetic Example 4 as a yellow solid (yield 65%).

$^1$H-NMR (ppm in DMSO-$d_6$)

δ=2.40 (s, 3H), 2.51 (s, 3H), 3.91 (s, 3H), 7.77 (d, 2H, J=8.5 Hz), 8.06 (d, 2H, J=8.5 Hz), 8.13 (d, 2H, J=8.5 Hz), 8.26 (d, 2H, J=8.5 Hz), 11.56 (bs, 1H), 12.46 (bs, 1H).

LC/MS

M$^+$=460.41 (2.62 min).

Synthetic Example 11

Synthesis of 4-carboxybenzoic N'-(1-(3-methyl-5-oxo-1-(4-trifluoromethylphenyl)-1,5-dihydropyrazol-4-ylidene)-ethyl)-hydrazide From the 4-methoxycarbonylbenzoic N'-(1-(3-methyl-5-oxo-1-(4-trifluoromethylphenyl)-1,5-dihydropyrazol-4-ylidene)-ethyl)-hydrazide synthesized in Synthetic Example 10, 18.6 mg of the desired product was obtained in the same manner as in Synthetic Example 5 as a pale yellow solid (yield 68%).

$^1$H-NMR (ppm in DMSO-$d_6$)

δ=2.40 (s, 3H), 2.51 (s, 3H), 7.77 (d, 2H, J=8.7 Hz), 8.03 (d, 2H, J=8.2 Hz), 8.10 (d, 2H, J=8.2 Hz), 8.23 (d, 2H, J=8.7 Hz), 11.53 (bs, 1H), 12.45 (bs, 1H).

LC/MS

M$^+$=446.38 (2.31 min).

Synthetic Example 12

Synthesis of 3-carboxybenzoic N'-(1-(1-(4-tert-butylphenyl)-3-methyl-5-oxo-1,5-dihydropyrazol-4-ylidene)-ethyl)-hydrazide 1) Synthesis of 3-methoxycarbonylbenzhydrazide The procedure in Synthetic Example 4 was followed using monomethyl isophthalate and tetramethylfluoroformamidinium hexafluorophosphate to 244.6 mg of a yellow solid (yield>99%).

$^1$H-NMR (ppm in DMSO-$d_6$)

δ=3.89 (s, 3H), 4.61 (bs, 2H), 7.62 (dd, 1H, J=8.0 Hz, 8.0 Hz), 8.08 (dd, 2H, J=1.8, 8.0 Hz), 8.42 (d, 1H, J=1.8 Hz), 9.98 (bs, 1H).

LC/MS

M$^+$=194 (0.51 min).

2) Synthesis of 3-methoxycarbonylbenzoic N'-(1-(1-(4-tert-butylphenyl)-3-methyl-5-oxo-1,5-dihydropyrazol-4-ylidene)-ethyl)-hydrazide From 1-(1-(4-tert-butylphenyl)-5-hydroxy-3-methyl-1H-pyrazol-4-yl)-ethanone and 3-methoxycarbonylbenzhydride, 64.6 mg of the desired product was obtained in the same manner as in Synthetic Example 4 as a yellow solid (yield 70%).

3) Synthesis of 3-carboxybenzoic N'-(1-(1-(4-tert-butylphenyl)-3-methyl-5-oxo-1,5-dihydropyrazol-4-ylidene)-ethyl)-hydrazide From the 3-methoxycarbonylbenzoic N'-(1-(1-(4-tert-butylphenyl)-3-methyl-5-oxo-1,5-dihydropyrazol-4-ylidene)-ethyl)-hydrazide synthesized in 2), 11.2 mg of the desired product was obtained in the same manner as in Synthetic Example 5 as a pale brown solid (yield 50%).

$^1$H-NMR (ppm in DMSO-$d_6$)

δ=1.29 (s, 9H), 2.37 (s, 3H), 2.45 (s, 3H), 7.42 (d, 2H, J=8.8 Hz), 7.70 (dd, 1H, J=7.8 Hz, 7.8 Hz), 7.89 (d, 2H, J=8.8 Hz), 8.16 (d, 1H, J=6.9 Hz), 8.19 (d, 1H, J=7.4 Hz), 8.51 (s, 1H), 11.46 (bs, 1H).

LC/MS

M$^+$=434.49 (2.37 min).

Synthetic Example 13

Synthesis of 3-carboxybenzoic N'-(1-(1-(3,4-dimethylphenyl)-3-methyl-5-oxo-1,5-dihydropyrazol-4-ylidene)-ethyl)-hydrazide 1) Synthesis of 3-methoxycarbonylbenzoic N'-(1-(1-(3,4-dimethylphenyl)-3-methyl-5-oxo-1,5-dihydropyrazol-4-ylidene)-ethyl)-hydrazide From 1-(1-(3,4-dimethylphenyl)-5-hydroxy-3-methyl-1H-pyrazol-4-yl)-ethanone and 3-methoxycarbonylbenzhydrazide, 27.4 mg of the desired product was obtained in the same manner as in Synthetic Example 4 as a pale yellow solid (yield 35%).

$^1$H-NMR (ppm in DMSO-$d_6$)

δ=2.21 (s, 3H), 2.25 (s, 3H), 2.34 (s, 3H), 2.36 (s, 3H), 3.92 (s, 3H), 7.14 (d, 1H, J=8.3 Hz), 7.70-7.77 (m, 3H), 8.20 (d, 2H, J=8.0 Hz), 8.51 (s, 1H), 11.49 (s, 1H).

2) Synthesis of 3-carboxybenzoic N'-(1-(1-(3,4-dimethylphenyl)-3-methyl-5-oxo-1,5-dihydropyrazol-4-ylidene)-ethyl)-hydrazide From the 3-methoxycarbonylbenzoic N'-(1-(1-(3,4-dimethylphenyl)-3-methyl-5-oxo-1,5-dihydropyrazol-4-ylidene)-ethyl)-hydrazide synthesized in 1), 17.2 mg of the desired product was obtained in the same manner as in Synthetic Example 5 as a pale yellow solid (yield 68%).

$^1$H-NMR (ppm in DMSO-$d_6$)

δ=2.21 (s, 3H), 2.25 (s, 3H), 2.36 (s, 3H), 2.45 (s, 3H), 7.14 (d, 1H, J=8.5 Hz), 7.68-7.77 (m, 3H), 8.15-8.20 (m, 2H), 8.19 (d, 1H, J=7.2 Hz), 8.50 (s, 1H).

LC/MS

M$^+$=406.43 (2.03 min).

Synthetic Examples 14 to 92

The structural formulae, yields, appearances, and molecular weights measured by LC/MS of the compounds synthesized by the following method based on Synthetic Example 1 are shown in Table 6.

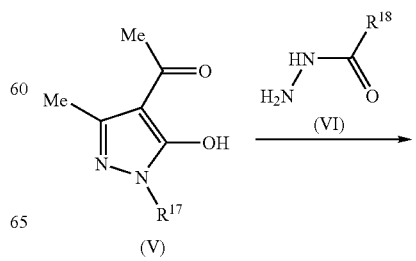

Formula 17

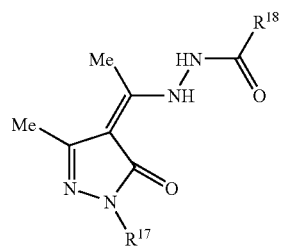

A pyrazole derivative (V) and a benzoic hydrazide (VI) were dissolved in a solvent such as DMF, EtOH and DMSO in a molar ratio of 1:1 and heated at 80 to 100° c. with stirring. The solvent was removed by evaporation, and the resulting crude product was dissolved in chloroform and recrystallized from a poor solvent or washed with chloroform to give the desired product.

TABLE 6

| Synthetic Ex. No. | $R^{17}$ | $R^{18}$ | Yield | Appearance | Molecular weight |
|---|---|---|---|---|---|
| 14 | Ph | 3-NO$_2$-Ph | 37.6% | Yellow solid | 379.38 |
| 15 | 4-t-Bu-Ph | 3-NO$_2$-Ph | 58.1% | Pale brown solid | 435.48 |
| 16 | Ph | 2-OH-Ph | 24.7% | Pale yellow solid | 350.38 |
| 17 | Ph | 4-OH-Ph | 65.1% | Pale pink solid | 350.38 |
| 18 | Ph | 3-OH-β-Naphthyl | 59.2% | Pale yellow solid | 400.44 |
| 19 | Ph | 2,4-(OH)$_2$-Ph | 41.1% | Pale yellow solid | 366.38 |
| 20 | Ph | 3,4-(OH)$_2$-Ph | 43.9% | Pale brown solid | 366.38 |
| 21 | Ph | 2-NO$_2$-Ph | 67.5% | Yellow solid | 379.38 |
| 22 | Ph | 4-NO$_2$-Ph | 53.4% | Yellow solid | 379.38 |
| 23 | 4-t-Bu-Ph | 2-OH-Ph | 29.4% | Pale yellow solid | 406.48 |
| 24 | 4-t-Bu-Ph | 4-OH-Ph | 24.1% | Pale brown solid | 406.48 |
| 25 | 4-t-Bu-Ph | 3-OH-β-Naphthyl | 11.0% | Yellow solid | 456.54 |
| 26 | 4-t-Bu-Ph | 2,4-(OH)$_2$-Ph | 27.5% | Pale yellow solid | 422.48 |
| 27 | 4-t-Bu-Ph | 3,4-(OH)$_2$-Ph | 40.2% | Brown solid | 422.48 |
| 28 | 4-t-Bu-Ph | 2-NO$_2$-Ph | 51.4% | Pale yellow solid | 435.48 |
| 29 | 4-t-Bu-Ph | 4-NO$_2$-Ph | 49.9% | Yellow solid | 435.48 |
| 30 | 4-CF$_3$-Ph | 2-OH-Ph | 48.5% | Yellow solid | 418.37 |
| 31 | 4-CF$_3$-Ph | 4-OH-Ph | 60.0% | Pink solid | 418.37 |
| 32 | 4-CF$_3$-Ph | 3-OH-β-Naphthyl | 8.2% | Pale yellow solid | 468.43 |
| 33 | 4-CF$_3$-Ph | 2,4-(OH)$_2$-Ph | 3.1% | Brown solid | 434.37 |
| 34 | 4-CF$_3$-Ph | 3,4-(OH)$_2$-Ph | 73.2% | Pale pink solid | 434.37 |
| 35 | 4-CF$_3$-Ph | 2-NO$_2$-Ph | 68.8% | Pale pink solid | 447.37 |
| 36 | 4-CF$_3$-Ph | 3-NO$_2$-Ph | 64.2% | Pale yellow solid | 447.37 |
| 37 | 4-CF$_3$-Ph | 4-NO$_2$-Ph | 60.1% | Pale yellow solid | 447.37 |
| 38 | 4-I-Ph | 2-OH-Ph | 22.9% | Yellow solid | 476.27 |
| 39 | 4-I-Ph | 4-OH-Ph | 36.6% | Pale brown solid | 476.27 |
| 40 | 4-I-Ph | 3-OH-β-Naphthyl | 46.5% | Yellow solid | 526.33 |
| 41 | 4-I-Ph | 3,4-(OH)$_2$-Ph | 52.5% | Pale pink solid | 492.27 |
| 42 | 4-I-Ph | 2-NO$_2$-Ph | 43.3% | Pale pink solid | 505.27 |
| 43 | 4-I-Ph | 3-NO$_2$-Ph | 51.4% | Yellow solid | 505.27 |
| 44 | 4-I-Ph | 4-NO$_2$-Ph | 27.6% | Yellow solid | 505.27 |
| 45 | 3-CF$_3$-Ph | 2-OH-Ph | 69.4% | Pale yellow solid | 418.37 |
| 46 | 3-CF$_3$-Ph | 4-OH-Ph | 25.7% | Pale brown solid | 418.37 |
| 47 | 3-CF$_3$-Ph | 3-OH-β-Naphthyl | 54.3% | Pale yellow solid | 468.43 |
| 48 | 3-CF$_3$-Ph | 2,4-(OH)$_2$-Ph | 13.2% | Pale brown solid | 434.37 |
| 49 | 3-CF$_3$-Ph | 3,4-(OH)$_2$-Ph | 57.3% | Pale pink solid | 434.37 |
| 50 | 3-CF$_3$-Ph | 2-NO$_2$-Ph | 53.9% | Pink solid | 447.37 |
| 51 | 3-CF$_3$-Ph | 3-NO$_2$-Ph | 57.4% | Pale yellow solid | 447.37 |
| 52 | 3-CF$_3$-Ph | 4-NO$_2$-Ph | 32.2% | Pale yellow solid | 447.37 |
| 53 | 3,4-Me$_2$-Ph | 2-OH-Ph | 52.2% | Pale yellow solid | 378.43 |
| 54 | 3,4-Me$_2$-Ph | 4-OH-Ph | 66.2% | Pale pink solid | 378.43 |
| 55 | 3,4-Me$_2$-Ph | 3-OH-β-Naphthyl | 65.9% | Pale yellow solid | 428.49 |
| 56 | 3,4-Me$_2$-Ph | 2,4-(OH)$_2$-Ph | 43.0% | Pale yellow solid | 394.43 |
| 57 | 3,4-Me$_2$-Ph | 3,4-(OH)$_2$-Ph | 40.4% | Pale yellow solid | 394.43 |
| 58 | 3,4-Me$_2$-Ph | 2-NO$_2$-Ph | 67.9% | Pale yellow solid | 407.43 |
| 59 | 3,4-Me$_2$-Ph | 3-NO$_2$-Ph | 50.8% | Pale yellow solid | 407.43 |
| 60 | 3,4-Me$_2$-Ph | 4-NO$_2$-Ph | 67.1% | Pale brown solid | 407.43 |
| 61 | 3,4-Cl$_2$-Ph | 2-OH-Ph | 45.6% | Pale yellow solid | 419.27 |
| 62 | 3,4-Cl$_2$-Ph | 4-OH-Ph | 63.7% | Pale yellow solid | 419.27 |
| 63 | 3,4-Cl$_2$-Ph | 3-OH-β-Naphthyl | 51.1% | Pale brown solid | 469.33 |
| 64 | 3,4-Cl$_2$-Ph | 2,4-(OH)$_2$-Ph | 17.0% | Pale yellow solid | 435.27 |

TABLE 6-continued

| Synthetic Ex. No. | R¹⁷ | R¹⁸ | Yield | Appearance | Molecular weight |
|---|---|---|---|---|---|
| 65 | 3,4-Cl$_2$-Ph | 3,4-(OH)$_2$-Ph | 66.1% | Pale pink solid | 435.27 |
| 66 | 3,4-Cl$_2$-Ph | 2-NO$_2$-Ph | 67.4% | Pale yellow solid | 448.27 |
| 67 | 3,4-Cl$_2$-Ph | 3-NO$_2$-Ph | 64.5% | Pale yellow solid | 448.27 |
| 68 | 3,4-Cl$_2$-Ph | 4-NO$_2$-Ph | 51.1% | Brown solid | 448.27 |
| 69 | 4-t-Bu-Ph | 4-NH$_2$-Ph | 74.8% | Pale brown solid | 405.53 |
| 70 | 4-t-Bu-Ph | 3-NH$_2$-Ph | 48.7% | Pale brown solid | 405.53 |
| 71 | 4-t-Bu-Ph | 4-CF$_3$-Ph | 69.1% | Pale yellow solid | 458.49 |
| 72 | 4-t-Bu-Ph | 4-t-Bu-Ph | 77.9% | Pink solid | 446.63 |
| 73 | 3,4-Me$_2$-Ph | 4-NH$_2$-Ph | 92.7% | Red solid | 377.48 |
| 74 | 3,4-Me$_2$-Ph | 3-NH$_2$-Ph | 61.1% | Pale orange solid | 377.48 |
| 75 | 3,4-Me$_2$-Ph | 4-CF$_3$-Ph | 67.7% | Pale orange solid | 430.44 |
| 76 | 3,4-Me$_2$-Ph | 4-t-Bu-Ph | 66.8% | Pale pink solid | 418.58 |
| 77 | 3,4-Cl$_2$-Ph | 4-NH$_2$-Ph | 51.2% | Orange solid | 418.32 |
| 78 | 3,4-Cl$_2$-Ph | 3-NH$_2$-Ph | 69.7% | Pink solid | 418.32 |
| 79 | 3,4-Cl$_2$-Ph | 4-CF$_3$-Ph | 69.6% | Pale orange solid | 471.28 |
| 80 | 3,4-Cl$_2$-Ph | 4-t-Bu-Ph | 79.8% | Pale pink solid | 459.42 |
| 81 | 4-t-Bu-Ph | 3-OH-Ph | 72.3% | Pale yellow solid | 406.53 |
| 82 | 3,4-Me$_2$-Ph | 3-OH-Ph | 42.0% | Pale pink solid | 378.48 |
| 83 | 3,4-Cl$_2$-Ph | 3-OH-Ph | 89.0% | Pink solid | 419.32 |
| 84 | 3-NO$_2$-Ph | 3-NO$_2$-Ph | 58% | Brown solid | 424.57 |
| 85 | 2-Py | 3-NO$_2$-Ph | 63% | Pale orange solid | 380.36 |
| 86 | 3-NO$_2$-Ph | 2,4-(OH)$_2$-Ph | 43% | Brown solid | 411.37 |
| 87 | 2-Py | 2,4-(OH)$_2$-Ph | 66% | Pale yellow solid | 367.36 |
| 88 | 3-NO$_2$-Ph | 4-t-Bu-Ph | 25% | Brown solid | 435.48 |
| 89 | 3-CF$_3$-Ph | 3-NH$_2$-Ph | 74% | Pale brown solid | 417.38 |
| 90 | 3-CF$_3$-Ph | 4-NH$_2$-Ph | 82% | Pale orange solid | 417.38 |
| 91 | 4-CF$_3$-Ph | 3-NH$_2$-Ph | 69% | Brown solid | 417.38 |
| 92 | 4-CF$_3$-Ph | 4-NH$_2$-Ph | 72% | Pale pink solid | 417.38 |

Synthetic Example 93

Synthesis of 2,4-dihydroxybenzoic N'-(1-(3,4-dimethylphenyl)-3-methyl-5-oxo-1,5-dihydropyrazol-4-ylidene-methyl)-hydrazide 1) Synthesis of 1-(3,4-dimethylphenyl)-5-hydroxy-3-methyl-1H-pyrazol-4-carbaldehyde 1.86 g (9.16 mmol) of 1-(3,4-dimethylphenyl)-3-methyl-3-pyrazolin-5-one was dissolved in 3.6 ml of dry dimethylformamide, and 1.02 ml (11.0 mmol) of phosphorus oxychloride was added gradually under cooling with ice at 20° C. or below. After the addition, the mixture was heated at 100° C. for 2 hours, cooled to room temperature and poured into 30 ml of ice-cold water. Then, the mixture was washed with 10 ml of water and 10 ml of dimethylformamide. The mixed solution was stirred for 18 hours, and the precipitated solid was collected by filtration, washed with 20 ml of water and dried to obtain 1.03 g of the desired product as a pale brown solid (yield 49%).

$^1$H-NMR (ppm in CDCl$_3$)

δ=2.29 (s, 3H), 2.32 (s, 3H), 2.43 (s, 3H), 7.20 (d, 1H, J=8 Hz), 7.48 (dd, 1H, J=8 Hz, 2 Hz), 7.54 (d, 1H, J=2 Hz), 9.60 (s, 1H)

2) Synthesis of 2,4-dihydroxybenzoic N'-[1-(3,4-dimethylphenyl)-3-methyl-5-oxo-1,5-dihydropyrazol-4-ylidene-methyl]-hydrazide 46 mg (0.2 mmol) of the 1-(3,4-dimethylphenyl)-5-hydroxy-3-methyl-1H-pyrazol-4-carbaldehyde synthesized in 1) and 34 mg (0.20 mmol) of 2,4-dihydroxybenzoic hydrazide were stirred in 1 ml of ethanol at room temperature for 96 hours. The precipitated solid was collected by filtration and washed with 1 ml of ethanol, 1 ml of ether and 1 ml of methanol successively to obtain 53 mg of the desired product (yield 70%).

LC/MS

M$^+$=380.40 (2.77 min)

Synthetic Example 94

Synthesis of 2,4-dihydroxybenzoic N'-(1-(1-(3,4-dimethylphenyl)-3-trifluoromethyl-5-oxo-1,5-dihydropyrazol-4-ylidene)-ethyl)-hydrazide 1-(1-(3,4-Dimethylphenyl)-5-hydroxy-3-trifluoromethyl-1H-pyrazol-4-yl)-ethanone (0.173 mmol, 51.5 mg) and 2,4-dihydroxybenzoic hydrazide (0.173 mmol, 30.6 mg) were stirred in ethanol (5 ml) at 80° C. for 19 hours. After the solvent was removed by evaporation, the residue was dried with a vacuum pump and filtered with chloroform, and the filtrate was concentrated and resolved by silica gel thin layer chromatography (CHCl$_3$/MeOH=10/1) to obtain 2,4-dihydroxybenzoic N'-(1-(1-(3,4-dimethylphenyl)-3-trifluoromethyl-5-oxo-1,5-dihydropyrazol-4-ylidene)-ethyl)-hydrazide as a pale yellow solid (67 mg, yield 87%, purity 80.7%).

LC-MS 448.40 (M$^+$)

Synthetic Example 95

Synthesis of 4-methoxycarbonylbenzoic N'-(1-(1-(3,4-dimethylphenyl)-3-trifluoromethyl-5-oxo-1,5-dihydropyrazol-4-ylidene)-ethyl)-hydrazide 1-(1-(3,4-Dimethylphenyl)-5-hydroxy-3-trifluoromethyl-1H-pyrazol-4-yl)-ethanone (0.189 mmol, 56.5 mg) and 4-methoxycarbonylbenzhydrazide (0.189 mmol, 36.8 mg) were stirred in DMF at 100° C. for 2.2 hours and at 120° C. for 17 hours. After the solvent was removed by evaporation, the residue was resolved by silica gel thin layer chromatography (CHCl$_3$/MeOH=10/1) to obtain 4-methoxycarbonylbenzoic N'-(1-(1-(3,4-dimethylphenyl)-3-trifluoromethyl-5-oxo-1,5-dihydropyrazol-4-ylidene)-ethyl)-hydrazide as a yellow solid (55.6 mg, 62%)

LC-MS 474.43 (M$^+$)

Synthetic Example 96

Synthesis of 4-carboxybenzoic N'-(1-(1-(3,4-dimethylphenyl)-3-trifluoromethyl-5-oxo-1,5-dihydropyrazol-4-ylidene)-ethyl)-hydrazide 4-Methoxycarbonylbenzoic N'-(1-(1-(3,4-dimethylphenyl)-3-trifluoromethyl-5-oxo-1,5-dihydropyrazol-4-ylidene)-ethyl)-hydrazide (0.107 mmol, 50.7 mg) was dissolved in methanol (2 ml) and stirred with 1M aqueous sodium hydroxide (0.534 mmol, 0.534 ml) at room temperature for 2 hours and at 60° C. for 1.5 hours. Then, the reaction vessel was cooled to 0° C., and 1M hydrochloric acid (0.534 mmol, 0.534 ml) and water were added. The precipitated solid was collected by filtration with water and dried to obtain 4-carboxybenzoic N'-(1-(1-(3,4-dimethylphenyl)-3-trifluoromethyl-5-oxo-1,5-dihydropyrazol-4-ylidene)-ethyl)-hydrazide as a yellow solid (43.8 mg, 89%).

LC-MS 460.41 (M$^+$)

Synthetic Example 97

Synthesis of 4-carboxybenzoic N'-(1-(4-tert-butylphenyl)-3-methyl-5-oxo-1,5-dihydropyrazol-4-ylidene-methyl)-hydrazide 1) Synthesis of 1-(4-tert-butylphenyl)-5-hydroxy-3-methyl-1H-pyrazole-4-carbaldehyde 1.89 g (9.33 mmol) of 1-(4-tert-butylphenyl)-5-hydroxy-3-methyl-1H-pyrazole was dissolved in 3.6 ml of dry dimethylformamide, and 1.05 ml (11.26 mmol) phosphorus oxychloride was added gradually at 20° C. or below under cooling with ice. After the addition, the mixture was heated at 100° C. for 3 hours, then cooled to room temperature and poured into 30 ml of ice-cold water. The mixed solution was stirred at room temperature for 18 hours, and the precipitated solid was collected by filtration, washed with 20 ml of water and dried to obtain 1.61 g of the above-identified desired product as a yellow solid (yield 70%).

$^1$H-NMR (ppm in DMSO-d$_6$)

δ=1.30-1.33 (m, 9H), 2.34-2.44 (m, 3H), 7.48-7.62 (m, 4H), 9.62-9.90 (m, 1H).

2) Synthesis of 4-methoxycarbonylbenzoic N'-(1-(4-tert-butylphenyl)-3-methyl-5-oxo-1,5-dihydropyrazol-4-ylidene-methyl)-hydrazide 1.0712 g (4.21 mmol) of the 1-(4-tert-butylphenyl)-5-hydroxy-3-methyl-1H-pyrazole-4-carbaldehyde synthesized in 1) and 819.6 mg (4.22 mmol) of 4-methoxycarbonylbenzhydrazide were stirred in 10 ml of dimethylformamide at room temperature for 3 hours. After the solvent was removed by evaporation, the precipitated solid was washed with a small amount of methanol and dried to obtain 765.9 mg of the above-identified desired product as a yellow solid (yield 42%).

$^1$H-NMR (ppm in DMSO-d$_6$)

δ=1.30 (s, 9H), 2.19-2.21 (m, 3H), 3.90 (s, 3H), 7.33 (s, 1H), 7.40-7.46 (m, 2H), 7.81-7.89 (m, 2H), 8.01-8.17 (m, 4H).

3) Synthesis of 4-carboxybenzoic N'-(1-(4-tert-butylphenyl)-3-methyl-5-oxo-1,5-dihydropyrazol-4-ylidene-methyl)-hydrazide 59.4 mg (0.14 mmol) of the 4-methoxycarbonylbenzoic N'-(1-(4-tert-butylphenyl)-3-methyl-5-oxo-1,5-dihydropyrazol-4-ylidene-methyl)-hydrazide synthesized in 2) was dissolved in 5.0 ml of methanol and stirred with 0.68 ml (0.68 mmol) of 1M aqueous sodium hydroxide at room temperature for 6 hours and then at 60° C. for 3 hours. After the stirring, 0.68 ml (0.68 mmol) of hydrochloric acid was added, and the precipitated solid was collected by filtration and dried to obtain 33.3 mg of the above-identified desired product as a yellow solid (yield 58%).

$^1$H-NMR (ppm in DMSO-d$_6$)

δ=1.30 (s, 9H), 2.19-2.21 (m, 3H), 7.33 (s, 1H), 7.40-7.46 (m, 2H), 7.80-7.89 (m, 2H), 7.99-8.14 (m, 4H).

LC/MS

M$^+$=420.46 (2.39 min)

Synthetic Example 98

Synthesis of 5-methoxycarbonyl-2-thiophenecarboxylic acid N'-(1-(1-(4-tert-butylphenyl)-3-methyl-5-oxo-1,5-dihydropyrazol-4-ylidene)-ethyl)-hydrazide 1) Synthesis of 5-methoxycarbonyl-2-thiophenecarboxylic acid 1.72 g (10 mmol) of thiophene-2,5-dicarboxylic acid and 3.18 g (30 mmol) of sodium carbonate suspended in 25 mL of DMF were stirred with 623 μL of methyl iodide at room temperature overnight. The sodium salt of the desired product was extracted with water, and 12M of hydrochloric acid was added to the combined aqueous layer. The desired product was extracted with ethyl acetate, and the combined organic layer was washed with saturated aqueous ammonium chloride and dried over anhydrous magnesium sulfate. The desired product was purified by silica gel column chromatography to give 0.49 g of a colorless solid (yield 28%).

$^1$H-NMR (ppm in CDCl$_3$)

δ=3.93 (s, 3H), 7.77 (d, 1H, J=4.2 Hz), 7.83 (d, 1H, J=4.2 Hz).

LC/MS

M$^+$=186 (0.92 min)

2) Synthesis of 5-methoxycarbonyl-2-thiophenecarboxylic acid hydrazide

The known procedure disclosed in the literature (J. Heterocyclic Chem., 28, 17, (1991).) was followed using 5-methoxycarbonyl-2-thiophenecarboxylic acid, thionyl chloride and hydrazine monohydrate to give 144 mg of a white solid (yield 72%).

$^1$H-NMR (ppm in DMSO-d$_6$)

δ=3.84 (s, 3H), 4.57 (brs, 2H), 7.72 (d, 1H, J=4.2 Hz), 7.79 (d, 1H, J=4.2 Hz), 10.06 (brs, 1H).

LC/MS

M$^+$=200 (3.09 min)

3) Synthesis of 5-methoxycarbonyl-2-thiophenecarboxylic acid N'-(1-(1-(4-tert-butylphenyl)-3-methyl-5-oxo-1,5-dihydropyrazol-4-ylidene)-ethyl)-hydrazide 54.5 mg (0.20 mmol) of 1-(1-(4-tert-butylphenyl)-5-hydroxy-3-methyl-1H-pyrazol-4-yl)-ethanone and 40.0 mg (0.20 mmol) of 5-methoxycarbonyl-2-thiophenecarboxylic acid hydrazide were dissolved in 2.0 mL of DMF and stirred at 110° C. for 12 hours. After cooling, the solvent was removed by evaporation, and the crude product was washed with ethyl acetate and collected by filtration to obtain 32.0 mg of the desired product as a yellow solid (yield 35%).

$^1$H-NMR (ppm in DMSO-$d_6$)

δ=1.29 (s, 9H), 2.36 (s, 3H), 2.43 (s, 3H), 3.87 (s, 3H), 7.41 (d, 2H, J=9.0 Hz), 7.87-7.90 (m, 4H).

LC/MS

M$^+$=454.54 (4.46 min)

Synthetic Example 99

Synthesis of 5-carboxy-2-thiophenecarboxylic acid N'-(1-(1-(4-tert-butylphenyl)-3-methyl-5-oxo-1,5-dihydropyrazol-4-ylidene)-ethyl)-hydrazide 14.9 mg (0.033 mmol) of 5-methoxycarbonyl-2-thiophenecarboxylic acid N'-(1-(1-(4-tert-butylphenyl)-3-methyl-5-oxo-1,5-dihydropyrazol-4-ylidene)-ethyl)-hydrazide in 1.5 mL of methanol was stirred with 164 μL (0.164 mmol) of 1M aqueous sodium hydroxide at room temperature for 17 hours. After the stirring, 164 μL (0.164 mmol) of 1M hydrochloric acid was added, and the precipitated solid was collected by filtration to obtain 6.8 mg of the desired product as a pale yellow solid (yield 47%).

$^1$H-NMR (ppm in DMSO-$d_6$)

δ=1.29 (s, 9H), 2.36 (s, 3H), 2.43 (s, 3H), 7.41 (d, 2H, J=9.0 Hz), 7.80 (d, 1H, J=3.9 Hz), 7.87-7.90 (m, 3H).

LC/MS

M$^+$=440.52 (4.23 min)

Synthetic Example 100

Synthesis of 4-carboxybenzoic N'-(1-(1-(quinolin-2-yl)-3-methyl-5-oxo-1,5-dihydropyrazol-4-ylidene)-ethyl)-hydrazide 1) Synthesis of 4-methoxycarbonylbenzoic N'-(1-(1-(quinolin-2-yl)-3-methyl-5-oxo-1,5-dihydropyrazol-4-ylidene)-ethyl)-hydrazide 2.0 mL of an isopropyl alcohol solution of 28.7 mg (0.11 mmol) of 1-(1-(quinolin-2-yl)-5-hydroxy-3-methyl-1H-pyrazol-4-yl)-ethanone, 20.8 mg (0.11 mmol) of 4-methoxycarbonylbenzhydrazide and 6.1 mg (0.03 mmol) of p-toluenesulfonic acid monohydrate was refluxed with heating for 48 hours. After cooling, the precipitate was collected by filtration and washed with methanol and acetonitrile to obtain 14.9 mg of the desired product as a purple solid (yield 31%).

$^1$H-NMR (ppm in DMSO-$d_6$)

δ=2.54 (s, 3H), 3.91 (s, 3H), 7.58-7.63 (m, 1H), 7.80-7.85 (m, 1H), 8.01-8.15 (m, 6H), 8.46 (d, 1H, J=6.3 Hz), 8.58 (d, 1H, J=6.3 Hz).

LC/MS

M$^+$=443.45 (3.21 min)

2) Synthesis of 4-carboxybenzoic N'-(1-(1-quinolin-2-yl)-3-methyl-5-oxo-1,5-dihydropyrazol-4-ylidene)-ethyl)-hydrazide 1.5 mL of a methanol solution of 14.9 mg (0.034 mmol) of the 4-methoxycarbonylbenzoic N'-(1-(1-(quinolin-2-yl)-3-methyl-5-oxo-1,5-dihydropyrazol-4-ylidene)-ethyl)-hydrazide synthesized in 1) was stirred with 168 μL (0.168 mmol) of 1M aqueous sodium hydroxide at 50° C. for 12 hours. After the stirring, 168 μL (0.168 mmol) of 1M hydrochloric acid was added, and the precipitated solid was collected by filtration to obtain 4.9 mg of the desired product as a dark yellow solid (yield 34%).

$^1$H-NMR (ppm in DMSO-$d_6$)

δ=2.44 (s, 3H), 7.52-7.56 (m, 1H), 7.75 (t, 1H, J=7.5 Hz), 7.94 (d, 1H, J=4.5 Hz), 7.96 (d, 1H, J=4.2 Hz), 8.05 (d, 2H, J=8.7 Hz), 8.10 (d, 2H, J=8.4 Hz), 8.33 (d, 1H, J=9.6 Hz), 8.42 (d, 1H, J=9.0 Hz).

LC/MS

M$^+$=429.43 (3.21 min)

Synthetic Example 101

Synthesis of methyl 4-[(2-{1-[1-(6-chloro-3-pyridazinyl)-3-methyl-5-oxo-1,5-dihydropyrazol-4-ylidene]-ethyl}hydrazino)carbonyl]benzoate 0.2 mmol of 1-[1-(6-chloro-3-pyridazinyl)-5-hydroxy-3-methyl-1H-pyrazol-4-yl]ethanone and 0.2 mmol of 4-methoxycarbonylbenzhydrazide were dissolved in 2 ml of DMSO and heated at 100° C. for 8 hours with stirring. After the solvent was removed by evaporation, the crude product was dissolved in chloroform and recrystallized from ether to obtain 55 mg of the desired product, methyl 4-[(2-{1-[1-(6-chloro-3-pyridazinyl)-3-methyl-5-oxo-1,5-dihydropyrazol-4-ylidene]-ethyl}hydrazino)carbonyl]benzoate (yield 64%).

$^1$H-NMR (ppm in DMSO-$d_6$)

δ=2.42 (s, 3H), 2.54 (s, 3H), 3.91 (s, 3H), 7.96 (d, 1H, J=9.3 Hz), 8.06 (d, 2H, J=8.4 Hz), 8.13 (d, 2H, J=8.4 Hz), 8.44 (d, 1H, J=9.3 Hz).

LC/MS

M$^+$=428.83 (2.88 min).

Synthetic Example 102

Synthesis of 4-[(2-{1-[3-methyl-5-oxo-1-(5-trifluoromethyl-2-pyridinyl)-1,5-hydropyrazol-4-ylidene]-ethyl}hydrazino)carbonyl]benzoic acid 1) Synthesis of methyl 4-{[2-{1-(5-hydroxy-3-methyl-1-[5-(trifluoromethyl)-2-pyridinyl]-1H-pyrazol-4-yl}ethylidene)hydrazino]carbonyl}benzoate 0.2 mmol of 1-{5-hydroxy-3-methyl-1-[5-(trifluoromethyl)-2-pyridinyl]-1H-pyrazol-4-yl}ethanone and 0.2 mmol of 4-methoxycarbonylbenzhydrazide were heated in 2 ml of DMF at 100° C. for 9 hours with stirring. After the solvent was removed by evaporation, the resulting crude product was dissolved in chloroform and recrystallized from hexane to obtain 66 mg of the desired product, methyl 4-{([2-(1-{5-hydroxy-3-methyl-1-[5-(trifluoromethyl)-2-pyridinyl]-1H-pyrazol-4-yl}ethylidene)hydrazino]carbonyl}benzoate (yield 72%).

$^1$H-NMR (ppm in DMSO-$d_6$)

δ=2.41 (s, 3H), 2.50 (s, 3H), 3.88 (s, 3H), 7.9-8.4 (m, 6H), 8.80 (s, 1H).

LC/MS

M$^+$=461.39 (3.00 min).

2) Synthesis of 4-[(2-{1-[3-methyl-5-oxo-1-(5-trifluoromethyl-2-pyridinyl)-1,5-dihydropyrazol-4-ylidene]-ethyl}hydrazino)carbonyl]benzoic acid 50 mg of the methyl 4-([2-(1-{5-hydroxy-3-methyl-1[5-(trifluoromethyl)-2-pyridinyl]-1H-pyrazol-4-yl}ethylidene) hydrazino]carbonyl)benzoate synthesized in 1) was heated in 3 ml of methanol and 0.3 ml of 1M aqueous sodium hydroxide at 60° C. for 8 hours with stirring. After it was cooled to room temperature, 0.3 ml of 1M hydrochloric acid was added to precipitate crystals, and crystals were collected by filtration and dried to obtain 30 mg of the desired product, 4-[(2-{1-[3-methyl-5-oxo-1-(5-trifluoromethyl-2-pyridinyl)-1,5-dihydropyrazol-4-ylidene]-ethyl}hydrazino)carbonyl]benzoic acid as a pale brown solid (yield 62%).

$^1$H-NMR (ppm in DMSO-$d_6$)

δ=2.41 (3H, s), 2.50 (3H, s), 8.04 (d, 2H, J=8.4 Hz), 8.10 (d, 2H, J=8.4 Hz), 8.26 (dd, 1H, J=9 Hz, J=2.4 Hz), 8.35 (d, 1H, J=9 Hz), 8.81 (brs, 1H), 11.6 (brs, 1H), 12.4 (brs, 1H)

LC/MS

M$^+$=447.37 (2.65 min).

Synthetic Example 103

Synthesis of 4-(1H-tetrazol-5-yl)-benzoic N'-(1-(1-(4-tert-butylphenyl)-3-methyl-5-oxo-1,5-dihydropyrazol-4-ylidene)-ethyl)-hydrazide A DMF solution (1 ml) of 27.2 mg (0.10 mmol) of 1-(1-(4-tert-butylphenyl)-5-hydroxy-3-methyl-1H-pyrazol-4-yl)-ethanone and 20.4 mg (0.10 mmol) of 4-(1H-tetrazol-5-yl)-benzoic hydrazide synthesized by the method disclosed in WO03/037328 was heated at 60° C. for 6 hours with one drop of concentrated hydrochloric acid, and the precipitated solid was washed with water and collected by filtration. The solid was mixed with 1M aqueous sodium hydroxide and filtered. 1M Hydrochloric acid was added to the filtrate, and the precipitated solid was collected by filtration to obtain 5.9 mg of the desired product as a brown solid (yield 12%).

$^1$H-NMR (ppm in DMSO-$d_6$)

δ=1.30 (s, 9H), 2.38 (s, 3H), 2.47 (s, 3H), 7.42 (d, 2H, J=8.6 Hz), 7.90 (d, 2H, J=8.6 Hz), 8.14 (d, 2H, J=8.4 Hz), 8.23 (d, 2H, J=8.4 Hz).

LC/MS

M$^+$=458.52 (2.62 min)

Synthetic Example 104

Synthesis of 4-methoxycarbonyl-3-nitrobenzoic N'-(1-(1-(4-tert-butylphenyl)-3-methyl-5-oxo-1,5-dihydropyrazol-4-ylidene)-ethyl)-hydrazide 1) Synthesis of 4-methoxycarbonyl-3-nitrobenzhydrazide The procedure described in reference (*J. Heterocyclic Chem.*, 28, 17, (1991).) was followed here using 1-methyl-2-nitroterephtalate, thionyl chloride and hydrazine hydrate to give the title compound (200 mg, 42%) as a white solid.

$^1$H-NMR (DMSO-$d_6$)

δ=3.88 (s, 3H), 4.67 (brs, 2H), 7.96 (d, 1H, J=7.8 Hz), 8.24 (dd, 1H, J=1.8, 7.8 Hz), 8.44 (d, 1H, J=1.8 Hz).

LC/MS

M$^+$=239

2) Synthesis of 4-methoxycarbonyl-3-nitrobenzoic N'-(1-(1-(4-tert-butylphenyl)-3-methyl-5-oxo-1,5-dihydropyrazol-4-ylidene)-ethyl)-hydrazide DMF solution (2.0 mL) of 1-(1-(4-tert-butylphenyl)-5-hydroxy-3-methyl-1H-pyrazol-4-yl)-ethanone (54.5 mg, 0.20 mmol) and 4-methoxycarbonyl-3-nitrobenzhydrazide (47.8 mg, 0.20 mmol) was heated at 110° C. for 6 hours After removing solvent, the residue was purified by column chromatography to give the title compound (53.8 mg, 55%) as a brown solid.

$^1$H-NMR (DMSO-$d_6$)

δ=1.29 (s, 9H), 2.31 (s, 3H), 2.59 (s, 3H), 3.86 (s, 3H), 7.35 (d, 2H, J=8.7 Hz), 7.83 (d, 1H, J=8.1 Hz), 7.98 (d, 2H, J=8.7 Hz), 8.35 (dd, 1H, J=1.5, 8.1 Hz), 8.45 (d, 1H, J=1.5 Hz).

LC/MS

M$^+$=493

Synthetic Example 105

Synthesis of 4-carboxy-3-nitrobenzoic N'-(1-(1-(4-tert-butylphenyl)-3-methyl-5-oxo-1,5-dihydropyrazol-4-ylidene)-ethyl)-hydrazide 1M aqueous sodium hydroxide (460 μL, 0.46 mmol) was added to a solution of 4-methoxycarbonyl-3-nitrobenzoic N'-(1-(1-(4-tert-butylphenyl)-3-methyl-5-oxo-1,5-dihydropyrazol-4-ylidene)-ethyl)-hydrazide (45.5 mg, 0.092 mmol) in methanol (1.5 mL) and the mixture was stirred at room temperature for 7 hours. After adding 1 M hydrochloric acid (460 μL, 0.46 mmol), the precipitate was filtered to give the title compound (24.3 mg, 55%) as a yellow solid.

$^1$H-NMR (DMSO-$d_6$)

δ=1.30 (s, 9H), 2.37 (s, 3H), 2.47 (s, 3H), 7.42 (d, 2H, J=9.0 Hz), 7.92 (d, 2H, J=9.0 Hz), 8.03 (d, 1H, J=8.1 Hz), 8.29 (dd, 1H, J=1.5, 8.1 Hz), 8.48 (d, 1H, J=1.5 Hz).

LC/MS

M$^+$=479

Reference Synthetic Example 1

Example 4 of WO01/34585

Synthesis of 5-(4-carboxybenzylidene)-3-[(1-{3,4-dimethylphenyl}-5-hydroxy-3-methyl-1H-pyrazol-4-ylmethylene)amino]-2-thioxothiazolidin-4-one 1) Synthesis of 1-(3,4-dimethylphenyl)-5-hydroxy-3-methyl-1H-pyrazol-4-carbaldehyde 1.86 g (9.16 mmol) of 1-(3,4-dimethylphenyl)-3-methyl-3-pyrazolin-5-one was dissolved in 3.6 ml of dry dimethylformamide, and 1.02 ml (11.0 mmol) of phosphorus oxychloride was added gradually under cooling with ice at 20° C. or below. After the addition, the mixture was heated at 100° C. for 2 hours, then cooled to room temperature and poured into 30 ml of ice-cold water. Then, it was washed with 10 ml of water and 10 ml of dimethylformamide. The mixed solution was stirred for 18 hours, and the precipitated solid was collected by filtration, washed with 20 ml of water and dried to obtain 1.03 g of the above-identified desired product as a pale brown solid (yield 49%).

$^1$H-NMR (ppm in CDCl$_3$)

δ=2.29 (s, 3H), 2.32 (s, 3H), 2.43 (s, 3H), 7.20 (d, 1H, J=8 Hz), 7.48 (dd, 1H, J=8 Hz, 2 Hz), 7.54 (d, 1H, J=2 Hz), 9.60 (s, 1H)

2) Synthesis of 5-(4-carboxybenzylidene)-3-[(1-{3,4-dimethylphenyl}-5-hydroxy-3-methyl-1H-pyrazol-4-ylmethylene)amino]-2-thioxothiazolidin-4-one 230 mg (1 mmol) of the 1-(3,4-dimethylphenyl)-5-hydroxy-3-methyl-1H-pyrazol-4-carbaldehyde synthesized in 1) and 148 mg (1 mmol) of 3-aminorhodanine were stirred in 10 ml of ethanol at room temperature for 96 hours. The resulting solid was collected by filtration, washed with ethanol and ether and dried to obtain 332 mg of a crude imine.

A liquid mixture of 160 mg (0.444 mmol) of the imine, 4 mg of piperidine, 66 mg of 4-formylbenzoic acid, 6 mg of benzoic acid and 20 ml of toluene was refluxed in a reactor equipped with a Dean-Stark tube packed with molecular sieve for 7 hours with heating. After cooling, the precipitated solid was collected by filtration and washed with 3 ml of toluene and 3 ml of ether to obtain 23.3 mg of a yellow solid. It was washed with a liquid mixture of methanol and chloroform to obtain 16.5 mg of the desired product (yield 7.5%).

$^1$H-NMR (ppm in DMSO-$d_6$)

δ=2.10-2.40 (s×3, 9H), 7.18 (d, 1H, J=8 Hz), 7.63 (d, 1H, J=8 Hz), 7.67 (s, 1H), 7.84 (d, 2H, J=8 Hz), 8.03 (d, 2H, J=8 Hz), 8.10 (d, 2H, J=8 Hz), 8.20 (s, 1H)

LC/MS $M^+$=493.0 (3.33 min)

Reference Synthetic Example 2

Example 5 of WO01/34585

Synthesis of 5-(3-carboxybenzylidene)-3-[(1-{3,4-dimethylphenyl}-5-hydroxy-3-methyl-1H-pyrazol-4-ylmethylene)amino]-2-thioxothiazolidin-4-one A liquid mixture of 160 mg (0.444 mmol) of the imine synthesized in 2) of Reference Synthetic Example 1, 4 mg of piperidine, 66 mg of 3-formylbenzoic acid, 6 mg of benzoic acid and 20 ml of toluene was refluxed in a reactor equipped with a Dean-Stark tube packed with molecular sieve for 7 hours with heating. After cooling, the precipitated solid was collected by filtration and washed with 3 ml of toluene and 3 ml of ether to obtain 38.5 mg of a yellow solid (yield 18%).

$^1$H-NMR (ppm in DMSO-$d_6$)

δ=2.00-2.30 (s×3, 9H), 7.18 (d, 1H, J=8 Hz), 7.64 (d, 1H, J=8 Hz), 7.68 (s, 1H), 7.73 (t, 1H, J=8 Hz), 7.97 (d, 2H, J=8 Hz), 8.06 (s, 1H), 8.08 (d, 1H, J=8 Hz), 8.23 (d, 2H, J=8 Hz)

LC/MS $M^+$=493.0 (3.32 min)

Reference Synthetic Example 3

Example 2 of WO01/34585

Synthesis of 3-(3-carboxyphenyl)-1-[(1-{3,4-dimethylphenyl}-5-hydroxy-3-methyl-1H-pyrazol-4-ylmethylene)amino]-2-thioxoimidazolidin-4-one 1) Synthesis of 1-amino-3-(3-carboxyphenyl)-2-thioxoimidazolidin-4-one 179 mg (1 mmol) of 3-isothiocyanatobenzoic acid and 523 μl (3 mmol) of diisopropylethylamine were stirred in 8 ml of dichloromethane and then with 155 mg (1 mmol) of ethyl hydrazinoacetate hydrochloride at room temperature for 96 hours. After the solvent was concentrated, the mixture was partitioned between ethyl acetate and 30% acetic acid. The aqueous layer was extracted with ethyl acetate again, and the organic layers were combined, washed with water and then with saturated aqueous sodium chloride, dried over magnesium sulfate and concentrated. The resulting solid was mixed with a 190:10:0.8 liquid mixture of ethyl acetate, methanol and acetic acid, and the insoluble was dried to obtain 55.7 mg of the desired product (yield 22%).

$^1$H-NMR (ppm in DMSO-$d_6$)

δ=4.44 (s, 2H), 5.46 (s, 2H), 7.57 (dd, 1H, J=8 Hz, J=1.5 Hz), 7.63 (t, 1H, J=8 Hz), 7.90 (s, 1H), 7.99 (d, 1H, J=8 Hz)

LC/MS $M^+$=251.30 (0.59 min).

2) Synthesis of 3-(3-caboxyphenyl)-1-[(1-{3,4-dimethylphenyl}-5-hydroxy-3-methyl-1H-pyrazol-4-ylmethylene)amino]-2-thioxoimidazolidin-4-one 50 mg (0.2 mmol) of the 1-amino-3-(3-carboxyphenyl)-2-thioxoimidazolidin-4-one synthesized above in 1) and 55 mg (0.22 mmol) of the 1-(3,4-dimethylphenyl)-5-hydroxy-3-methyl-1H-pyrazole-4-carbaldehyde synthesized in 1) of Reference Synthetic Example 1 were stirred in a liquid mixture of 10 ml of ethanol and 5 ml of methanol at room temperature for 96 hours. The resulting insoluble was collected by filtration to obtain 73 mg of the desired product as a yellow solid (yield 72%).

$^1$H-NMR (ppm in DMSO-$d_6$)

δ=2.24 (s, 3H), 2.27 (s, 3H), 2.38 (s, 3H), 4.74 (s, 2H), 7.21 (d, 1H, J=8 Hz), 7.40-7.80 (m, 4H), 7.95 (s, 1H), 8.02 (d, 1H, J=8 Hz), 8.14 (s, 1H)

LC/MS $M^+$=463.51 (2.77 min).

Reference Synthetic Example 4

Example 3 of WO01/34585

Synthesis of 3-(4-carboxyphenyl)-1-[(1-{3,4-dimethylphenyl}-5-hydroxy-3-methyl-1H-pyrazol-4-ylmethylene)amino]-2-thioxoimidazolidin-4-one 1) Synthesis of 1-amino-3-(4-carboxyphenyl)-2-thioxoimidazolidin-4-one 179 mg (1 mmol) of 4-isothiocyanatobenzoic acid and 523 μl (3 mmol) of diisopropylethylamine were stirred in 8 ml of dichloromethane and then with 155 mg (1 mmol) of ethyl hydrazinoacetate hydrochloride at room temperature for 96 hours. After the solvent was concentrated, the mixture was partitioned between ethyl acetate and 30% acetic acid. The aqueous layer was extracted with ethyl acetate again, and the organic layers were combined, washed with water and then with saturated aqueous sodium chloride, dried over magnesium sulfate and concentrated. The resulting solid was mixed with a 190:10:0.8 liquid mixture of ethyl acetate, methanol and acetic acid, and the insoluble was dried to obtain 132 mg of the desired product (yield 53%).

$^1$H-NMR (ppm in DMSO-$d_6$)

δ=4.46 (s, 2H), 5.47 (s, 2H), 7.46 (d, 2H, J=8 Hz), 8.04 (d, 2H, J=8 Hz)

LC/MS $M^+$=251.26 (0.95 min)

2) Synthesis of 3-(4-carboxyphenyl)-1-[(1-{3,4-dimethylphenyl}-5-hydroxy-3-methyl-1H-pyrazol-4-ylmethylene)amino]-2-thioxoimidazolidin-4-one 50 mg (0.2 mmol) of the 1-amino-3-(4-carboxyphenyl)-2-thioxoimidazolidin-4-one synthesized above in 1) and 55 mg (0.22 mmol) of the 1-(3,4-dimethylphenyl)-5-hydroxy-3-methyl-1H-pyrazole-4-carbaldehyde synthesized in 1) of Reference Synthetic Example 1 were stirred in a liquid mixture of 10 ml of ethanol and 5 ml of methanol at room temperature for 96 hours. The resulting insoluble was collected by filtration to obtain 87 mg of the desired product as a yellow solid (yield 85%).

$^1$H-NMR (ppm in DMSO-$d_6$)

δ=2.24 (s, 3H), 2.27 (s, 3H), 2.50 (s, 3H), 4.75 (s, 2H), 7.21 (d, 1H, J=8 Hz), 7.40-7.70 (m, 4H), 8.08 (d, 2H, J=8.8 Hz), 8.14 (brs, 1H)

LC/MS

M$^+$=463.51 (2.76 min).

The structural formulae of the compounds obtained in the Synthetic Examples are as follows.

Formula 18

SYNTHETIC EX. 1

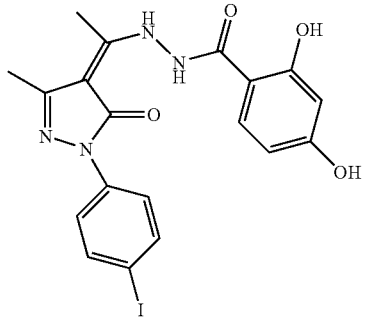

SYNTHETIC EX. 2

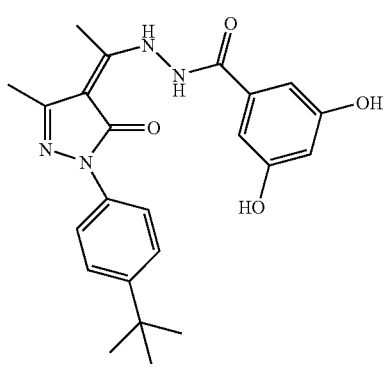

SYNTHETIC EX. 3

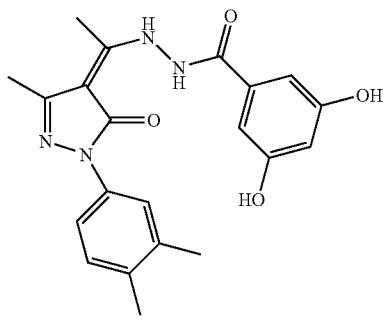

-continued

SYNTHETIC EX. 4

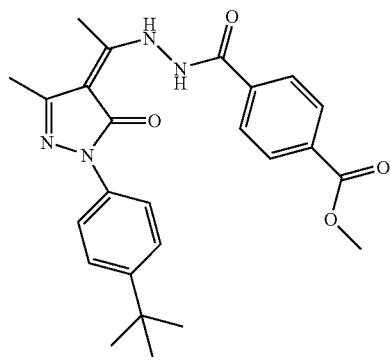

SYNTHETIC EX. 5

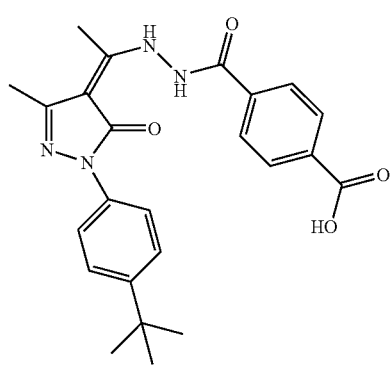

SYNTHETIC EX. 6

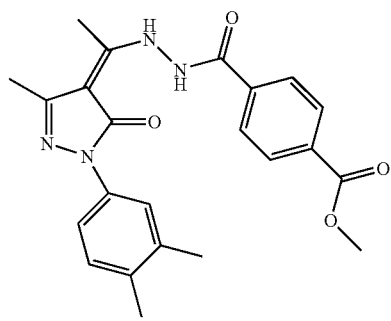

SYNTHETIC EX. 7

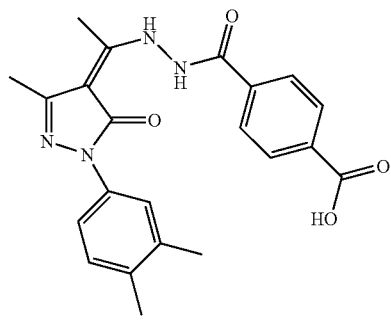

-continued
SYNTHETIC EX. 8
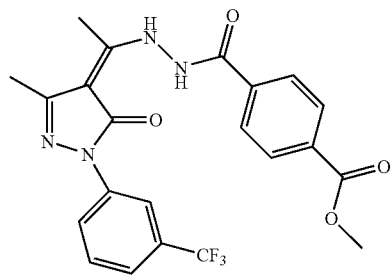
SYNTHETIC EX. 9
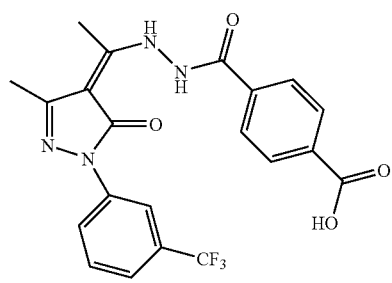
SYNTHETIC EX. 10
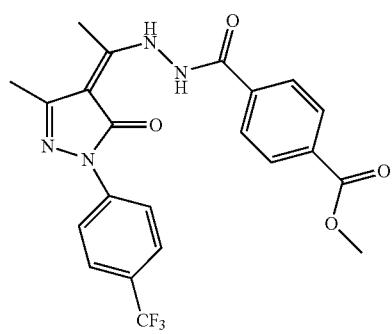
SYNTHETIC EX. 11
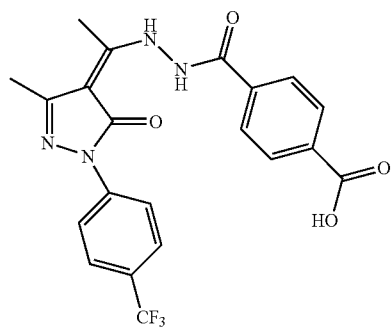
SYNTHETIC EX. 12
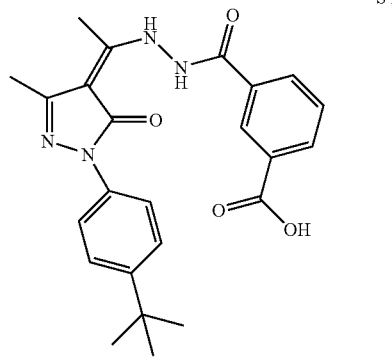
-continued
SYNTHETIC EX. 13
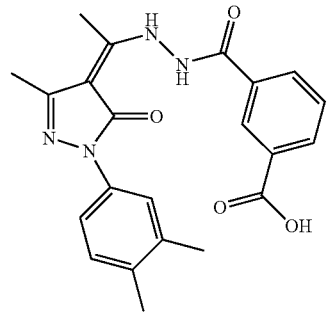
SYNTHETIC EX. 14
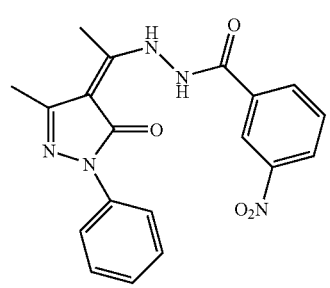
SYNTHETIC EX. 15
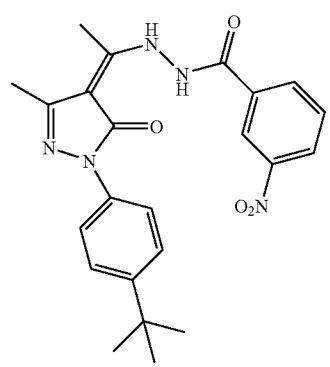
SYNTHETIC EX. 16
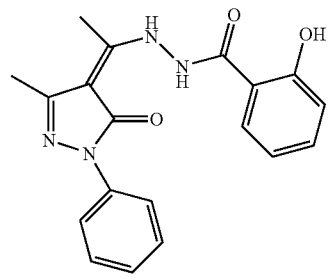
SYNTHETIC EX. 17
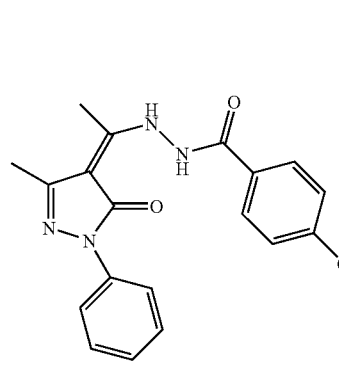

SYNTHETIC EX. 18
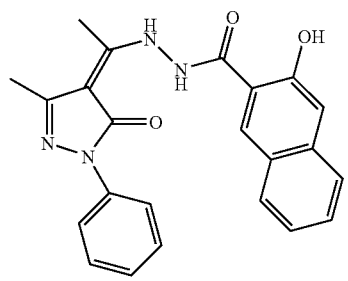
SYNTHETIC EX. 23
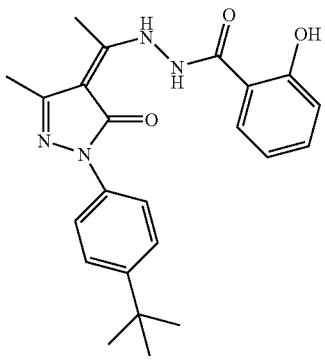
SYNTHETIC EX. 19
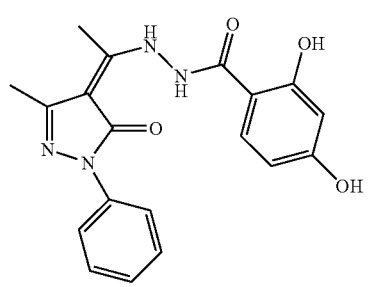
SYNTHETIC EX. 20
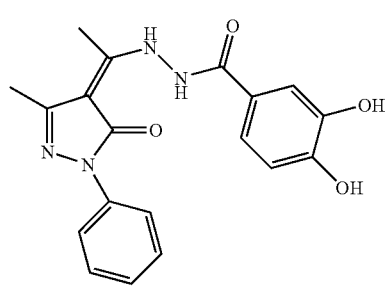
SYNTHETIC EX. 24
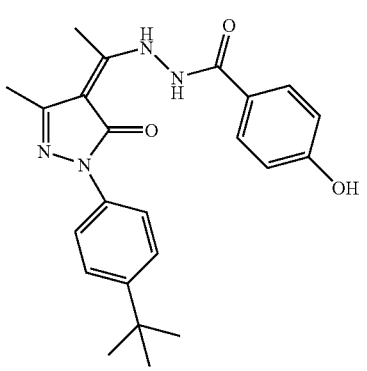
Formula 19
SYNTHETIC EX. 21
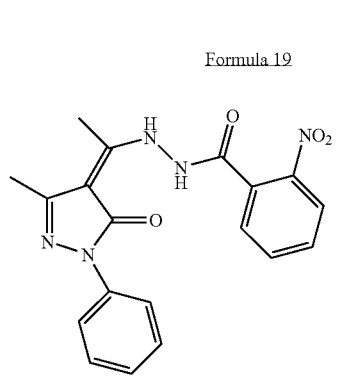
SYNTHETIC EX. 25
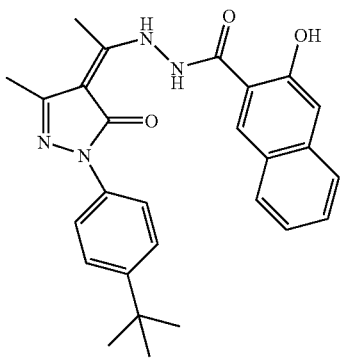
SYNTHETIC EX. 22
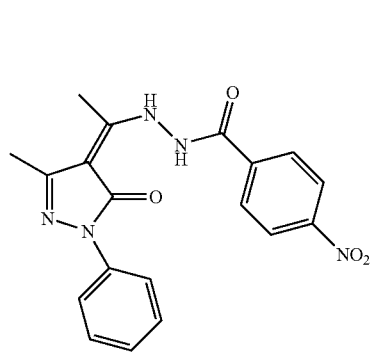
SYNTHETIC EX. 26
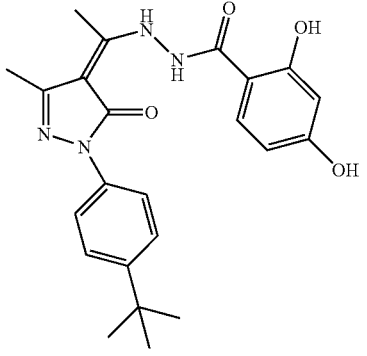

SYNTHETIC EX. 27
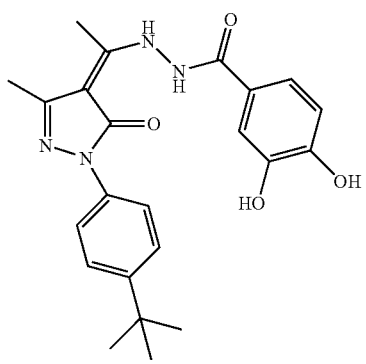
SYNTHETIC EX. 28
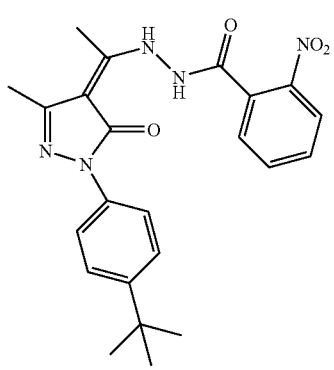
SYNTHETIC EX. 29
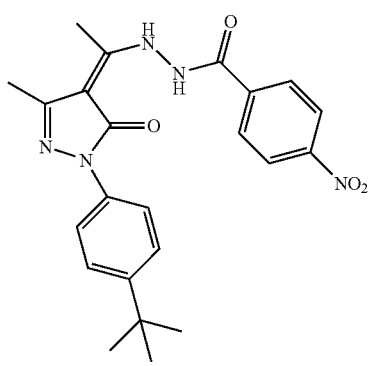
SYNTHETIC EX. 30
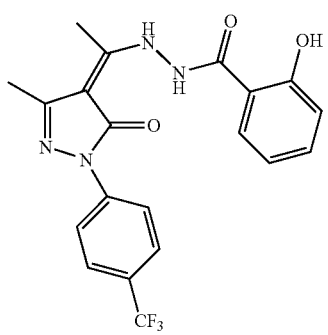
SYNTHETIC EX. 31
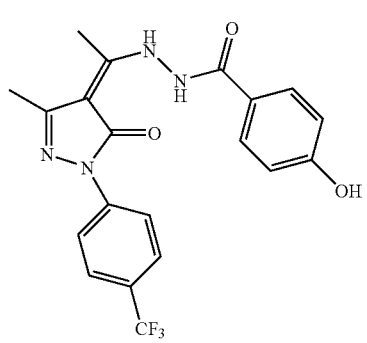
SYNTHETIC EX. 32
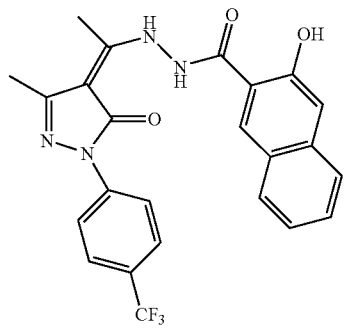
SYNTHETIC EX. 33
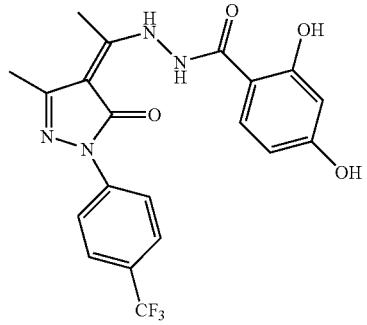
SYNTHETIC EX. 34
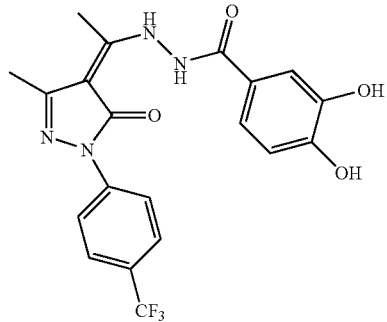

-continued
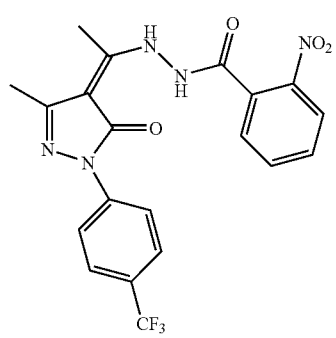
SYNTHETIC EX. 35
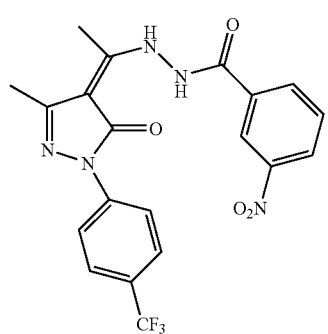
SYNTHETIC EX. 36
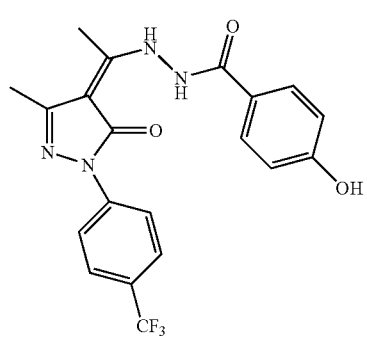
SYNTHETIC EX. 37
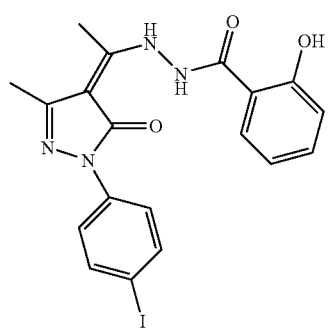
SYNTHETIC EX. 38
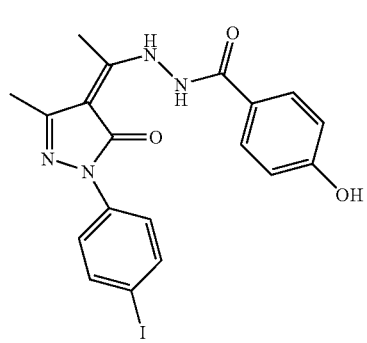
SYNTHETIC EX. 39
-continued
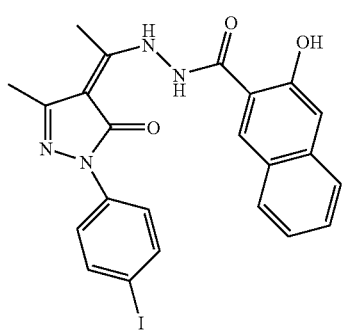
SYNTHETIC EX. 40
Formula 20
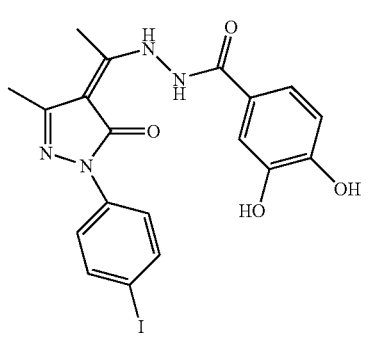
SYNTHETIC EX. 41
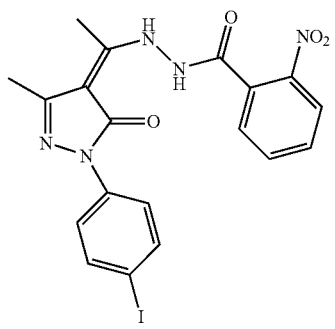
SYNTHETIC EX. 42
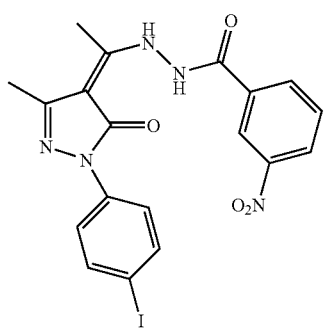
SYNTHETIC EX. 43

SYNTHETIC EX. 44
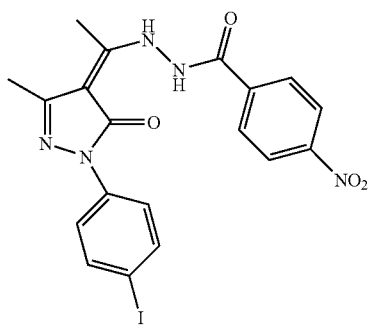
SYNTHETIC EX. 45
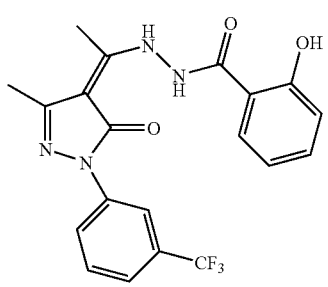
SYNTHETIC EX. 46
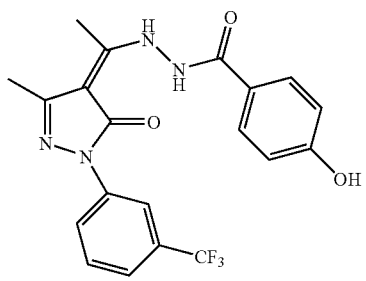
SYNTHETIC EX. 47
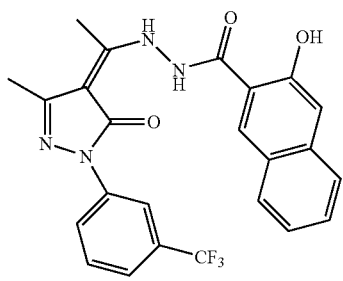
SYNTHETIC EX. 48
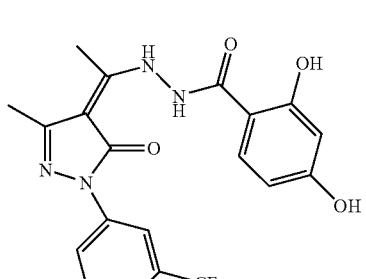
SYNTHETIC EX. 49
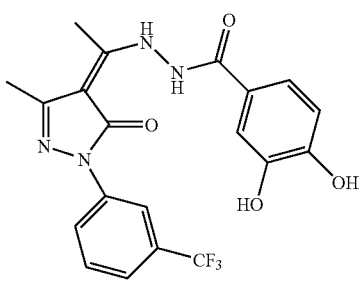
SYNTHETIC EX. 50
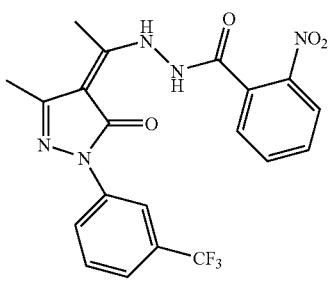
SYNTHETIC EX. 51
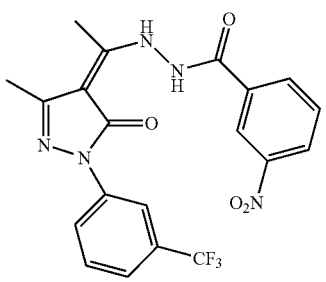
SYNTHETIC EX. 52
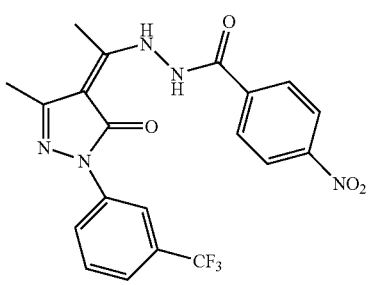
SYNTHETIC EX. 53
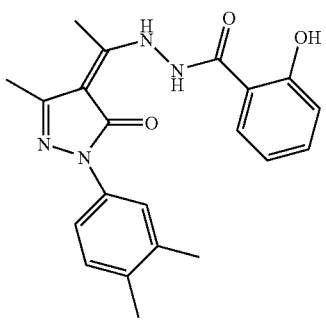

SYNTHETIC EX. 54
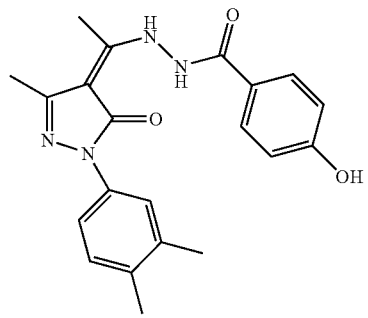
SYNTHETIC EX. 55
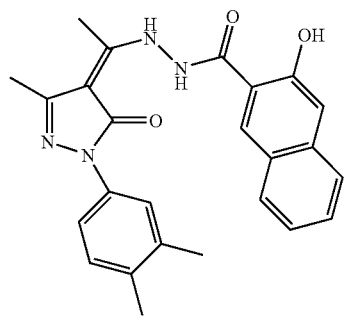
SYNTHETIC EX. 56
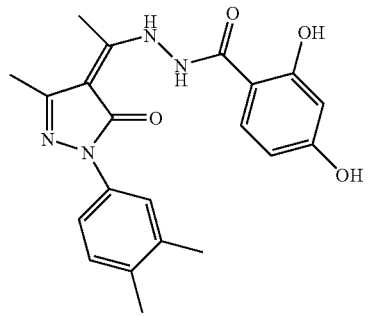
SYNTHETIC EX. 57
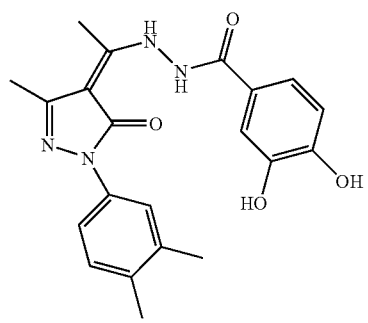
SYNTHETIC EX. 58
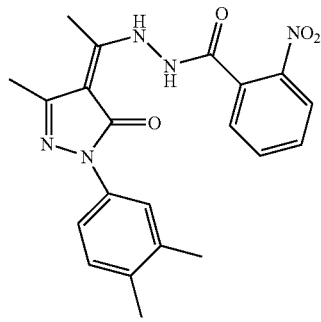
SYNTHETIC EX. 59
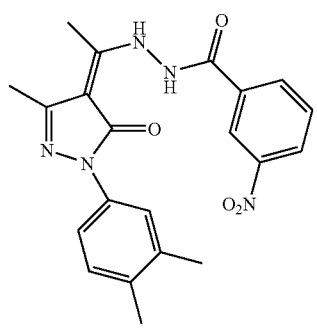
SYNTHETIC EX. 60
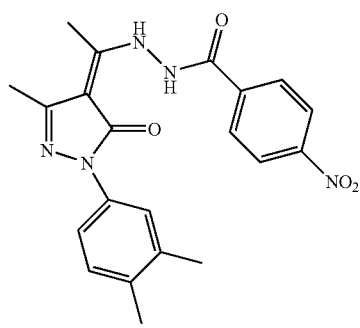
Formula 21
SYNTHETIC EX. 61
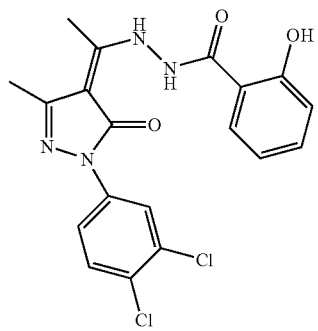

-continued
SYNTHETIC EX. 62
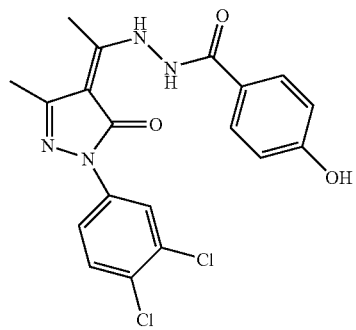
SYNTHETIC EX. 63
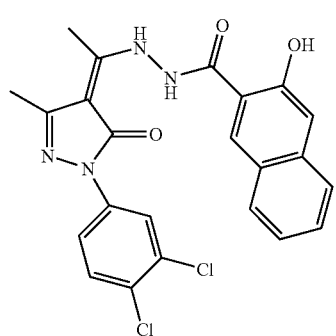
SYNTHETIC EX. 64
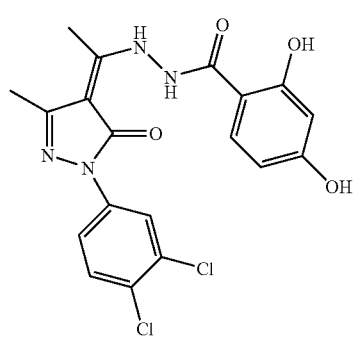
SYNTHETIC EX. 65
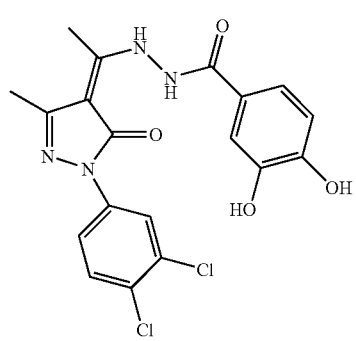
SYNTHETIC EX. 66
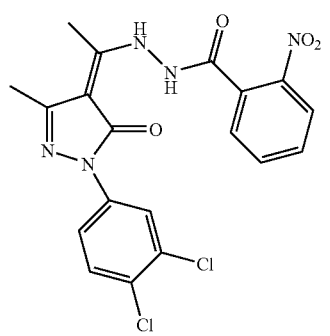
-continued
SYNTHETIC EX. 67
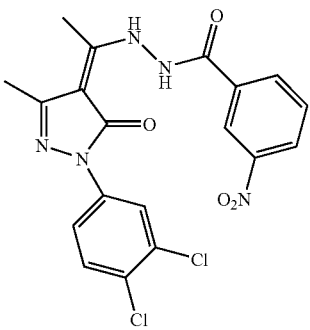
SYNTHETIC EX. 68
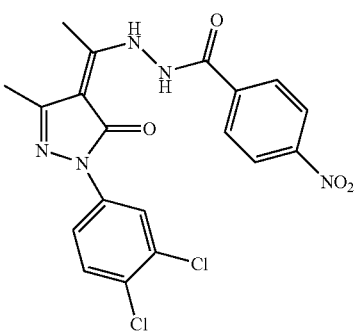
SYNTHETIC EX. 69
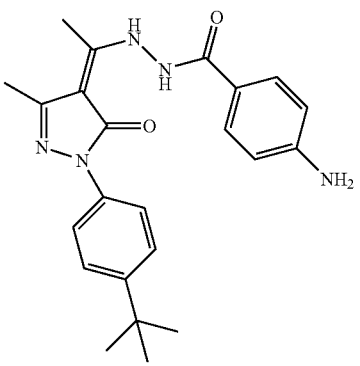
SYNTHETIC EX. 70
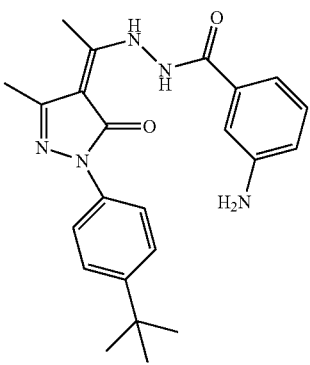

SYNTHETIC EX. 71
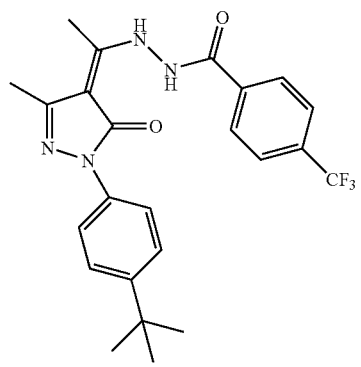
SYNTHETIC EX. 72
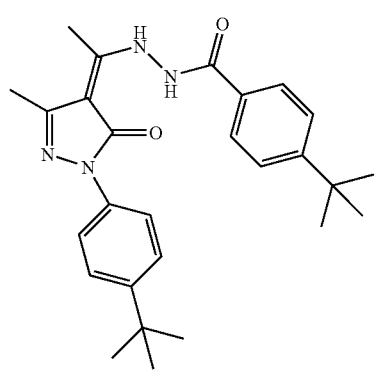
SYNTHETIC EX. 73
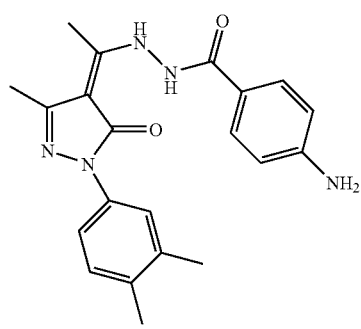
SYNTHETIC EX. 74
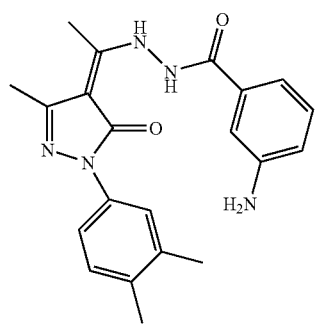
SYNTHETIC EX. 75
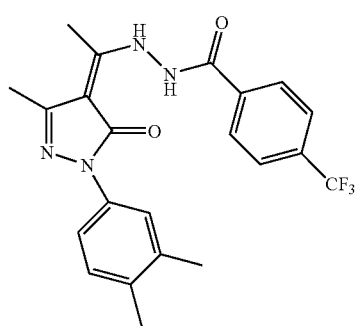
SYNTHETIC EX. 76
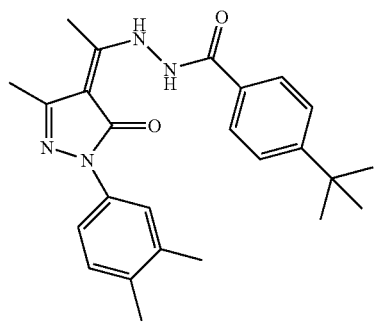
SYNTHETIC EX. 77
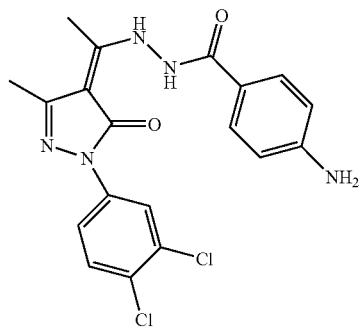
SYNTHETIC EX. 78
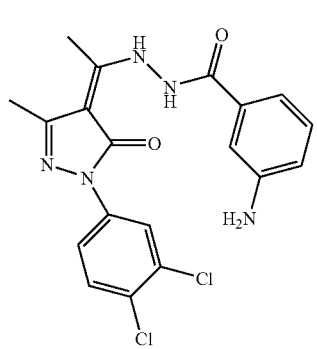

-continued
SYNTHETIC EX. 79
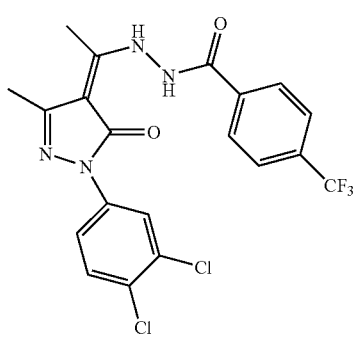
SYNTHETIC EX. 80
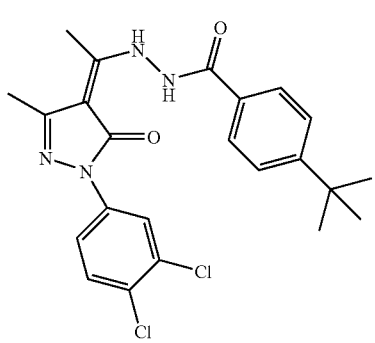
Formula 22
SYNTHETIC EX. 81
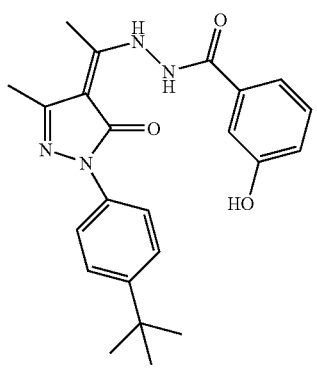
SYNTHETIC EX. 82
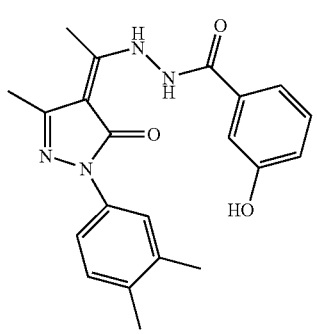
-continued
SYNTHETIC EX. 83
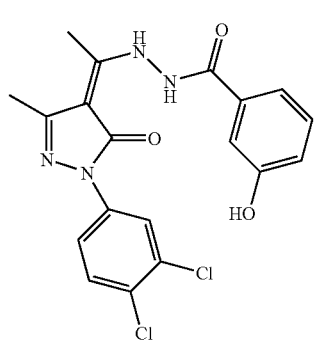
SYNTHETIC EX. 84
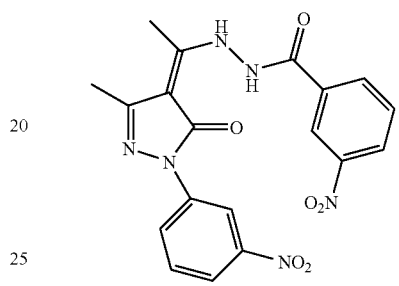
SYNTHETIC EX. 85
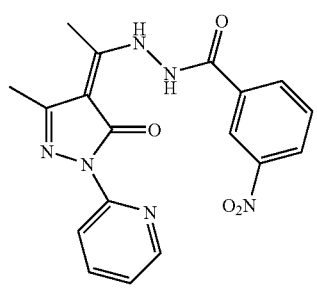
SYNTHETIC EX. 86
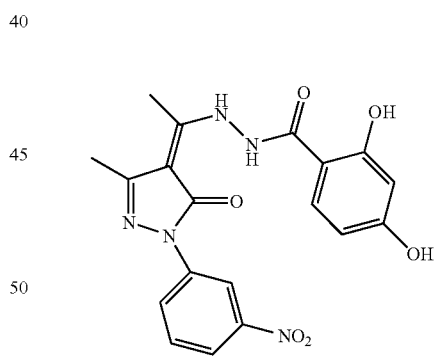
SYNTHETIC EX. 87
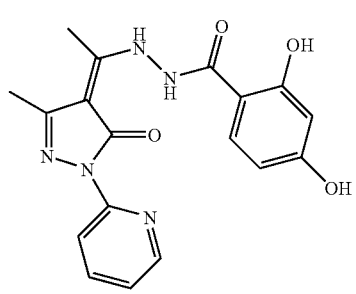

SYNTHETIC EX. 88
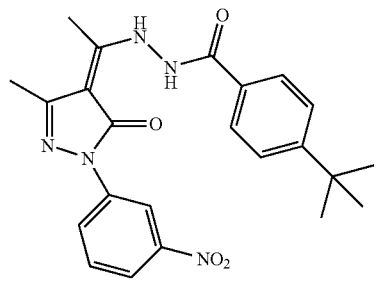
SYNTHETIC EX. 89
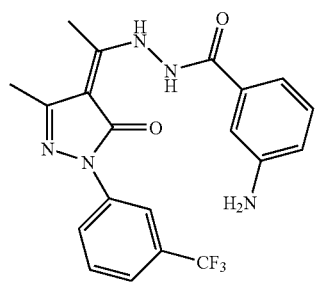
SYNTHETIC EX. 90
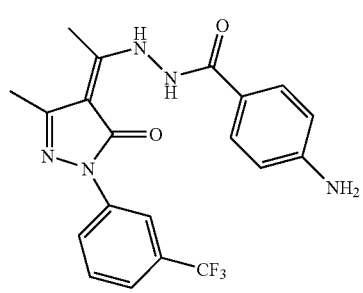
SYNTHETIC EX. 91
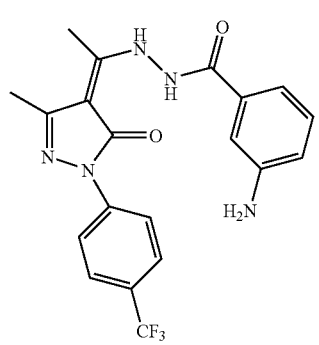
SYNTHETIC EX. 92
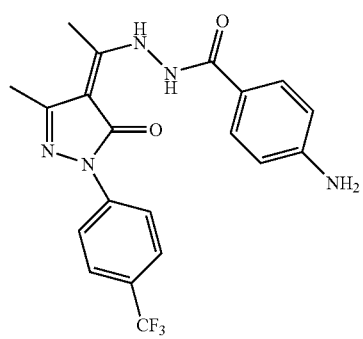
SYNTHETIC EX. 93
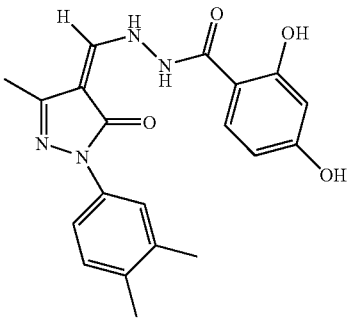
Formula 23
SYNTHETIC EX. 94
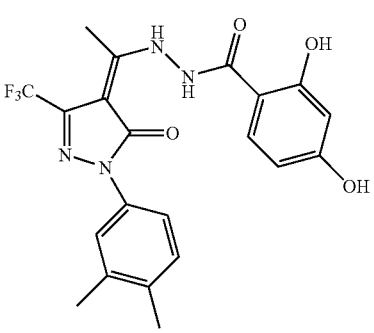
SYNTHETIC EX. 95
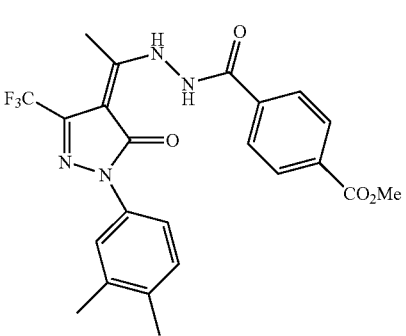
SYNTHETIC EX. 96
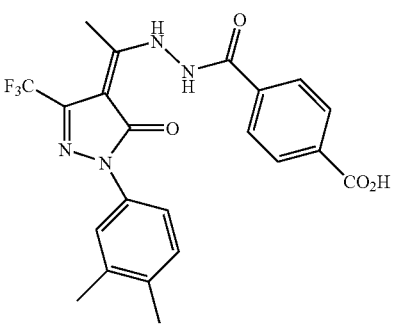

SYNTHETIC EX. 97
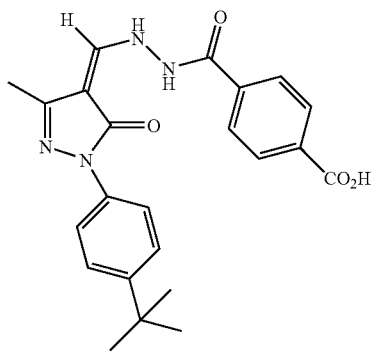
SYNTHETIC EX. 98
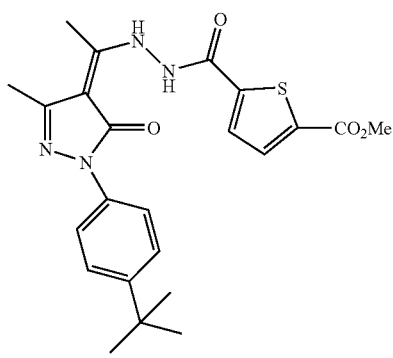
SYNTHETIC EX. 99
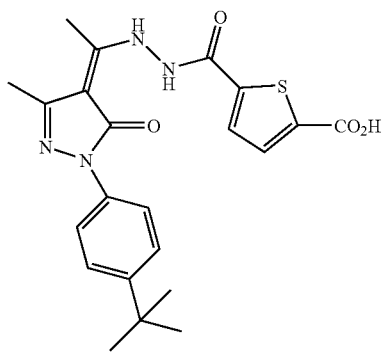
SYNTHETIC EX. 100
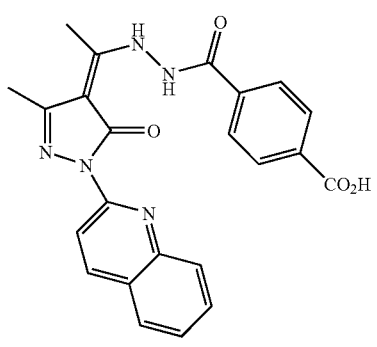
SYNTHETIC EX. 101
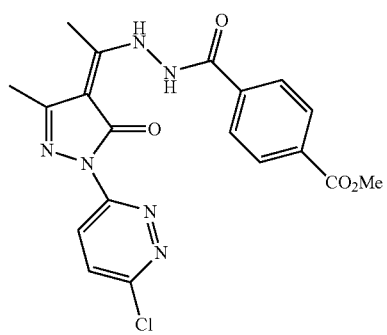
SYNTHETIC EX. 102
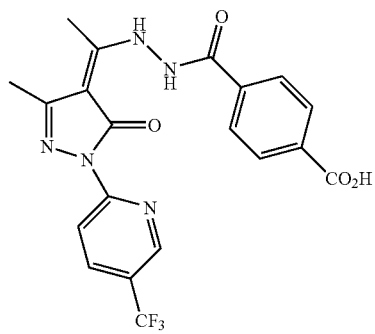
SYNTHETIC EX. 103
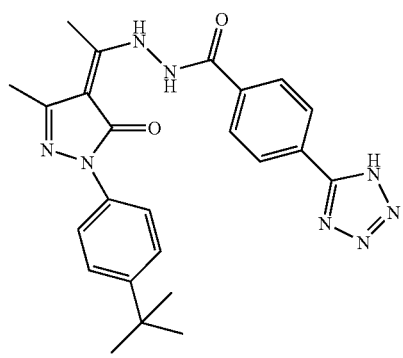
SYNTHETIC EX. 104
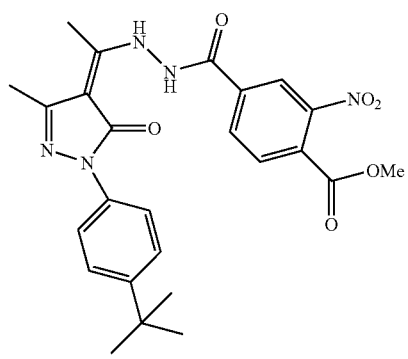

SYNTHETIC EX. 105

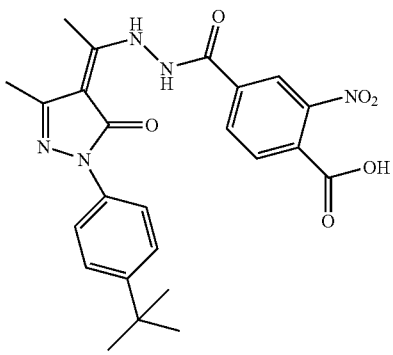

Assay Example 1

Stimulation of Proliferation of a Thrombopoietin (TPO)-Dependent Cell Line (1)

The reactivity of Synthetic Example 56, the compound of the present invention, with thrombopoietin (TPO) receptor was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human TPO receptor (c-mp1) under control of a cytomegaloviral promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in Iscove's modified Dulbecco's medium (IMDM; GIBCO) containing 10% fetal bovine serum (FBS; TRACE SCIENTIFIC) using a $CO_2$ incubator (5% $CO_2$, 37° C.).

(2) Cell Proliferation Assay by the MTT Method

Figure 2:
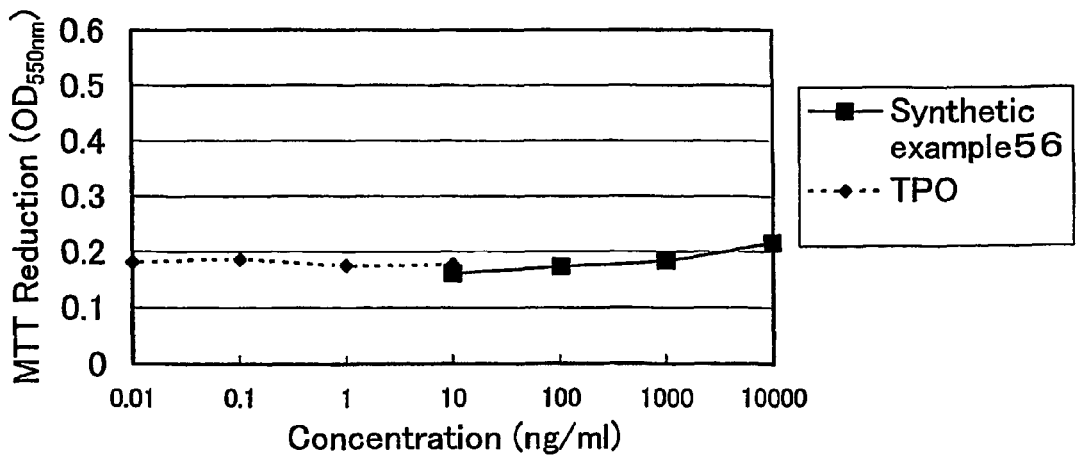
FIG. 2: The proliferation of UT7/EPO cells when stimulated by Synthetic Example 56 assayed by the MTT method is shown in FIG. 2.

The subcultured cells described above were washed twice with phosphate buffered saline (PBS) and suspended in IMDM containing 10% FBS at a cell density of $6 \times 10^4$ cells/ml. The cell suspension was transferred to a 96-well tissue culture plate (CORNING) in 100-µl aliquots. Then either TPO (PeproTech EC) or Synthetic Example 56 dissolved in dimethylsulfoxide (DMSO) was diluted 83-fold with IMDM containing 10% FBS and added to the aforementioned cell suspension in 20-µl aliquots. The suspension was incubated in a $CO_2$ incubator (5% $CO_2$, 37° C.) for 4 days. Cell proliferation was assayed according to the method of Mosmann et al. (J. Immunol. Methods, 65:55-63 (1983)). A 10-µl aliquot of 5 mg/ml MTT reagent (SIGMA) was added to each well of the tissue culture plate and the plate was incubated at 37° C. for 4 h. The formazan pigment generated was dissolved by adding 150 µl per well of 0.1 M HCl/isopropanol solution and the absorbance of the resulting pigment solution was measured at 550 nm with a 96-well microplate reader (BIO-RAD, M450). FIG. 1 shows the results with UT7/EPO-mp1 cells, while FIG. 2 shows data obtained with UT7/EPO cells expressing no TPO receptor. FIG. 1 demonstrated that proliferation of UT7/EPO-mp1 cells was stimulated by Synthetic Example 56 in a concentration-dependent manner, while no effect of this compound on proliferation was observed with UT7/EPO, the mother cell line, as shown in FIG. 2.

Assay Example 2

Activity of Signal Transduction Mediated by TPO Receptor

The signal-transducing activity of Synthetic Example 56, the compound of the present invention, mediated by TPO receptor was assayed according to the method of Komatsu et al. (Blood, 87:4552-4560 (1996)). Human leukemic cell line UT7/EPO-mp1 was washed three times with PBS and suspended in IMDM containing 10% FBS at a cell density of $9 \times 10^5$ cells/ml. The cell suspension was incubated in a $CO_2$ incubator (5% $CO_2$, 37° C.) for 18 h. To 2 ml of this cell suspension ($7 \times 10^6$ cells/ml), either TPO (final concentration, 30 ng/ml) or a DMSO solution of Synthetic Example 56 (final concentration, 1 µg/ml) was added. After incubating the mixture at 37° C. for 1-15 min, the cells were lysed in 1.4 ml of TNE buffer (20 mM Tris-HCl buffer (pH 7.4) containing 150 mM NaCl, 1 mM EDTA, 1% Triton X-100, 1 mM PMSF, 1 mM $Na_3VO_4$, and 1/400-diluted Protease Inhibitor Cocktail (SIGMA)). The cell lysate was centrifuged to collect the supernatant for immunoprecipitation with antibodies against proteins involved in signal transduction (anti-STAT3 (SANTA CRUZ BIOTECHNOLOGY) and anti-STAT5A (UPSTATE BIOTECHNOLOGY)) and protein G Sepharose (PHARMACIA). The immunoprecipitated protein fraction was collected and denatured in a sample buffer for separation by SDS-polyacrylamide gel electrophoresis (7.5%). The separated proteins were transferred onto polyvinylidene difluoride (PVDF) membrane (Atto Corporation, 0.2 µm pore size) at 100 V for 1 h for detection of tyrosine phosphorylation using an alkaline phosphatase-labelled antibody against phosphorylated tyrosine (RC20, TRANSDUCTION LABORATORIES). The antigen-antibody complex formed on the PVDF membrane was visualized with 150 µg/ml NBT (BIO-RAD) and 300 µg/ml BCIP (BIO-RAD). The results are summarized in Table 7.

TABLE 7

|  | DMSO | SYNTHETIC EXAMPLE No. 56 | TPO |
|---|---|---|---|
| STAT 3 | − | + | + |
| STAT 5A | − | + | + |

Assay Example 3

The following Synthetic Examples were tested according to the method of Assay Example 1 to determine the maximal growth rate (efficacy), expressed by taking the value with human leukemic cell line UT7/EPO-mp1 observed in the presence of 10 ng/ml TPO as 100% standard, and the concentration of each compound that yields a growth rate corresponding to 50% of the maximum cell growth observed with the same compound ($EC_{50}$). The results are summarized in Table 8. Here, "-" indicates that $EC_{50}$ was not determined because the value of efficacy was below the detection limit.

TABLE 8

| Synthetic Example No. | Efficacy (%) | $EC_{50}$ (ng/ml) |
|---|---|---|
| 1 | 74 | 7.4 |
| 2 | 89 | 6.3 |
| 3 | 82 | 15 |
| 4 | 53 | 15 |

TABLE 8-continued

| Synthetic Example No. | Efficacy (%) | EC$_{50}$ (ng/ml) |
|---|---|---|
| 5 | 86 | 3.4 |
| 6 | 64 | 7.4 |
| 7 | 99 | 2.2 |
| 8 | 52 | 31 |
| 9 | 90 | 5.1 |
| 10 | 78 | 20 |
| 11 | 83 | 2.0 |
| 12 | 100 | 76 |
| 13 | 99 | 280 |
| 14 | 91 | 72 |
| 15 | 109 | 23 |
| 16 | 58 | 61 |
| 17 | 73 | 79 |
| 18 | 94 | 55 |
| 19 | 100 | 14 |
| 20 | 91 | 38 |
| 21 | 39 | 290 |
| 22 | 50 | 190 |
| 23 | 129 | 28 |
| 24 | 89 | 7.2 |
| 25 | 54 | 200 |
| 26 | 78 | 2.9 |
| 27 | 75 | 5.6 |
| 28 | 99 | 37 |
| 29 | 67 | 230 |
| 30 | 106 | 19 |
| 31 | 63 | 5.2 |
| 32 | 90 | 37 |
| 33 | 96 | 1.1 |
| 34 | 99 | 5.2 |
| 35 | 99 | 34 |
| 36 | 97 | 59 |
| 37 | 63 | 140 |
| 38 | 93 | 36 |
| 39 | 97 | 28 |
| 40 | 37 | 250 |
| 41 | 115 | 32 |
| 42 | 71 | 250 |
| 43 | 87 | 83 |
| 44 | 26 | 250 |
| 45 | 74 | 30 |
| 46 | 82 | 15 |
| 47 | 48 | 190 |
| 48 | 62 | 8.0 |
| 49 | 62 | 9.1 |
| 50 | 89 | 37 |
| 51 | 73 | 33 |
| 52 | 22 | 120 |
| 53 | 120 | 12 |
| 54 | 61 | 7.5 |
| 55 | 53 | 220 |
| 56 | 96 | 1.1 |
| 57 | 97 | 5.9 |
| 58 | 110 | 32 |
| 59 | 82 | 24 |
| 60 | 62 | 100 |
| 61 | 91 | 29 |
| 62 | 57 | 6.4 |
| 63 | 21 | 190 |
| 64 | 74 | 7.7 |
| 65 | 70 | 8.9 |
| 66 | 133 | 33 |
| 67 | 80 | 33 |
| 68 | 26 | 210 |
| 69 | 89 | 5.7 |
| 70 | 87 | 23 |
| 71 | 89 | 69 |
| 72 | 88 | 75 |
| 73 | 84 | 10 |
| 74 | 77 | 25 |
| 75 | 89 | 63 |
| 76 | 79 | 46 |
| 77 | 78 | 5.1 |
| 78 | 69 | 15 |
| 79 | 81 | 160 |
| 80 | 71 | 640 |
| 81 | 84 | 7.2 |
| 82 | 84 | 26 |
| 83 | 78 | 6.1 |
| 84 | 109 | 130 |
| 86 | 105 | 21 |
| 87 | 71 | 600 |
| 88 | 70 | 130 |
| 89 | 68 | 39 |
| 90 | 76 | 21 |
| 91 | 81 | 24 |
| 92 | 82 | 5.5 |
| 93 | 84 | 4.3 |
| Reference Synthetic Example 1 | 7 | — |
| Reference Synthetic Example 2 | 12 | — |
| Reference Synthetic Example 3 | 7 | — |
| Reference Synthetic Example 4 | 67 | 1400 |

Assay Example 4

Figure 3:
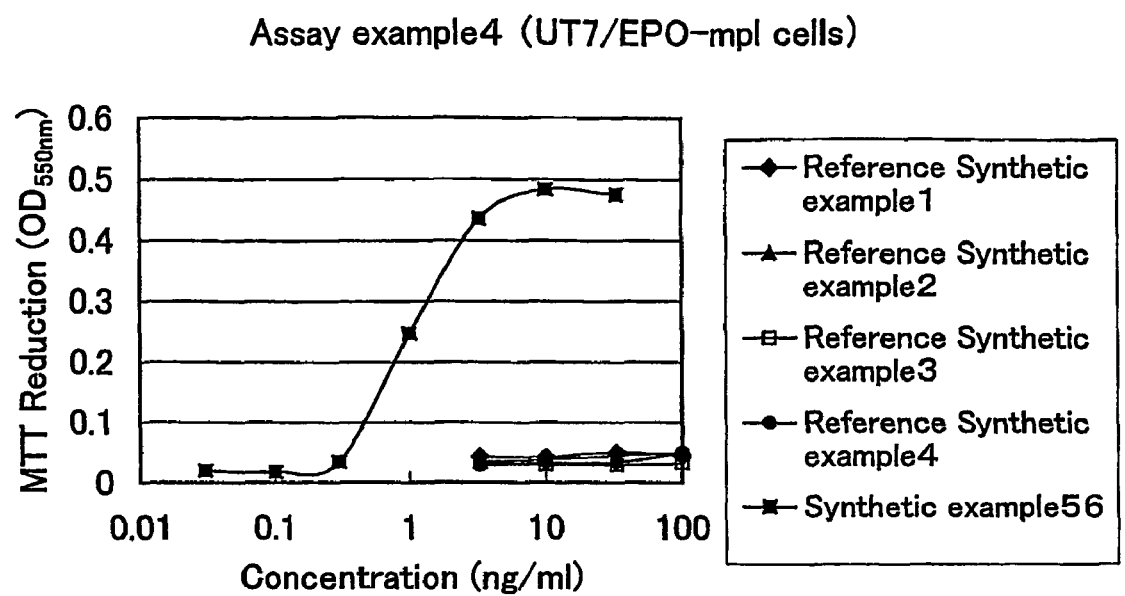
FIG. 3: The proliferation of UT7/EPO-mpl cells when stimulated by Synthetic Example 56 or the compounds described in a publication of international patent application (Reference Synthetic Examples 1 to 4) assayed by the MTT method is shown in FIG. 3.

Synthetic Example 56, the compound of the present invention, and four compounds (Reference Synthetic Examples 1 to 4) described in a publication of international patent application (Publication No. WO01/34585, applied by SmithKline Beecham Corp.) were tested according to the method of Assay Example 1. FIG. 3 shows the results.

Assay Example 5

Activity of Stimulating Proliferation of a TPO-Dependent Cell Line (2)

Human leukemic cell line UT7/EPO-mpl was washed twice with PBS and suspended in IMDM containing 10% FBS at a cell density of $6\times10^4$ cells/ml. The cell suspension was transferred to a 96-well tissue culture plate (CORNING) in 100-μl aliquots. Then either TPO or the following Synthetic Examples, each dissolved in DMSO, were diluted 83-fold with IMDM containing 10% FBS and added to the aforementioned cell suspension in 20-μl aliquots. The suspension was incubated in a $CO_2$ incubator (5% $CO_2$, 37° C.) for 4 days. Cell proliferation was assayed using WST-8 reagent (Kishida Chemical, Co. Ltd.) according to instructions by the manufacturer. A 10-μl aliquot of 5 mM WST-8 reagent solution was added to each well of the tissue culture plate and the plate was incubated at 37° C. for 4 h. The formazan pigment generated was detected by measuring the absorbance at 450 nm with a 96-well microplate reader (Nihon Molecular Devices, SpectraMax 190). The concentration of each compound that yields a growth rate corresponding to 50% of the growth of human leukemic cell line UT7/EPO-mpl observed in the presence of 10 ng/ml TPO ($EC_{50}T$) and the maximal growth rate achieved by the same compound (efficacy), expressed by taking the value with human leukemic cell line UT7/EPO-mpl in the presence of 10 ng/ml TPO as 100% standard, are summarized in Table 9.

TABLE 9

| Synthetic Example No. | Efficacy (%) | EC$_{50}$T (ng/ml) |
|---|---|---|
| 94 | 95 | 3.3 |
| 95 | 71 | 52 |

TABLE 9-continued

| Synthetic Example No. | Efficacy (%) | EC$_{50}$T (ng/ml) |
| --- | --- | --- |
| 96 | 93 | 3.3 |
| 97 | 94 | 25 |
| 98 | 96 | 31 |
| 99 | 110 | 3.9 |
| 100 | 107 | 59 |
| 101 | 100 | 18 |
| 102 | 100 | 69 |
| 103 | 90 | 4.8 |

Formulation Example 1

A granule preparation containing the following ingredients is prepared.

| Ingredients | |
| --- | --- |
| Compound represented by the formula (1) | 10 mg |
| Lactose | 700 mg |
| Corn Starch | 274 mg |
| HPC-L | 16 mg |
| | 1000 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
| --- | --- |
| Compound represented by the formula (1) | 10 mg |
| Lactose | 79 mg |
| Corn Starch | 10 mg |
| Magnesium Stearate | 1 mg |
| | 100 mg |

A compound represented by the formula (1) and lactose are sifted through a 60-mesh sieve. Corn starch is sifted though a 120-mesh sieve. They are mixed with magnesium stearate in a V-type blender. The 10% powder is put in hard capsules No. 5, 100 mg each.

Formulation Example 3

A granule preparation for capsulation containing the following ingredients is prepared.

| Ingredients | |
| --- | --- |
| Compound represented by the formula (1) | 15 mg |
| Lactose | 90 mg |
| Corn Starch | 42 mg |
| HPC-L | 3 mg |
| | 150 mg |

A compound represented by the formula (1) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
| --- | --- |
| Compound represented by the formula (1) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (1), lactose, microcrystalline cellulose and CMC-NA (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

A intravenous preparation is prepared as follows.

| | |
| --- | --- |
| Compound represented by the formula (1) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The invention claimed is:

1. A pyrazolone compound represented by formula (2):

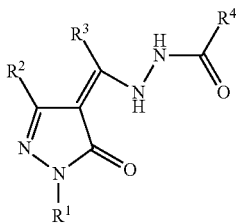

Formula (2)

wherein
R$^1$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups, and
wherein the hydroxyl group and the amino group may be substituted with a C$_{1-6}$ alkyl group or a C$_{1-6}$ alkylcarbonyl group;
R$^2$ is a hydrogen atom, a C$_{1-6}$ alkyl group, a C$_{1-3}$ alkyl group substituted with one or more fluorine atoms or a C$_{2-14}$ aryl group;
R$^3$ is a hydrogen atom, a C$_{1-6}$ alkyl group or a C$_{1-3}$ alkyl group substituted with one or more fluorine atoms, and
R$^4$ is a C$_{2-14}$ aryl group substituted with NR$^5$R$^6$ (wherein R$^5$ and R$^6$ are independently hydrogen atoms, formyl groups, C$_{1-6}$ alkyl groups or C$_{1-6}$ alkylcarbonyl groups),
a tautomer, prodrug or pharmaceutically acceptable salt of the compound.

2. A pyrazolone compound represented by formula (2):

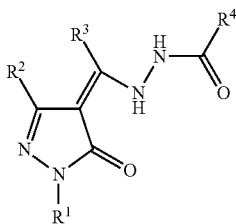

Formula (2)

wherein
R$^1$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups, and
wherein the hydroxyl group and the amino group may be substituted with a C$_{1-6}$ alkyl group or a C$_{1-6}$ alkylcarbonyl group;
R$^2$ is a hydrogen atom, a C$_{1-6}$ alkyl group, a C$_{1-3}$ alkyl group substituted with one or more fluorine atoms or a C$_{2-14}$ aryl group;
R$^3$ is a hydrogen atom, a C$_{1-6}$ alkyl group or a C$_{1-3}$ alkyl group substituted with one or more fluorine atoms, and
R$^4$ is a C$_{2-14}$ aryl group substituted with one or more nitro groups,
a tautomer, prodrug or pharmaceutically acceptable salt of the compound.

3. A pyrazolone compound represented by formula (3):

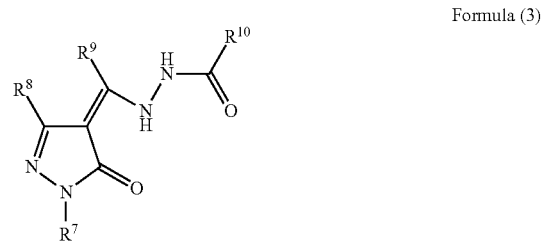

Formula (3)

wherein
R$^7$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups,
wherein the hydroxyl group and the amino group may be substituted with a C$_{1-6}$ alkyl group or a C$_{1-6}$ alkylcarbonyl group;
R$^8$ is a hydrogen atom, a C$_{1-6}$ alkyl group, a C$_{1-3}$ alkyl group substituted with one or more fluorine atoms or a C$_{2-14}$ aryl group;
R$^9$ is a hydrogen atom, a C$_{1-6}$ alkyl group or a C$_{1-3}$ alkyl group substituted with one or more fluorine atoms, and
R$^{10}$ is a C$_{2-14}$ aryl group substituted with one or more carboxyl groups;
a tautomer, prodrug or pharmaceutically acceptable salt of the compound.

4. A pyrazolone compound represented by formula (3):

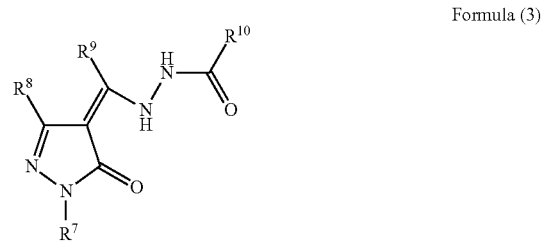

Formula (3)

wherein

R$^7$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups,
wherein the hydroxyl group and the amino group may be substituted with a C$_{1-6}$ alkyl group or a C$_{1-6}$ alkylcarbonyl group;

R$^8$ is a hydrogen atom, a C$_{1-6}$ alkyl group, a C$_{1-3}$ alkyl group substituted with one or more fluorine atoms or a C$_{2-14}$ aryl group;

R$^9$ is a hydrogen atom, a C$_{1-6}$ alkyl group or a C$_{1-3}$ alkyl group substituted with one or more fluorine atoms, and R$^{10}$ is a C$_{2-14}$ aryl group substituted with X(CYZ)$_n$CO$_2$H, wherein X is CH$_2$, O, S or NR$^{11}$; and R$^{11}$ is a hydrogen atom, a C$_{1-6}$ alkyl group, a formyl group or a C$_{1-6}$ alkylcarbonyl group, wherein Y and Z are independently hydrogen atoms or C$_{1-3}$ alkyl groups, and n is 0, 1, 2 or 3;

a tautomer, prodrug or pharmaceutically acceptable salt of the compound.

5. A pyrazolone compound represented by formula (3):

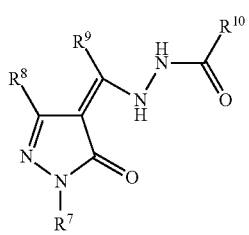

Formula (3)

wherein

R$^7$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups,
wherein the hydroxyl group and the amino group may be substituted with a C$_{1-6}$ alkyl group or a C$_{1-6}$ alkylcarbonyl group;

R$^8$ is a hydrogen atom, a C$_{1-6}$ alkyl group, a C$_{1-3}$ alkyl group substituted with one or more fluorine atoms or a C$_{2-14}$ aryl group;

R$^9$ is a hydrogen atom, a C$_{1-6}$ alkyl group or a C$_{1-3}$ alkyl group substituted with one or more fluorine atoms, and R$^{10}$ is a C$_{2-14}$ aryl group substituted with one or more sulfonic acid groups;

a tautomer, prodrug or pharmaceutically acceptable salt of the compound.

6. A pyrazolone compound represented by formula (3):

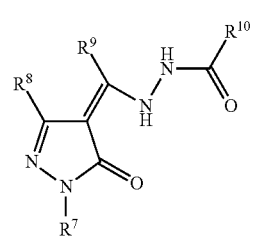

Formula (3)

wherein

R$^7$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups,
wherein the hydroxyl group and the amino group may be substituted with a C$_{1-6}$ alkyl group or a C$_{1-6}$ alkylcarbonyl group;

R$^8$ is a hydrogen atom, a C$_{1-6}$ alkyl group, a C$_{1-3}$ alkyl group substituted with one or more fluorine atoms or a C$_{2-14}$ aryl group;

R$^9$ is a hydrogen atom, a C$_{1-6}$ alkyl group or a C$_{1-3}$ alkyl group substituted with one or more fluorine atoms, and R$^{10}$ is a C$_{2-14}$ aryl group substituted with one or more phosphonic acid groups;

a tautomer, prodrug or pharmaceutically acceptable salt of the compound.

7. A pyrazolone compound represented by formula (3):

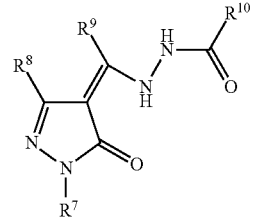

Formula (3)

wherein

R$^7$ is a C$_{2-14}$ aryl group,
wherein the C$_{2-14}$ aryl group may be optionally substituted with one or more C$_{1-6}$ alkyl groups, one or more C$_{1-3}$ alkyl groups substituted with one or more fluorine atoms, one or more halogen atoms, one or more nitro groups, one or more C$_{1-6}$ alkylcarbonyl groups, one or more hydroxyl groups or one or more amino groups,
wherein the hydroxyl group and the amino group may be substituted with a C$_{1-6}$ alkyl group or a C$_{1-6}$ alkylcarbonyl group;

R$^8$ is a hydrogen atom, a C$_{1-6}$ alkyl group, a C$_{1-3}$ alkyl group substituted with one or more fluorine atoms or a C$_{2-14}$ aryl group;

R$^9$ is a hydrogen atom, a C$_{1-6}$ alkyl group or a C$_{1-3}$ alkyl group substituted with one or more fluorine atoms, and $R^{10}$ is a $C_{2-14}$ aryl group substituted with one or more tetrazole groups;

a tautomer, prodrug or pharmaceutically acceptable salt of the compound.

8. A pyrazolone compound represented by formula (4):

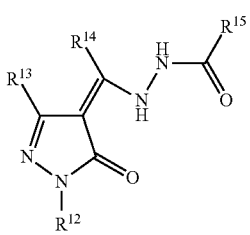

Formula (4)

wherein $R^{12}$ is a $C_{2-14}$ aryl group,
wherein the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups,
wherein the hydroxyl group and the amino group may be substituted with a $C_{1-6}$ alkyl group or a $C_{1-6}$ alkylcarbonyl group;

$R^{13}$ is a hydrogen atom, a $C_{1-6}$ alkyl group, a $C_{1-3}$ alkyl group substituted with one or more fluorine atoms or a $C_{2-14}$ aryl group;

$R^{14}$ is a hydrogen atom, a $C_{1-6}$ alkyl group or a $C_{1-3}$ alkyl group substituted with one or more fluorine atoms, and $R^{15}$ is a $C_{2-14}$ aryl group substituted with an amino group and a carboxyl group;

a tautomer, a prodrug or pharmaceutically acceptable salt of the compound.

9. A pyrazolone compound represented by formula (4):

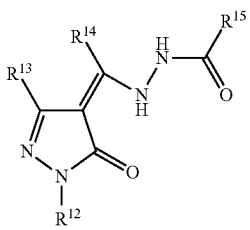

Formula (4)

wherein $R^{12}$ is a $C_{2-14}$ aryl group,
wherein the $C_{2-14}$ aryl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups,
wherein the hydroxyl group and the amino group may be substituted with a $C_{1-6}$ alkyl group or a $C_{1-6}$ alkylcarbonyl group;

$R^{13}$ is a hydrogen atom, a $C_{1-6}$ alkyl group, a $C_{1-3}$ alkyl group substituted with one or more fluorine atoms or a $C_{2-14}$ aryl group;

$R^{14}$ is a hydrogen atom, a $C_{1-6}$ alkyl group or a $C_{1-3}$ alkyl group substituted with one or more fluorine atoms, and $R^{15}$ is a $C_{2-14}$ aryl group substituted with a substituent selected from the group consisting of a nitro group, a halogen atom, a cyano group, a $C_{1-3}$ alkyl group substituted with one or more fluorine atoms;

a tautomer, prodrug or pharmaceutically acceptable salt of the compound.

10. A pharmaceutical preparation comprising the pyrazolone compound according to claim 1 and at least one pharmaceutically acceptable additive selected from the group consisting of an excipient, a lubricant, a binder, a disintegrant, a humectant, a plasticizer, and a coating agent.

11. A pharmaceutical preparation comprising the pyrazolone compound according to claim 2 and at least one pharmaceutically acceptable additive selected from the group consisting of an excipient, a lubricant, a binder, a disintegrant, a humectant, a plasticizer, and a coating agent.

12. A pharmaceutical preparation comprising the pyrazolone compound according to claim 3 and at least one pharmaceutically acceptable additive selected from the group consisting of an excipient, a lubricant, a binder, a disintegrant, a humectant, a plasticizer, and a coating agent.

13. A pharmaceutical preparation comprising the pyrazolone compound according to claim 4 and at least one pharmaceutically acceptable additive selected from the group consisting of an excipient, a lubricant, a binder, a disintegrant, a humectant, a plasticizer, and a coating agent.

14. A pharmaceutical preparation comprising the pyrazolone compound according to claim 5 and at least one pharmaceutically acceptable additive selected from the group consisting of an excipient, a lubricant, a binder, a disintegrant, a humectant, a plasticizer, and a coating agent.

15. A pharmaceutical preparation comprising the pyrazolone compound according to claim 6 and at least one pharmaceutically acceptable additive selected from the group consisting of an excipient, a lubricant, a binder, a disintegrant, a humectant, a plasticizer, and a coating agent.

16. A pharmaceutical preparation comprising the pyrazolone compound according to claim 7 and at least one pharmaceutically acceptable additive selected from the group consisting of an excipient, a lubricant, a binder, a disintegrant, a humectant, a plasticizer, and a coating agent.

17. A pharmaceutical preparation comprising the pyrazolone compound according to claim 8 and at least one pharmaceutically acceptable additive selected from the group consisting of an excipient, a lubricant, a binder, a disintegrant, a humectant, a plasticizer, and a coating agent.

18. A pharmaceutical preparation comprising the pyrazolone compound according to claim 9 and at least one pharmaceutically acceptable additive selected from the group consisting of an excipient, a lubricant, a binder, a disintegrant, a humectant, a plasticizer, and a coating agent.

19. A pyrazolone compound represented by formula (1):

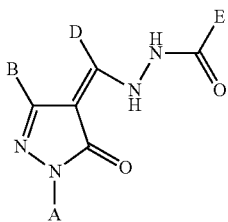

Formula (1)

wherein
A is a phenyl group,
wherein the phenyl group may be optionally substituted with one or more $C_{1-6}$ alkyl groups, one or more $C_{1-3}$ alkyl groups substituted with one or more fluorine atoms, one or more halogen atoms, one or more nitro groups, one or more $C_{1-6}$ alkylcarbonyl groups, one or more hydroxyl groups or one or more amino groups, and
wherein the hydroxyl group and the amino group may be substituted with a $C_{1-6}$ alkyl group or a $C_{1-6}$ alkylcarbonyl group;
B is a hydrogen atom, a $C_{1-6}$ alkyl group, a $C_{1-3}$ alkyl group substituted with one or more fluorine atoms or a phenyl group;
D is a hydrogen atom, a $C_{1-6}$ alkyl group or a $C_{1-3}$ alkyl group substituted with one or more fluorine atoms; and
E is a phenyl,
wherein the phenyl group is optionally substituted with one or more hydroxyl groups, one or more nitro groups, $NG^1G^2$,
wherein $G^1$ and $G^2$ are independently hydrogen atoms, formyl groups, $C_{1-6}$ alkyl groups or $C_{1-6}$ alkylcarbonyl groups,
one or more carboxyl groups, and one or more $C_{1-6}$ alkoxycarbonyl groups or $X(CYZ)_nCO_2H$,
wherein X is $CH_2$, O, S or $NG^3$,
wherein $G^3$ is a hydrogen atom, a $C_{1-6}$ alkyl group, a formyl group or a $C_{1-6}$ alkylcarbonyl group,
wherein Y and Z are independently hydrogen atoms or $C_{1-3}$ alkyl groups, and n is 0, 1, 2 or 3;
a tautomer, prodrug or pharmaceutically acceptable salt of the compound.

20. A pharmaceutical preparation comprising the pyrazolone compound according to claim 19 and at least one pharmaceutically acceptable additive selected from the group consisting of an excipient, a lubricant, a binder, a disintegrant, a humectant, a plasticizer, and a coating agent.

21. A medicament comprising at least one pyrazolone compound of formula (1) according to claim 19.

* * * * *